(12) United States Patent
Alfonso et al.

(10) Patent No.: US 9,486,484 B2
(45) Date of Patent: *Nov. 8, 2016

(54) METHODS OF USING ADIPOSE TISSUE-DERIVED CELLS IN THE TREATMENT OF THE LYMPHATIC SYSTEM AND MALIGNANT DISEASE

(71) Applicant: CYTORI THERAPEUTICS, INC., San Diego, CA (US)

(72) Inventors: Zeni Alfonso, Temecula, CA (US); John K. Fraser, San Diego, CA (US)

(73) Assignee: Cytori Therapeutics, Inc., San Diego, CA (US)

( * ) Notice: Subject to any disclaimer, the term of this patent is extended or adjusted under 35 U.S.C. 154(b) by 173 days.

This patent is subject to a terminal disclaimer.

(21) Appl. No.: 14/336,755

(22) Filed: Jul. 21, 2014

(65) Prior Publication Data

US 2014/0369970 A1  Dec. 18, 2014

Related U.S. Application Data

(63) Continuation of application No. 13/031,031, filed on Feb. 18, 2011, now Pat. No. 8,784,801, which is a continuation of application No. PCT/US2009/054055, filed on Aug. 17, 2009.

(60) Provisional application No. 61/090,186, filed on Aug. 19, 2008.

(51) Int. Cl.

| | |
|---|---|
| *C12N 5/00* | (2006.01) |
| *A61K 35/28* | (2015.01) |
| *A61K 35/35* | (2015.01) |
| *C12N 5/078* | (2010.01) |
| *C12N 5/071* | (2010.01) |
| *A61K 45/06* | (2006.01) |
| *A61K 35/12* | (2015.01) |

(52) U.S. Cl.
CPC .............. *A61K 35/28* (2013.01); *A61K 35/35* (2013.01); *A61K 45/06* (2013.01); *C12N 5/069* (2013.01); *C12N 5/0651* (2013.01); *A61K 35/12* (2013.01); *A61K 2035/124* (2013.01)

(58) Field of Classification Search
None
See application file for complete search history.

(56) References Cited

U.S. PATENT DOCUMENTS

| | | |
|---|---|---|
| 3,917,515 A | 11/1975 | Goldberg |
| 4,000,275 A | 12/1976 | Lunn |
| 4,146,172 A | 3/1979 | Cullis et al. |
| 4,418,691 A | 12/1983 | Yannas et al. |
| 4,458,678 A | 7/1984 | Yannas et al. |
| 4,466,888 A | 8/1984 | Verkaart |
| 4,734,269 A | 3/1988 | Clarke et al. |
| 4,820,626 A | 4/1989 | Williams et al. |
| 4,834,703 A | 5/1989 | Dubrul et al. |
| 4,883,755 A | 11/1989 | Carabasi et al. |
| 4,897,185 A | 1/1990 | Schuyler et al. |
| 4,963,489 A | 10/1990 | Naughton et al. |
| 5,034,135 A | 7/1991 | Fischel |
| 5,035,708 A | 7/1991 | Alchas et al. |
| 5,079,160 A | 1/1992 | Lacy et al. |
| 5,087,244 A | 2/1992 | Wolinsky et al. |
| 5,092,883 A | 3/1992 | Eppley et al. |
| 5,131,907 A | 7/1992 | Williams et al. |
| 5,143,063 A | 9/1992 | Fellner |
| 5,158,867 A | 10/1992 | McNally et al. |
| 5,226,914 A | 7/1993 | Caplan et al. |
| 5,234,608 A | 8/1993 | Duff |
| 5,261,612 A | 11/1993 | Ftaiha |
| 5,312,380 A | 5/1994 | Alchas et al. |
| 5,372,945 A | 12/1994 | Alchas et al. |
| 5,409,833 A | 4/1995 | Hu et al. |
| 5,436,135 A | 7/1995 | Tayot et al. |
| 5,470,307 A | 11/1995 | Lindall |
| 5,486,359 A | 1/1996 | Caplan et al. |
| 5,521,087 A | 5/1996 | Lee et al. |
| 5,562,646 A | 10/1996 | Goldman et al. |
| 5,591,625 A | 1/1997 | Gerson et al. |

(Continued)

FOREIGN PATENT DOCUMENTS

| | | |
|---|---|---|
| CN | 1287166 | 3/2001 |
| CN | 101258237 | 9/2008 |

(Continued)

OTHER PUBLICATIONS

Abbate, A., Biondi-Zoccai, G.G. and Baldi, A. (2002) "Pathophysiologic role of myocardial apoptosis in post-infarction left ventricular remodeling" J Cell Physiol 193, 145-53.

(Continued)

*Primary Examiner* — Blaine Lankford

(74) *Attorney, Agent, or Firm* — Knobbe Martens Olson & Bear LLP

(57) ABSTRACT

Aspects of the invention provides methods for preparing and using adipose-tissue-derived stem and progenitor cells, adipose-tissue-derived lymphatic endothelial cells, and cells capable of differentiating into lymphatic endothelial cells to treat disorders of the lymphatic system and to modulate expansion, repair, and/or regeneration of the lymphatic system. The invention further provides using adipose-tissue-derived lymphatic endothelial cells and cells capable of differentiating into lymphatic endothelial cells for delivery of therapeutic agents to tumor cells as a means for treating malignant disease, and assays to screen for drugs that modulate lymphatic system expansion, repair or regeneration.

20 Claims, 22 Drawing Sheets

(56) References Cited

U.S. PATENT DOCUMENTS

| | | | |
|---|---|---|---|
| 5,641,622 A | 6/1997 | Lake et al. |
| 5,653,689 A | 8/1997 | Buelna et al. |
| 5,654,186 A | 8/1997 | Cerami et al. |
| 5,686,262 A | 11/1997 | Fink et al. |
| 5,686,289 A | 11/1997 | Humes et al. |
| 5,688,531 A | 11/1997 | Benayahu |
| 5,713,860 A | 2/1998 | Kaplan et al. |
| 5,728,739 A | 3/1998 | Ailhaud et al. |
| 5,736,396 A | 4/1998 | Bruder et al. |
| 5,744,360 A | 4/1998 | Hu et al. |
| 5,783,408 A | 7/1998 | Hamilton et al. |
| 5,785,965 A | 7/1998 | Pratt et al. |
| 5,786,207 A | 7/1998 | Katz et al. |
| 5,811,094 A | 9/1998 | Caplan et al. |
| 5,817,050 A | 10/1998 | Klein |
| 5,827,735 A | 10/1998 | Young et al. |
| 5,827,740 A | 10/1998 | Pittenger |
| 5,827,897 A | 10/1998 | Ailhaud et al. |
| 5,830,714 A | 11/1998 | Swaminathan et al. |
| 5,830,741 A | 11/1998 | Dwulet et al. |
| 5,837,235 A | 11/1998 | Mueller et al. |
| 5,837,444 A | 11/1998 | Shah et al. |
| 5,837,539 A | 11/1998 | Caplan et al. |
| 5,851,832 A | 12/1998 | Weiss et al. |
| 5,854,292 A | 12/1998 | Ailhaud et al. |
| 5,869,037 A | 2/1999 | Crystal et al. |
| 5,906,934 A | 5/1999 | Grande et al. |
| 5,908,784 A | 6/1999 | Johnstone et al. |
| 5,916,743 A | 6/1999 | Lake et al. |
| 5,952,215 A | 9/1999 | Dwulet et al. |
| 5,968,356 A | 10/1999 | Morsiani |
| 5,980,887 A | 11/1999 | Isner et al. |
| 6,001,642 A | 12/1999 | Tsao |
| 6,010,696 A | 1/2000 | Caplan et al. |
| 6,020,196 A | 2/2000 | Hu et al. |
| 6,030,836 A | 2/2000 | Thiede et al. |
| 6,043,066 A | 3/2000 | Mangano et al. |
| 6,086,582 A | 7/2000 | Altman et al. |
| 6,090,121 A | 7/2000 | Weber et al. |
| 6,129,853 A | 10/2000 | Sasayama et al. |
| 6,139,757 A | 10/2000 | Ohmura |
| 6,197,325 B1 | 3/2001 | MacPhee et al. |
| 6,200,606 B1 | 3/2001 | Peterson et al. |
| 6,206,873 B1 | 3/2001 | Paolini et al. |
| 6,221,315 B1 | 4/2001 | Giesler et al. |
| 6,232,345 B1 | 5/2001 | Hiraide et al. |
| 6,238,908 B1 | 5/2001 | Armstrong et al. |
| 6,251,295 B1 | 6/2001 | Johnson |
| 6,261,549 B1 | 7/2001 | Fernandez et al. |
| 6,277,060 B1 | 8/2001 | Neumann |
| 6,316,247 B1 | 11/2001 | Katz et al. |
| 6,322,784 B1 | 11/2001 | Pittenger et al. |
| 6,355,239 B1 | 3/2002 | Bruder et al. |
| 6,368,356 B1 | 4/2002 | Zhong et al. |
| 6,387,369 B1 | 5/2002 | Pittenger et al. |
| 6,429,013 B1 | 8/2002 | Halvorsen et al. |
| 6,436,639 B1 | 8/2002 | Kiefer et al. |
| 6,451,207 B1 | 9/2002 | Sterman et al. |
| 6,475,764 B1 | 11/2002 | Burtscher et al. |
| 6,517,526 B1 | 2/2003 | Tamari |
| 6,576,464 B2 | 6/2003 | Gold et al. |
| 6,589,728 B2 | 7/2003 | Csete et al. |
| 6,623,959 B2 | 9/2003 | Harris |
| 6,689,352 B2 | 2/2004 | Achen et al. |
| 6,777,231 B1 | 8/2004 | Katz et al. |
| 6,804,558 B2 | 10/2004 | Haller et al. |
| 7,078,230 B2 | 7/2006 | Wilkison |
| 7,390,484 B2 | 6/2008 | Fraser et al. |
| 7,514,075 B2 | 4/2009 | Hedrick et al. |
| 7,585,670 B2 | 9/2009 | Hedrick et al. |
| 7,651,684 B2 | 1/2010 | Hedrick et al. |
| 7,767,452 B2 | 8/2010 | Kleinsek |
| 7,771,716 B2 | 8/2010 | Hedrick et al. |
| 7,887,795 B2 | 2/2011 | Fraser et al. |
| 7,901,672 B2 | 3/2011 | Fraser et al. |
| 8,053,248 B2 | 11/2011 | Bakaltcheva et al. |
| 8,105,580 B2 | 1/2012 | Fraser et al. |
| 8,119,121 B2 | 2/2012 | Fraser et al. |
| 8,163,276 B2 | 4/2012 | Hedrick et al. |
| 8,246,947 B2 | 8/2012 | Hedrick et al. |
| 8,404,229 B2 | 3/2013 | Fraser et al. |
| 8,691,216 B2 | 4/2014 | Fraser |
| 8,771,678 B2 | 7/2014 | Hedrick et al. |
| 8,784,801 B2 * | 7/2014 | Alfonso ............... A61K 35/28 424/93.7 |
| 8,883,499 B2 | 11/2014 | Hedrick et al. |
| 9,198,937 B2 | 12/2015 | Fraser et al. |
| 2001/0000802 A1 | 5/2001 | Soykan et al. |
| 2001/0009757 A1 | 7/2001 | Bischof et al. |
| 2002/0103542 A1 | 8/2002 | Bilbo |
| 2002/0111694 A1 | 8/2002 | Ellingsen et al. |
| 2002/0142909 A1 | 10/2002 | Sakota |
| 2002/0182211 A1 | 12/2002 | Peach et al. |
| 2003/0014126 A1 | 1/2003 | Patel et al. |
| 2003/0026759 A1 | 2/2003 | Ferrell et al. |
| 2003/0054331 A1 | 3/2003 | Fraser et al. |
| 2003/0069168 A1 | 4/2003 | Xu et al. |
| 2003/0075516 A1 | 4/2003 | Rothman et al. |
| 2003/0082152 A1 | 5/2003 | Hedrick et al. |
| 2003/0100105 A1 | 5/2003 | Poo et al. |
| 2003/0152558 A1 | 8/2003 | Luft et al. |
| 2003/0161816 A1 | 8/2003 | Fraser et al. |
| 2003/0161817 A1 | 8/2003 | Young et al. |
| 2003/0162707 A1 | 8/2003 | Fraser et al. |
| 2003/0211085 A1 | 11/2003 | Sanberg et al. |
| 2003/0211602 A1 | 11/2003 | Atala |
| 2003/0212024 A1 | 11/2003 | Keating et al. |
| 2004/0067218 A1 | 4/2004 | Casteilla et al. |
| 2004/0076604 A1 | 4/2004 | Stein-Streilein et al. |
| 2004/0122710 A1 | 6/2004 | Holte |
| 2004/0197304 A1 | 10/2004 | Chen et al. |
| 2005/0008626 A1 | 1/2005 | Fraser et al. |
| 2005/0084961 A1 | 4/2005 | Hedrick et al. |
| 2005/0186261 A1 | 8/2005 | Avelar et al. |
| 2005/0271636 A1 | 12/2005 | Oliver et al. |
| 2006/0025338 A1 * | 2/2006 | Alitalo ............... A61K 38/1858 435/44 |
| 2006/0083720 A1 | 4/2006 | Fraser et al. |
| 2006/0088532 A1 | 4/2006 | Alitalo et al. |
| 2007/0111935 A1 | 5/2007 | Franco et al. |
| 2007/0116674 A1 | 5/2007 | Casteilla et al. |
| 2007/0148766 A1 | 6/2007 | Yoshimura et al. |
| 2007/0212676 A1 | 9/2007 | Takakura et al. |
| 2007/0233038 A1 | 10/2007 | Pruitt et al. |
| 2007/0274960 A1 | 11/2007 | Harman et al. |
| 2007/0274967 A1 | 11/2007 | Cao |
| 2008/0119410 A1 | 5/2008 | King et al. |
| 2008/0206208 A1 | 8/2008 | Casteilla et al. |
| 2009/0104159 A1 | 4/2009 | Prosper et al. |
| 2009/0217396 A1 | 8/2009 | Kyrkanides et al. |
| 2010/0003272 A1 | 1/2010 | Sieweke |
| 2010/0015104 A1 | 1/2010 | Fraser et al. |
| 2010/0119496 A1 | 5/2010 | Wilkison et al. |
| 2011/0293642 A1 | 12/2011 | Mays |
| 2012/0077751 A1 | 3/2012 | Wang et al. |
| 2012/0157410 A1 | 6/2012 | Watterson et al. |
| 2012/0177619 A1 | 7/2012 | Di Nicola |
| 2013/0060338 A1 | 3/2013 | Hedrick et al. |
| 2013/0108592 A1 | 5/2013 | Pinkernell et al. |
| 2013/0156726 A1 | 6/2013 | Ichim et al. |
| 2013/0164731 A1 | 6/2013 | Cimino et al. |
| 2013/0165392 A1 | 6/2013 | Harding et al. |
| 2013/0269701 A1 | 10/2013 | Lurie et al. |
| 2013/0288290 A1 | 10/2013 | Hedrick et al. |
| 2013/0344035 A1 | 12/2013 | Fraser et al. |
| 2014/0227234 A1 | 8/2014 | Fraser et al. |
| 2014/0227341 A1 | 8/2014 | Fraser et al. |
| 2015/0152375 A1 | 6/2015 | Hedrick et al. |

FOREIGN PATENT DOCUMENTS

| | | |
|---|---|---|
| CN | 101415451 | 4/2009 |
| EP | 0 040 427 | 11/1981 |
| EP | 0 341 966 | 11/1989 |

(56) References Cited

FOREIGN PATENT DOCUMENTS

| | | |
|---|---|---|
| EP | 0 399 340 | 11/1990 |
| EP | 0 418 979 | 3/1991 |
| EP | 0 446 450 | 9/1991 |
| EP | 0 448 770 | 10/1991 |
| EP | 0 512 769 | 11/1992 |
| EP | 0 515 726 | 12/1992 |
| EP | 0 570 331 | 11/1993 |
| EP | 0 919 249 | 6/1999 |
| EP | 0 987 325 | 3/2000 |
| EP | 1 077 253 | 2/2001 |
| EP | 1 077 254 | 2/2001 |
| EP | 1 011 752 | 10/2004 |
| EP | 1 712 616 | 10/2006 |
| EP | 2 450 433 | 5/2012 |
| EP | 1 678 295 | 3/2013 |
| JP | 59-090649 | 5/1984 |
| JP | 01-141583 | 6/1989 |
| JP | 02-002884 | 1/1990 |
| JP | 02-295484 | 12/1990 |
| JP | 04-183381 | 6/1992 |
| JP | 04-267873 | 9/1992 |
| JP | 7-255469 | 10/1995 |
| JP | 08-208401 | 8/1996 |
| JP | 08-259604 | 10/1996 |
| JP | 9-255588 | 9/1997 |
| JP | 10-17310 | 1/1998 |
| JP | 11-4682 | 1/1999 |
| JP | 11-57731 | 3/1999 |
| JP | 2000-325068 | 11/2000 |
| JP | 2001-103965 | 4/2001 |
| JP | 2003-024040 | 1/2003 |
| JP | 2001-231539 | 8/2003 |
| JP | 2004-99471 | 4/2004 |
| JP | 2004-272762 | 9/2004 |
| KR | 10-2004-0063167 | 7/2004 |
| WO | WO 86/01111 | 2/1986 |
| WO | WO 87/03812 | 7/1987 |
| WO | WO 94/02156 | 2/1994 |
| WO | WO 94/03645 | 2/1994 |
| WO | WO 94/27698 | 12/1994 |
| WO | WO 96/38482 | 12/1996 |
| WO | WO 97/18299 | 5/1997 |
| WO | WO 97/26326 | 7/1997 |
| WO | WO 97/39104 | 10/1997 |
| WO | WO 97/40137 | 10/1997 |
| WO | WO 97/41208 | 11/1997 |
| WO | WO 97/49827 | 12/1997 |
| WO | WO 98/04682 | 2/1998 |
| WO | WO 98/20731 | 5/1998 |
| WO | WO 98/32333 | 7/1998 |
| WO | WO 98/51317 | 11/1998 |
| WO | WO 99/01145 | 1/1999 |
| WO | WO 99/02654 | 1/1999 |
| WO | WO 99/03973 | 1/1999 |
| WO | WO 99/11789 | 3/1999 |
| WO | WO 99/28444 | 6/1999 |
| WO | WO 99/37340 | 7/1999 |
| WO | WO 99/43286 | 9/1999 |
| WO | WO 99/43787 | 9/1999 |
| WO | WO 00/53795 | 9/2000 |
| WO | WO 01/21767 | 3/2001 |
| WO | WO 01/62901 | 8/2001 |
| WO | WO 02/055678 | 7/2002 |
| WO | WO 02/064157 | 8/2002 |
| WO | WO 02/068010 | 9/2002 |
| WO | WO 02/075302 | 9/2002 |
| WO | WO 02/081007 | 10/2002 |
| WO | WO 03/001329 | 1/2003 |
| WO | WO 03/022988 | 3/2003 |
| WO | WO 03/024215 | 3/2003 |
| WO | WO 03/039481 | 5/2003 |
| WO | WO 03/053346 | 7/2003 |
| WO | WO 03/053362 | 7/2003 |
| WO | WO 03/073998 | 9/2003 |
| WO | WO 03/080801 | 10/2003 |
| WO | WO 2004/013275 | 2/2004 |
| WO | WO 2004/029230 | 4/2004 |
| WO | WO 2004/052418 | 6/2004 |
| WO | WO 2004/072828 | 8/2004 |
| WO | WO 2004/074457 | 9/2004 |
| WO | WO 2004/093934 | 11/2004 |
| WO | WO 2004/101015 | 11/2004 |
| WO | WO 2005/012480 | 2/2005 |
| WO | WO 2005/025584 | 3/2005 |
| WO | WO 2005/034843 | 4/2005 |
| WO | WO 2005/035738 | 4/2005 |
| WO | WO 2005/035742 | 4/2005 |
| WO | WO 2005/063967 | 7/2005 |
| WO | WO 2006/014156 | 2/2006 |
| WO | WO 2006/121445 | 11/2006 |
| WO | WO 2006/127007 | 11/2006 |
| WO | WO 2007/135284 | 11/2007 |
| WO | WO 2009/020650 | 2/2009 |
| WO | WO 2009/076548 | 6/2009 |
| WO | WO 2013/116041 | 8/2013 |

OTHER PUBLICATIONS

Aharinejad, S., Mars, S.C., Jr., Bock P., Mason-Savas, A., MacKay, C.A. Larson, E.K., Jackson, M.E., Luftensteiner, M. and Weisbauer, E. (1995) "CSF-1 treatment promotes angiogenesis in the metaphysics of osteopetrotic (toothless, tl) rats" Bone 16, 315-324.

Ahrens, Patricia Buckley et al., "Stage-Related Capacity for Limb Chondrogenesis in Cell Culture," *Developmental Biology*, 1977, 60:69-82.

Ailhaud, et al., 1983, "Hormonal requirements for growth and differentiation of OB17 preadipocyte cells in vitro," *Diabete & Metabolisme*, vol. 9:125-133.

Ailhaud, et al., 1985, "Lipoprotiene lipase et differenciation adipocytaire," *Reprod. Nutr. Develop.*, vol. 25:153-158.

Alameddine, Hale S. et al., "Regeneration of Skeletal Muscle Fibers from Autologous Satellite Cells Multiplied In Vitro. An Experimental Model for Testing Cultured Cell Myogenicity," *Muscle & Nerve*, 1989, 12:544-55.

Alhadlaq et al. "Engineered adipose tissue from human mesenchymal stem cells maintains predefined shape and dimension: implications in soft tissue augmentation and reconstruction." *Tissue Eng* 11, 556-566 (2005).

Anderson, Apr. 30, 1998, Human Gene Therapy, Nature, 392 Supp (6679):25-30.

Angele, P. et al., "Engineering of Osteochondral Tissue with Bone Marrow Mesenchymal Progenitor Cells in a Derivatized Hyaluronan-Gelatin Composite Sponge," *Tissue Engineering*, 1999, 5:545-53.

Ankrom et al., 1998, Age-related changes in human oestrogen receptor function and levels in osteoblasts, *Biochem J.* 333:787-794.

Aragona, F., L. D'Urso et al (1998) "Immunologic aspects of bovine injectable collagen in humans. A review" Eur Urol 33(2): 129-33.

Arts et al., 2002, Contaminants from the Transplant Contribute to Intimal Hyperplasia Associated with Microvascular Endothelial Cell Seeding, Eur. J. Endovasc. Surg. 23:29-38.

Arvidsson, A., Collin, T., Kirik, D., Kokaia, Z., and Lindvall, O. (2002) "Neuronal replacement from endogenous precursors in the adult brain after stroke" Nat Med 8, 963-70.

Ashjian et al., 2003, In vitro differentiation of human processed lipoaspirate cells into early neural progenitors Plast Reconstr Surg 111 1922-1931.

Asken, S. (1990) "Microliposuction and autologous fat transplantation for aesthetic enhancement of the aging face" J Dermatol Surg Oncol 16(10): 965-72.

Aso et al., Aug. 15, 1995, A Preadipocyte Clonal Line from bovine Intramuscular Adipose Tissue: Nonexpression of GLUT-4 protein during Adipocyte Differentiation, *Biochem. Biophys. Res. Commun.* 213:369-375.

Asou, Y., Rittling, S.R., Yoshitake, H., Tsuji, K., Shinomiya, K., Nifuji, A., Denhardt, D.T., and Noda, M. (2001) "Osteopontin facilitates angiogenesis, accumulation of osteoclasts, and resorption in ectopic bone" Endocrinology 142, 1325-1332.

(56) References Cited

OTHER PUBLICATIONS

Assady, S., Maor, G., Amit, M., ltskovitz-Eldor, J., Skorecki, K.L., and Tzukerman, M. (2001) "Insulin production by human embryonic stem cells" Diabetes 50, 1691-7.
Assmus et al., 2002, Transplantation of Progenitor Cells and Regeneration Enhancement in Acute Myocardial Infarction (TOPCARE-AMI) Circulation 106, pp. 3009-3017.
Athanasopoulos, T., Fabb, S., and Dickson, G. (2000) "Gene therapy vectors based on adeno-associated virus: characteristics and applications to acquired and inherited diseases (review)" Int J Mol Med 6, 363-75.
ATTC Preservation Methods: Freezing and Free-Drying, ATCC, 2nd Edition, 1991.
Avital, I. D. lnderbitzin, et al. (2001) "Isolation, characterization and transplantation of bone marrow-derived hepatocyte stem cells" Biochem Biophys Res Commun 288(1): 156-64.
Badiavas, et al. "Participation of bone marrow derived cells in cutaneous would healing." Journal of Cellular Physiology. 196(2): 245-250 (2003).
Bagnato et al., Jan. 2002, Emerging role of endothelin-1 in tumor angiogenesis, Trends in Endocrinology and Metabolism, 14(1):44-50.
Bailey, A. J. et al., "Age-Related Changes in the Biochemical Properties of Human Cancellous Bone Collagen: Relationship to Bone Strength," *Calcified Tissue International*, 1999, 65:203-10.
Banerji et al., Feb. 22, 1999, LYVE-1, a New Homologue of the CD44 Glycoprotein, Is a Lymph-specific Receptor for Hyaluronan, J. Cell Biology, 144(4):789-801.
Banfi, A., Bianchi, G., Galotto, M., Cancedda, R., and Quarto, R. (2001) "Bone marrow stromal damage after chemo/radiotherapy: occurrence, consequences and possibilities of treatment" Leuk Lymphoma 42, 863-70.
Barghorn, A. et al., "a-Smooth Muscle Actin Distribution in the Pulmonary Vasculature Comparing Hypoplastic and Normal Fetal Lungs," *Pediatric Pathology & Laboratory Medicine*, 1998, 18:5-22.
Barker et al., 2001, Survival after transplantation of unrelated donor umbilical cord blood is comparable to that of huan leukocyte antigen-matched unrelated donor bone marrow: results of a matched-pair analysis, Blood, 97:2957-61.
Baron et al., 1999, Acute Necrotizing Pancreatitis, The New Engl. J. Med. 340:1412-1417.
Barry et al., (1999) "The monoclonal antibody SH-2, raised against human mesenchymal stem cells, recognizes an epitope on endoglin (CD105)" Biochem Biophys Res Commun 265, 134-9.
Bartynski, J.M., S. Marion et al. (1990) "Histopathologic evaluation of adipose autografts in a rabbit ear model" Otolaryngol Hea Neck Surg 102(4): 314-21.
Bastard, J. P. et al., "A Mini-Liposuction Technique Adapted to the Study of Human Adipocyte Glucose Transport System," *Diabetologia*, 36(Suppl. 1):A135, 1993.
Baylink, David J., "Glucocorticoid-Induced Osteoporosis," *The New England Journal of Medicine*, 1983, 309:306-8.
BD Biosciences, Feb. 15, 2002, Product Specification Sheet: BD Matrigel™ Basement Membrane Matrix, 3 pp.
Becerra, José et al., "Demineralized Bone Matrix Mediates Differentiation of Bone Marrow Stromal Cells In Vitro: Effect of Age of Cell Donor," *Journal of Bone and Mineral Research*, 1996, 11:1703-14.
Beecken, W.D., Kramer, W., and Jonas, D. (2000) "New molecular mediators in tumor angiogenesis" J Cell Mol Med 4, 262-269.
Geiser, Ian H. and Irvin O. Kanat, "Subchondral Bone Drilling: a Treatment for Cartilage Defects," *Journal of Foot Surgery*, 1990, 29:595-601.
Bender et al., 1991, Identification and comparison of CD34-positive cells and their subpopulations from normal peripheral blood and bone marrow using multicolor flow cytometry, Blood 77(12): 2591-2596.
Bennett, JH, et al., 1991 *J. Cell Sci*. "Adipocytic cells cultured from marrow have osteogenic potential," 99(Pt1):131-139.

Berdel et al., 1982, Purification of human monocytes by adherence to polymeric fluorocarbon. Characterization of the monocyte-enriched cell fraction, Immunobiology, 163:511-520.
Beresford, et al., 1986 *Endo*. "1,25-Dihydroxyvitamin D3 and Human Bone-Derived Cells in Vitro: Effects on Alkaline Phosphatase, Type I Collagen and Proliferation," 119:1776-1785.
Bergan et al., 1996, Electroporation of synthetic oligodeoxynucleotides: a novel technique for ex vivo bone marrow purging, Blood, 88(2):731-741.
Bergeon, M.T. (1967) "Collagen: a review" J Okla State Med Assoc 60(6): 330-2.
Bernlohr, David A. et al., "Tissue Specific Expression of p422 protein , a putative Lipid Carrier, in Mouse Adipocytes," *Biochem. Biophys. Res. Commun.* 1985 132:850-855.
Berry et al., 2005, The Establishment of a Predictive Mutational Model of the Forkhead Domain through the Analyses of FOXC2 Missense Mutations Identified in Patients with Hereditary Lymphedema with Distichiasis, Human Molecular Genetics 14(18):2619-2627.
Bhagavati, et al., 2004, Isolation and enrichment of skeletal muscle progenitor cells from mouse bone marrow, Biochem. Biophys. Res. Comm. 318(1):318-24.
Bianco et al., Apr. 2008, Mesenchymal stem cells: revisiting history, concepts, and assays, Cell Stem Cell, 2:313-319.
Bickenbach, J.R. and Dunnwald, M. (2000) "Epidermal stem cells: characteristics and use in tissue engineering and gene therapy" Adv Dermatol 16, 159-83.
Bjornson, et al., 1999 *Science* "Turning Brain into Blood: A Hematopoetic Fate Adopted by Adult Neural Stem Cells in Vivo," 283:534-537.
Bjorntorp et al., 1980, Differentiation and function of rat adipocyte precursor cells in primary culture, J. Lipid Research 21:714-723.
Björntrop, et al. "Isolation and characterization of cells from rat adipose tissue developing into adipocytes." J. Lipid Res. 19:316-324 (1978).
Black et al., 2000, Adult Rat and Human Bone Marrow Stromal cells Differentiate Into Neurons, *J. Neurosci. Res. Science* 61:364-370.
Block, C.A., C.S. Cooper (2003) "Long-term Efficacy of periurethral collagen injection for the treatment of urinary incontinence secondary to myelomeningocele" J Urol 169(1): 327-329.
Boering, G. and A.J. Huffstadt (1967) "The use of derma-fat grafts in the face" Br J Plast Surg 20(2): 172-8.
Boerner, C.F. (1988) "Allergic response to a porcine collagen corneal shield. Case report" Arch Ophthalmol 106(2): 171.
Boghossian et al, 2005, Suppression of fat deposition for the life time with gene therapy, Peptides 26(8):1512-1519.
Bond et al., 1999, "Human Subcutaneou spreadipocytes Differentiate Into osteoblasts," *FASEB Journal* 13:600A.
Bonner-Weir, S. and Sharma, A. (2002) "Pancreatic stem cells" J Pathol 197, 519-526.
Boskey, et al., 1985, "The Effect of Osteocalcin on In Vitro Lipid-Induced Hydroxyapatite Formation and Seeded Hydroxyapatite Growth," *Calc. Tiss. Int.* 37:75.
Breen, Ellen C. et al., "TGFb Alters Growth and Differentiation Related Gene Expression in Proliferating Osteoblasts In Vitro, Preventing Development of the Mature Bone Phenotype," *Journal of Cellular Physiology*, 1994, 160:323-35.
Breiteneder-Geleff et al., Feb. 1999, Angiosarcomas Express Mixed Endothelial Phenotypes of Blood and Lymphatic Capillaries, Am. J. Path. 154(2): 385-394.
Bruder, et al., 1997 J. Cell Biochem. "Growth Kinetics, Self-Renewal, and the Osteogenic Potential of Purified Human Mesenchymal Stem Cells During Extensive Subcultivation and Following Cryopreservation," 64:278-294.
Bruder, Scott P. et al., "Bone Regeneration by Implantation of Purified, Culture-Expanded Human Mesenchymal Stem Cells," *Journal of Orthopaedic Research*, 1998, 16:155-62.
Bulleid, J.J., D.C. John et al (2000) "Recombinant expression systems for the production of collagen" Biochem Soc Trans 28(4): 350-3.
Burres, S. (2001) "Soft-tissue augmentation with fascian" Clin Plast Surg 28(1): 101-10.

(56) References Cited

OTHER PUBLICATIONS

Buschmann, I.R. Busch, H.J., Mies, G., and Hossmann, K.A. (2003) "Therapeutic induction of arteriogenesis in hypoperfused rat brain via granulocyte-macrophage colony-stimulating factor" Circulation 108, 610-615.
Butler-Browne, et al., 1990 Anat. Embryol. (Berl) "Myosin heavy and light chain expression during human skeletal muscle development and precocious muscle maturation induced by thyroid hormone," 181:513-522.
Butnariu-Ephrat, Miriam et al., "Resurfacing of Goat Articular Cartilage by Chondrocytes Derived From Bone Marrow," Clinical Orthopaedics and Related Research, 1996, 330:234-43.
Campion, Dennis R., "The Muscle Satellite Cell: A Review," Internationals Review of Cytology, 1984, 87:225-51.
Caplan and Goldberg, 1999, Principles of tissue engineered regeneration of skeletal tissues, Clin Orthop Suppl. 367: 12-16.
Caplan, A.I. and Bruder, S.P. (2001) "Mesenchymal stem cells: building blocks for molecular medicine in the 21st century" Trends Mol Med 7, 259-64.
Caplan, Arnold I., "Mesenchymal Stem Cells," Journal of Orthopaedic Research, 1991, 9:641-50.
Caplan, Arnold I., "The Mesengenic Process," Clinics in Plastic Surgery, 21:429-35, 1994.
Carano, R.A. and Filvaroff, E.H. (2003) "Angiogenesis and bone repair" Drug Discov. Today 8, 980-989.
Carmeliet, P. (2000) "Mechamisms of angiogenesis and arteriogenesis" Nat Med 6, 389-395.
Carmeliet, P. and A. Luttun (2001) "The emerging role of the bone marrow-derived stem cells in (therapeutic angiogenesis" Thromb Haemost 86(1): 289-97.
Carpandena, C.A. "Collagen alterations in adipose autograft's." Aesthetic Plastic Surgery vol. 18, 11-15 (1994).
Carranza-Bencano, A. et al., "Comparative Study of the Reconstruction of Articular Cartilage Defects with Free Costal Perichondrial Grafts and Free Tibial Periosteal Grafts: An Experimental Study on Rabbits," Calcified Tissue International, 1999, 65:402-7.
Casteilla et al., Apr. 26, 2011, Adipose-derived stromal cells: their identity and uses in clinical trials, an update, World J. Stem Cells, 3(4):25-33.
Castro, et al. "Failure of Bone Marrow Cells to Transdifferentiate into Neural Cells in Vivo." Science. 297:1299 (2002).
Castro, et al. "Response to Comment on 'Failure of Bone Marrow Cells to Transdifferentiate into Neural Cells in Vivo.'" Science. 299:1184c (2003).
Castro-Malaspina, H., W. Ebell, et al. (1984) "Human bone marrow fibroblast colony-forming units (CFU-F" Prog Clin Ciol Res 154: 209-36.
Cavallini, 2007, Autologous Fibroblasts to Treat Deep and Complicated Leg Ulcers in Diabetic Patients, Wound Repair Regen. 15(1):35-8.
Chang et al., Jan. 2006, Characterization of two populations of mesenchymal progenitor cells in umbilical cord blood, Cell Biology International, 40:495-499.
Cheifetz et al., 1988, Analysis of intracellular osteopontin as a marker of osteoblastic cell differentiation and mesenchymal cell migration,European Journal of Oral Sciences, 106(Supp. 1):401-7.
Cheifetz, S. et al., "Endoglin Is a Component of the Transforming Growth Factor-β Receptor System in Human Endothelial Cells," J. Biol. Chem., 1992 267:19027-19030.
Chen et al., Dec. 2005, Novel Expression and Characterization of Lymphatic Vessel Endothelial Hyaluronate Receptor 1 (LYVE-1) by Conjunctival Cells, Invest. Ophthalmol. Vis. Sci. 46(12):4536-4540.
Chen, J. et al. Intravenous Administration of Human Bone Marrow Stromal Cells Induces Angiogenesis in the Ischemic Boundary Zone After Stroke in Rats, Circulation Research, Apr. 2003, vol. 92, pp. 692-699.
Chen, J. et al. Intravenous Bone Marrow Stromal Cell Therapy Reduces Apoptosis and Promotes Endogenous Cell Proliferation After Stroke in Femal Rat, J. Neuroscience Research, Sep 2003, vol. 73 pp. 778-786.
Chen, Theresa L. et al., "1α,25-Dihydroxyvitamin D3 Receptors in Cultured Rat osteoblast-like Cells," J. Biol. Chem. 1983 258:4350-4355.
Chen, Xiaoli et al., "Differentiation-dependent expression of obese (ob) gene by preadipocytes and adipocytes in primary cultures of porcine stromal-vascular cells," Biochimica et Biophysica Acta, 1997, 1359:136-42.
Cheng S-L., et al., 1994 Endo "Differentiation of Human Bone Marrow Osteogenic Stromal Cells in Vitro: Induction of the Osteoblast Phenotype by Dexamethasone," 134: 277-286.
Chimal-Monroy et al., 1999, Expression of N-cadherin, N-CAM, fibronectin tenascin is stimulated by TGF-b1, b2, b3 and b5 during the formation of precartilage condensations, The International Journal of Developmental Biology, 43:59-67.
Cho. et al. "Engineering of volume-stable adipose tissues." Biomaterials 26, 3577-3585 (2005).
Cho. et al. "Enhancement of adipose tissue formation by implantation of adipogenic-differentiated preadipocytes." Biochem Biophys Res Commun 345, 588-594 (2006).
Choi et al. "Adipose tissue engineering using mesenchymal stem cells attached to injectable PLGA spheres." Biomaterials 26, 5855-5863 (2005).
Choi. et al. "Adipogenic differentiation of adipose tissue derived adult stem cells in nude mouse." Biochem Biophys Res Commun 345, 631-637 (2006).
Chyun, et al., 1984 Endo. "Cortisol Decreases Bone Formation by Inhibiting Periosteal Cell Proliferation," 114:477-480.
Civin, C.I., Strauss, L.C., Fackler, M.J., Trischmann, T.M., Wiley, J.M., and Loken, M.R. (1990) "Positive stem cell selection-basic science" Prog Clin Biol Res 333, 387-401.
Clarke, D. and Frisen, J. (2001) "Differentiation potential of adult stem cells" Curr Opin Genet Dev 11, 575-80.
Clavijo-Alvarez,J.A. et al. "A novel perfluoroelastomer seeded with adipose-derived stem cells for soft-tissue repair." Plast Reconstr Surg 118, 1132-1142 (2006).
Coleman III, et al. "Autologous Collagen? Lipocytic Dermal Augmentation. A Histopathologic Study". J. Dermatol Surg Oncol. vol. 19, 1032-1040 (1993).
Coleman, S.R. (1995) "Long-term survival of fat transplants: controlled demonstrations" Aesthetic Plast Surg 19(5): 421-5.
Coleman, S.R. (2001). "Structural fat grafts: the ideal filler?" Clin Plast Surg 28(1): 111-9.
Coleman, W.P., 3rd (1991) "Autologous fat transplantation" Plast Reconstr Surg 88(4): 736.
Colombo et al., Feb. 7, 2003, Opposite effects of background genotype on muscle and liver insulin sensitivity of lipoatrophic mice, J Biol Chern. 278(6):3992-3999.
Commons, G.W., Halperin, B., and Chang, C.C. (2001) "Large-vol. liposuction: a review of 631 consecutive cases over 12 years" Plast Reconstr Surg 108, 1753-63.
Conget, PA and JJ Minguell 1999 J. Cell. Physiol "Phenotypical and Functional Properties of Human Bone Marrow Mesenchymal Progenitor Cells," 181:67-73.
Connolly, J.F. (1998) "Clinical use of marrow osteoprogenitor cells to stimulate osteogenesis" Clin Orthop(355 Suppl): S257-66.
Considine, et al., "Paracrine stimulation of preadipocyte-enriched cell cultures by mature adipocytes," American Journal of Physiology 1996 270(5) E895-E899.
Cooper, et al., 1999 J. Endocrinol. "Glucocorticoid activity, inactivity and the osteoblast," 163: 159-164.
Cousin et al., Jul. 2009, Adult stromal cells dervied from human adipose tissue provoke pancreatic cancer cell death both in vitro and in vivo, PLoS One, 4(7), e6278.
Cousin, et al. (2003), "Reconstitution of Lethally Irradiated Mice by Cells Isolated From Adipose Tissue", Biochem. Biomed. Res. Comm. 310:1016-1022.
Craiu, et al., 2005, Flowing cells through pulsed electric fields efficiently purges stem cell preparations of contaminating myeloma cells while preserving stem cell function, Blood 105(5):2235-2238.

(56) References Cited

OTHER PUBLICATIONS

Crandall, David L. et al., "Identification of Estrogen Receptor b RNA in Human Breast and Abdominal Subcutaneous Adipose Tissue," *Biochemical and Biophysical Research Communications*, 248:523-6, 1998.

Crevensten et al. "Intervertebral Disc Cell Therapy for Regeneration: Mesenchymal Stem Cell Implantation in Rat Intervertebral Discs." Annals of Biomedical Engineering. 32(3):430-434 (2004).

Cronin,K.J. et al. "New murine model of spontaneous autologous tissue engineering, combining an arteriovenous pedicle with matrix materials." *Plast Reconstr Surg* 113, 260-269 (2004).

Cui, et al., 2006, Effects of low-intensity ultrasound on chondrogenic differentiation of mesenchymal stem cells embedded in polyglycolic acid: an in vivo study, Tissue Eng. 12(1):75-82.

Dani, et al., "Differentiation of embryonic stem cells into adipocytes in vitro," *J.Cell Sci.* 1997 110, 1279-1285.

Davis, P.F. and Z.M. Mackie (1981) "A simple procedure for the separation of insoluble collagen and elastin" Anal Biochem 115(1): 11-7.

Dawra et al., Apr. 2007, Development of a new mouse model of acute pancreatitis induced by administration of L-arginine, Am J Physiol Gastrointest Liver Physiol. 292(4):G1009-1018.

de la Fuente et al., 2004, Dedifferentiated adult articular chondrocytes: a population of human multipotent primitive cells, Exp. Cell Res. 297(2): 313-28.

De Ugarte et al., 2003, Differential expression of stem cell mobilization-associated molecules on multi-lineage cells from adipose tissue and bone marrow, Immunology Letters, 89:267-270.

De Ugarte et al., 2003, Future of fat as raw material for tissue regeneration, Ann Plast Surg 50, 215-9.

De Ugarte, "Comparison of Multi-Lineage Cells from Human Adipose Tissue and Bone Marrow," Cells Tissues Organs, 2003.

Deng, Weiwen et al., "In Vitro Differentiation of Human Marrow Stromal Cells into Early Progenitors of Neural Cells by Conditions That Increase Intracellular Cyclic AMP," *Biochemical and Biophysical Research Communications*, 2001, 282:148-52.

Dengler T et al. 2002. Stem Cell Therapy for the Infarcted Heart ("Cellular Cardiomyoplasty"), Herz 27:598-610.

Denker, A.E., et al., 1995 *Differentiation* "Formation of cartilage-like spheroids by micromass cultures of murine C3H101/2 cells upon treatment with transforming growth factor-b1," 59: 25-34.

Denker, et al., 1999 *Differentiation* "Chondrogenic differentiation of murine C3H10T1/2 multipotential mesenchymal cells: I. Stimulation by bone morphogenetic protein-2 in high-density micromass cultures," 64:67-76.

Dennis, James E. et al., "A Quadripotential Mesenchymal Progenitor Cell Isolated from the Marrow of an Adult Mouse," *Journal of Bone and Mineral Research*, 1999, 14:700-9.

Di Carlo, et al., 2004, Hypoxia inhibits myogenic differentiation through accelerated MyoD degradation, The Journal of Biological Chemistry, 279(16):16332-338.

Dias, Peter et al., "The Molecular Basis of Skeletal Muscle Differentiation," *Seminars in Diagnostic Pathology*, 1994, 11:3-14.

Diefenderfer, David L. and Carl T. Brighton, "Microvascular Pericytes Express Aggrecan Message Which is Regulated by BMP-2," *Biochemical and Biophysical Research Communications*, 2000, 269:172-8.

Dimri, et, al., 1995 *Proc. Natl. Acad. Sci. USA* "A biomarker that identifies a senescent human cells in culture and in aging skin in vivo," 92: 9363-9367.

D'Ippolito, G., Schiller, P.C., Ricordi, C., Roos, B.A., and Howard, G.A. (1999) "Age-related osteogenic potential of mesenchymal stromal stem cells from human vertebral bone marrow" J Bone Miner Res 14, 1115-22.

Donovan, D., Brown, N.J., Bishop, E.T. and Lewis, C.E. (2001) "Comparison of three in vitro human 'angiogenesis' assays with capillaries formed in vivo" Angiogenesis 4, 113-121.

Dragoo et al., 2003, Bone induction by BMP-2 transduced stem cells derived from human fat, J. Orth. Res., 21:622-629.

Dragoo et al. "Tissue-engineered cartilage and bone using stem cells from human infrapatellar fat pads." The Journal of Bone and Joint Surgery. 85(5):740-747 (2003).

Duan, "Treatment of Myocardial Ischemia with Bone Marrow-Derived Mesenchymal Stem Cells Overexpressing Hepatocyte Growth Factor," Molecular Therapy, 2003.

Ducy, et, al., 1997 *Cell* "Osf2/Cbfa1: A Transcriptional Activator of Osteoblast Differentiation," 89:747-754.

Duxbury et al., 2004, Lymphangiogenesis in tissue-engineered small intestine, Transplantation 77(8):1162-6.

Ebisawa, et al., 2004, Ultrasound enhances transforming growth factor B-mediated chondrocyte differentiation of human mesenchymal stem cells, Tissue Eng. 10(5-6):921-9.

Eichler, et al., 2003, Engraftment capacity of umbilical cord blood cells processed by either whole blood preparation or filtration, Stem Cells 21:208-216.

Eisenberg, Shlomo, "High density lipoprotein metabolism," *Journal of Lipid Research*, 1984, 25:1017-58.

Ei-Ghalbzouri et al., 2004, Cutaneous biology: human adipose tissue-derived cells delay re-epithelialization in comparison with skin fibroblasts in organotypic skin culture, British Journal of Dermatology, 150(3):444-454.

Engleholm, S.A., Spang-Thomsen, M., Brunner N., Nohr, I., and Vindelov, L.L. (1985) "Disaggregation of human solid tumors by combined mechanical and enzymatic methods" Br J Cancer 51, 93-8.

Enomoto, Hirayuki et al., "Cbfa1 Is a Positive Regulatory Factor in Chondrocyte Maturation," J. Biol. Chem. 2000 275:8695-8702.

Entenmann, et al., "Relationship between replication and differentiation cultured human adipocyte precursor cells," *American Phys. Soc.* 1996 270,C1011-C1016.

Eppich, et al., 2000, Pulsed electric fields for selection of hematopoietic cells and depletion of tumor cell contaminants, Nature Biotechnology 18:882-887.

Eppley, B.L., Smith, P.G., Sadove, A.M., and Delvino, J.J. (1990) "Experimental effects of graft revascularization and consistency on cervicofacial fat transplant survival" J Oral Maxillofac Surg 48, 54-62.

Eremia, S. and N. Newman (2000). "Long-term follow-up after autologous fat grafting: analysis of results from 116 patients followed at least 12 months after receiving the last of a minimum of two treatments" Dermatol Surg 26(12): 1150-8.

Erickson et al. "Chondrogenic potential of adipose tissue derived stromal cells in vitro and in vivo." Biochemical and Biophysical Research Communications. 290(2):763-769 (2002).

Ersek, Robert A. "Transplantation of Purified Autologous Fat: A 3-Year Follow-Up is Disappointing." Plast. Reconst. Surg. 87(2):219-228 (1991).

Eschenhagen, T., Didie, M., Muzel, Fi, Schubert, P., Schneiderbanger, K., and Zimmermann, W.H. (2002) "3D engineered hear tissue for replacement therapy" Basic Res Cardiol 97 Suppl 1, 1146-1152.

Fain et al. "Comparison of the Release of Adipolines by Adipose Tissue, Adipose Tissue Matrix, and Adipocytes from Visceral and Subcutaneous Abdominal Adipose Tissues of Obese Humans." Endocrinology. 145(5):2273-2282, at 2278, col. 2 (2004).

Fajas, Lluis, et al., "Transcriptional control of adipogenesis," *Current Opinion in Cell Biology*, 1998, 10:165-73.

Fella, N., Van V., Bierkens, J., Borremans, B., Schoeters, G., and Van Gorp, J. (1993) "Characterization of a 5-flurorouracil-enriched osteoprogenitor population of the murine bone marrow" Blood 82, 3580-91.

Farndale, Richard W. et al., "Improved quantitation and discrimination of sulphated glycosaminoglycans by use of dimethylene blue," *Biochimica et Biophysica Acta*, 1986, 883:173-7.

Ferrari G., et al., 1998 *Science* "Muscle Regeneration by Bone Marrow-Derived Myogenic Progenitors," 279: 1528-1530.

Fink, et al., 2004, Induction of adipocyte-like phenotype in human mesenchymal stem cells by hypoxia, Stem Cells 22:1346-1355.

Folkman, J. (1995) "Angiogenesis in cancer, vascular, rheumatoid and other disease" Nat Med 1, 27-31.

(56) References Cited

OTHER PUBLICATIONS

Ford, C.N., P.A. Staskowski et al. (1995) "Autologous collagen vocal fold injection: a preliminary clinical study" Laryngoscope 105(9 Pt 1): 944-8.
Formanek et al., 1998, Magnetic cell separation for purification of human oral keratinocytes: an effective method for functional studies without prior cell subcultivation, Eur Arch Otorhinolaryngol, 255:211-215.
Fortier, Lisa, et al., 2000, "Isolation and chondrocytic differentiation of equine bone marrow-derived mesenchymal stem cells," Am. J. Vet. Res. 59:1182-1187.
Fraser et al. "Adult Stem Cell Therapy for the Heart." The International Journal of Biochemistry & Cell Biology. 36(4):658-666 (2004).
Fraser et al., Mar. 1992, Proliferation of totipotent hematopoietic stem cells in vitro with retention of long-term competitive in vivo reconstituting ability, Cell Biology, 89(5):1968-72.
Fraser JK. Adipose Tissue: Challenging the Marrow Monopoly. Cytotherapy. 4(6):509-510 (2002).
Frederikson and McKay 1988 J. Neurosci. "Proliferation and Differentiation of Rat Neuroepithelial Precursor Cells in vivo," 8:1144-1151.
Fridman, et al., 1992 Int. J. Cancer "Malignant Transformation of NIH-3T3 Cells After Subcutaneous co-Injection With a Reconstituted Basement Membrane (Matrigel)," 51(5), 740-44.
Friedmann, 1989, Progress toward human gene therapy, Science, 244(4910):1275-1281.
Fukuda, et al. (2006), "Stem Cells as a Source of Regenerative Cardiomyocytes", Circ. Res. 98:1002-1013.
Fukuda, K. (2001). "Development of regenerative cardiomyocytes from mesenchymal stem cells for cardiovascular tissue engineering" Artif Organs 25(3): 187-93.
Fukumura et al., Oct. 31, 2003, Paracrine regulation of adipogenesis and adipocyte differentiation during in vivo adipogensis,, Circ Res., 17 pp.
Fülöp, Csaba et al., "Expression of Alternatively Spliced Epidermal Growth Factor-like Domains in Aggrecans of Different Species," The Journal of Biological Chemistry, 1993, 268:17377-83.
Fulton et al., "Fat Grafting" Fundamentals of Cosmetic Surgery. 19(3):523-530 (Jul. 2001).
Ganey et al. "A potential role for cell-based therapeutics in the treatment of intervertebral disc herniation." Eur Spine J. 11(Suppl. 2):S206-214 (2002).
Ganey et al. "Intervertebral Disc Repair Using Adipose Tissue-Derived Stem and Regenerative Cells." 34(21):2297-2304 (2009).
Garcia-Olmo et al., "Autologous Stem Cell Transplantation for Treatment of Rectovaginal Fistula in Perianal Crohn's Disease: A New Cell-Based Therapy", Int. J Colorectal Dis (2003), 18:451-454.
Garrafa et al., 2006, Isolation and characterization of lymphatic microvascular endothelial cells from human tonsils, J Cell Physiol 207(1):107-113.
Gaustad, K.G., Boquest, A.C., Anderson, B.E., Gerdes, A.M., and Collas, P. (2004) "Differentiation of human adipose tissue stem cells using extracts of rat cardiomyocytes" Biochem. Biophys. Res Commun. 314, 420-427.
Geiselhart, A., Neu, S., Buchholz, F., Lang, P., Niethammer, D., and Handgretinger, R. (1996) "Postive selection of CD56+ lymphocytes by magnetic cell sorting" Nat Immun. 15, 227-233.
Gelse et al., Feb. 2003, Articular cartilage repair by gene therapy using growth factor-producing mesenchymal cells, Arthritis Rheum. 48:430-441.
Gimble et al. "Adipose-Derived Adult Stem Cells: Isolation, Characterization, and Differentiation Potential." Cytotherapy. 5(5):362-369 (2003).
Gimble et al., 1995, Bone morphogenetic proteins inhibit adipocyte differentiation by bone marrow stromal cells, J. Cell Biochem. 58(3):393-402.
Gimble et al., 2007, Adipose-derived stem cells for regenerative medicine, Circulation Research, 100:1249-1260.
Gimble, Jeffery M. et al., "Adipose tissue-derived therapeutics," Expert Opin. Biol., 2003, 3(5)705-713.
Glowacki, J., "Influence of Age on Human Marrow," Calcified Tissue International, 1995, 56(Supp. 1):S50-1.
Goldman et al., 2005, Overexpression of VEGF-C causes transient lymphatic hyperplasia but not increased lymphangiogenesis in regenerating skin, Circ. Res. 96(11):1193-1199.
Graepler et al., 1998, Magnetic cell sorting for parietal cell purification using a new monoclonal antibody without influence on cell function, J. Biochem. Biophys. Methods 36(2-3):143-55.
Greenberg, A.W. and Hammer, D.A. (2001) "Cell separation mediated by differential rolling adhesion" Biotechnol Bioeng 73 111-24.
Grigoradis A., et al., 1988 J. Cell Biol. "Differentiation of Muscle, Fat, Cartilage, and Bone from Progenitor Cells Present in a Bone-derived Clonal Cell Population: Effect of Dexamethasone," 106: 2139-2151.
Grigoriadis, Agamemnon E. et al., "Analysis of chondroprogenitor frequency and cartilage differentiation in a novel family of clonal chondrogenic rat cell lines," Differentiation, 1996, 60:299-307.
Gronthos et al., 2001, Surface protein characterization of human adipose tissue-derived stromal cells, Journal of Cellular Physiology, 189:54-63.
Groutz, A., J.G. Blavias et al (2000) "Outcome results of transurethral collagen injection for female stress incontinence: assessment by urinary incontinence score" J Urol 164(6): 2006-9.
Guerrerosantos, J., A. Gonzalez-Mendoza, et al. (1996). "Long-term survival of free fat grafts in muscle: an experimental study in rats." Aesthetic Plast Surg 20(5): 403-8.
Guerriero, V and JR Florini 1980 Endocrinology "Dexamethasone Effects on Myoblast Proliferation and differentiation," 106:1198-1202.
Haab, F., P.E. Zimmern et al (1997) Urinary stress incontinence due to intrinsic sphincteric deficiency: experience with fat and collagen periurethral injections: J Urol 157(4): 1283-6.
Hagege, A.A., Carrion, C., Menasche, P., Vilquin, J.T., Duboc, D., Marolleau, J.P., Desnos, M., and Bruneval, P. (2003) "Viability and differentiation of autologous skeletal myoblast grafts in ischaemic cardiomyopathy" Lancet 361, 491-2.
Hak et al., "Toxic effects of DMSO on cultured beating heart cells at temperatures above zero," Cryobiology, 1973, 10:244-250.
Hall, BK 1981 "Intracellular and extracellular control of differentiation of cartilage and bone," Histochem. J. 13:599-614.
Hamano et al. The induction of angiogenesis by the implantation of autologous bone marrow cells: A novel and simple therapeutic method. Surgery. 130(1):44-54 (2001).
Hamel, M., T. Shaarawy et al (2001) "Deep sclerectomy with collagen implant in patients with glaucoma and high myopia" J Cataract Refract Surg 27(9): 1410-7.
Hardingham, Tim et al., "Studies on the Synthesis, Secretion and Assembly of Proteoglycan Aggregates by Chondrocytes," Matrices and Cell Differentiation, 1984, 151:17-29.
Harvey et al., 2005, Lymphatic Vascular Defects Promoted by Prox1 Haploinsufficiency Cause Adult-Onset Obesity, Nature Genetics 37[10]:1072-1081.
Hauner et al. "Cultures of Human Adipose Precursor Cells." Methods in Molecular Biology. 155(1):239-247 (2001).
Hauner H. et al., "Glucocorticoids and Insulin Promote the Differentiation of Human Adipocyte Precursor Cells into Fat Cells," Journal of Clinical Endocrinology and Metabolism, 64:832-5, 1987.
Hauner, et al., "Endothelin-1 Inhibits the Adipose Differentiation of Cultured Human Adipocyte Precursor Cells," Metabolism 1994 43(2) pp. 227-232.
Hauner, Hans et al., "Promoting Effect of Glucocorticoids on the Differentiation of Human Adipocyte Precursor Cells Cultured in a Chemically Defined Medium," Journal of Clinical Investigation, 84:1663-70, 1989.
Hausman et al., 2001, The biology of white adipocyte proliferation, Obesity Reviews, 2(4):239-254.
Hausman et al., 2004, Adipose tissue angiogenesis, Journal of Animal Science 82:925-934.

(56) References Cited

OTHER PUBLICATIONS

Hausman, et al., "The Influence of Extracellular Matrix Substrata on Preadipocyte Development in Serum-Free Cultures of Stromal-Vascular Cells," *J. Anim.Sci.* 1996 74(9), 2117-2128.
Haynes, 1988, Principles of flow cytometery, Cytometry Supplement, 3:7-17.
Haynesworth, S. E. et al., "Cell Surface Antigen on Human Marrow-Derived Mesenchymal Cells are Detected by Monoclonal Antibodies," *Bone*, 1992, 13:69-80.
Hemmrich,K. et al. "Implantation of preadipocyte-loaded hyaluronic acid-based scaffolds into nude mice to evaluate potential for soft tissue engineering." *Biomaterials* 26, 7025-7037 (2005).
Hemstreet, G.P. 3, Enoch, P.G., and Pretlow, T.G. 2 (1980) "Tissue disaggregation of human renal cell carcinoma with further isopyknic and isokinetic gradient purification" Cancer Res 40, 1043-9.
Herman, Ira M. and Patricia D'Amore, "Microvascular Pericytes Contain Muscle and Nonmuscle Actins," *J. Cell Biol.* 1985 101:43-52.
Herzenberg et al., 2002, The history and future of the fluorescence activated cell sorter and flow cytometry: a view from Stanford, Clinical Chemistry, 48(10):1819-1827.
Hess, "Bone Marrow as a Source of Endothelial Cells an NeuN-Expressing Cells After Stroke," Stroke, 2002.
Hess, D.C. et al. Hematopoietic Origin of Microglial and Perivascular Cells in Brain, Experimental Neurology, Apr. 2004, vol. 186, pp. 134-144.
Hewitson et al., 2006, Histochemical localization of cell proliferation using in situ hybridization for histone mRNA, Methods Mol. Biol. 326:219-26.
Hong et al. "Adipose tissue engineering by human adipose-derived stromal cells." *Cells Tissues Organs* 183, 133-140 (2006).
Horwitz et al, 2001, Clinical responses to bone marrow transplantation in children with severe osteogenesis imperfecta, Blood, 97(5):1227-31.
Horwitz et al., 2005, Clarification of the nomenclature for MSC: The International Society for Cellular Therapy position statement, 7(5):393-395.
Horwitz, E. M., D.J. Prockop, et al. (1999). "Transplantability and therapeutic effects of bone marrow-derived mesenchymal cells in children with osteogenesis imperfecta." Nat Med 5(3): 309-13.
Houtgraff, et al. (2011), "First Experience in Humans Using Adipose-Derived Regenerative Cells in the Treatment of Patents With STSegment Elevation Myocardial infarction", J. Am. Coll. Cardiol. 59:539-540.
Hsiung, M. W., P. Woo et al (2000) "Fat augmentation for glottic insufficiency" Laryngoscope 110(6): 1026-33.
Huang, J.I., S.R. Beanes, et al. (2002) "Rat extramedullary adipose tissue as a source of osteochondrogenic progenitor cells" Plast Reconstr Surg 109(3): 1033-41; discussion 1042-3.
Huard et al, 2002, Muscle-derived cell-mediated ex vivo gene therapy for urological dysfunction, Gene Therapy, 9:1617-1626.
Huibregtse, Barbara, et al., 1998, "Effect of Age and Sampling Site on the Chondro-Osteogenic Potential of Rabbit Marrow-derived Mesenchymal Progenitor Cells," *Journal of Orthopaedic Research.* 18:18-24.
Hur et al. Akt Is a Key Modulator of Endothelial Progenitor Cell Trafficking in Ischemic Muscle. Stem Cells. 25:1769-1778 (2007).
Huss, Ralf, "Isolation of Primary and Immortalized CD34-Hematopoietic and Mesenchymal Stem Cells from Various Sources," *Stem Cells*, 2000, 18:1-9.
Hutley, L.J., A.C. Herington, et al. (2001) "Human adipose tissue endothelial cells promote preadipocyte proliferation" Am J. Physiol Endocrinol Metab 281(5): E1037-1044.
Ito et al., 2001, A new continuous-flow cell separation method based on cell density: principle, apparatus, and preliminary application to separation of human buffy coat, Journal of Clinical Apheresis, 16(4):186-191.
Iwasaki, Motoki et al., "Regulation of Proliferation and Osteochondrogenic Differentiation of Periosteum-Derived Cells by Transforming Growth Factor-b and Basic Fibroblast Growth Factor," *Journal of Bone and Joint Surgery*, 1995, 77A:543-54.
Jackson et al. Regeneration of ischemic cardiac muscle and vascular endothelium by adult stem cells. Journal Clinical Investigation. 107(11): 1395-1402 (2001).
Jaiswal et al., 2000, Adult human mesenchymal stem cell differentiation to the osteogenic or adipogenic lineage is regulated by mitogen-activated protein kinase, J Biol Chem, 275:9645-52.
Jaiswal, et al., 1997 "Osteogenic Differentiation of Purified, Culture-Expanded Human Mesenchymal Stem Cells In Vitro," J. Cell Biochem. 64:295-312.
Ji, 2006, Lymphatic Endothelial Cells, Lymphangiogenesis, and Extracellular Matrix, Lymphat. Res. Biol. 4(2):83-100.
Jiang, Y., Jahagirdar, B.N., Reinhardt, R.L., Schwartz, R.E., Keene, C.D., Ortiz-Gonzalez, X.R., Reyes, M., Lenvik, T., Lund, T., Blackstad, M., Du, J., Aldrich, S., Lisberg, A., Low, W.C., Largaespada, D.A., and Verfaillie, C.M. (2002a) "pluripotency of mesenchymal stem cells derived from adult marrow" Nature 418, 41-9.
Jiang, Y., Vaessen, B., Lenvik, T., Blackstad, M., Reyes, M., and Verfaillie, C.M. (2002b)"Multipotent progenitor cells can be isolated from postnatal murine bone marrow, muscle, and brain" Exp Hematol 30, 896-904.
Johnson, P. R. et al., "Uncontrolled adipocyte proliferation is not the primary lesion in the genetically-obese Zucker rat," *International Journal of Obesity*, 5:563-70, 1981.
Johnstone B., et al., 1998 "In Vitro Chondrogenesis of Bone Marrow-Derived Mesenchymal Progenitor Cells," Exp. Cell Res. 238: 265-272.
Joyner, C.J., Triffitt, J., Puddle, B., and Athanasou, N.A. (1999) "Development of a monoclonal antibody to the aP2 protein to identify adipocyte precursors in tumours of adipose differentiation" Pathol. Res Pract. 195, 461-466.
Jurgens et al. "Effect of tissue-harvesting site on yield of stem cells derived from adipose tissue: implications for cell-based therapies." Cell Tiss. Res. 332:415-426 (2008).
Kale et al. "Bone marrow stem cells contribute to repair of the ischemically injured renal tubule" J. Clinical Investigation, vol. 112, No. 1 42-49 (Jul. 2003).
Kamer, F.M. and M.M. Churukian (1984) "Clinical use of injectable collagen. A three-year retrospective review" Arch Otolaryngol 110(2): 93-8.
Kamihata et al. "Improvement of collateral perfusion and regional function by implantation of peripheral blood mononuclear cells into ischemic hibernating myocardium." Thromb Vascular Biology. 22:1804-1810 (2002).
Kang et al. "Improvement of neurological deficits by intracerebral transplantation of human adipose tissue-derived stromal cells after cerebral ischemia in rats." Experimental Neurology. 183(2):355-366 (2003).
Kang et al. "Interactions between human adipose stromal cells and mouse neural stem cells in vitro." Developmental Brain Research. 145(1): 141-149 (2003).
Kania, et al., 1990 "The *Drosophila* segmentation gene runt encodes a novel nuclear regulatory protein that is also expressed in the developing nervous system," Genes Dev. 4:1701-1713.
Karkkainen et al., 2002, Lymphatic endothelial regulation, lymphoedema, and lymph node metastasis, Semin Cell Dev Biol 13(1):9-18.
Karlsson et al., "Long-term storage of tissues by cryopreservation: critical issues," Biomaterials 1996, 17(3):243-256.
Katz et al. 2005, Cell surface and transcriptional characterization of human adipose-derived adherent stromal (hADAS) cells, Stem Cells 23(3):412-23.
Katz, A.J., Hedrick, M.H., Llull, R., and Futrell, J.W. (2001) "A novel device for the simple and efficient refinement of liposuctioned tissue" Plast Reconstr Surg 107, No. 2, 595-597.
Katz, Adam J. et al., "Emerging Approaches to the Tissue Engineering of Fat," *Clinics in Plastic Surgery*, 1999, 26:587-603.
Katz, B.E., Bruck, M.C. and Coleman, W. P. 3 (2001b) "The benefits of powered liposuction versus traditional liposuction: a paired comparison analysis" Dermatol Surg 27, 863-7.

(56) References Cited

OTHER PUBLICATIONS

Kaushal et al., 2001, Functional small-diameter neovessels cretaed using endothelial progenitor cells expanded ex vivo, Nat Med 7:1035-40.

Kawamoto et al., 2001, Therapeutic potential of ex vivo expanded endothelial progenitor cells for myocardial ischemia, Circulation, 103:634-637.

Kawamoto et al., 2003, Intramyocardial transplantation of autologous endothelial progenitor cells for therapeutic neovascularization of myocardial ischemia, Circulation 107:461-8.

Kehlen, A. et al., 2000 *J. Cell Biochem.* "Increased Lymphocytic Aminopeptidase N/CD13 Promoter Activity After Cell-Cells Contact," 80:115-123.

Kerjaschki et al., 2006, Lymphatic endothelial progenitor cells contribute to de novo lymphangiogenesis in human renal transplants, Nature Medicine 12(2):230-4.

Kern, P.A., A. Knedler, et al. (1983) Isolation and culture of microvascular endothellium from human adipose tissue: J Clin Invest 71(6): 1822-9.

Killinger, D. W. et al., "Influence of Adipose Tissue Distribution on the Biological Activity of Androgens," *Annals New York Academy of Sciences*, 595:199-211, 1990.

Killinger, Donald W. et al., "The Relationship Between Aromatase Activity and Body Fat Distribution," *Steroids*, 50:61-72, 1987.

Kim et al., 2002, Ex vivo gene delivery of IL-1Ra and soluble TNF receptor confers a distal synergistic therapeutic effect in antigen-induced arthritis, Mol. Ther. 6:591-600.

Kim et al., 2007, Systemic transplantation of human adipose stem cells attenuated cerebral inflammation and degeneration in a hemorrhagic stroke model, Brain Research, 1183:42-50.

Kim, et al. "Wound healing effect of adipose-derived stem cells: A critical role of secretory factors on human dermal fibroblasts." Journal of Dermatological Science. 48(1): 15-24 (2007).

Kimura et al. "Adipose tissue engineering based on human preadipocytes combined with gelatin microspheres containing basic fibroblast growth factor." *Biomaterials* 24, 2513-2521 (2003).

Kirsch, Thorsten and Klaus von der Mark, "Remodelling of collagen types I, II and X and calcification of human fetal cartilage," *Bone and Mineral*, 1992, 18:107-17.

Klar et al., 2005, RAR-related orphan receptor a isoform 1 (RORa1) is disrupted by a balanced translocation t(4;15)(q22.3;121.3) associated with severe obesity, Eur. J. Hum. Genet. 13(8):928-934.

Klein et al., 2006, Adipose tissue as source and target for novel therapies, Trends Endocrin. Metab., 17(1):26-32.

Klein, A.W. (2001) "Skin filling. Collagen and other injectables of the skin" Dermatol Clin 19(3): 491-508, ix.

Knutson, et al., 1999, Increased anticoagulant osmolality improves separation of leukocytes from red blood cells (RBC), Transfusion Science 21: 185-191.

Kobari et al., 2001, CD133+ cell selection is an alternative to CD34+ cell selection for ex vivo expansion of hematopoietic stem cells, J. Hematother. Stem Cell Res. 10(2):273-81.

Kong et al., 2005, Effect of cardiac lymph flow obstruction on cardiac collagen synthesis and interstitial fibrosis, Physiol Res. 55:253-258.

Kosher, RA, et al., 1986 *J. Cell Biol.* "Collagen Gene Expression During Limb Cartilage Differentiation," 102:1151-1156.

Kosher, Robert A. and Michael Solursh, "Widespread Distribution of Type II Collagen during Embryonic Chick Development," *Developmental Biology*, 1989, 131:558-66.

Koufman, J.A. (1991) "Lipoinjection for vocal cord paralysis" Laryngoscope 101(12 Pt 1): 1385.

Kriehuber et al., 2001, Isolation and characterization of dermal lymphatic and blood endothelial cells reveal stable and functionally specialized cell lineages, J Exp Med 194(6):797-808.

Kumano et al, 1997, Effects of osmotic agents on hyaluronan synthesis in human peritoneal mesothelial cells and fibroblasts, Adv. Perit. Dial. 13:58-63.

Kuri-Harcuch et al., 1984, Extracellular matrix production by mouse 3T3-F442A cells during adipose differentiation in culture, Differentiation, 28:173-178.

Lafontan, M. et al., "Réflexions sur une nouvelle approche de chirurgie plastique réparatrice: la réimplantation de fragments de tissu adipeux prélevés par liposuccion," *Ann. Chur. Plast. Esthet.*, 34:77-81, 1989.

Lam, Anson and Ronald Moy, "The Potential for Fat Transplantation," *J. Dermatol. Surg. Oncol.*, 18:432-4, 1992.

Lambert et al., 1993, Local drug delivery catheters: functional comparison of porous and microporous designs, Coron. Artery Dis. 4:469-475.

Lamouille, S., Mallet, C., Feige, J.J., and Bailly, S. (2002) "Activin receptor-like kinase 1 is implicated in the maturation phase of angiogenesis" Blood 100, 4495-4501.

Lanier, L.L. et al, 1991 *J. Immunol.* "Molecular and Functional Analysis of Human Natural Killer Cell-Associated Neural Cells Adhesion Molecule (N-Cam/CD56)," 146:4421-4426.

Lasch, J., Kullertz, G., and Opalka, J.R. (2000) "Separation of erythrocytes into age-related fractions by density or size? Counterflow centrifugation" Clin Chem Lab Med 38, 629-632.

Latoni, J.D., D.M. Marshall et al (2000 "Overgrowth of fat autotransplanted for correction of localized steroid-induced atrophy" Plast Reconstr Surg 106(7): 1566-9.

Lawson-Smith, M.J. and McGeachie, J.K. 1998 *J. Anat.* "The identification of myogenic cells in skeletal muscle, with emphasis on the use of tritiated thymidine autoradiography and desmin antibodies," 192:161-171.

Lazarus, Hillard M. et al., "Human Bone Marrow-Derived Mesenchymal (Stromal) Progenitor Cells (MPCs) Cannot Be Recovered from Peripheral Blood Progenitor Cell Collections," *Journal of Hematotherapy*, 1997, 6:447-55.

Leboy, et al., 1991 *J. Cell Physiol.* "Dexamethasone Induction of Osteoblast mRNAs in Rat Marrow Stromal Cell Cultures," 146:370-378.

Leboy, Phoebe S. et al., "Ascorbic Acid Induces Alkaline Phosphatase, Type X Collagen, and Calcium Deposition in Cultured Chick Chondrocytes," *The Journal of Biological Chemistry*, 1989, 264:17281-6.

Lecoeur, L. and J. P. Ouhayoun, "In vitro induction of osteogenic differentiation from non-osteogenic mesenchymal cells," *Biomaterials*, 18:989-93, 1997.

Lee et al., 1992, Adhesion Molecules in Skeletogenesis: I. Transient Expression of Neural Cell Adhesion Molecules (NCAM) in Osteoblasts During Endochondral and Intramembranous Ossification, *Journal of Bone and Mineral Research*, 7:1435-46.

Lee et al., 2001, Periurethral autologous fat injection as treatment for female stress urinary incontinence: a randomized double-blind controlled trial, J Urol 165(1): 153-158.

Lee et al., Jan. 2006, Human adipose-derived stem cells display myogenic potential and perturbed function in hypoxic conditions, Biochemical and Biophysical Research Communications, 341:882-888.

Lee, J. H., Z. Ilic, et al. (1996) "Cell kinetics of repair after allyl alcohol-induced liver necrosis in mice" Int J Exp Pathol 77(2): 63-72.

Lehner, M. and Holter, W. (2002) "Endotoxin-free purification of monocytes for dendritic cell generation via discontinuous density gradient centrifugation based on diluted Ficoll-Paque Plus" Int Arch Allergy Immunol 128, 73-76.

Lendahl, et al., 1990 *Cell* "CNS Stem Cells Express a New Class of Intermediate Filament Protein," 60:585-595.

Lennon et al., 1995, A chemically defined medium supports in vitor proliferation and maintains the osteochondral potential of rat marrow-derived mesenchymal stem cells, Exp Cell Res, 219:211-22.

Lennon, Donald P. et al., "Human and Animal Mesenchymal Progenitor Cells from Bone Marrow: Identification of Serum for Optimal Selection and Proliferation," *In Vitro Cell. Dev. Biol.— Animal*, 1996, 32:602-11.

Lennon, et al., 2001, Cultivation of rat marrow-derived mesenchymal stem cells in reduced oxygen tension: effects on in vitro and in vivo osteochondrogenesis, J. Cell Phys. 187(3):345-55.

(56) References Cited

OTHER PUBLICATIONS

Lenoir, N. 2000 Science "Europe Confronts the Embryonic Stem Cell Research Challenge," 287:1425-1427.
Leo et al., 2004, In vivo bioluminescent imaging of virus-mediated gene transfer and transduced cell transplantation in the intervertebral disc, Spine, 29(8):838-844.
Lev, Robert and S. S. Spicer, "Specific Staining of Sulphate Groups with Alcian Blue at Low pH," *J. Histochem. Cytochem.*, 1964, 12:309-10.
Lin, et al. "Hematopoietic Stem Cells Contribute to the Regeneration of Renal Tubules After Renal Ischmia-Reperfusion Injury in Mice." Journal of the American Society of Nephrology. 14: 1188-1199 (2003).
Lincoff et al., 1994, Local drug delivery for the prevention of restenosis. Fact, fancy, and future, Circulation, 90:2070-2084.
Linsenmayer, Thomas et al., 1998, "Type X Collagen: A Hypertrophic Cartilage-Specific Molecule," *Pathol. Immunopathol.* 7:14-19.
Liu, S.H., R.S. Yang et al (1995) "Collagen in tendon, ligament and bone healing. A current review" Clin Orthop (318): 265-78.
Loncar, 1992, Ultrastructural analysis of differentiation of rat endoderm in vitro. Adipose vascular-stromal cells induce endoderm differentiation, which in turn induces differentiation of the vascular-stromal cells into chondrocytes, *J. Submicrosc. Cytol. Pathol.*, 24:509-19.
Long, Michael W. et al., "Age-Related Phenotypic Alterations in Populations of Purified Human Bone Precursor Cells," *The Journals of Gerontology*, 1999, 54A:B54-62.
Lucas, P. A. et al., "Isolation of Putative Mesenchymal Stem Cells from Rat Embryonic and Adult Skeletal Muscle," *In Vitro Cell Dev. Biol.*, 1992, 28:154A.
Lucas, Paul A. et al., "Mesenchymal Stem Cells From Granulation Tissue," *J. Cell Biochem*, 1993 17E:122, R212.
Lumelsky, N., et al. 2001 Science "Differentiation of Embryonic Stem Cells to Insulin-Secreting Structures Similar to Pancreatic Islets," 292:1389-1394.
Lund et al. "Granulocyte colony-stimulating factor mobilized CFU-F can be found in the peripheral blood but have limited expansion potential." Haematologica. 93(6):908-912 (2008).
Luskey, B.D., Lim, B., Apperley, J.F., Orkin, S.H., and Williams, D.A. (1990) "Gene transfer into murine hematopoietic stem cells and bone marrow stromal cells" Ann NY Acad Sci 612, 398-406.
Luttun et al., 2002, Revascularization of ischemic tissues by PlGF treatment, and inhibition of tumor angiogenesis, arthritis and atherosclerosis by anti-Fltl, Nat Med 8:831-40.
Lynch, et al., 1995, the Influence of Type I Collagen on the Development and Maintenance of the Osteoblast Phenotype in Primary and Passaged Rat Calvarial Osteoblasts: Modification of Expression of Genes Supporting Cell Growth, Adhesion, and Extracelluar Matrix Mineralization, Exp. Cell Res, 216:35-45.
MacDougald, Ormond A. and M. Daniel Lane, "Transcriptional Regulation of Gene Expression During Adipocyte Differentiation," *Annu. Rev. Biochem.*, 1995, 64:345-73.
Mainwaring, G. and Rowley, A.F. (1985) "Separation of leucocytes in the dogfish (*Scyliorhinus canicula*) using density gradient centrifugation and differential adhesion to glass coverslips" Cell Tissue Res 241, 283-90.
Majeska, Robert J. and Gideon A. Rodan, "The Effect of 1,25(OH)2D3 on Alkaline Phosphates in Osteoblastic Osteosarcoma Cells," *J. Biol. Chem.* 1982 257:3362-3365.
Majumdar, M.K., Thiede, M.A., Mosca, J.D., Moorman, M., and Gerson, S.L. (1998) "Phenotypic and functional comparison of cultures of marrow-derived mesenchymal stem cells (MSCs) and stromal cells" J Cell Physiol 176, 57-66.
Malaval, et al., 1994 *J. Cell. Physiol.* "Cellular Expression of Bone-Related Proteins During In Vitro Ostegenesis in Rat Bone Marrow Stromal Cell Culture," 158:555-572.
Manduca, et al., 1992 *Eur. J. Cell Biol.* "Chondrogenic differentiation in chick embryo osteoblast cultures," 57:193-201.
Manetti et al. (2000) "Fibroblast growth factors and their inhibitors" Curr. Pharm. Des 6, 1897-1924.

Marchlinski et al., 1987,Experimental myocardial cryoinjury: local electromechanical changes, arrhythmogenicity, and methods for determining depth of injury, Pacing Clin Electrophysiol 10:886-901.
Marko, et al., "Isolation of a Preadipocyte Cell Line from Rat Bone Marrow and Differentiation to Adipocytes," *Endocrinology* 1995 136(10), 4582-4588.
Martin, et al., 1999 *Exp. Cell Res.* "Mammalian Chondrocytes Expanded in the Presence of Fibroblast Growth Factor 2 Maintain the Ability to Differentiate and Regenerate Three-Dimensional Cartilaginous Tissue," 253:681-688.
Martinez-Estrada et al. "Human adipose tissue as a source of Flk-1 <+> cells: new method of differentiation and expansion." Cardiovascular Research. 65(2):328-333 (2005).
Maruyama et al., Apr. 2007, Decreased Macrophage Number and Activation Lead to Reduced Lymphatic Vessel Formation and Contribute to Impaired Diabetic Wound Healing, Am J Pathol. 170(4):1178-1191.
Massi et al., 2006, Tumour lymphangiogenesis is a possible predictor of sentinel lymph node status in cutaneous melanoma: a case-control study, J Clin Pathol, 59(2):166-173.
Masuda et al. "Novel strategy for soft tissue augmentation based on transplantation of fragmented omentum and preadipocytes." *Tissue Eng* 10, 1672-1683 (2004).
Masuda et al. "Photocured, styrenated gelatin-based microspheres for de novo adipogenesis through corelease of basic fibroblast growth factor, insulin, and insulin-like growth factor I." *Tissue Eng* 10, 523-535 (2004).
Mazo et al. (2008), "Transplantation of Adipose-Derived Stromal Cells is Associated With Functional Improvement in a Rat Model of Chronic Myocardial Infarction", Eur. J. Heart Failure 10:454-462.
Mazur et al., 1994, Coronary restenosis and gene therapy, Texas Heart Institute Journal, 21:104-111.
McMurray, Jan. 21, 2010, Systolic heart failure, The New England Journal of Medicine, 362(3):228-238, Supplementary Appendix.
Megeney, et al., 1996 *Genes Dev.* "MyoD is required for myogenic stem cell function in adult skeletal muscle," 10:1173-1183.
Mehlhorn et al., 2001, Myocardial Fluid Balance, Eur. J. Cardiothoracic Surg. 20:1220-1230.
Mezey, et al. "Comment on 'Failure of Bone Marrow Cells to Transdifferentiate into Neural Cells in Vivo.'" Science. 299:1184b (2003).
Miller, 1992, Human gene therapy comes of age, Nature, 357:455-460.
Miller, J.J. and J.C. Poop (2002) "Fat hypertrophy after autologous fat transfer" Opthal Plast Reconstr Surg 18(3): 228-31.
Mills, J.D., Fischer, D., and Villeneuve, F.S. (2000) "Coronary collateral development during chronic ischemia: serial assessment using harmonic myocardial contrast echocardiography" J Am Coll Cardiol 36(2):618-24.
Miranville et al. "Human adipose tissue-derived stem cells improve postnatal neovascularization." International Journal of Obesity. 28(Suppl 1):S100 (May 2004).
Miranville et al. "Human adipose tissue-derived stem cells improve blood flow in the ischemic mouse hind-limb" Circulation, vol. 108, No. 17, Supp. IV, 164 (Oct. 2003).
Miranville, et al. "Improvement of postnatal neovascularization by human adipose tissue-derived stem cells." Circulation, American Heart Association. 110(3):349-355 (2004).
Miyagi, et al., 2001, Application of hypothermia to autologous stem cell purging, Cryobiology 42:190-95.
Mizuno, H., P.A. Zuk, et al. (2002) "Myogenic differentiation by human processed lipoaspirate cells" Plast Reconstr Surg 109(1): 199-209; discussion 210-1.
Mohr et al., 2001, Simultaneous immunomagnetic CD34+ cell selection and B-cell depletion in peripheral blood progenitor cell samples of patients suffering from B-cell non-Hodgkin's lymphoma Clin Cancer Res 7:51-57.
Moitra et al., 1998, Life without white fat: a transgenic mouse, Genes Dev. 12(20):3168-3181.
Molkentin and Olson 1996 *Curr. Opin. Genet. Dev.* "Defining the regulatory networks for muscle development," 6:445-453.

(56) References Cited

OTHER PUBLICATIONS

Monteiro, P., Antunes, A., Goncalves, L.M., and Providencia, L.A. (2003) "Long-term clincal impact of coronary-collateral vessels after acute myocardial infarction" Rev. Port. Cardiol 22, 1051-1061.
Morizono et al., 2003, Multilineage cells from adipose tissue as gene delivery vehicles, Hum Gene Ther 14, 59-66.
Mosca et al., 2000, Mesenchymal stem cells as vehicles for gene delivery, Clin Orthop, 379S:71-90.
Mullen, Richard J. et al., "NeuN, a neuronal specific nuclear protein in vertebrates," *Development*, 1992, 116:201-11.
Muller et al. "Selection of ventricular-like cardiomyocytes from ES cells in vitro." The FASEB Journal. 14:2540-2548 (2000).
Mullins et al., 1996, Allergic reactions to oral, surgical and topical bovine collagen. Anaphylactic risk for surgeons, Aust N Z J Ophthalmol 24(3):257-260.
Mundlos, et al., 1997 *Cell* "Mutations Involving the Transcription Factor CBFA12 Cause Cleidocranial Dysplasia," 89:773-779.
Muramatsu, T., Nakamura, A., and Park, H.M. (1998) "In vivo electroportion: a powerful and convenient means of nonviral gene transfer to tissues of living animals (Review)" Int J Mol Med 1, 55-62.
Murayama, T., O.M. Tepper, et al. (2002) "Determination of bone marrow-derived endothelial progenitor cells significance in angiogenic growth factor-induced neovascularization in vivo" Exp Hematol 30(8): 967-72.
Murry CE et al. 2004. Hematopoietic stem cells do not transdifferentiate into cardiac myocytes in myocardial infarcts. Nature 428: 664-668.
Murry et al., 1996, Skeletal myoblast transplantation for repair of myocardial necrosis, J Clin Invest 98(11):2512-2523.
Muschler, G.F., Nitto, H., Boehm, C.A., and Easley, K.A. (2001) "Age-and gender-related changes in the cellularity of human bone marrow and the prevalence of osteoblastic progenitors" J Orthop Res 19(1), 117-25.
Muskhelishvili et al., 2003, Evaluation of cell proliferation in rat tissues with BrdU, PCNA, Ki-67(MIB-5) immunohistochemistry and in situ hybridization for histone mRNA, J. Histochem. & Cytochem. 51(12):1681-1688.
Myllyharju, J. (2000) "Recombinant collagen trimers from insect cells and yeast" Methods Mol Biol 139: 39-48.
Nagle, R. B. et al., "Factor VII-Associated Antigen in Human Lymphatic Endothelium," *Lymphology*, 1987, 20:20-4.
Nagy, J.A., Dvorak, A. M., and Dvorak, H.F. (2003) VEGF-A (164/165) and PIGF: roles in angiogenesis and arteriogenesis: Trends Cardiovasc Med 13, 169-175.
Nakahara, H. et al., "Bone and Cartilage Formation in Diffusion Chambers by Subcultured Cells Derived from the Periosteum," *Bone*, 1990, 11:181-8.
Nakajima, I. et al., 1998, "Adipose tissue extracellar matrix: newly organized by adipocytes during differentiation," *Differentiation* 63:193-200.
Nakano, Hirotaka et al., "RT-PCR Suggests Human Skeletal Muscle Origin of Alveolar Soft-Part Sarcoma," *Oncology*, 2000, 58:319-23.
Nathan, Suresh et al. "Cell-Based Therapy in the Repair of Osteochrondral Defects: A Novel Use for Adipose Tissue", Tissue Engineering, vol. 9, No. 4, 2003.
Nehls, A. and D Drenckhahn 1991 *J. Cell Biol.* "Heterogeneity of Microvascular Pericytes for Smooth Muscle Type Alpha-Actin," 113:147-154.
Nerem, R.M. and Ensely, A.E. (2004) "The tissue engineering of blood vessels and the heart" Am J Transplant 4 Supp 6, 36-42.
Ng et al., Nov. 2004, Interstitial flow differentially stimulates blood and lymphatic endothelial cell morphogenesis in vitro, Microvasc Res. 68(3):258-64.
Nguyen, A., K.A. Pasyk et al. (1990) "Comparative study of survival of autologous adipose tissue taken and transplanted by different techniques" Plast Reconstr Surg 85(3): 378-86; discussion 387-9.
Nishimori et al., 2002, "Health-related quality of life of unrelated bone marrow donors in Japan" Blood 99(6), 1995-2001.
Novakofski, Jan E., "Primary Cell Culture of Adipose Tissue," *Biology of the Adipocyte: Research Approaches*, Van Nostrand Reinhold Company, NY, 1987 160-97.
O'Driscoll, Shawn W., "Current Concepts Review: The Healing and Regeneration of Articular Cartilage," *Journal of Bone and Joint Surgery*, 1998, 80A:1795-812.
Odorico, J.S., Kaufman, D.S., and Thomson, J.A. (2001) "Multilineage differentiation from human embryonic stem cells lines" Stem Cells 19, 193-204.
Ogawa, 2006, The importance of adipose-derived stem cells and vascularized tissue regeneration in the field of tissue transplantation, Current Stem Cell Research & Therapy, 1:13-20.
Ohgushi, H. and Caplan, A.I. (1999) "Stem cell technology and bioceramics: from cell to gene engineering" J Biomed Mater Res 48, 913-27.
Olson, E. N. et al., "Know Your Neighbors: Three Phenotypes in Null Mutants of the Myogenic bHLH Gene MRF4," *Cell*, 1996, 85:1-4.
Ooi, K., M.P. Lacy et al (1991) "salt-soluble collagen and elastin in the human aorta and pulmonary artery" Exp Mol Pathol 55(1): 25-9.
Orlic, "Bone marrow stem cells regenerate infarcted myocardium," Pediatric Transplantation, 2003.
Orlic, "Stem Cell Repair in Ischemic Heart Disease: An Experimental Model," International Journal of Hematology, Supplement I, 2002.
Orlic, D., J. Kajstura, et al. (2001) "Bone marrow cells regenerate infarcted myocardium" Nature 410(6829): 701-5.
Orlic, D., J. Kajstura, et al. (2001) "Transplanted adult bone marrow cells repair myocardial infarcts in mice" Ann N Y Acad Sci 938: 221-9, discussion 229-30.
Owen et al., 1990, Progressive Development of the Rat Osteoblast Phenotype in Vitro: Reciprocal Relationships in Expression of Genes Associated with Osteoblast Proliferation and Differentiation During Formation of the Bone Extracellular Matrix, J. Cell Physiol., 143:420-430.
Pairault, Jacques and Howard Green, "A study of the adipose conversion of suspended 3T3 cells by using glycerophosphate dehydrogenase as differentiation marker," *Proc. Natl. Acad. Sci. USA*, 1979, 76:5138-42.
Pajvani et al., 2005, Fat apoptosis through targeted activation of caspase 8: a new mouse model of inducible and reversible lipoatrophy, Nature Medicine, 11(7):797-803.
Palma, P.C., C.L. Riccetto, et al. (1997) "Repeated lipoinjections for stress urinary incontinence" J Endourol 11(1): 67-70.
Park, S. R. et al., "Interconversion Potential of Clone Human Marrow Adipocytes In Vitro," *Bone*, 1999, 24:549-54.
Patrick et al. "Long-term implantation of preadipocyte-seeded PLGA scaffolds." Tissue Eng. 8(2):283-93 (2002).
Patrick et al. "Preadipocyte Seeded PLGA Scaffolds for Adipose Tissue Engineering." Tissue Eng. 5(2): 139-151 (1999).
Patrick et al., 2000, Adipose tissue engineering: the future of breast and soft tissue reconstruction following tumor resection, Semin. Surg. Oncol. 19(3):302-11.
Paul S.R., et al., 1991 *Blood* "Stromal Cell-Associated Hematopoiesis: Immortalization and Characterization of Primate Bone Marrow-Derived Stromal Cell Line," 77: 1723-33.
Pavcnik et al., 2004, Second-generation percutaneous bioprosthetic valve: a short-term study in sheep, Eur. J. Endovasc. Surg. 40:1223-1227.
Pedersen, S. B. et al., "Identification of oestrogen receptors and oestrogen receptor mRNA in human adipose tissue," *European Journal of Clinical Investigation*, 26:262-9, 1996.
Pera, M.F., Reubinoff, B., and Trounson, A. (2000) "Human embryonic stem cells" J Cell Sci 113 (Pt 1) 5-10.
Perbeck et al., Mar. 2006, Lymph Circulation in the Breast after Radiotherapy and Breast Conservation, Lymphology, 39(1):33-40 (abstract).
Periasamy, Muthu et al., "Regulation of myosin heavy-chain gene expression during skeletal-muscle hypertrophy," *Biochem. J.* 1989 257:691-698.
Perin et al. "Transendocardial, autologous bone marrow cell transplantation for severe, chronic ischemic heart failure." Circulation. 107(18):2294-2302 (2003).

(56) References Cited

OTHER PUBLICATIONS

Pettengell et al. "Peripheral Blood Progenitor Cell Transportation in Lymphoma and Leukemia Using a Single Apheresis." Blood. 82:3770-3777 (1993).
Pettersson, Per et al., "Adipocyte Precursor Cells in Obese and Nonobese Humans," *Metabolism*, 34:808-12, 1985.
Pettersson, Per et al., "Cells in Human Adipose Tissue Developing into Adipocytes," *Acta Med Scand*, 1984, 215:447-51.
Pierelli, Luca et al., "CD34+/CD105+ cells are enriched in primitive circulating progenitors residing in the G0 phase of the cell cycle and contain all bone marrow and cord blood CD34+/CD38low/-precursors," *British Journal of Haematology*, 2000, 108:610-20.
Piersma et al. "Migration of fibroblastoid stromal cells in murine blood." Cell Tissue Kinet. 18:589-595 (1985).
Pipp et al., 2003, VEGFR-1-selective VEGF homologue PlGF is arteriogenic: evidence for a monocyte-mediated mechanism, Circ. Res 92:378-385.
Pittenger, M.F. A.M. Mackay, et al. (1999) "Multilineage potential of adult human mesenchymal stem cells" Science 284(5411): 143-7.
Planat-Benard et al. "Spontaneous Cardiomyocyte Differentiation from Adipose Tissue Stroma Cells." Circulation Research. 94(2):223-229 (2004).
Planat-Bernard, et al. "Plasticity of Human Adipose Lineage Cells toward Endothelial Cells Physiological and Therapeutic Perspectives." Circulation, American Heart Association. 109(5):656-663 (2004).
Podgrabinska et al., Dec. 10, 2002, Molecular characterization of lymphatic endothelial cells, PNAS 99(25):16069-16074.
Poliard, A. et al., "Controlled Conversion of an Immortalized Mesodermal progenitor Cell Towards osteogenic, Chondrogenic, or Adipogenic Pathways," *J. Cell Biol.* 1995 130;1461-1472.
Ponce, 2001, 14. In vitro Matrigel Angiogenesis Assays, in Methods in Molecular Medicine, vol. 46: Angiogenesis Protocols, Edited by JC Murray, Humana Press, Totowa, NJ, pp. 205-209.
Price, Paul A. and Sharon A. Baukol, "1,25-Dihydroxyvitamin D3 Increases Synthesis of the Vitamin K-dependent Bone Protein by Osteosarcoma Cells," *The Journal of Biological Chemistry*, 1980, 255:11660-3.
Price, Paul A. et al., "Matrix GLA Protein, a New γ-Carboxyglutamic Acid-Containing Protein Which is Associated With the Organic Matrix of Bone," *Biochem. Biophys. Res. Commun.*, 1983 117:765-771.
Price, Paul A., "GLA-Containing Proteins of Bone," *Connective Tissue Research*, 1989, 21:51-60.
Prince et al., 2002, Isolex 300i CD34-selected cells to support multiple cycles of high-dose therapy, Cytotherapy 4:137-45.
Probst, M. et al., "Homologous bladder augmentation in dog with the bladder acellular matrix graft," *BJU International*, 2000, 85:362-71.
Prockop D.J. 1997 *Science* "Marrow Stromal Cells as Stem Cells for Nonhematopoietic Tissues," 276: 71-74.
Prockop, D.J., S.A. Azizi, et al. (2000) Potential use of marrow stromal cells as therapeutic vectors for diseases of the central nervous system: Prog Brain Res 128:293-7.
Purna, S.K. and M. Babu (2000) "Collagen based dressings—a review" Burns 26(1): 54-62.
Qian, X., Jin, L., and Lloyd, R.V. (1998) Percoll Density Gradient-Enriched Populations of Rat Pituitary Cells: Interleukin 6 Secretion, Proliferative Activity, and Nitric Oxide Synthase Expression: Endocr. Pathol. 9, 339-346.
Quirici, N., Soligo, D., Bossolasco, P., Servida, F., Lumini, C., and Deliliers, G.L. (2002) "Isolation of bone marrow mesenchymal stem cells by anti-nerve growth factor receptor antiobidies" Exp Hematol 30, 783-91.
Rajnoch, C., Chachques, J.C., Berrebi, A., Bruneval, P., Benoit, M.O., and Carpentier, A. (2001) "Cellular therapy reverses myocardial dysfunction" J Thorac Cardiovasc Surg 121(5), 871-8.
Rajpurohit, et al., 2002, Phenotypic characteristics of the nucleus pulposus: expression of hypoxia inducing factor-1, glucose transporter-1 and mmp-2, Cell Tissue Res. 308(3):401-7.

Rambaldi, et al., 1998, Innovative two-step negative selection of granulocyte colony-stimulating factor-mobilized circulating progenitor cells: adequacy for autologous and allogeneic transplantation, Blood 91(6):2189-2196.
Ramirez-Zacarias et al., 1992, Quantitation of adipose conversion and triglycerides by staining intracytoplasmic lipds with Oil red O, Histochemistry 97(6):493-497.
Ramsay, T. G. et al., "Pre-Adipocyte Proliferation and Differentiation in Response to Hormone Supplementation of Decapitated Fetal Pig Sera," *J. Anim. Sci.*, 64:735-44, 1987.
Rando, et al., 1995 *Exp. Cell Res.* "The Fate of Myoblasts Following Transportation into Mature Muscle," 220:383-389.
Rando, Thomas A. and Helen M. Blau, "Primary Mouse Myoblast Purification, Characterization, and Transplantation for Cell-mediated Gene Therapy," *J. Cell Biol* 1994 125:1275-1287.
Rangappa et al., 2003, Transformation of adult mesenchymal stem cells isolated from the fatty tissue into cardiomyocytes, Ann Thorac. Surg 75, 775-779.
Rehman et al., 2007, Human adipose stromal cells express the angiogenic factor VEGF and its receptor VEGFR-2, Arterioscler Thromb Vasc Biol, 22:878, Poster Presentation P111, p. a-19.
Rehman, et al. "Angiogenic potential of subcutaneous adipose stromal cells for autologous cell therapy." Journal of the American College of Cardiology. 41(6)(Suppl A): 308A (Mar. 19, 2003).
Rehman, et al. "Secretion of angiogenic and antiapoptotic factors by human adipose stromal cells." Circulation. 109(10):1292-1298 (2004).
Reinecke H et al. 2002. Skeletal muscle stem cells do not transdifferentiate into cardiomyocytes after cardiac grafting. J. Mol. Cell. Cardiol. 34: 241-249.
Reitman et al., 2000, A-ZIP/F-1 mice lacking white fat: a model for understanding lipoatrophic diabetes, Int. J. Obes. Relat. Metab. Disord. 24 (Supp14):S11-514.
Religa et al., 2005, Presence of bone marrow-derived circulating progenitor endothelial cells in the newly formed lymphatic vessels, Blood 106(13):4184-4190.
Remacle, M., G. Lawson et al (1999) "Correcting vocal fold immobility by autologous collagen injection for voice rehabilitation. A short-term study." Ann Otol Rhinol Laryngol 108(8): 788-83.
Remme, W.J. (2000) "Overview of the relationship between ischemia and congestive heart failure" Clin Cardiol 23, 4-8.
Reyes, M., Lund, T., Lenvik, T., Aguiar, D., Koodie, L., and Verfaillie, C.M. (2001) "Purification and ex vivo expansion of postnatal human marrow mesodermal progenitor cells" Blood 98, 2615-2625.
Richardson, J. B. et al., "Repair of human articular cartilage after implantation of autologous chondrocytes," *The Journal of Bone and Joint Surgery*, 1999, 81:1064-8 ).
Rickard, David J. et al., "Isolation and Characterization of Osteoblast Precursor Cells from Human Bone Marrow," *Journal of Bone and Mineral Research*, 1996, 11:312-24.
Rim et al., 2005, Mesenchymal stem cells from the outer ear: a novel adult stem cell model system for the study of adipogenesis, FASEB J. 19(9):1205-1207.
Rivard et al., 1998, Angiogenesis and vasculogenesis in treatment of cardiovascular disease, Molecular Medicine, 4:429-440.
Rodriguez et al. "The human adipose tissue is a source of multipotent stem cells." Biochimie. 87(1):125-128 (2005).
Rolovic, et al., 1990, Megakaryocytopoiesis in experimentally induced chronic normobaric hypoxia, Exp. Hematol. 18(3):190-4.
Rubens, F. D. et al., "Tissue Factor Expression by Cells Used for Sodding of Prosthetic Vascular Grafts," *Journal of Surgical Research*, 72:22-8, 1997.
Rupnick et al., 2002, Adipose tissue mass can be regulated through the vasculature, PNAS 99(16):10730-10735.
Russell, S.W., Doe, W.F., Hoskins, R.G. and Cochrane, C.G. (1976) "inflammatory cells in solid murine neoplasms. I. Tumor disaggregation and identification of constituent inflammatory cells" Int J Cancer 18, 322-30.
Ryden et al., Jan. 11, 2002, Mapping of early signaling events in tumor necrosis factor-alpha-mediated lipolysis in human fat cells, J. Biol. Chem. 277(2):1085-1091.

(56) References Cited

OTHER PUBLICATIONS

Saalbach, A., et al., 1997 *Cell and Tiss. Res.* "The Fibroblast-specific MAb AS02: a novel tool for detection and elimination of human fibroblasts," 290:593-599.

Safford et al. "In vivo engraftment and differentiation of murine adipose derived stromal cells" Blood, vol. 100, No. 11, 731a, (Nov. 2002).

Safford, Kristine M. et al., "Neurogenic differentiation of murine and human adipose-derived stromal cells," *Biochemical and Biophysical Research Communications*, 2002, 371-379.

Saha, et al. 2006, Inhabition of human embryonic stem cell differentiation by mechanical strain, J. Cell Phys. 206(1):126-137.

Saito et al. "Transcoronary implantation of bone marrow stromal cells ameliorates cardiac function after myorcardial infarction." The Journal of Thoracic and Cardiovascular Surgery. 126(1):114-122 (2003).

Sallam et al., 1973, A new surgical approach to myocardial revascularization-internal mammary artery to coronary vein anastomosis, Thorax, 28:613-616.

Saluja et al., Mar. 2003, Pancreatitis and associated lung injury: when MIF miffs, Gastroenterology, 124(3):844-847.

Salven et al., 2003, VEGFR-3 and CD133 identify a population of CD34+ lymphatic/vascular endothelial precursor cells, Blood 101(1):168-172.

Sanchez-Ramos, et al., 2000 "Adult Bone Marrow Stromal Cells Differentiate into Neural Cells in Vitro," Exp. Neurol. 164:247-256.

Sarnat, Harvey B. et al., "Neuronal nuclear antigen (NeuN): a marker of neuronal maturation in the early human fetal nervous system," *Brain & Development*, 1998, 20:88-94.

Sattler et al. "Liporecycling: a technique for facial rejuvination and body contouring" Dermantol. Surg. vol. 26, No. 12, 1140-1144 (Dec. 2000).

Savitz et al. "Cell Transplantation for stroke." Annals of Neurology. 52(3):266-275 (2002).

Schenke-Layland et al., May 15, 2009, Adipose tissue-derived cells improve cardiac function following myocardial infarction, Journal of Surgical Research, 153(2):217-223.

Scherberich, A. and A. Beretz (2000) "Culture of vascular cells in tridimensional (3-D) collagen: a methodological review" Therapie 55(1): 35-41.

Schmidt et al., Jan. 1992, A better model of acute pancreatitis for evaluating therapy, Ann Surg. 215(1):44-56.

Schoeller et al. "Histomorphologic and volumetric analysis of implanted autologous preadipocyte cultures suspended in fibrin glue: a potential new source for tissue augmentation." Aesthetic Plastic Surgery. 25(1):57-63 (2001).

Scholz et al. (2003) "Bone marrow transplantation abolishes inhibition of arteriogenesis in placenta growth factor (PIGF)—mice" J Mol Cell Cardiol 35, 177-184.

Scholz et al., (2002) "Contribution of arteriogenesis and angiogenesis to postocculsive hindlimb perfusion in mice" J Mol Cell Cardiol 34, 775-787.

Scholz, D., Cai, W.J., and Schaper, W. (2001) "Arteriogenesis, a new concept of vascular adaptation in occlusive disease" Angiogenesis 4, 247-257.

Schwartz et al., 2002, Multipotent adult progenitor cells from bone marrow differentiate into functional hepatocyte-like cells J Clin Invest 109:1291-302.

Schwartzmann, M. (2000) "Use of collagen membranes for guided bone regeneration: a review" Implant Dent 9(1): 63-6.

Schweitzer et al., (1995) "Isolation and culture of human bone marrow endothelial cells" Exp Hematol 23, 41-8.

Sclafani, A.P. and T. Romo, 3rd (2001) "Collagen, human collagen and fat: the search for a three-dimensional soft tissue filler" Facial Plast Surg 17(1): 79-85.

Sclafani, A.P., T. Romo, 3rd et al. (2002) "Rejuvenation of the aging lip with an injectable acellular dermal graft (cymetra)" Arch Facial Plast Surg 4(4): 252-7.

Scott, Douglas M. et al., "Collagen Synthesis in Cultured Osteoblast-like Cells," *Archives of Biochemistry and Biophysics*, 1980, 201:384-91.

Seale and Rudnicki 2000 Dev. Biol. "A New Look at the Origin, Function, and "Stem-Cell" Status of Muscle Satellite Cells," 218:115-124.

Sekiya et al., (2002) "Expansion of human adult stem cells from bone marrow stroma: conditions that maximize the yields of early progenitors and evaluate their quality" Stem Cells 20, 530-541.

Sekiya et al., 2004, Adipogenic differentiation of human adult stem cells from bone marrow stroma (MSCs), J. Bone and Min. Res. 19(2):256-264.

Sergeant, P., Blackstone, E., and Meyns, B. (1997) "Early and late outcome after CABG in patients with evolving myocardial infarction" Eur J Cardiothorac. Surg 11, 848-856.

Shalhoub, Victoria et al., "Downregulation of Cell Growth and Cell Cycle Regulated Genes during Chick Osteoblast Differentiation with the Reciprocal Expression of Histone Gene Variants," *Biochemistry*, 1989, 28:5318-22.

Shi, Q., S. Rafil, et al. (1998) "Evidence for circulating bone marrow-derived endothelial cells" Blood 92(2): 362-7.

Shigematsu, S., Yamauchi, K., Nakajima, K., Iijima, S., Aizawa, T., and Hashizume, K. (1999) "IGF-1 regulates migration and angiogenesis of human endothelial cells" Endocr. J 46 Suppl, S59-S62.

Shillabeer, et al., "A novel method for studying preadipocyte differentiation in vitro," *Intl. J. Obesity* 1996 20(Supp. 3), S77-S83.

Shimazaki, et al., 1998, Elimination of myeloma cells from bone marrow by using monoclonal antibodies and magnetic immunobeads, Blood 72(4):1248-54.

Shore, J.W. (2000) "Injectable lyophilized particulate human fascia lata (Fascian) for lip, perioral and glabellar enhancement" Opthal Plast Reconstr Surg 16(1): 23-7.

Shukunami C., et. al., 1996 *Journ. of Cell Bio.* "Chrondrogenic Differentiation of Clonal Mouse Embryonic Cell Line ATDC5 In Vitro: Differentiation-dependent Gene Expression of Parathyroid Hormone (PTH)/PTH-related Peptide Receptor," 133:2:457-468.

Shukunami, C., et al., 1998 *Exp. Cell Res.* "Sequential Progression of the Differentiation Program by Bone Morphogenetic Protein-2 in Chondrogenic Cell Line ATDC5," 241:1-11.

Siffert, Robert S., "The Role of Alkaline Phosphatase in Osteogenesis," *The Journal of Experimental Medicine*, 1951, 93:415-26.

Silberstein, L., et al., 1986 *Cell* "Developmental Progression of Myosin Gene Expression in Cultured Muscle Cells," 46:1075-1081.

Silver, F.H. and G. Pins (1992) "Cell growth on collagen: a review of tissue engineering using scaffolds containing extracellular matrix" J Long Term Eff Med Implants 2(1): 67-80.

Sivan-Loukianova et al. "CD34+ Blood cells accelerate vascularization and healing of diabetic mouse skin wounds" J. Vascular Research, vol. 40, No. 4, 368-377 (Jul.-Aug. 2003).

Šmahel, J., "Aspiration lipectomy and adipose tissue injection: pathophysiologic commentary," *European Journal of Plastic Surgery*, 14:126-31, 1991.

Smith et al., 1995, A mononuclear cell dose of 3×10(8)/kg predicts early multilineage recovery in patients with malignant lymphoma treated with carmustine, etoposide, Ara-C and melphalan (BEAM) and peripheral blood progenitor cell transplantation, Exp Hematol 23:1581-1588.

Smith et al., 2000, "Mesenchymal Stem Cells Derived From Bone Marrow and Human Adipose Tissue Exhibit Multilineage Potential," *Journal of Investigative Medicine*, 95A.

Smith, J.W. (1997) "Apheresis techniques and cellular immunomodulation" Ther. Apher. 1, 203-206.

Smits, G., Holzgreve, W., and Hahn, S. (2000) "An examination of different Percoll density gradients and magnetic activated cell sorting (MACS) for the enrichment of fetal erythroblasts from maternal blood" Arch. Cynecol. Obstet. 263, 160-163.

Soda, et al., 1983, "Adipocyte stem cell: A brief review," *Int. J. of Cell Cloning*, 1:79-84.

Sodian, R., Lemke, T., Fritsche, C., Hoerstrup, S.P, Fu, P., Potapov, E.V., Hausmann, H., and Hetzer, R. (2002) "Tissue-engineering

(56) References Cited

OTHER PUBLICATIONS bioreactors: a new combined cell-seeding and perfusion system for vascular tissue engineering" Tissue Eng 8, 863-870.

Soli et al., 2001, A multicentre evaluation of a new filtration protocol for leucocyte depletion of high-haematocrit red blood cells collected by an utomated blood collection system, Vox Sang. 81:108-112.

Sommer et al. "Current Concepts of Fat Graft Survival: Histology of Aspirated Adipose Tissue and Review of the Literature." Dermatologic Surgery. 26(12):1159-1166 (2000).

Sorisky et al., "From preadipocyte to Adipocyte: Differentiation-Directed Signals of Insulin from the Cell Surface to the Nucleus," *Critical Review in Clinical Laboratory Sciences* 1999 36(1), 1-34.

Speranza, M.L. and G. Valentini (1986) "A simple procedure for the purification of neutral salt soluble type I collagen from skin" Ital J Biochem 35(1): 42-8.

Springhorn, Jeremy P. et al., "Human Capillary Endothelial Cells from Abdominal Wall Adipose Tissue: Isolation Using an Anti-Pecam Antibody," *In Vitro Cellular & Developmental Biology—Animal*, 31:473-81, 1995.

Stamm, C., Westphal, B., Kleine, H.D., Petzsch, M., Kittner, C., Klinge, H., Schumichen, C., Nienaber, C.A., Freund, M. and Steinhoffm G. (2003) "Autologous bone-marrow stem-cell transplantation for myocardial regeneration" Lancet 4, 45-46.

Stashower et al., 1999, "Stromal progenitor cells present within liposuction and reduction abdominoplasty fat for autologous transfer to aged skin," *Dermatologic Surgery*, 25:12:945-949.

Steffgen et al, 2003, Osmoregulation of aldose reductase and sorbitol dehydrogenase in cultivated interstitial cells of rat renal inner medulla, Nephrol. Dial. Transplant. 18(11):2255-61.

Stosich et al. "Adipose tissue engineering from human adult stem cells: clinical implications in plastic and reconstructive surgery." *Plast Reconstr Surg* 119, 71-83 (2007).

Strauer, B.E., M. Brehm, et al. (2002) "Repair of infarcted myocardium by autologous intracoronary mononuclear bone marrow cell transplantation in humans" Circulation 106(15): 1913-8.

Strem et al., 2005, Multipotential differentian of adipose tissue-derived stem cells, Keio J. Med 54(3):132-141.

Strutt et al., 1996, "Growth and differentiation of human adipose stromal cells in culture," *methods in Molecular Medicine: Human Cell Culture Protools*, 41-51.

Su et al., "Increased expression of G in mouse embryo stem cells promotes terminal differentiation to adipocytes," *American Physiological Society* 1993 265(6), C1729-C1735.

Suga, S., et al., 1996,"*Eur. J. Cell Biol.* "Intracellular localization of antigens recognized by anti-vimentin monoclonal antibodies (mAbs): Cross-reactivities of anti-vimentin mAbs with other cellular components 70:84-91.

Sundberg et al., 2002, Stable expression of antiopoietin-1 and other markers by cultured pericytes: phenotypic similarities to a subpopulation of cells in maturing vessels during later stages of angiogenesis in vivo, Lab invest 82:387-401.

Symmons et al., 2006, The world of biologics, Lupus, 15(3):122-126.

Syrjälä, M. et al., "A flow cytometric assay of CD34-postitive cell populations in the bone marrow," *British Journal of Haematology*, 1994, 88:679-84.

Tabata,Y. et al. "De novo formation of adipose tissue by controlled release of basic fibroblast growth factor." *Tissue Eng.* 6:6279-289 (2000).

Tacchetti, C, et al., 1992 *Exp Cell Res.* "Cell Condensation in Chondrogenic Differentiation," 200:26-33.

Tacchetti, C. et al., "In Vitro Morphogenesis of Chick Embryo Hypertrophic Cartilage," *The Journal of Cell Biology*, 1987, 105:999-1006.

Tafech et al., 2006, Destroying RNA as a Therapeutic Approach, Current Medicinal Chemistry, 13(8):863-81.

Takahashi, T., C. Kalka, et al. (1999) "Ischemia and cytokine-induced mobilization of bone marrow-derived endothelial progentiro cells for neovascularization" Nat Med 5(4): 434-8.

Takasaki, et al (1995) "Human type VI collagen: purification from human subcutaneous fat tissue and an immunohistochemical study of morphea and systemic sclerosis" J Dermatol 22(7): 480-5.

Tang et al., 2004, Commitment of C3H10T1/2 pluripotent stem cells to the adipocyte lineage, PNAS 101(26):9607-9611.

Tapscott, et al., 1988 *Science* "MyoD1: A Nuclear Phosphoprotein Requiring a Myc Homology Region to Convert Fibroblasts to Myoblasts," 242:405-411.

Tavassoli et al., 1981, "The Nature of Fibroblasts Derived From Adipose Tissue In-Vitro," *Clinical Research*, 29:5:871A.

Tavassoli, Mehdi, "In Vivo Development of Adipose Tissue Following Implantation of Lipid-Depleted Cultured Adipocyte," *Experimental Cell Research*, 137:55-62, 1982.

Thomas, E.D. (1994) "Stem Cell Transplantation: Past, Present and Future" Stem Cells 12: 539-544.

Thornell, et al., 1984 *J. Neurol. Sci.* "Development of Fiber Types in Human Fetal Muscle," 66:107-115.

Tintut et al., 2003, Multilineage potential of cells from the artery wall, Circulation, 108(20):2505-2510.

Toma, J.G., Akhavan, M., Fernandes, K.J., Barnabe-Heider, F., Sadikot, A., Kaplan, D.R. and Miller, F.D. (2001) "Isolation of multipotent adult stem cells from the dermis of mammalian skin" Nat Cell Biol 3, 778-84.2.

Tondreau et al., 2004, Isolation of BM mesenchymal stem cells by plastic adhesion or negative selection: phenotype, proliferation kinetics and differentiation potential, Cytotherapy, 6(4):372-379.

Tontonoz, Peter et al., "mPPARg2: tissue-specific regulator of an adipocyte enhancer," *Genes & Development*, 1994, 8:1224-34.

Torio-Padron et al. "Engineering of adipose tissue by injection of human preadipocytes in fibrin." *Aesthetic Plast Surg* 31, 285-293 (2007).

Tosh, et al. "Conversion of pancreatic cells to hepatocytes." Biochem Soc Trans 30:51-55 (2002).

Totonoz, et al., 1995 *Nucl. Acid Res* "mPPARg2: tissue-specific regulator of an adipocyte enhancer."

Trayhurn, P. and Margaret Ashwell, "Control of white and brown adipose tissues by the autonomic nervous system," *The Proceedings of the Nutrition Society*, 1987, 46:135-42.

Trujillo et al., 2005, Apoptosis through targeted activation of Caspase8 ("ATTAC-mice"): novel mouse models of inducible and reversible tissue ablation, Cell Cycle 4(9):1141-1145.

Tschopp et al, 1983, Hypergravity promotes cell proliferation, Experientia 39(12):1323-9.

Tsonis and Goetinck 1990 *Exp. Cell Res.* "Cell Density Dependent Effect of a Tumor Promoter on Proliferation and Chondrogenesis of Limb Bud Mesenchymal Cells," 190:247-253.

Twentyman, P.R. and Yuhas, J.M. (1980) "Use of bacterial neutral protease for disaggregation of mouse tumours and multicellular tumor spheroids" Cancer Lett 9, 225-8.

Uitto, J. (1971) "Collagen biosynthesis in human skin. A review with emphasis on scleroderma" Ann Clin Res 3(5): 250-8.

Urban et al. "Degeneration of the intervertebral disc." Arthritis Research & Therapy. 5(3):120-130 (2003).

Urbich et al. "Endothelial Progenitor Cells." Trends in Cardiovascular Medicine. 14(8):318-322 (2004).

Urs et al., 2004, Gene expression profiling in human preadipocytes and adipocytes by microarray analysis, J. Nutr. 134:762-770.

Van et al., 1978, "Complete Differentiation of Adipocyte Precursors," *Cell Tissue*, 195:317-329.

Van Merris et al., 2001, "Separation of bovine bone marrow into maturation-related myeloid cell fractions" Vet. Immunol. Immunopathol. 83, 11-17.

Van, "Cytological and enzymological characterization of adult human adipocyte precursors in culture," J Clin Invest 1976.

Vandenburgh, Herman H. and Patricia Karlisch, "Longitudinal Growth of Skeletal Myotubes In Vitro in a New Horizontal Mechanical Cell Stimulator," *In Vitro Cellular & Developmental Biology*, 1989, 25:607-16.

Varzaneh et al., 1994, Extracellular Matrix Components Secreted by Microvascular Endothelial Cells Stimulate Preadipocyte Differentiation In Vitro, Metabolism 43(7):906-912.

(56) References Cited

OTHER PUBLICATIONS

Vassaux et al., 1994, Proliferation and differentiation of rat adipose precursor cells in chemically defined medium: differential action of anti-adipogenic agents, Journal of Cellular Physiology, 161(2):249-256.
Verma (1990), "Gene therapy." Scientific American 263(5): 68-84.
Vojtassak, et al., 2006; "Autologous Biograft and Mesenchymal Stem Cells in Treatment of the Diabetic Foot," Neuro Endocrinol Lett. 27 Suppl 2:134-7.
von der Mark, et al., 1977 *Nature* "Relationship between cell shape and type of collagen synthesised as chondrocytes lose their cartilage phenotype in culture," 267:531-532.
von Heimburg, D. et al. "Human preadipocytes seeded on freeze-dried collagen scaffolds investigated in vitro and in vivo." *Biomaterials* 22, 429-38 (2001).
Vukicevic et al., 1992, Identification of Multiple Active Growth factors in Basement Membrane Matrigel Suggests Caution in Interpretation of Cellular Activity Related to Extracellular Matrix Components, Exp. Cell Res, 202(1):1-8.
Wabitsch, et al., "Biological Effects of Human Growth Hormone in Rat Adipocyte Precursor Cells and Newly Differentiated Adipocytes in primary Culture," *Metabolism* 1996 vol. 45,No. 1 pp. 34-42.
Wagner et al., 2005, Comparative characteristics of mesenchymal stem cells from human bone marrow, adipose tissue, and umbilical cord blood, Experimental Hematology 33:1402-1416.
Wakitani, Shigeyuki et al., "Mesenchymal Cell-Based Repair of Large, Full-Thickness Defects of Articular Cartilage," *The Journal of Bone and Joint Surgery*, 1994, 76A:579-92.
Wakitani, Shigeyuki et al., "Myogenic Cells Derived from Rat Bone Marrow Mesenchymal Stem Cells Exposed to 5-Azacytidine," *Muscle & Nerve*, 1995, 18:1417-26.
Walther, W. and Stein, U. (2000) Viral vectors for gene transfer: a review of their use in the treatment of human diseases: Drugs 609, 249-71.
Walton et al. "De novo adipose formation in a vascularized engineered construct." *Microsurgery* 24, 378-384 (2004).
Wang "Human Progenitor cells from bone marrow or adipose tissue produce VEGF, HGF, and IGF-1 in response to TNF by a p38 MAPK-dependent mechanism." Am J. Physiol/Regul Integ 2006.
Wang, et al., 1992, An effective immunomagnetic method for bone marrow purging in T cell malignancies, Bone Marrow Transplant. 9(5):319-23 (abstract).
Wang, L., Zeng, H., Wang, P., Soker, S., and Mukhopadhyay, D. (2003) "Neuropilin-1 mediated vascular permeability factor/vascular endothelial growth factor-dependent endothelial cell migration" J Biol Chem 278, 48848-48860.
Watts et al., 2002, Variable product purity and functional capacity after CD34 selection: a direct comparison of the CliniMACS (v2.1) and Isolex 300i(v2.5) clinical scale devices, Br J Haematol 118:117-23.
Weiner, Francis R. et al. "Regulation of collagen Gene Expression in 3T3-L1 Cells. Effects of Adipocyte Differentiation and Tumor necrosis Factor a," Biochem 1989 28:4094-4099.
Weintraub, et al., 1991 *Science* "The myoD Gene Family: Nodal Point During Specification of the Muscle Cell Lineage," 251:761-766.
Weintraub, Harold et al. "Tissue-specific gene activation by MyoD: determination of specificity by cis-acting repression elements," *Genes & Development*, 1994, 8:2203-11.
Werlich, T., K.J. Stiller, et al. (1999) "Experimental studies on the stem cell concept of liver regeneration II" Exp Toxicol Pathol 51(1): 93-8.
Williams, Irene H. and S. Efthimios Polakis, "Differentiation of 3T3-L1 Fibroblasts to Adipocytes, the Effect of Indomethacin, Prostaglandin $E_1$ and Cyclic AMP on the Process of Differentiation" *Biochem Biophys. Res.Commun.* 1977 77:175-186.
Williams, John T. et al., "Cells Isolated from Adult Human Skeletal Muscle Capable of Differentiating into Multiple Mesodermal Phenotypes," *The American Surgeon*, 65:22-6, 1999.

Williams, S.K., McKenney, S. and Jarrell, B.E. (1995) "Collagenase lot selection and purification for adipose tissue digestion" Cell Transplant 4, 281-9.
Williams, Stuart K. et al., "Liposuction-derived human fat used for vascular graft sodding contains endothelial cells and not mesothelial cells as the major cell type," *Journal of Vascular Surgery*, 19:916-23, 1994.
Wilting et al., 2007, The Proepicardium Delivers Hemangioblasts but not Lymphangioblasts to the Developing Heart, Developmental Biology 305:451-459.
Wilting et al., Aug. 2002, The transcription factor Prox1 is a marker for lymphatic endothelial cells in normal and diseased human tissues, The FASEB Journal, 16:1271-1273.
Wise, Leigh S. and Howard Green, "Participation of One Isozyme of Cytosolic Glycerophosphate Dehydrogenase in the Adipose Conversion of 3T3 Cells," *J. Biol. Chem.* 1979 254:273-275.
Wlodarski, Krzysztof H., "Section III. Basic Science and Pathology. Properties and Origin of Osteoblasts," *Clinical Orthopaedics and Related Research*, 252:276-93, 1990.
Wolinsky et al., Feb. 1990, Use of a perforated balloon catheter to deliver concentrated heparin into the wall of the normal canine artery, J. Am. Coll. Cardiol. 15(2):475-481.
Wollert et al. "Intracoronary autologous bone-marrow cell transfer after myocardial infarction: the BOOST randomised controlled clinical trial." The Lancet Limited. 364(9429):141-148 (2004).
Worster et al., 2001, Chondrocytic differentiation of mesenchymal stem cells sequentially exposed to transforming growth factor-B1 in monolayer and insulin-like growth factor-I in a three dimensional matrix, J. Orthop. Res. 19(4):738-49.
Wu et al. "Preparation and assessment of glutaraldehyde-cross-linked collagen-chitosan hydrogels for adipose tissue engineering." *J Biomed Mater Res A* 81, 59-65 (2007).
Xie et al., 2006, Preparation of bupleurum nasal spray and evaluation on its safety and efficacy, Chem. Pharm. Bull., 54(1):48-53.
Xiong, B., Gong, L.L., Zhang, F., Hu, M.B. and Yuan, H.Y. (2002) "TGF beta1 expression and angiogenesis in colorectal cancer tissue" World J Gastroenterol. 8, 496-498.
Yavorkovsky, L., E. Lai, et al. (1995) "Participation of small intraportal stem cells in the restitutive response of the liver to periportal necrosis induced by allyl alochol" Hepatology 21(6): 1702-12.
Ye, Q., Zund, G., Benedikt, P., Jockenhoevel, S., Hoerstrup, S.P., Sakyama, S., Hubbell, J.A. and Turina, M. (2000) "Fibrin gel a three dimensional matrix in cardiovascular tissue engineering" Eur J Cardiothorac Surg 17, 587-91.
Yin, L., D. Lynch, et al. (1999) "Participation of different cell types in the restitutive response of the rat liver to periportal injury induced by allyl alcohol" J Hepatol 31(3): 497-507.
Yokoyama, T., N. Yoshimural et al (2001) "Persistence and survival of autologous muscle derived cells versus bovine collagen as potential treatment of stress urinary incontinence" J Urol 165(1): 271-6.
Yoo, Jung U. and Brian Johnstone, "The Role of Osteochondral Progenitor Cells in Fracture Repair," *Clinical Orthopaedics and Related Research*, 1998, 355S:S73-81 ).
Yoon, Kyonggeun et al., "Characterization of the Rat osteocalcin Gene: Stimulation of Promoter Activity by 1,25-Dihydroxyvitamin D3," *Biochem.* 1988 27:8521-8526.
Young et al., "Mesenchymal Stem Cells Reside Within the Connective Tissues of Many Organs," *Developmental Dynamics* 1995 202(2), 137-144.
Young et al., 2001, Human reserve pluripotent mesenchymal stem cells are present in the connective tissues of skeletal muscle and dermis derived from fetal, adult and geriatric donors, Anat Rec 264:51-62.
Young, 2000 Science "A Time for Restraint," 287:1424.
Young, Henry E. et al., "Human Pluripotent and Progenitor Cells Display Cell Surface Cluster Differentiation Markers CD10, CD13, CD56, and MHC Class-I," *Proc. Soc. Exp. Biol. Med.*, 1999, 221:63-71.
Yuksel et al., Apr. 2000, De novo adipose tissue generation through long-term, local delivery of insulin and insulin-like growth factor-1

(56) References Cited

OTHER PUBLICATIONS by PLGA/PEG microspheres in an in vivo rat model: a novel concept and capability, Plastic and Reconstructive Surgery, 105:1721-1729.
Zalin, RJ 1987 *Exp. Cell Res.* "The Role of Hormones and Prostanoids in the in Vitro Proliferation and differentiation of Human Myoblasts," 172:265-281.
Zezulak, Kathleen M. and Howard Green, "Specificity of Gene Expression in Adipocytes," *Molecular and Cellular Biology*, 1985, 5:419-21.
Zhang, "Bone marrow-derived endothelial progenitor cells participate in cerebral neovascularization after focal cerebral ischemia in the adult mouse," Circ Res. (2002) 90:284-288.
Zimmerman et al., (2002) "Cardiac grafting of engineered heart tissue in syngenic rats" Circulation 106, 1151-1157.
Zimmermann et al., (2004) "Engineered heart tisue for regeneration of diseased hearts" Biomaterials 25, 1639-1647.
Zuk, Patricia A. et al., "Human Adipose Tissue Is a Source of Multipotent Stem Cells," *Molecular Biology of the Cell*, 2002, 13:4279-4295.
Zuk, Patricia Z. et al., "Multilineage Cells from Human Adipose Tissue: Implication for Cell-Based Therapies," *Tissue Engineering*, Apr. 2001, 7:211-228.
Zvaifler, et al., 2000, "Mesenchymal precursor cells in the blood of normal individuals," *Arthritis Res.* 2:477-488.
Ando et al., Autologous Tissue-Fragmented Extracardiac Conduit With Rapid, Stable Endothelialization due to Angiogenesis, Mar. 2000, The Japanese Journal of Thoracic and Cardiovascular Surgery, 48(3):153-160.
Arts et al., Jan. 2001, A novel method for isolating pure microvascular endothelial cells from subcutaneous fat tissue ideal for direct cell seeding, Laboratory Investigation, 81(10):1461-1465.
Chen et al., Therapeutic Benefit of Intravenous Administration of Bone Marrow Stromal Cells After Cerebral Ischemia in Rats, Apr. 2001, Stroke, 32:1005-1011.
Duckers et al., 2006, The bedside celution system for isolation of adipose derived regenerative cells, EuroIntervention, 2:395-298.
Efrat, 1998, Cell-based therapy for insulin-dependent diabetes mellitus, European Journal of Endocrinology, 138:129-133.
Frye et al., Apr. 2002, Isolation and culture of rat microvascular endothelial cells, In Vitro Cell. Dev. Biol.—Animal, 38:208-212.
Hoying et al., Angiogenic Potential of Microvessel Fragments Established in Three-Dimensional Collagen Gels, 1996, In Vitro Cell. Dev. Biol.—Animal, 32:409-419.

Kilroy et al., 2007, Cytokine profile of human adipose-derived stem cells: expression of angiogenic, hematopoietic, and pro-inflammatory factors, Journal of Cellular Physiology, 212:702-707.
Liu et al., Dec. 1, 2008, Tissue-engineered skin containing mesenchymal stem cells improves burn wounds, Artif Organs, 32(12):925-931.
Pardridge, 2011, Drug transport in brain via the cerebrospinal fluid, Fluids and Barriers of the CNS, 8:7.
Pereboeva et al., 2003, Approaches to utilize mesenchymal progenitor cells as cellular vehicles, Stem Cells, 21:389-404.
Puregraft LLC, 2013, Puregraft: Behind Every Curve, 11 pp.
Sell S, Nov. 2001, The role of progenitor cells in repair of liver injury and in liver transplantation, Wound Repair and Regeneraiton, 9(6):467-482 Database accession No. NLM11896898.
Shang et al., Strong Neurogenesis, Angiogenesis, Synaptogenesis, and Antifibrosis of Hepatocyte Growth Factor in Rats Brain After Transient Middle Cerebral Artery Occlusion, 2011, Journal of Neuroscience Research, 89:86-95.
Shokrgozar et al., Apr. 1, 2012, Health potential of mesenchymal stem cells cultured on a collagen-based scaffold for skin regeneraiton, Iran Biomed J., 16(2):68-76.
Singer et al., Apr. 1, 2013, The effects of rat mesenchymal stem cells on injury progression in a rat model, Acad Emerg Med, 29(4):398-402.
Tateishi-Yuyama et al., Therapeutic angiogenesis for patients with limb ischaemia by autologous transplantation of bone-marrow cells: a pilot study and a randomised controlled trial, Aug. 10, 2002, The Lancet, 360:427-35.
Yamamoto et al., Jul. 2012, Periurethral injection of authologous adipose-derived rengenerative cells for the treatment of male stress urinary incontinence: report of three initial cases, International Journal of Urology, 19(7):652-659.
Zeyda et al., 2007, Human adipose tissue macrophages are of an anti-imflammatory phenotype but capable of excessive pro-inflammatory mediator production, International Journal of Obesity, 31:1420-1428.
Zhang et al., 1997, Mitogenic and anti-proliferative signals for neural crest cells and the neurogenic action of TGB-Beta1, Developmental Dynamics, 208:375-386.
Zhu et al., Apr. 2013, Comparison of three different fat graft preparation methods: gravity separation, centrifugation, and simultaneous washing with filtration in a closed system, Plastic and Reconstructive Surgery, pp. 873-880.
Zuk et al., 2004, Stem Cells From Adipose Tissue, in Handbook of Stem Cells, vol. 2: Adult and Fetal, Blau et al., eds. Elsevier Academic Press, Burlington, MA, pp. 425-447.

\* cited by examiner

TANGENTIAL CROSS-FLOW FILTRATION
(HIGH PERMEATE RATE)

DEAD-END FILTRATION
(LOW PERMEATE RATE)

METHODS OF USING ADIPOSE TISSUE-DERIVED CELLS IN THE TREATMENT OF THE LYMPHATIC SYSTEM AND MALIGNANT DISEASE

RELATED APPLICATIONS

The present application is a continuation of U.S. patent application Ser. No. 13/031,031, entitled "METHODS OF USING ADIPOSE TISSUE-DERIVED CELLS IN THE TREATMENT OF THE LYMPHATIC SYSTEM AND MALIGNANT DISEASE," filed Feb. 18, 2011, which is a continuation of International Patent Application No. PCT/US2009/054055, entitled "METHODS OF USING ADIPOSE TISSUE-DERIVED CELLS IN THE TREATMENT OF THE LYMPHATIC SYSTEM AND MALIGNANT DISEASE," filed Aug. 17, 2009, which designated the United States and was published in English, which claims priority under 35 U.S.C. §119 to U.S. Provisional Application No. 61/090,186, entitled "METHODS OF USING ADIPOSE TISSUE-DERIVED CELLS IN THE TREATMENT OF THE LYMPHATIC SYSTEM AND MALIGNANT DISEASE," filed Aug. 19, 2008, the entire contents of each of which are herein incorporated by reference in their entireties.

FIELD OF THE INVENTION

Aspects of the present invention relate to compositions that comprise cells derived from adipose tissue, specifically, adipose-tissue-derived lymphatic endothelial cells (LECs) and cells capable of differentiating into lymphatic endothelial cells (pre-LECs). Methods of making and use of the foregoing compositions are also provided.

BACKGROUND OF THE INVENTION

The lymphatic system plays a dual role in fluid transport and immune surveillance. In fluid transport, extravasated fluid and macromolecules pass into lymphatic vessels that are lined by a single layer of lymphatic endothelial cells (LECs) surrounded by an incomplete basement membrane. Fluid is transferred from these vessels into larger vessels, many of which are lined by lymphatic smooth muscle that exhibit spontaneous beating, which, in concert with the action of adjacent skeletal muscle, pumps the lymph fluid back to the venous system through the thoracic duct. A healthy adult will drain one to two liters of lymph every 24 hours.

Despite apparent similarities, lymphatic vessels are very different from blood vessels, e.g., arteries, veins, and capillaries. In order to facilitate fluid uptake, initial lymph vessels are extremely permeable, are largely devoid of a basement membrane, and lack supporting pericytes and smooth muscle cells. Further, recent studies have demonstrated that, in the post-natal setting, certain molecules are expressed by LECs but not by blood endothelial cells (BECs). These molecules include, e.g., FLT-4 (also referred to as VEGF receptor-3, or VEGFR-3), D2-40, the homeobox-containing gene Prox-1, podoplanin, and the CD44 homolog LYVE-1 (Karkkainen, et al., 2002 "Lymphatic endothelial regulation, lymphoedema, and lymph node metastasis," Semin Cell Dev Biol 13(1): 9-18). FLT-4, the protein product of the fms-like tyrosine kinase-4 gene, specifically recognizes and is activated by VEGF-C and other ligands.

Other differences between LECs and BECs have been described (Kriehuber, et al., 2001, "Isolation and characterization of dermal lymphatic and blood endothelial cells reveal stable and functionally specialized cell lineages," J Exp Med 194(6): 797-808, incorporated herein by reference in its entirety). For example, LECs and BECs have been reported not to be functionally interchangeable. According to Kriehuber, et al., 2001, co-cultured isolated LECs and BECs form only homotypic structures. The vessel-like structures formed in these cultures segregate into structures formed entirely of LECs and structures formed entirely of BECs. Thus, BECs and cells capable of differentiating into BECs would not necessarily be expected to function in lymphatic repair and LECs and cells capable of differentiating into LECs would not necessarily be expected to function in microvascular repair.

Furthermore, it has been reported that in the vertebrate heart coronary blood and lymph vessels are derived from different sources. (See Wilting, et al., 2007, "The Proepicardium Delivers Hemangioblasts but not Lymphangioblasts to the Developing Heart," Developmental Biology doi: 101016/j.ydbio.2007.02.026).

A number of pathological conditions exist in which the ability of the lymphatic system to transport fluid is insufficient to meet demand. This leads to tissue edema that is disfiguring, disabling, and, on occasion, life-threatening. There are thus a number of settings in which modulation of expansion or repair of the lymphatic system are clinically desirable. Acute myocardial infarction leads to increased vascular permeability, thereby increasing the amount of fluid and macromolecules in the interstitial space for removal by the lymphatic system. This edema leads to tissue injury throughout the ventricle, causing histologically visible gaps between vascular endothelial cells and activation of platelets that reduce blood vessel patency. Myocardial edema is evident in many clinical states and can be caused or worsened by cardiac surgery and myocardial infarction. Myocardial edema is also implicated in rejection following heart transplant. The consequences of edema have been studied in animal models of chronic lymphatic obstruction. These studies indicate myofibrillar disruption resulting from edema-induced separation of cardiac myocytes and formation of non-elastic scar tissue which can, in turn, lead to impaired conductance and arrythmia (Kong, et al., 2005, "Effect of cardiac lymph flow obstruction on cardiac collagen synthesis and interstitial fibrosis," Physiol Res. 55:253-258).

Severe tissue edema is frequently present following lymph node dissection, e.g., that which occurs as a routine part of surgical therapy for breast cancer. Chemotherapy and radiotherapy can also induce or worsen edema. In addition, lymphatic regeneration is an important part of wound healing. The inclusion of lymphatic vessels within tissue-engineered constructs will be an important factor in the success of these constructs and related products (Duxbury, et al., 2004, "Lymphangiogenesis in tissue-engineered small intestine," Transplantation 77(8): 1162-6).

Effecting lymphatic expansion by administering a ligand specific for FLT-4 has been proposed (e.g., U.S. Pat. No. 6,730,658, incorporated herein by reference in its entirety). However, cellular over-expression of the FLT-4 ligand, VEGF-C, within a repairing wound reportedly induced only transient lymphatic proliferation (Goldman, et al., 2005, "Overexpression of VEGF-C causes transient lymphatic hyperplasia but not increased lymphangiogenesis in regenerating skin," Circ. Res. 96(11): 1193-9). Further, these studies showed that VEGF-C had no ability to induce LEC migration into the area of injury. It appears that lymph vessel generation and stabilization is a multi-factorial process for which VEGF-C (or another FLT-4 ligand) is not alone sufficient.

Another important aspect of lymphatic system biology is that the lymphatics are involved in tumor metastasis. Invasion of the lymphatic system by malignant cells is well known as a means of staging tumors. In one recent study it was shown that tumor lymph vessel density was a strong predictor of positivity at adjacent sentinel lymph nodes (Massi, et al., 2006, "Tumour lymphangiogenesis is a possible predictor of sentinel lymph node status in cutaneous melanoma: a case-control study," J Clin Pathol 59(2): 166-73). Thus, methods of altering tumor lymphangiogenesis may be applied to the management and treatment of malignancy.

LECs isolated from human palatine tonsils were reported to form tube-like structures in vitro (Garrafa, et al., 2006, "Isolation and characterization of lymphatic microvascular endothelial cells from human tonsils." J Cell Physiol 207(1): 107-13, incorporated herein by reference in its entirety). However, harvesting of skin and tonsil LECs in sufficiently large quantities to allow for clinical use creates harvest site morbidity. The therapeutic use of LECs harvested from tumors is limited in that there is a risk of contamination with tumor cells. Adipose tissue is well-known as a source of BECs but has not previously been recognized as a source of LECs.

Data derived from kidney transplant patients have been interpreted to suggest that circulating lymphatic progenitor cells exist (Religa, et al., 2005, "Presence of bone marrow-derived circulating progenitor endothelial cells in the newly formed lymphatic vessels," Blood 106(13): 4184-90; Kerjaschki, et al., 2006, "Lymphatic endothelial progenitor cells contribute to de novo lymphangiogenesis in human renal transplants," Nature Medicine 12(2): 230-4, incorporated herein by reference). Religa, et al., 2005, reported that following gender-mismatched kidney transplants, approximately 4.5% of the recipient's lymphatic endothelial nuclei were found to be donor-derived. It has been reported that these cells, while circulating, exhibited certain markers of the mononuclear phagocyte lineage, including CD45 and CD14 (Kerjaschki, et al., 2006). Two other populations have been hypothesized as lymphatics EPC candidates: the FLT-$4^+$/CD$34^+$ population and the CD$133^+$/FLT-$4^+$ (e.g., Salven, et al., 2003, "VEGFR-3 and CD133 identify a population of CD34+ lymphatic/vascular endothelial precursor cells," Blood 101(1): 168-72). However, the frequency of these populations in human peripheral blood appears to be extremely low. It has been reported that the frequency of CD$34^+$ cells in the blood is approximately 0.2% (Bender, et al., 1991, "Identification and comparison of CD34-positive cells and their subpopulations from normal peripheral blood and bone marrow using multicolor flow cytometry," Blood 77(12): 2591-6), and that only 0.2%±0.1% of CD$34^+$ cells in the normal adult blood express FLT-4 (Salven, et al., 2003). Accordingly, the frequency of CD$34^+$/FLT-$4^+$ cells in normal blood would be only 0.04%.

Adipose tissue contains a population of cells with the ability to differentiate into multiple cell lineages, that is frequently referred to as Adipose-tissue-Derived Stem Cells (ADSC) (Zuk, et al., 2002, "Human adipose tissue is a source of multipotent stem cells," Mol Biol Cell 13(12): 4279-95 incorporated herein by reference in its entirety and U.S. Pat. No. 6,777,231, incorporated herein by reference in its entirety.) Katz, et al., have reported performing a low density gene expression microarray analysis of ADSC (Katz, et al. 2005, "Cell surface and transcriptional characterization of human adipose-derived adherent stromal (hADAS) cells," Stem Cells 23(3): 412-23 incorporated herein by reference in its entirety). VEGF-C, a ligand for FLT-4, was among the many genes that this study showed to be expressed in ADSC. The frequency of ADSC within the adipose-derived cell population as a whole, as measured by generally recognized clonogenic assays (fibroblastic colony-forming unit and alkaline phosphatase expressing colony-forming unit), has been reported to be approximately 1-8% (Fraser, et al., 1992, "Proliferation of totipotent hematopoietic stem cells in vitro with retention of long-term competitive in vivo reconstituting ability," Proc Natl Acad Sci USA 89(5): 1968-72 and U.S. Pub. No. 2003/0161816, titled "Systems and Methods for Treating Patients with Processed Lipoaspirate Cells," both incorporated herein by reference). The need for a rich source of LECs and pre-LECs, for tissue transplantation and the treatment of lymphatic diseases and disorders is manifest.

SUMMARY OF THE INVENTION

Embodiments described herein relate to the discovery that LECs and cells capable of differentiating into LECS (pre-LECs) can be obtained, enriched, isolated and/or purified from adipose tissue. The ease and low morbidity of adipose tissue removal makes this discovery particularly unique and a significant clinical advance. Further, the ability to obtain, enrich, isolate and/or purify LECs and/or pre-LECs from adipose tissue, and reintroduce the LECs and/or pre-LECs into the same subject from which the adipose tissue was removed (e.g., autologous transfer) provides substantial clinical benefit since one can more easily avoid contamination, tissue rejection, and infection. Accordingly, in light of the disclosure herein, adipose tissue can now be thought of as a rich source of lymphatic cells for expansion, repair, and regeneration of the lymphatic system. The LECs and pre-LECs obtained according to the methods provided herein can be used in therapeutic preparations, cosmetics, and as biotechnological tools (e.g., to identify compounds that modulate expansion, repair, or regeneration of the lymphatic system).

Some embodiments concern methods of processing adipose tissue to obtain a cell population that comprises an enriched, isolated, or concentrated amount of LECs and/or pre-LECs. By some approaches, adipose tissue is removed from a subject (e.g., a mammal, a domestic animal, a rodent, a horse, a dog, cat, or human) and an adipose-derived cell population containing LECs and/or pre-LECs is separated from collagen, adipocytes, blood, and saline (e.g., by employing a disaggregation enzyme, filtration, or centrifugation or any combination of these approaches). Preferably, a cell processing unit is used (e.g., U.S. application Ser. No. 10/316,127, U.S. Pub. No. 2003/0161816, entitled SYSTEMS AND METHODS FOR TREATING PATIENTS WITH PROCESSED LIPOASPIRATE CELLS, filed Dec. 9, 2002, and U.S. application Ser. No. 10/877,822, U.S. Pat. App. Pub. No. 2005/0084961, entitled SYSTEMS AND METHODS FOR SEPARATING AND CONCENTRATING REGENERATIVE CELLS FROM TISSUE, filed Jun. 25, 2004; both of which are hereby expressly incorporated by reference in their entireties). In embodiments, the adipose-derived LEC and/or pre-LEC cells express an amount of, e.g., FLT-4, and/or CD45, and/or CD31, and/or CD34, and/or podoplanin, and/or LYVE-1, and/or Prox-1.

In some embodiments, once the adipose-derived cell population that comprises LECs and/or pre-LECs is obtained, it is further refined, concentrated, enriched, isolated, or purified using a cell sorting device (e.g., FACS) and/or gradient sedimentation (e.g., ficoll-hypaque). In some embodiments, the obtained, refined, enriched, isolated, or purified adipose-derived cell population comprising LECs and/or pre-LECs has a cell population that is greater than or equal to 0.5%-1%, 1-2%, 2%-4%, 4%-6%, 6%-8%, 8%-10%, 10%-20%, 20%-30%, 30%-40%, 40%-50%, 50%-60%, 60%-70%, 70%-80%, 80%-90%, or 90%-100% LECs and/or pre-LECs, as compared to the total adipose-derived cell population. Compositions that comprise, consist, or consist essentially of an adipose-derived cell population with greater than or equal to 0.5%-1%, 1-2%, 2%-4%, 4%-6%, 6%-8%, 8%-10%, 10%-20%, 20%-30%, 30%-40%, 40%-50%, 50%-60%, 60%-70%, 70%-80%, 80%-90%, or 90%-100% LECs and/or pre-LECs, as compared to the total adipose-derived cell population, can be made by isolating the LECs and/or pre-LECs using a cell processing device, gradient sedimentation or a cell sorting device or a combination of any of these techniques and, in some embodiments, mixing said obtained, refined, enriched, isolated, or purified LECs and/or pre-LECs with a support, biological material, prosthetic, or medical device. Preferably, compositions that comprise, consist, or consist essentially of the adipose derived cell population comprising one or more of the foregoing amounts/concentrations of LECs and/or pre-LECs are made by mixing the LECs and/or pre-LECs with unprocessed adipose tissue, a collagen matrix or biological prosthetic or support, processed adipose tissue containing adipose-derived stem cells and/or progenitor cells, and cell populations already containing an enriched amount of LECs and/or pre-LECs.

Accordingly, aspects of the invention include compositions that comprise, consist, or consist essentially of a refined, enriched, concentrated, isolated, or purified adipose-derived cell population comprising LECs and/or pre-LECs and mixtures of these cells with a biological material, support, prosthetic, or medical device, including but not limited to, unprocessed adipose tissue, collagen matrix or support, processed adipose tissue containing adipose-derived stem cells and/or progenitor cells, and cell populations already containing an enriched amount of LECs and/or pre-LECs. In some embodiments, the aforementioned compositions comprise an amount or concentration of refined, isolated, or purified adipose-derived LECs and/or pre-LECs that is greater than or equal to 0.5%-1%, 1-2%, 2%-4%, 4%-6%, 6%-8%, 8%-10%, 10%-20%, 20%-30%, 30%-40%, 40%-50%, 50%-60%, 60%-70%, 70%-80%, 80%-90%, or 90%-100% LECs and/or pre-LECs, as compared to the total adipose-derived cell population. In some embodiments, the adipose-derived LEC and/or pre-LECs express an amount of, e.g., FLT-4, and/or CD45, and/or CD31, and/or CD34, and/or podoplanin, and/or LYVE-1, and/or Prox-1. Methods of making and using the foregoing compositions are also embodiments and in some aspects of the invention, the biological material, support, prosthetic, or medical device is provided separately from the cell population comprising adipose-derived LECs and/or pre-LECs (e.g., the biological material, support, prosthetic, or medical device is co-administered with said LECs and/or pre-LECs).

In some embodiments, the cell population that comprises LECs and/or pre-LECs is processed in a cell processing unit that operates in a closed system (see e.g., U.S. application Ser. No. 10/316,127 (U.S. Pub. No. 2003/0161816), entitled SYSTEMS AND METHODS FOR TREATING PATIENTS WITH PROCESSED LIPOASPIRATE CELLS, filed Dec. 9, 2002, and U.S. application Ser. No. 10/877,822 (U.S. Pat. App. Pub. No. 2005/0084961), entitled SYSTEMS AND METHODS FOR SEPARATING AND CONCENTRATING REGENERATIVE CELLS FROM TISSUE, filed Jun. 25, 2004). In more embodiments, the cell collection chamber of said cell processing unit is attached to a cell sorter such that the cell processing unit and cell sorter are within a closed system. Accordingly, a sample of cells or the entire cell population obtained from the cell processing unit can be transferred through a conduit, while maintaining a closed system, to the cell sorter, which then identifies and/or confirms the presence of said LECs and/or pre-LECs in the adipose-derived cell population and/or separates, isolates, and purifies said LECs and/or pre-LECs.

In more embodiments, the cell collection chamber of said cell processing unit is attached to a purification chamber via a conduit such that a closed system is maintained. The purification chamber contains a centrifuge loaded with tubes containing an LEC and/or pre-LEC selective gradient (e.g., ficoll-hypaque) such that once the population of cells obtained at the cell collection chamber is passed through the conduit, while maintaining a closed system, to the purification chamber, said cell population is layered on the gradient. Centrifugation is conducted and the portion of the gradient containing the purified LECs and/or pre-LECs is removed. The removed LECs and/or pre-LECs or a portion thereof can be cryopreserved and stored or analyzed for the presence or absence of a marker that confirms the presence of LECs and/or pre-LECs in the cell population by transferring a sample of said cells to a testing chamber, as detailed below. The removed purified LECs and/or pre-LECs can also be immediately introduced into a subject, or mixed with or co-administered to said subject with a biological material, support, prosthetic, or medical device.

In some embodiments, once an adipose-derived cell population suspected of containing LECs and/or pre-LECs has been obtained, refined, enriched, isolated, or purified it is desired that said cell population is analyzed or measured for the presence or absence of an LEC and/or pre-LEC marker, which identifies and/or confirms that the adipose derived cell population, in fact, comprises LECs and/or pre-LECs. In some embodiments, the marker used to identify the presence or absence of LECs and/or pre-LECs in an adipose-derived cell population is selected from the group consisting of, e.g., FLT-4, and/or CD45, and/or CD31, and/or CD34, and/or podoplanin, and/or LYVE-1, and/or Prox-1. Markers used to identify or confirm the presence or absence of LECs and/or pre-LECs in an adipose-derived cell population also include an RNA encoding one or more of the aforementioned proteins. The presence or absence of these markers can be identified using conventional techniques in immunology and molecular biology, including but not limited to, immunolabeling, immunohistochemistry, immunoprecipitation, immunoblots, PCR, Northern hybridization, gene chips, arrays and the like. A measurement of the presence or absence of a marker or markers that indicates that an adipose-derived cell population comprises LECs and/or pre-LECs provides one of skill in the art with an understanding of the nature of the preparation, the level of refinement, enrichment, isolation or purification, and whether the adipose tissue used to generate the cell preparation was a good source from which to prepare the compositions described herein.

In some embodiments, the measurement for the presence or absence of a marker that indicates that said cell population comprises LECs and/or pre-LECs is conducted within the cell processing unit while maintaining a closed system and in other embodiments, a sample of the processed cell population is removed from the cell processor and a measurement for the presence or absence of a marker that indicates that said cell population comprises LECs and/or pre-LECs is conducted outside of the closed system.

By some approaches, a portion of the adipose-derived cell population is transferred through a conduit from a cell collection chamber to a cell testing chamber that contains a buffer comprising a detectably labeled antibody (e.g., a fluorescently labeled antibody) that binds to, e.g., FLT-4, and/or CD45, and/or CD31, and/or CD34, and/or podoplanin, and/or LYVE-1, and/or Prox-1. such that a closed system is maintained. Once the labeled antibody has had sufficient time to interact with said cells, the buffer containing said antibody is removed through an outlet port leading to a waste container and a wash buffer is introduced into said testing chamber via an inlet port. A plurality of wash cycles can be employed. Attached to the cell testing chamber or incorporated therein is a detector, which detects the presence or absence of LECs and/or pre-LECs bound to said detectably labeled antibody in the washed sample.

Additionally, the methods of processing adipose tissue to obtain a cell population that comprises LECs and/or pre-LECs described herein can include cryopreservation such that, in some approaches, before or after the cells have been measured or analyzed for the presence or absence of a marker that indicates the cell population comprises LECs and/or pre-LECs, said cells can be cryopreserved and stored or banked for future use. Conventional approaches to cryopreservation and storage can be used such that the cell population that comprises LECs and/or pre-LECs can be removed from a cell processor and cryopreserved outside of the closed system and in some embodiments, a cryopreservation chamber including a cryopreservation liquid or gas (e.g., liquid nitrogen) is attached to said cell processor such that said cell population can be cryopreserved within a closed system.

Aspects of the invention also concern methods of tissue transplantation, wherein an adipose-derived cell population that comprises LECs and/or pre-LECs obtained by an approach described herein is provided to a subject (e.g., a mammal, a domestic animal, a horse, a rodent, a dog, cat, or human) in need of lymphatic cells, lymphatic vessels, or lymphatic tissue. Accordingly, said subject is identified as one in need of lymphatic cells, lymphatic vessels, or lymphatic tissue (e.g., by clinical evaluation by a technician, veterinarian, or physician) and said subject is provided an amount of an adipose-derived cell population that comprises LECs and/or pre-LECs (e.g., in an enriched, concentrated, isolated, refined, or purified form, as described herein) sufficient to induce formation of lymphatic vessels or lymphatic tissue. In some embodiments, the adipose-derived LEC and/or pre-LEC cells express an amount of FLT-4, CD45, CD31, CD34, podoplanin, LYVE-1, or Prox-1. In some embodiments, said identified subject has a disease or disorder selected from the group consisting of obesity; lymphatic vessel aplasia; edema; lymphatic vessel loss or damage due to surgical intervention; lymphatic vessel loss, damage or deficiency due to organ or tissue transplant; reduced lymphatic vessel function due to lymphatic vessel blockage; lymphatic vessel occlusion; elephantiasis; cardiovascular disease; heart disease; chronic granulomatous disease (CGD); lymphatic malignancies, including Hodgkin's Disease, non-Hodgkin's lymphoma, and Castleman Disease; non-lymphatic malignancies, including breast cancer, ovarian cancer, colorectal cancer, lung cancer, liver cancer, stomach cancers, pancreatic cancer, and CNS cancer.

In some methods of tissue transplantation, the adipose-derived cell population that comprises LECs and/or pre-LECs, which is provided to said subject, comprises greater than or equal to 0.5%-1%, 1-2%, 2%-4%, 4%-6%, 6%-8%, 8%-10%, 10%-20%, 20%-30%, 30%-40%, 40%-50%, 50%-60%, 60%-70%, 70%-80%, 80%-90%, or 90%-100% LECs and/or pre-LECs as compared to the total adipose-derived cell population. The adipose-derived cell population comprising LECs and/or pre-LECs used in these methods can be obtained by isolating the LECs and/or pre-LECs using a cell processing device, filtration, gradient sedimentation or a cell sorting device or a combination of any of these techniques. Further, the adipose derived cell population comprising LECs and/or pre-LECs used in these methods can be obtained by mixing or coadministering a refined, enriched, isolated, or purified cell population that comprises LECs and/or pre-LECs obtained in accordance with an embodiment described herein with a medical device, prosthetic, tissue, graft, support, unprocessed adipose tissue, collagen matrix, support, processed adipose tissue containing adipose-derived stem cells and/or progenitor cells, and cell populations already containing an enriched amount of LECs and/or pre-LECs.

By some approaches, said cell population that comprises LECs and/or pre-LECs obtained, refined, enriched, isolated, or purified in accordance with the teachings herein can be re-introduced into the same subject from which the adipose tissue used to obtain said population that comprises LECs and/or pre-LECs was removed (autologous transfer). By some approaches, the adipose-derived cell population that comprises LECs and/or pre-LECs is cryopreserved and subsequently thawed prior to re-introduction into the same subject from which said cells were removed. In more embodiments, an induction of lymphatic cell growth or differentiation or the production of lymphatic vessels or tissue is analyzed and/or measured in said subject that received said adipose-derived cell population that comprises LECs and/or pre-LECs. Such measurement or analysis can be conducted days (e.g., 1, 2, 3, 4, 5, 6, 7, 8, 9, 10, 11, 12, 13, or 14 days) or weeks (e.g., 1, 2, 3, 4, 5, 6, 7, 8, 9, 10, 11, 12, 13, or 14 weeks) after the subject receives said adipose-derived cell population that comprises LECs and/or pre-LECs and such measurement and analysis can be conducted by conventional techniques (e.g., clinical evaluation or biopsy).

Some embodiments described herein relate to methods of inducing expansion of lymph vessels, wherein a subject (e.g., a mammal, a domestic animal, a horse, a rodent, a dog, cat, or human) is identified as one in need of an expansion of lymph vessels and said identified subject is provided a population of adipose-derived LEC and/or pre-LEC cells that express an amount of, e.g., FLT-4, and/or CD45, and/or CD31, and/or CD34, and/or podoplanin, and/or LYVE-1, and/or Prox-1. Said subject can be identified as one in need of an induction of expansion of lymph vessels through the clinical evaluation of a technician, veterinarian, or physician. In some embodiments said identified subject suffers from a disease or disorder selected from the group consisting of obesity; lymphatic vessel aplasia; edema; lymphatic vessel loss or damage due to surgical intervention; lymphatic vessel loss, damage or deficiency due to organ or tissue transplant; reduced lymphatic vessel function due to lymphatic vessel blockage; lymphatic vessel occlusion; elephantiasis; cardiovascular disease; heart disease; chronic granulomatous disease (CGD); lymphatic malignancies, including Hodgkin's Disease, non-Hodgkin's lymphoma, and Castleman Disease; non-lymphatic malignancies, including breast cancer, ovarian cancer, colorectal cancer, lung cancer, liver cancer, stomach cancers, pancreatic cancer, and CNS cancer.

The population of cells that comprise adipose-derived LEC and/or pre-LEC cells, which express an amount of, e.g., FLT-4, and/or CD45, and/or CD31, and/or CD34, and/or podoplanin, and/or LYVE-1, and/or Prox-1 given to said identified subject can be refined, concentrated, enriched, isolated or purified (e.g., greater than or equal to 0.5%-1%, 1-2%, 2%-4%, 4%-6%, 6%-8%, 8%-10%, 10%-20%, 20%-30%, 30%-40%, 40%-50%, 50%-60%, 60%-70%, 70%-80%, 80%-90%, or 90%-100% LECs and/or pre-LECs). The adipose-derived cell population comprising LECs and/or pre-LECs used in these methods can be obtained by isolating the LECs and/or pre-LECs using a cell processing device, gradient sedimentation, filtration, or a cell sorting device or a combination of any of these techniques. Further, the adipose derived cell population used in these methods can be obtained by mixing or co-administering an enriched or isolated cell population that comprises LECs and/or pre-LECs obtained in accordance with an embodiment described herein with unprocessed adipose tissue, collagen matrix, support, processed adipose tissue containing adipose-derived stem cells and/or progenitor cells, and cell populations already containing an enriched amount of LECs and/or pre-LECs.

By some approaches, said methods of inducing expansion of lymph vessels require re-introduction of a cell population that comprises LECs and/or pre-LECs obtained, refined, enriched, concentrated, isolated, or purified in accordance with the teachings herein into the same subject from which the adipose tissue used to obtain said population that comprises LECs and/or pre-LECs was removed (autologous transfer). By some approaches, the adipose-derived cell population that comprises LECs and/or pre-LECs is cryopreserved and subsequently thawed prior to re-introduction into the same subject from which said cells were removed. In more embodiments, an induction of lymphatic cell growth or differentiation or the production of lymphatic vessels or tissue is analyzed or measured in said subject that received said adipose-derived cell population that comprises LECs and/or pre-LECs. Such measurement or analysis can be conducted days (e.g., 1, 2, 3, 4, 5, 6, 7, 8, 9, 10, 11, 12, 13, or 14 days) or weeks (e.g., 1, 2, 3, 4, 5, 6, 7, 8, 9, 10, 11, 12, 13, or 14 weeks) after the subject receives said adipose-derived cell population that comprises LECs and/or pre-LECs and such measurement and analysis can be conducted by conventional techniques (e.g., clinical evaluation or biopsy).

Aspects of the invention also concern methods of treating a patient having a disease or disorder involving the lymphatic system, said disease or disorder selected from the group consisting of obesity; lymphatic vessel aplasia; edema; lymphatic vessel loss or damage due to surgical intervention; lymphatic vessel loss, damage or deficiency due to organ or tissue transplant; reduced lymphatic vessel function due to lymphatic vessel blockage; lymphatic vessel occlusion; elephantiasis; cardiovascular disease; heart disease; chronic granulomatous disease (CGD); lymphatic malignancies, including Hodgkin's Disease, non-Hodgkin's lymphoma, and Castleman Disease; non-lymphatic malignancies, including breast cancer, ovarian cancer, colorectal cancer, lung cancer, liver cancer, stomach cancers, pancreatic cancer, and CNS cancer. By some approaches, said patient is identified as having one of the aforementioned diseases or disorders using clinical evaluation or diagnostic techniques and said patient is provided an effective amount of an adipose-derived cell population comprising refined, concentrated, isolated, enriched, or purified LECs and/or pre-LECs, obtained as described herein, preferably a population of adipose-derived LEC and/or pre-LEC cells that express an amount of FLT-4, a ligand for FLT-4, such as VEGF-C, CD45, CD31, CD34, podoplanin, LYVE-1, or Prox-1. In some embodiments, the improvement of the disease or disorder is measured, analyzed, or observed, and in other embodiments, the expansion or induction of lymphatic cell, vessel, or tissue growth is measured, analyzed, or observed. In more embodiments, said cells have been modified to deliver an agent with the ability to reduce progression of the disease.

In accordance with more embodiments, the adipose-derived cell population that comprises LECs and/or pre-LECs is provided to a subject as an anti-tumor agent delivery vehicle. For example, by engineering the cells to express one or more pro-drugs or pro-drug converting enzymes, agents suitable for treating malignant disease can be targeted to lymphatic vessels developing within the tumor. The adipose-derived cell population that comprises LECs and/or pre-LECs can be engineered to release one or more chemotherapeutic agents, for example. In some embodiments, especially when a lymphatic disorder results from the inability to express a factor involved in a lymphatic function, an adipose-derived cell population that comprises LECs and/or pre-LECs engineered to express and deliver that factor can be provided. In a related approach, an adipose-derived cell population that comprises LECs and/or pre-LECs from a patient having normal expression of that factor can be administered to the patient. U.S. Pat. App. Pub. No. 2006/0088532, titled "Lymphatic and Blood Endothelial Cell Genes," hereby expressly incorporated by reference, describes a number of genes that can be introduced into an adipose-derived cell population that comprises LECs and/or pre-LECs prepared as described herein and said transfected cells can be used to treat various lymphatic disorders Aspects of the present invention also concern methods of identifying a compound that modulates expansion or induction of adipose-derived LECs and/or pre-LECs, lymphatic vessels, or lymphatic tissue. By some approaches these methods require identification of a candidate compound, contacting said candidate compound with a population of adipose-derived LECs and/or pre-LECs, obtained as described herein, and measuring, analyzing, or observing, a difference in the expansion of said cells or the induction of lymphatic vessel or lymphatic tissue formation in the presence of the candidate compound, as compared to expansion of said cells or the induction of lymphatic vessel or lymphatic tissue formation in the absence of said candidate compound. Preferably, adipose-derived LECs and/or pre-LECs that express an amount of, e.g., FLT-4, and/or CD45, and/or CD31, and/or CD34, and/or podoplanin, and/or LYVE-1, and/or Prox-1 are used.

Accordingly, some embodiments provided herein relate to an isolated population of adipose-derived cells comprising lymphatic endothelial cells (LECs) and pre-LECs, wherein greater than 5%, greater than 10%, greater than 20%, greater than 30%, greater than 40%, or more of the isolated population of adipose-derived cells express FLT-4.

Some embodiments provided herein relate to an isolated population of adipose-derived cells comprising lymphatic endothelial cells (LECs) and pre-LECs, wherein greater than 5%, greater than 10%, or more of the population of adipose-derived cells also express CD45. Some embodiments, provided herein relate to an isolated population of adipose-derived cells comprising lymphatic endothelial cells (LECs)

and pre-LECs, wherein greater than 5%, greater than 10%, or more of the population of adipose-derived cells also express CD34.

Some embodiments provided herein relate to compositions comprising the isolated population of adipose-derived cells described herein, mixed with a biological material, an additive, a support, a medical device, a prosthetic, a cell differentiation factor, a growth promoter, an immunosuppressive agent, an anti-apoptosis agent, a biological tissue, a tissue graft, a portion of unprocessed adipose tissue, a collagen, a population of adipose-derived stem cells, a population of adipose-derived endothelial cells, or a population of adipose derived progenitor cells.

Some embodiments provided herein relate to a method of lymphatic endothelial cell (LEC) and pre-LEC transplantation in a mammal. A mammal in need of LECs or pre-LECs can be identified, and provided or administered an isolated population of adipose-derived cells comprising lymphatic endothelial cells (LECs) and pre-LECs, wherein greater than 5% of said population of adipose-derived cells express FLT-4. In some embodiments, the isolated population of adipose-derived cells can be mixed with a biological material, an additive, a medical device, a prosthetic, a cell differentiation factor, a growth promoter, an immunosuppressive agent, an anti-apoptosis agent, a biological tissue, a tissue graft, a portion of unprocessed adipose tissue, a collagen, a population of adipose-derived stem cells, a population of adipose-derived endothelial cells, or a population of adipose derived progenitor cells.

In some embodiments, the mammal can be assessed for one or more of the following: induction of lymphatic cell proliferation, lymphatic cell expansion, lymphatic vessel formation, and lymphatic tissue formation. In some embodiments, the cell transplantation accompanies a breast augmentation procedure. In some embodiments, the mammal identified has a disease or disorder selected from the group consisting of obesity, lymphatic vessel aplasia, edema, lymphatic vessel loss or damage due to surgical intervention, lymphatic vessel loss, damage or deficiency due to organ or tissue transplant, reduced lymphatic vessel function due to lymphatic vessel blockage, lymphatic vessel occlusion, elephantiasis, cardiovascular disease, heart disease, chronic granulomatous disease (CGD), a lymphatic malignancy, Hodgkin's Disease, a non-Hodgkin's lymphoma, Castleman Disease; a non-lymphatic malignancy, a breast cancer, an ovarian cancer, a colorectal cancer, a lung cancer, a liver cancer, a stomach cancer, a pancreatic cancer, and a cancer of the central nervous system.

Some embodiments relate to methods of inducing expansion of lymph vessels in a mammal. In some embodiments, a mammal in need of an expansion of lymph vessels is identified, and provided an isolated population of adipose-derived cells comprising lymphatic endothelial cells (LECs) and pre-LECs, wherein greater than 5% of said population of adipose-derived cells express FLT-4.

In some embodiments, the isolated population of adipose-derived cells can be mixed with a biological material, an additive, a medical device, a prosthetic, a cell differentiation factor, a growth promoter, an immunosuppressive agent, an anti-apoptosis agent, a biological tissue, a tissue graft, a portion of unprocessed adipose tissue, a collagen, a population of adipose-derived stem cells, a population of adipose-derived endothelial cells, or a population of adipose derived progenitor cells In some embodiments, the mammal can be assessed for one or more of the following: induction of lymphatic cell proliferation, lymphatic cell expansion, lymphatic vessel formation, and lymphatic tissue formation. In some embodiments, the providing or administration step accompanies a breast augmentation procedure.

In some embodiments, the mammal has a disease or disorder selected from the group consisting of obesity, lymphatic vessel aplasia, edema, lymphatic vessel loss or damage due to surgical intervention, lymphatic vessel loss, damage or deficiency due to organ or tissue transplant, reduced lymphatic vessel function due to lymphatic vessel blockage, lymphatic vessel occlusion, elephantiasis, cardiovascular disease, heart disease, chronic granulomatous disease (CGD), a lymphatic malignancy, Hodgkin's Disease, a non-Hodgkin's lymphoma, Castleman Disease; a non-lymphatic malignancy, a breast cancer, an ovarian cancer, a colorectal cancer, a lung cancer, a liver cancer, a stomach cancer, a pancreatic cancer, and a cancer of the central nervous system.

Some embodiments relate to methods of treating a disease or disorder selected from the group consisting of obesity, lymphatic vessel aplasia, edema, lymphatic vessel loss or damage due to surgical intervention, lymphatic vessel loss, damage or deficiency due to organ or tissue transplant, reduced lymphatic vessel function due to lymphatic vessel blockage, lymphatic vessel occlusion, elephantiasis, cardiovascular disease, heart disease, chronic granulomatous disease (CGD), a lymphatic malignancy, Hodgkin's Disease, a non-Hodgkin's lymphoma, Castleman Disease; a non-lymphatic malignancy, a breast cancer, an ovarian cancer, a colorectal cancer, a lung cancer, a liver cancer, a stomach cancer, a pancreatic cancer, and a cancer of the central nervous system. A mammal can be identified as having the disease or disorder, and provided or administered an isolated population of adipose-derived cells comprising lymphatic endothelial cells (LECs) and pre-LECs, wherein greater than 5% of said population of adipose-derived cells express FLT-4.

In some embodiments, the isolated population of adipose-derived cells can be mixed with a biological material, an additive, a medical device, a prosthetic, a cell differentiation factor, a growth promoter, an immunosuppressive agent, an anti-apoptosis agent, a biological tissue, a tissue graft, a portion of unprocessed adipose tissue, a collagen, a population of adipose-derived stem cells, a population of adipose-derived endothelial cells, or a population of adipose derived progenitor cells.

In some embodiments, the mammal can be assessed for one or more of the following: induction of lymphatic cell proliferation, lymphatic cell expansion, lymphatic vessel formation, and lymphatic tissue formation.

Some embodiments herein provide a method of processing adipose tissue to obtain an isolated population of adipose-derived cells that comprises lymphatic endothelial cell (LECs) and pre-LECs for transplantation in a mammal in need thereof. Adipose tissue from a mammal can be provided and processed by filtration or centrifugation or both to obtain an adipose-derived cell population that is substantially separated from collagen, adipocytes, and blood cells. The presence or absence of LECs or pre-LECs in the adipose-derived cell population can be determined or assessed, for example by determining the presence or absence of a marker for LECs or pre-LECs. For example, the presence or absence of markers such as FLT-4, CD45, CD31, CD34, Podoplanin, LYVE-1, and Prox-1 or an RNA encoding FLT-4, CD45, CD31, CD34, Podoplanin, LYVE-1, and Prox-1 or fragments thereof can be determined.

In some embodiments, the processing is performed in a closed system.

In some embodiments, the isolated population of adipose-derived cells that comprises lymphatic endothelial cell (LECs) and pre-LECs can be mixed said with a biological material, an additive, a support, a medical device, a prosthetic, a cell differentiation factor, a growth promoter, an immunosuppressive agent, an anti-apoptosis agent, a biological tissue, a tissue graft, a portion of unprocessed adipose tissue, a collagen, a population of adipose-derived stem cells, a population of adipose-derived endothelial cells, or a population of adipose derived progenitor cells.

In some embodiments, the cells, e.g., lymphatic endothelial cells (LECs) and pre-LECs, wherein greater than 5% of said population of adipose-derived cells express FLT-4, can be provided to a mammal in need of a transplantation of LECs or pre-LECs. In some embodiments, the isolated population of adipose-derived cells can be mixed with a biological material, an additive, a medical device, a prosthetic, a cell differentiation factor, a growth promoter, an immunosuppressive agent, an anti-apoptosis agent, a biological tissue, a tissue graft, a portion of unprocessed adipose tissue, a collagen, a population of adipose-derived stem cells, a population of adipose-derived endothelial cells, or a population of adipose derived progenitor cells.

In some embodiments, the mammal has a disease or disorder selected from the group consisting of obesity, lymphatic vessel aplasia, edema, lymphatic vessel loss or damage due to surgical intervention, lymphatic vessel loss, damage or deficiency due to organ or tissue transplant, reduced lymphatic vessel function due to lymphatic vessel blockage, lymphatic vessel occlusion, elephantiasis, cardiovascular disease, heart disease, chronic granulomatous disease (CGD), a lymphatic malignancy, Hodgkin's Disease, a non-Hodgkin's lymphoma, Castleman Disease; a non-lymphatic malignancy, a breast cancer, an ovarian cancer, a colorectal cancer, a lung cancer, a liver cancer, a stomach cancer, a pancreatic cancer, and a cancer of the central nervous system.

In some embodiments, the mammal that is provided the adipose derived cell population is the same mammal from which the adipose derived cell population was obtained.

Some embodiments disclosed herein relate to a method of delivering a chemotherapeutic agent to a mammal. A mammal in need of a chemotherapeutic agent can be identified and provided an isolated population of adipose-derived cells comprising lymphatic endothelial cells (LECs) and pre-LECs, wherein greater than 5% of said population of adipose-derived cells express FLT-4, to said identified mammal, wherein said isolated population of adipose derived cells expresses said chemotherapeutic agent.

In some embodiments, the isolated population of adipose-derived cells can be mixed with a biological material, an additive, a support, a medical device, a prosthetic, a cell differentiation factor, a growth promoter, an immunosuppressive agent, an anti-apoptosis agent, a biological tissue, a tissue graft, a portion of unprocessed adipose tissue, a collagen, a population of adipose-derived stem cells, a population of adipose-derived endothelial cells, or a population of adipose derived progenitor cells.

Some embodiments disclosed herein relate to a method of identifying a compound that modulates expansion or induction of cells or tissue selected from the group consisting of adipose-derived LECs, adipose-derived pre-LECs, lymphatic vessels, and lymphatic tissue. A candidate compound can be provided, and contacted with an isolated population of adipose-derived cells comprising lymphatic endothelial cells (LECs) and pre-LECs, wherein greater than 5% of said population of adipose-derived cells express FLT-4. The method can include the step of determining a difference in the expansion of the population of adipose-derived cells or the induction of lymphatic vessels or lymphatic tissue formation in the presence of the candidate compound, as compared to expansion of the population of adipose-derived cells or the induction of lymphatic vessel or lymphatic tissue formation in the absence of the candidate compound. Thus, a candidate compound can be identified as a compound that modulates expansion or induction of adipose-derived LECs or pre-LECs, lymphatic vessels, or lymphatic tissue when a difference in the expansion of the population of adipose-derived cells or the induction of lymphatic vessels or lymphatic tissue formation in the presence of the candidate compound, as compared to expansion of the population of adipose-derived cells or the induction of lymphatic vessel or lymphatic tissue formation in the absence of the candidate compound.

In some embodiments, the isolated population of adipose-derived cells can be mixed with a biological material, an additive, a medical device, a prosthetic, a cell differentiation factor, a growth promoter, an immunosuppressive agent, an anti-apoptosis agent, a biological tissue, a tissue graft, a portion of unprocessed adipose tissue, a collagen, a population of adipose-derived stem cells, a population of adipose-derived endothelial cells, or a population of adipose derived progenitor cells.

Other embodiments relate to the use of the isolated population of adipose-derived cells described herein to prepare a medicament for transplantation, such as a breast augmentation procedure. In some embodiments, the medicament can also include a biological material, an additive, a medical device, a prosthetic, a cell differentiation factor, a growth promoter, an immunosuppressive agent, an anti-apoptosis agent, a biological tissue, a tissue graft, a portion of unprocessed adipose tissue, a collagen, a population of adipose-derived stem cells, a population of adipose-derived endothelial cells, or a population of adipose-derived progenitor cells. In some embodiments Some embodiments relate to the use of the isolated population of adipose-derived cells described herein to prepare a medicament for inducing expansion of lymph vessels in a mammal. In some embodiments, the medicament can also include a biological material, an additive, a medical device, a prosthetic, a cell differentiation factor, a growth promoter, an immunosuppressive agent, an anti-apoptosis agent, a biological tissue, a tissue graft, a portion of unprocessed adipose tissue, a collagen, a population of adipose-derived stem cells, a population of adipose-derived endothelial cells, or a population of adipose-derived progenitor cells.

Some embodiments relate to the use of the isolated population of adipose-derived cells described herein to prepare a medicament for the treatment of a disease or disorder selected from the group consisting of: obesity, lymphatic vessel aplasia, edema, lymphatic vessel loss or damage due to surgical intervention, lymphatic vessel loss, damage or deficiency due to organ or tissue transplant, reduced lymphatic vessel function due to lymphatic vessel blockage, lymphatic vessel occlusion, elephantiasis, cardiovascular disease, heart disease, chronic granulomatous disease (CGD), a lymphatic malignancy, Hodgkin's Disease, a non-Hodgkin's lymphoma, Castleman Disease; a non-lymphatic malignancy, a breast cancer, an ovarian cancer, a colorectal cancer, a lung cancer, a liver cancer, a stomach cancer, a pancreatic cancer, and a cancer of the central nervous system. In some embodiments, the medicament can also include a biological material, an additive, a medical device, a prosthetic, a cell differentiation factor, a growth promoter, an immunosuppressive agent, an anti-apoptosis agent, a biological tissue, a tissue graft, a portion of unprocessed adipose tissue, a collagen, a population of adipose-derived stem cells, a population of adipose-derived endothelial cells, or a population of adipose-derived progenitor cells.

BRIEF DESCRIPTION OF THE DRAWINGS

FIGS. 14-1 and 14-2 are an illustration of an exemplary re-usable component for a system of the invention.

FIGS. 15A-1 and 15A-2 are an illustration of an exemplary device of the invention assembled using the disposable set of FIG. 13 and a re-usable component of FIG. 14.

A. Flow graph showing FLT-4$^+$ cells in Sample 503 plotted according to their expression of CD34 and CD31. Three subpopulations were identified based on their expression of CD34 and CD31 and designated Q1-Q3. The gates were drawn based in part on analysis of a negative control.

Figure 16:
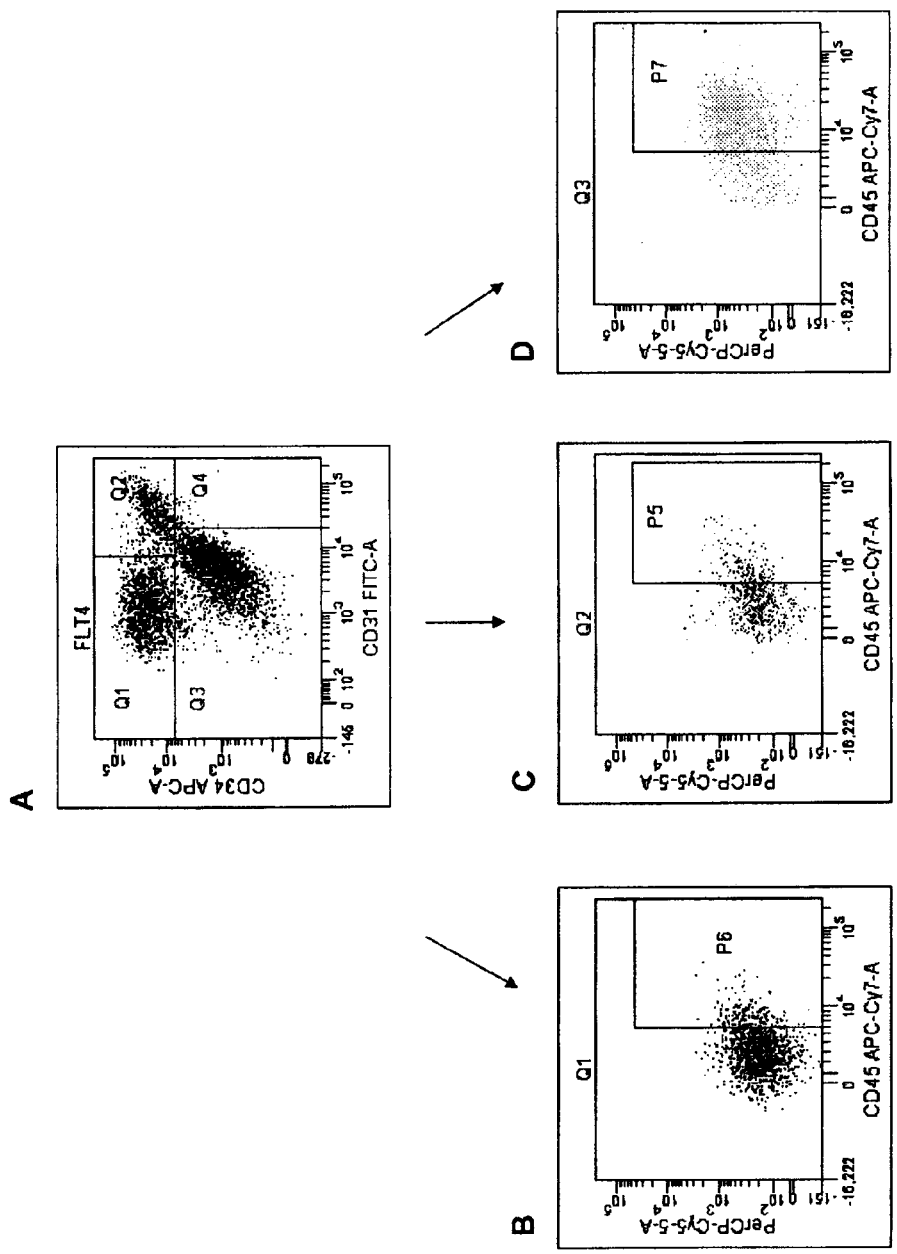
FIG. 16 Expression of CD45 by FLT-4$^+$ Subpopulations of Sample 503.

B. Graph showing cells in Q1 of FIG. 16A, additionally indicating expression of CD45 (P6).

C. Graph showing cells in Q2 of FIG. 16A, additionally indicating expression of CD45 (P5).

D. Graph showing cells in Q3 of FIG. 16A, additionally indicating expression of CD45 (P7).

The CD45 gates P5, P6 and P7 were drawn based on a CD45 gate drawn based in part on analysis of a negative control.

Figure 17:
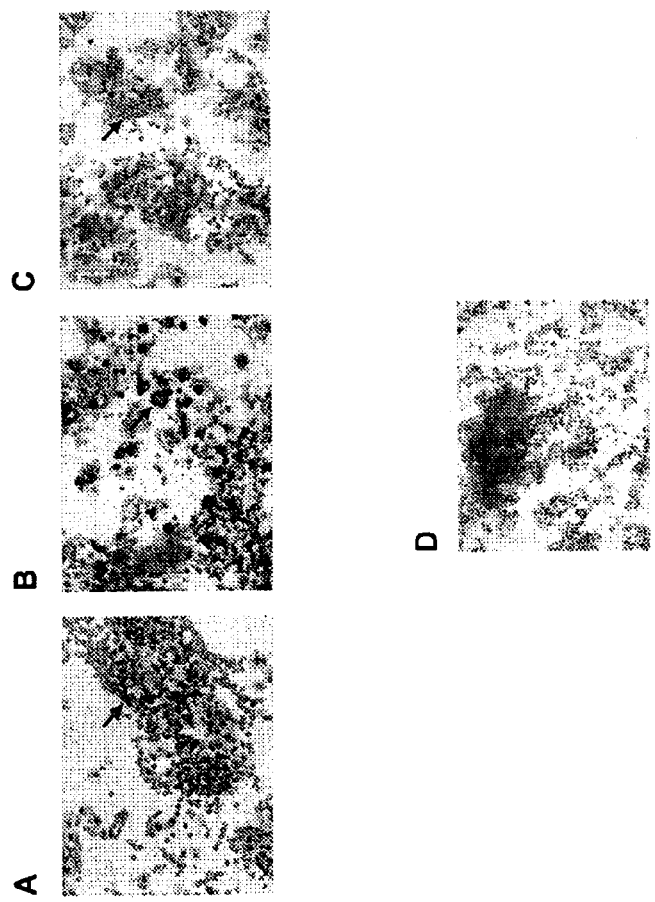

FIG. 17 Expression of Prox-1 and Lyve 1 by Fresh Adipose Tissue Digestates.

Arrows indicate examples of cells that stain with marker-specific antibody; in the original color images these cells appear as reddish brown. All samples were costained with hematoxylin.

A. Lyve-1 immunohistochemical staining. The stained cell indicated by the arrow point appears rounded in the original color image.

B. CD45 immunohistochemical staining. The positive cells stained with deep intensity, making them visible in the grayscale image.

C. Prox-1 immunohistochemical staining. The stained cell indicated by the arrow is elongated and extends from the arrow point downward and slightly toward the right side of the image.

D. Negative staining (hematoxylin only).

Figure 18:
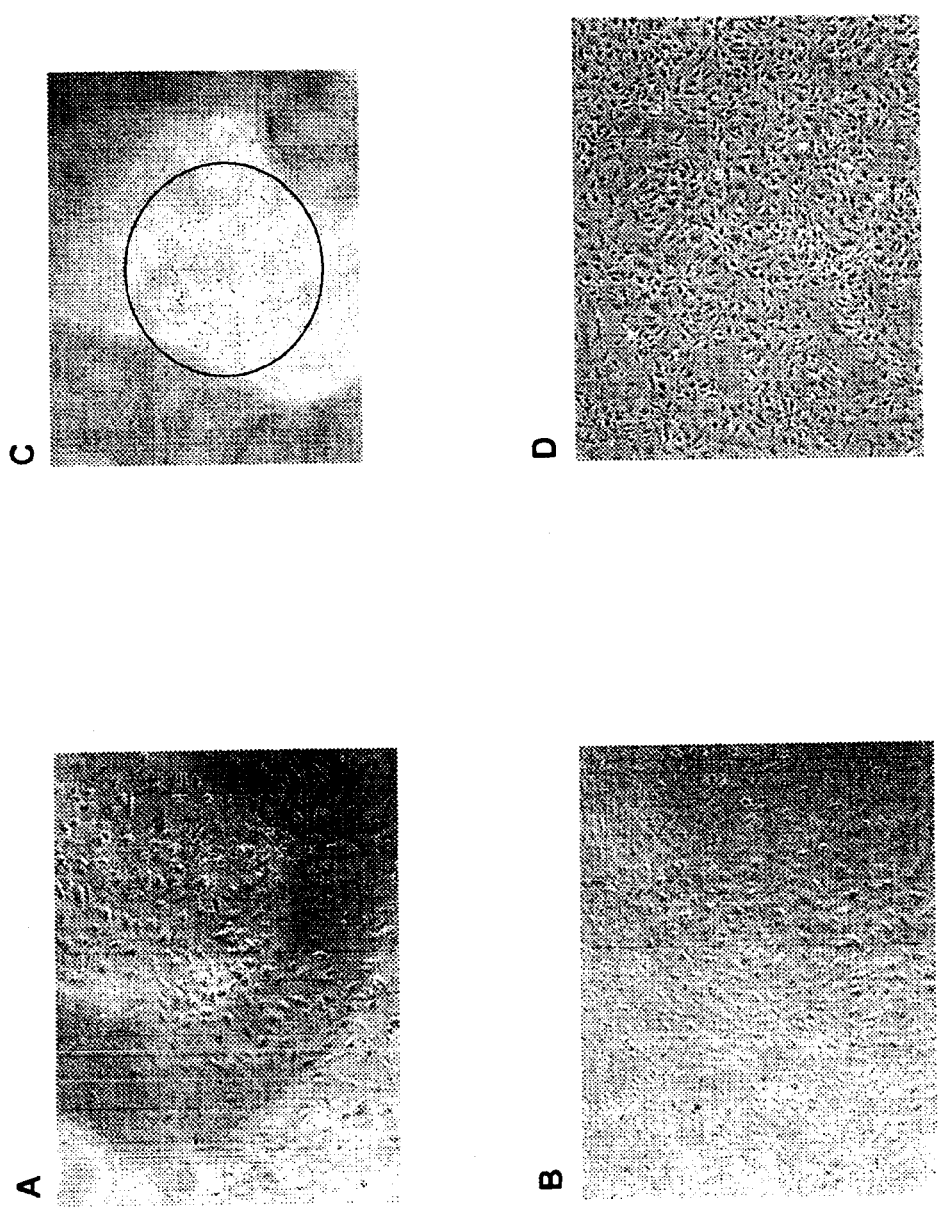

FIG. 18 Morphological Analysis of CFU-Endo Colonies.

The colonies presented cobblestone morphology typical of endothelial cells. Magnification was 40× for all four images.

A. A CFU-Endo colony first detected at 14 days of culture.
B. A CFU-Endo colony first detected at 28 days of culture.
C. A CFU-Endo colony first detected at 7 days of culture.
D. The colony of FIG. 18C at passage three.

Figure 1:
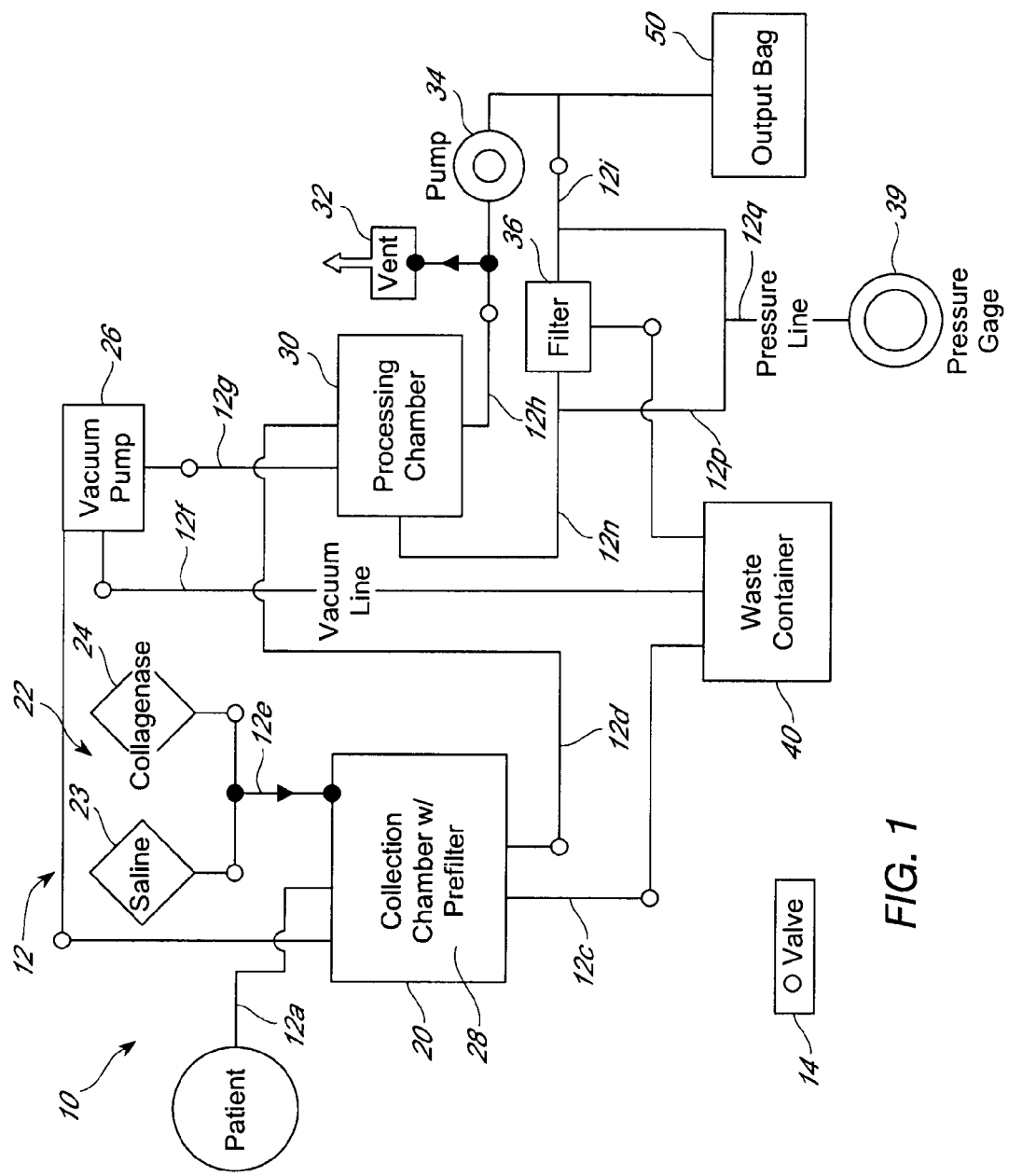
FIG. 1 is an illustration of a system for separating and concentrating regenerative cells from tissue which includes one filter assembly.
Figure 2:
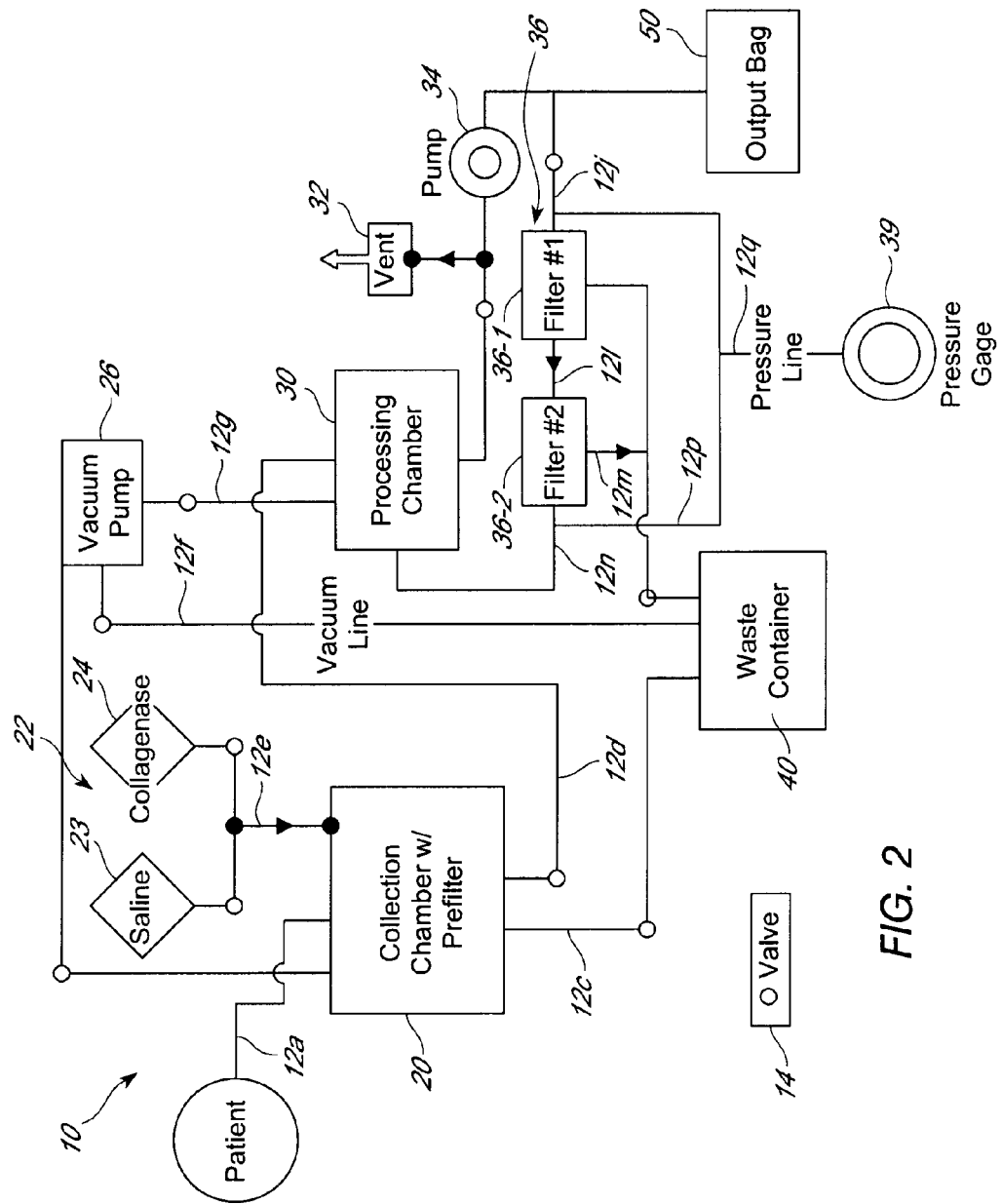
FIG. 2 is an illustration of a system similar to FIG. 1 having a plurality of filter assemblies in a serial configuration.
Figures 1, 19:
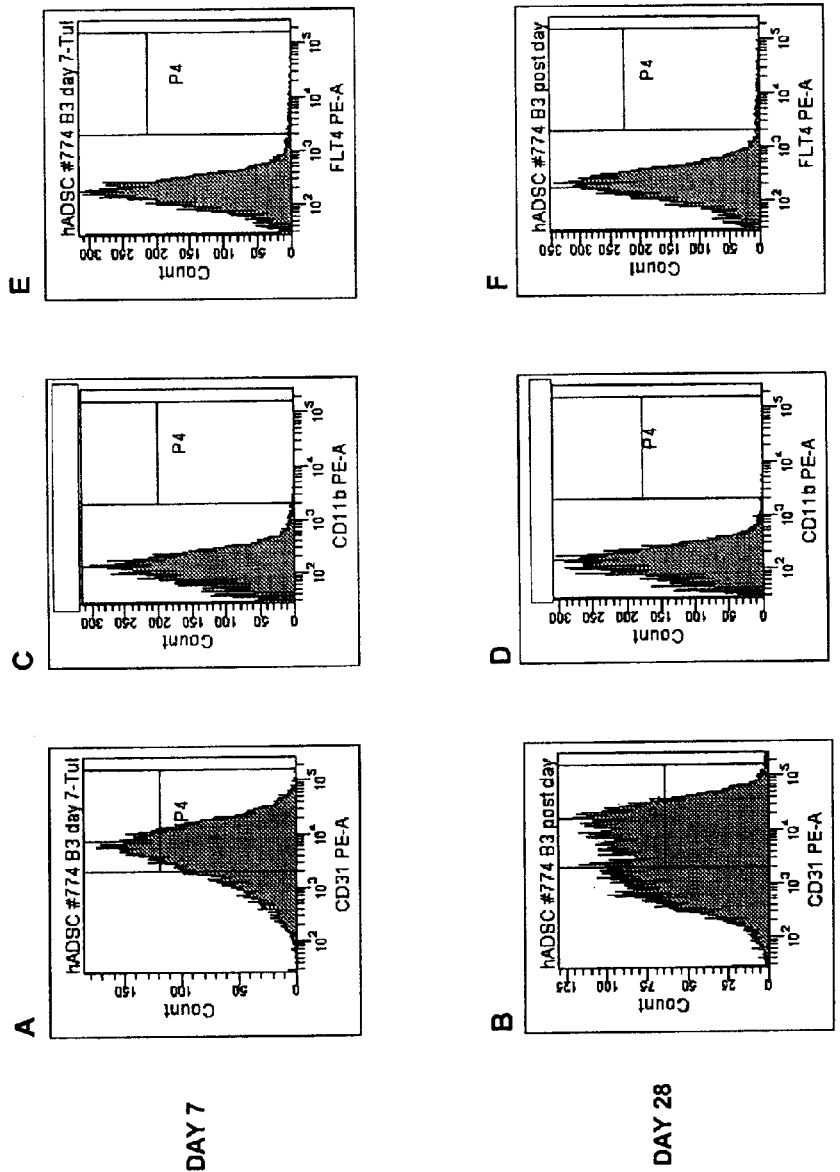
Figures 2, 19:
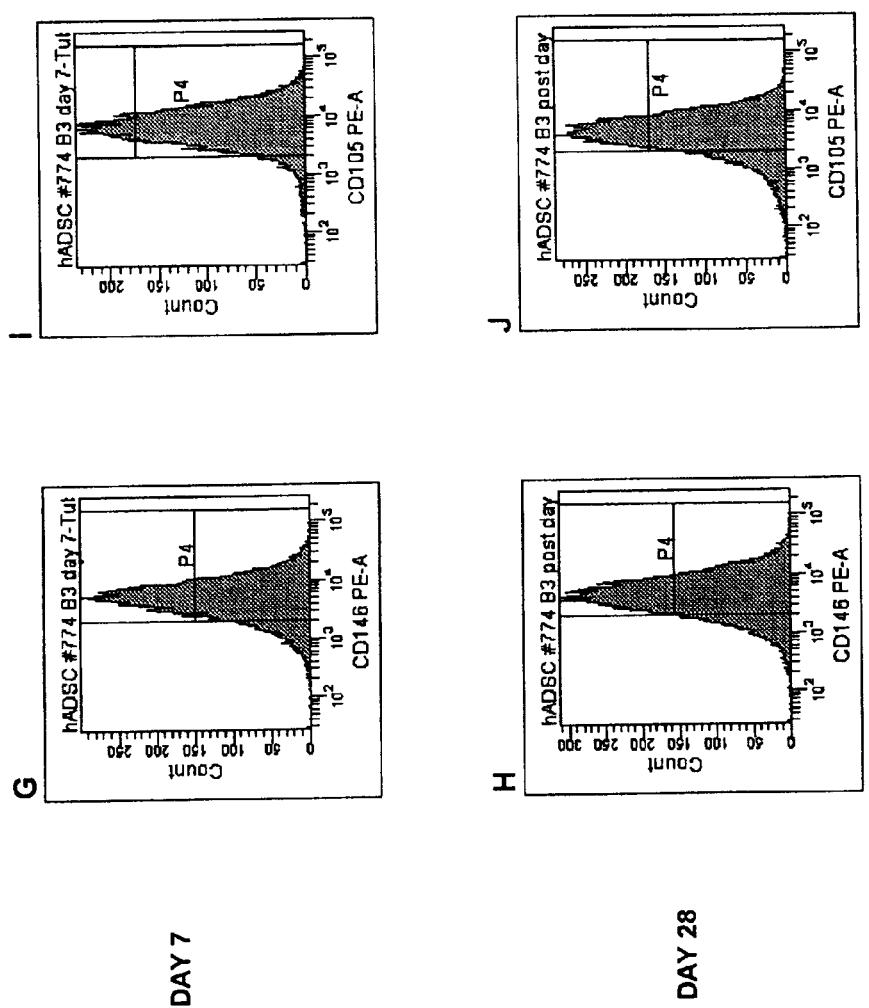

FIGS. 19-1 and 19-2. Cytofluorometric Analysis of Cells Expanded from CFU-Endo Colonies Detected at 7 and 28 Days of Culture. Cytofluorometric assays were performed on a FACSAria™ (Becton Dickinson) and analyses were performed using FACSDIVA™ software (Becton Dickinson). The presence or absence of each antigen was determined by comparison to the appropriate isotype or FMO (fluorescence minus one) control. Gate P4 was drawn based on the respective control and included no more that the 0.5% of the control population.

A. CD31 expression in cells from colony detected at 7 days of culture.
B. CD31 expression in cells from colony detected at 28 days of culture.
C. CD11b expression in cells from colony detected at 7 days of culture.
D. CD11b expression in cells from colony detected at 28 days of culture.
E. FLT-4 expression in cells from colony detected at 7 days of culture.
F. FLT-4 expression in cells from colony detected at 28 days of culture.
G. CD146 expression in cells from colony detected at 7 days of culture.
H. CD146 expression in cells from colony detected at 28 days of culture.

I. CD105 expression in cells from colony detected at 7 days of culture.

J. CD105 expression in cells from colony detected at 28 days of culture.

Figure 20:
Figure 20:
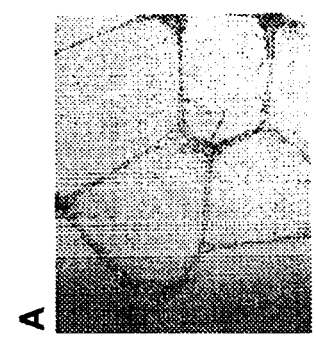

FIG. 20. Tube Formation by Cells CFU-Endo Colonies Detected at 7 and 28 Days of Culture.

A. Tube formation by cells from colony detected at 7 days of culture.

B. Tube formation by cells from colony detected at 28 days of culture.

DETAILED DESCRIPTION OF THE INVENTION

Aspects of the present invention stem from the discovery that adipose tissue is a rich source of lymphatic endothelial cells (LECs) and cells capable of differentiating into lymphatic endothelial cells (pre-LECs). Compositions and methods of obtaining, refining, concentrating, isolating, and purifying said LECs and/or pre-LECs, especially adipose derived cell populations that express an amount of, e.g., FLT-4, and/or CD45, and/or CD31, and/or CD34, and/or podoplanin, and/or LYVE-1, and/or Prox-1. are disclosed. In some embodiments, the cells are stored and/or cryopreserved and stored and, in other embodiments, the cells are immediately introduced into a subject in need thereof. Particularly preferred are methods of re-introducing LECs and/or pre-LECs obtained as described herein into the same subject from which the cells were obtained (e.g., autologous transfer) and some of these methods can be practiced using a cell processing unit that maintains a closed pathway. The LECs and/or pre-LECs made in accordance with the teachings herein can be used in methods of tissue transplantation, methods of inducing expansion of lymph vessels, and methods of treating diseases and disorders of the lymphatic system, with or without the presence of another biological material, cell population, support, prosthetic, or medical device. The LECs and/or pre-LECs made in accordance with the teachings herein can also be used to deliver therapeutic agents to the lymphatic system, or to identify compounds that modulate expansion, repair, or regeneration of the lymphatic system.

In some contexts, the term "adipose tissue" refers to a tissue containing multiple cell types including adipocytes and vascular cells. Adipose tissue includes lymphatic cells, including LECs, and pre-LECs, including LEC progenitor cells. Accordingly, adipose tissue refers to fat, including the connective tissue that stores the fat.

In some contexts, the term "unit of adipose tissue" refers to a discrete or measurable amount of adipose tissue. A unit of adipose tissue may be measured by determining the weight and/or volume of the unit. In reference to the disclosure herein, a unit of adipose tissue may refer to the entire amount of adipose tissue removed from a subject, or an amount that is less than the entire amount of adipose tissue removed from a subject. Thus, a unit of adipose tissue may be combined with another unit of adipose tissue to form a unit of adipose tissue that has a weight or volume that is the sum of the individual units.

In some contexts, the term "portion" refers to an amount of a material that is less than a whole. A minor portion refers to an amount that is less than 50%, and a major portion refers to an amount greater than 50%. Thus, a unit of adipose tissue that is less than the entire amount of adipose tissue removed from a subject is a portion of the removed adipose tissue.

In some contexts, the term "lymphatic endothelial cell" (also referred to as a LEC) refers to endothelial cells that line lymph vessels and that are related to, but distinct from, those endothelial cells that line blood vessels which are referred to as "blood endothelial cells" or "BECs."

In some contexts, the term "progenitor cell" refers to a cell that is unipotent, bipotent, or multipotent with the ability to differentiate into one or more cell types, which perform one or more specific functions and which have limited or no ability to self-renew. A "pre-LEC" is any cell on the pathway to differentiating into a LEC. A LEC progenitor cell is therefore one kind of pre-LEC. Some of the progenitor cells disclosed herein may be pluripotent. A specific form of progenitor cell referred to herein is the "lymphatic endothelial progenitor cell" or "LEC progenitor cell" or, more simply, "LEC progenitor." These terms are used to define a progenitor cell that has the ability to differentiate into a lymphatic endothelial cell. Some LEC progenitors may be bipotent or multipotent.

In some contexts, the term "cells capable of differentiating into lymphatic endothelial cells" refers to all cells that are not fully differentiated or mature lymphatic endothelial cells but that have the potential to differentiate or mature into such cells. Thus, the terms "pre-LEC" and "cells capable of differentiating into lymphatic endothelial cells" can be synonymous as used herein.

In some contexts, the term "adipose tissue-derived cells" refers to cells extracted from adipose tissue that has been processed to separate the active cellular component (e.g., the component containing LECs and pre-LECs) from the mature adipocytes and connective tissue. Separation may be partial or full. That is, the "adipose tissue-derived cells" may or may not contain some adipocytes and connective tissue. This fraction is referred to herein as "adipose tissue-derived cells," "adipose derived cells," or "ADC." Typically, ADC refers to the pellet of cells obtained by washing and separating the cells from the adipose tissue. The pellet is typically obtained by centrifuging a suspension of cells so that the cells aggregate at the bottom of a centrifuge container.

In some contexts, "lymphatic condition, disease or disorder" is intended to include all disorders characterized by insufficient or abnormal lymphatic function, including but not limited to, wounding, lymphangitis, obesity, primary or secondary lymphedema, congenital lymphatic insufficiency, lymphatic vessel aplasia, cardiovascular disease, heart disease, chronic granulomatous disease (CGD), lymphatic malignancies (including but not limited to Hodgkin's Disease, non-Hodgkin's lymphoma, and Castleman Disease), Milroy's disease, Meige's disease, elephantiasis, disorders of the lymphatic system arising secondarily to tissue damage, e.g., an infarction, injury from surgery, organ or tissue transplant, radiation therapy, chemotherapy, and occlusion or blockage (full or partial) of lymph vessels. Also included are non-lymphatic malignancies that nonetheless affect the lymphatic system, including, but not limited to, breast cancer, ovarian cancer, colorectal cancer, lung cancer, liver cancer, stomach cancers, pancreatic cancer, and CNS cancer. Insufficient or abnormal lymphatic function can result, e.g., from a defect in or deficiency of any component of the lymphatic system, including valves, capillaries, ducts, etc. Repairing or modulating expansion of any of these and any other lymphatic system components are contemplated using the methods described herein.

In some contexts, the term "lymphangiogenesis" refers to the process by which lymphatic vessels are expanded, generated, regenerated, or repaired.

In some contexts, the term "expansion," is used to encompass repair, regeneration, proliferation, differentiation, migration, survival, or any growth parameter of any lymphatic structure, including lymphatic endothelial cells and any structures composed in whole or in part of lymphatic endothelial cells. Cells that enhance expansion of the lymphatic system are cells that enhance expansion of the lymphatic system by any mechanism, either direct or indirect. "Modulation of expansion" is meant to encompass an influencing expansion in either a stimulatory or inhibitory manner, as is necessary for treating a disorder characterized by anomalous, abnormal, undesirable, or insufficient lymphatic function. It is understood that the various functions or components of the lymphatic system can become more or less active, and therefore can require different levels of modulation, at different times, even within the same patient. These requirements are affected, e.g., by disease type, disease stage, patient variation due to age, gender, health status, genetic factors, environmental factors, drugs and combinations of drugs administered currently or formerly to the patient, etc.

In some contexts, the term "treating" includes reducing or alleviating at least one adverse effect or symptom of a lymphatic system condition, disease or disorder, i.e., any disorder characterized by abnormal, anomalous or insufficient lymphatic function. Adverse effects or symptoms of lymphatic disorders are well-known in the art and include, but are not limited to, tissue edema, which can be disfiguring, disabling, and, on occasion, life threatening.

In some contexts, the terms "administering," "introducing" and "transplanting" are used interchangeably and refer to the placement of a cell population as described herein into a subject by a method or route, which results in localization of a cell population, as described herein at a desired site. The cell population, as described herein, can be administered by any appropriate route which results in delivery to a desired location in the subject where at least a portion of the cells remain viable. The period of viability of the cells after administration to a subject can be as short as a few hours, e.g., twenty-four hours, to a few days, to as long as several years.

In some contexts, the term "subject" includes warm-blooded animals, preferably mammals, including humans. In a preferred embodiment, the subject is a primate. In a more preferred embodiment, the subject is a human.

In some contexts, the term "immunosuppressive drug or agent" is intended to include pharmaceutical agents, which inhibit or interfere with normal immune function. Examples of immunosuppressive agents suitable with the methods disclosed herein include agents that inhibit T-cell/B-cell co-stimulation pathways, such as agents that interfere with the coupling of T-cells and B-cells via the CTLA4 and B7 pathways, as disclosed in U.S. Pub. No. 2002/0182211. A preferred immunosuppressive agent is cyclosporin A. Other examples include myophenylate mofetil, rapamicin, and anti-thymocyte globulin. In one embodiment, the immunosuppressive drug is administered with at least one other therapeutic agent. The immunosuppressive drug can be administered in a formulation, which is compatible with the route of administration and is administered to a subject at a dosage sufficient to achieve the desired therapeutic effect. In another embodiment, the immunosuppressive drug is administered transiently for a sufficient time to induce tolerance to a cell population described herein.

In some contexts, the phrase "pharmaceutically or pharmacologically acceptable" refers to molecular entities and compositions that do not produce adverse, allergic, or other untoward reactions when administered to an animal or a human. As used herein, "pharmaceutically acceptable carrier" includes any and all solvents, dispersion media, coatings, antibacterial and antifungal agents, isotonic and absorption delaying agents and the like. The use of such media and agents for pharmaceutically active substances is well known in the art. Except insofar as any conventional media or agent is incompatible with the vectors or cells of the present invention, its use in therapeutic compositions is contemplated. Supplementary active ingredients also can be incorporated into the compositions.

In some contexts, the term "unit dose" is used to refer to a discrete amount of a therapeutic composition dispersed in a suitable carrier. Those of ordinary skill in the art will readily optimize effective dosages and administration regimens as determined, e.g., by good medical practice and the characteristics of the individual patient. Further refinement of dosages can be made by those of ordinary skill in the art based, e.g., on data observed in animals or human clinical trials. The section below describes several approaches to obtain, refine, enrich, concentrate, isolate, or purify LECs and/or pre-LECs.

Methods of Making an Adipose-Derived Cell Population Comprising LECs and/or Pre-LECs In some embodiments, adipose-derived cells (ADCs) are processed to obtain a refined, enriched, concentrated, isolated, or purified population of LECs and/or pre-LECs using a cell processing unit, gradient sedimentation, filtration, or a combination of any one or more of these approaches. In general, adipose tissue is first removed from a subject (e.g., a mammal, a domestic animal, a rodent, a horse, a dog, cat, or human) then it is processed to obtain a cell population comprising LECs and/or pre-LECs. For allogeneic transplantation, an appropriate donor can be selected using methods known in the art, for example, methods used for selection of bone marrow donors. The volume of adipose tissue collected from the patient can vary from about 1 cc to about 2000 cc and in some embodiments up to about 3000 cc. The volume of tissue removed will vary from patient to patient and will depend on a number of factors including but not limited to: age, body habitus, coagulation profile, hemodynamic stability, severity of insufficiency or injury, co-morbidities, and physician preference.

The adipose tissue can be obtained by any method known to a person of ordinary skill in the art. For example, the adipose tissue may be removed from a subject by suction-assisted lipoplasty, ultrasound-assisted lipoplasty, or excisional lipectomy. In addition, the procedures may include a combination of such procedures, such as a combination of excisional lipectomy and suction-assisted lipoplasty. If the tissue or some fraction thereof is intended for re-implantation into a subject, the adipose tissue should be collected in a manner that preserves the viability of the cellular component and that minimizes the likelihood of contamination of the tissue with potentially infectious organisms, such as bacteria and/or viruses. Thus, the tissue extraction should be performed in a sterile or aseptic manner to minimize contamination. Suction-assisted lipoplasty may be desired to remove the adipose tissue from a patient as it provides a minimally invasive method of collecting tissue with minimal potential for stem cell damage that may be associated with other techniques, such as ultrasound-assisted lipoplasty.

The extraction of LECs from skin or tonsillar tissue yields a cell population that contains many different contaminating cell types. Separation of LECs from tonsil material has been reported to require cell culturing to remove non-adherent cells, followed by immunoselection and then cell culturing in selective medium to expand the number of LECs to significant numbers (Garrafa, et al., 2006). Similarly, extraction from dermal tissue is associated with contamination by nucleated blood cells and by numerous non-endothelial cell types (keratinocytes, fibroblasts, etc.) (Kriehuber, et al., 2001, incorporated herein by reference in its entirety).

Accordingly, adipose tissue provides a rich source of a population of cells that is easily enriched for LECs and pre-LECs as compared to tonsils or dermal tissue. Collection of adipose tissue is also more patient-friendly and is associated with lower morbidity than collection of a similar volume of skin or a much larger volume of tonsil. Adipose tissue also contains pre-LECs, which have been described as having the ability to integrate into lymphatic vessels (Kerjaschki, et al., 2006).

For suction-assisted lipoplastic procedures, adipose tissue is collected by insertion of a cannula into or near an adipose tissue depot present in the patient followed by aspiration of the adipose into a suction device. In some embodiments, a small cannula may be coupled to a syringe, and the adipose tissue may be aspirated using manual force. Using a syringe or other similar device may be desirable to harvest relatively moderate amounts of adipose tissue (e.g., from 0.1 ml to several hundred milliliters of adipose tissue). Procedures employing these relatively small devices require only local anesthesia. Larger volumes of adipose tissue (e.g., greater than several hundred milliliters) may require general anesthesia at the discretion of the donor and the person performing the collection procedure. When larger volumes of adipose tissue are to be removed, relatively larger cannulas and automated suction devices may be employed.

Excisional lipectomy procedures include, and are not limited to, procedures in which adipose tissue-containing tissues (e.g., skin) is removed as an incidental part of the procedure; that is, where the primary purpose of the surgery is the removal of tissue (e.g., skin in bariatric or cosmetic surgery) and in which adipose tissue is removed along with the tissue of primary interest. Subcutaneous adipose tissue may also be extracted by excisional lipectomy in which the adipose tissue is excised from the subcutaneous space without concomitant removal of skin.

The amount of tissue collected can depend on a number of variables including, but not limited to, the body mass index of the donor, the availability of accessible adipose tissue harvest sites, concomitant and pre-existing medications and conditions (such as anticoagulant therapy), and the clinical purpose for which the tissue is being collected. Experience with transplant of hematopoietic stem cells (bone marrow or umbilical cord blood-derived stem cells used to regenerate the recipient's blood cell-forming capacity) shows that engraftment is cell dose-dependent with threshold effects (Smith, et al., 1995; Barker, et al., 2001, both incorporated herein by reference in their entirety). Thus, it is possible that the general principle that "more is better" will be applied within the limits set by other variables and that where feasible the harvest will collect as much tissue as possible.

The adipose tissue that is removed from a patient is then collected into a device (e.g., cell processing unit, centrifuge, or filtration unit) for further processing so as to remove collagen, adipocytes, blood, and saline, thereby obtaining an adipose-derived cell population comprising LECs and/or pre-LECs. Preferably the population of adipose derived cells containing LECs and/or pre-LECs is free from contaminating collagen, adipocytes, blood, and saline. The major contaminating cells in adipose tissue (adipocytes) have low density and are easily removed by flotation.

Adipose tissue processing to obtain a refined, concentrated, and isolated population of adipose-derived LECs and/or pre-LECs and modifications thereto are preferably performed using methods described, for example, in U.S. application Ser. No. 10/316,127 (U.S. Pat. App. Pub. No. 2003/0161816), entitled SYSTEMS AND METHODS FOR TREATING PATIENTS WITH PROCESSED LIPOASPIRATE CELLS, filed Dec. 9, 2002, and U.S. application Ser. No. 10/877,822 (U.S. Pat. App. Pub. No. 2005/0084961), entitled SYSTEMS AND METHODS FOR SEPARATING AND CONCENTRATING REGENERATIVE CELLS FROM TISSUE, filed Jun. 25, 2004; U.S. application Ser. No. 10/242,094, entitled PRESERVATION OF NON EMBRYONIC CELLS FROM NON HEMATOPOIETIC TISSUES, filed Sep. 12, 2002, which claims the benefit of U.S. App. Ser. No. 60/322,070 filed Sep. 14, 2001; U.S. application Ser. No. 10/884,638, entitled SYSTEMS AND METHODS FOR ISOLATING AND USING CLINICALLY SAFE ADIPOSE DERIVED REGENERATIVE CELLS, filed on Jul. 2, 2004; U.S. Pat. App. Pub. No. 2006/0025338, entitled "Compositions and Methods for Treatment of Lymphatic and Venous Vessel Arterialization;" U.S. Pat. No. 6,316,247; and U.S. Pat. No. 5,372,945, all of which are hereby expressly incorporated by reference in their entireties. The applications above disclose the processing of adipose-derived cells in a system that is configured to maintain a closed, sterile fluid/tissue pathway. This can be achieved by use of a pre-assembled, linked set of closed, sterile containers and tubing allowing for transfer of tissue and fluid elements within a closed pathway. This processing set can be linked to a series of processing reagents (e.g., saline, enzymes, etc.) inserted into a device, which can control the addition of reagents, temperature, and timing of processing thus relieving operators of the need to manually manage the process. In a preferred embodiment, the entire procedure from tissue extraction through processing and placement into the recipient is performed in the same facility, indeed, even within the same room, of the patient undergoing the procedure.

For many applications, preparation of the active cell population requires depletion of the mature fat-laden adipocyte component of adipose tissue. This can be achieved by a series of washing and disaggregation steps in which the tissue is first rinsed to reduce the presence of free lipids (released from ruptured adipocytes) and peripheral blood elements (released from blood vessels severed during tissue harvest), and then disaggregated to free intact adipocytes and other cell populations from the connective tissue matrix. In certain embodiments, the entire adipocyte component, or non-LEC/pre-LEC component, is separated from the LEC/pre-LEC component of the adipose tissue. In other embodiments, only a portion or portions of the non-LEC/pre-LEC component is separated from the LEC/pre-LECs. Thus, in some embodiments, LEC/pre-LECs are provided with BECs, BEC progenitors (EPCs), and adipose tissue-derived stem cells, adipose tissue-derived stromal cells, and other cellular elements.

Rinsing is an optional but preferred step, wherein the tissue is mixed with a solution to wash away free lipid and single cell components, such as those components in blood, leaving behind intact adipose tissue fragments. In one embodiment, the adipose tissue that is removed from the patient is mixed with isotonic saline or other physiologic solution(s), e.g., Plasmalyte® of Baxter Inc. or Normosol® of Abbott Labs. Intact adipose tissue fragments can be separated from the free lipid and cells by any means known to persons of ordinary skill in the art including, but not limited to, filtration, decantation, sedimentation, or centrifugation. In some embodiments, the adipose tissue is separated from non-adipose tissue by employing a filter disposed within a tissue collection container, as discussed herein. In other embodiments, the adipose tissue is separated from non-adipose tissue using a tissue collection container that utilizes decantation, sedimentation, and/or centrifugation techniques to separate the materials.

The intact tissue fragments are then disaggregated using any conventional techniques or methods, including mechanical force (mincing or shear forces), ultrasonic or other physical energy, lasers, microwaves, enzymatic digestion with single or combinatorial proteolytic enzymes, such as collagenase, trypsin, lipase, liberase H1, nucleases, or members of the Blendzyme family as disclosed in U.S. Pat. No. 5,952,215, "Enzyme composition for tissue dissociation," expressly incorporated herein by reference in its entirety, and pepsin, or a combination of mechanical and enzymatic methods. For example, the cellular component of the intact tissue fragments may be disaggregated by methods using collagenase-mediated dissociation of adipose tissue, similar to the methods for collecting microvascular endothelial cells in adipose tissue, as disclosed in U.S. Pat. No. 5,372,945, expressly incorporated herein by reference in its entirety. Additional methods using collagenase that may be used are disclosed in, e.g., U.S. Pat. No. 5,830,741, "Composition for tissue dissociation containing collagenase I and II from clostridium histolyticum and a neutral protease" and by Williams, et al., 1995, "Collagenase lot selection and purification for adipose tissue digestion," Cell Transplant 4(3):281-9, both expressly incorporated herein by reference in their entirety. Similarly, a neutral protease may be used instead of collagenase, as disclosed in Twentyman, et al. (Twentyman, et al., 1980, "Use of bacterial neutral protease for disaggregation of mouse tumours and multicellular tumor spheroids," Cancer Lett. 9(3):225-8, expressly incorporated herein by reference in its entirety). Furthermore, the methods described herein may employ a combination of enzymes, such as a combination of collagenase and trypsin or a combination of an enzyme, such as trypsin, and mechanical dissociation.

Adipose tissue-derived cells may then be obtained from the disaggregated tissue fragments by reducing the number of mature adipocytes. A suspension of the disaggregated adipose tissue and the liquid in which the adipose tissue was disaggregated is then passed to another container, such as a cell collection container. The suspension may flow through one or more conduits to the cell collection container by using a pump, such as a peristaltic pump, that withdraws the suspension from the tissue collection container and urges it to the cell collection container. Other embodiments may employ the use of gravity or a vacuum while maintaining a closed system. Separation of the cells in the suspension may be achieved by buoyant density sedimentation, centrifugation, elutriation, filtration, differential adherence to and elution from solid phase moieties, antibody-mediated selection, differences in electrical charge, immunomagnetic beads, fluorescence activated cell sorting (FACS), or other means. Examples of these various techniques and devices for performing the techniques may be found in U.S. Pat. Nos. 6,277,060; 6,221,315; 6,043,066; 6,451,207; 5,641,622; and 6,251,295, all incorporated herein by reference in their entirety. Many of these devices can be incorporated within the cell processing unit, while maintaining a closed system.

In some embodiments, the cells in the suspension are separated from the acellular component of the suspension using a spinning membrane filter. In other embodiments, the cells in the suspension are separated from the acellular component using a centrifuge. In one such exemplary embodiment, the cell collection container may be a flexible bag that is structured to be placed in a centrifuge (e.g., manually or by robotics). In other embodiments, a flexible bag is not used. After centrifugation, the cellular component containing LECs and/or pre-LECs forms a pellet, which may then be resuspended with a buffered solution so that the cells can be passed through one or more conduits to a mixing container, as discussed herein. The resuspension fluids may be provided by any suitable means. For example, a buffer may be injected into a port on the cell collection container, or the cell collection container may include a reserve of buffer that can be mixed with the pellet of cells by rupturing the reserve. When a spinning membrane filter is used, resuspension is optional since the cells remain in a volume of liquid after the separation procedure.

Although some embodiments described herein are directed to methods of fully disaggregating the adipose tissue to separate the active cells from the mature adipocytes and connective tissue, additional embodiments are directed to methods in which the adipose tissue is only partially disaggregated. For example, partial disaggregation may be performed with one or more enzymes, which are removed from at least a part of the adipose tissue early relative to an amount of time that the enzyme would otherwise be left thereon to fully disaggregate the tissue. Such a process may require less processing time and would generate fragments of lymphatic vessels within which multiple LECs remain in partial or full contact.

In some embodiments, the tissue is washed with sterile buffered isotonic saline and incubated with collagenase at a collagenase concentration, a temperature, and for a period of time sufficient to provide adequate disaggregation. In a preferred embodiment, the collagenase enzyme used will be approved for human use by the relevant authority (e.g., the U.S. Food and Drug Administration). Suitable collagenase preparations include recombinant and non-recombinant collagenase. Non-recombinant collagenase may be obtained from F. Hoffmann-La Roche Ltd., Indianapolis, Ind. and/or Advance Biofactures Corp., Lynbrook, N.Y. Recombinant collagenase may also be obtained as disclosed in U.S. Pat. No. 6,475,764.

In one embodiment, solutions contain collagenase at concentrations of about 10 µg/ml to about 50 µg/ml (e.g., 10 µg/ml, 20 µg/ml, 30 µg/ml, 40 µg/ml, or 50 µg/ml) and are incubated at from about 30° C. to about 38° C. for from about 20 minutes to about 60 minutes. These parameters will vary according to the source of the collagenase enzyme, optimized by empirical studies, in order to confirm that the system is effective at extracting the desired cell populations in an appropriate time frame. A particular preferred concentration, time and temperature is 20 µg/ml collagenase (mixed with the neutral protease dispase; Blendzyme 1, Roche) and incubated for 45 minutes at about 37° C. An alternative preferred embodiment applies 0.5 units/mL collagenase (mixed with the neutral protease thermolysin; Blendzyme 3). In a particularly preferred embodiment the collagenase enzyme used is material approved for human use by the relevant authority (e.g., the U.S. Food and Drug Administration). The collagenase used should be free of microorganisms and contaminants, such as endotoxin.

Following disaggregation the active cell population can be washed/rinsed to remove additives and/or by-products of the disaggregation process (e.g., collagenase and newly-released free lipid). The active cell population can then be concentrated by centrifugation or other methods known to persons of ordinary skill in the art, as discussed above. These post-processing wash/concentration steps may be applied separately or simultaneously. In one embodiment, the cells are concentrated and the collagenase removed by passing the cell population through a continuous flow spinning membrane system or the like, such as, for example, the system disclosed in U.S. Pat. Nos. 5,034,135 and 5,234,608, all incorporated herein by reference in their entirety.

In addition to the foregoing, there are many known post-wash methods that may be applied for further purifying the adipose-derived cell population that comprises LECs and/or pre-LECs. These include both positive selection (selecting the target cells), negative selection (selective removal of unwanted cells), or combinations thereof. In addition to separation by flow cytometry as described herein and in the literature, cells can be separated based on a number of different parameters, including, but not limited to, charge or size (e.g., by dielectrophoresis or various centrifugation methods, etc.).

Many other conformations of the staged mechanisms used for cell processing will be apparent to one skilled in the art. For example, mixing of tissue and saline during washing and disaggregation can occur by agitation or by fluid recirculation. Cell washing may be mediated by a continuous flow mechanism such as the spinning membrane approach, differential adherence, differential centrifugation (including, but not limited to differential sedimentation, velocity, or gradient separation), or by a combination of means. Similarly, additional components allow further manipulation of cells, including addition of growth factors or other biological response modifiers, and mixing of cells with natural or synthetic components intended for implant with the cells into the recipient.

Post-processing manipulation may also include cell culture or further cell purification (Kriehuber, et al., 2001; Garrafa, et al., 2006). In some embodiments, once the adipose-derived cell population that comprises LECs and/or pre-LECs is obtained, it is further refined, concentrated, enriched, isolated, or purified using a cell sorting device and/or gradient sedimentation. Mechanisms for performing these functions may be integrated within the described devices or may be incorporated in separate devices.

In a preferred embodiment of the invention, the tissue removal system and processing set would be present in the vicinity of the patient receiving the treatment, such as the operating room or out-patient procedure room (effectively at the patient's bedside). This allows rapid, efficient tissue harvest and processing, and decreases the opportunity for specimen handling/labeling error, thereby allowing for performance of the entire process in the course of a single surgical procedure.

As described in U.S. application Ser. No. 10/884,638, entitled SYSTEMS AND METHODS FOR ISOLATING AND USING CLINICALLY SAFE ADIPOSE DERIVED REGENERATIVE CELLS, filed on Jul. 2, 2004, one or more additives may be added to the cells during and/or after processing. Some examples of additives include agents that optimize washing and disaggregation, additives that enhance the viability of the active cell population during processing, anti-microbial agents (e.g., antibiotics), additives that lyse adipocytes and/or red blood cells, or additives that enrich for cell populations of interest (by differential adherence to solid phase moieties or to otherwise promote the substantial reduction or enrichment of cell populations). Other examples of additives that potentially enhance development of the lymphatic vasculature are discussed in U.S. Pat. App. Pub. No. 2006/0025338, "Compositions and Methods for Treatment of Lymphatic and Venous Vessel Arterialization," hereby expressly incorporated by reference in its entirety.

The LECs and pre-LECs obtained as described herein can be cultured according to approaches known in the art, and the cultured cells can be used in several of the embodied methods. For example, LECs can be cultured on collagen-coated dishes or 3D collagen gel cultures in endothelial cell basal medium in the presence of low or high fetal bovine serum or similar product, as described in Ng, et al., November 2004, "Interstitial flow differentially stimulates blood and lymphatic endothelial cell morphogenesis in vitro," Microvasc Res. 68(3):258-64, incorporated herein by reference. Alternatively, LECs can be cultured on other extracellular matrix protein-coated dishes. Examples of extracellular matrix proteins that may be used include, but are not limited to, fibronectin, laminin, vitronectin, and collagen IV. Gelatin or any other compound or support, which similarly promotes adhesion of endothelial cells into culture vessels may be used to culture LECs, as well.

Examples of basal culture medium that can be used to culture LECs and pre-LECs in vitro include, but are not limited to, EGM, RPMI, M199, MCDB131, DMEM, EMEM, McCoy's 5A, Iscove's medium, modified Iscove's medium or any other medium known in the art to support the growth of blood endothelial cells. Examples of supplemental factors or compounds that can be added to the basal culture medium that could be used to culture LECs and pre-LECs include, but are not limited to, ascorbic acid, heparin, endothelial cell growth factor, endothelial growth supplement, glutamine, HEPES, Nu serum, fetal bovine serum, human serum, equine serum, plasma-derived horse serum, iron-supplemented calf serum, penicillin, streptomycin, amphotericin B, basic and acidic fibroblast growth factors, insulin-growth factor, astrocyte conditioned medium, fibroblast or fibroblast-like cell conditioned medium, sodium hydrogencarbonate, epidermal growth factor, bovine pituitary extract, magnesium sulphate, isobutylmethylxanthine, hydrocortisone, dexamethasone, dibutyril cyclic AMP, insulin, transferrin, sodium selenite, oestradiol, progesterone, growth hormone, angiogenin, angiopoietin-1, Del-1, follistatin, granulocyte colony-stimulating factor (G-CSF), erythropoietin, hepatocyte growth factor (HGF)/scatter factor (SF), leptin, midkine, placental growth factor, platelet-derived endothelial cell growth factor (PD-ECGF), platelet-derived growth factor-BB (PDGF-BB), pleiotrophin (PTN), progranulin, proliferin, transforming growth factor-alpha (TGF-alpha), transforming growth factor-beta (TGF-beta), tumor necrosis factor-alpha (TNF-alpha), vascular endothelial growth factor (VEGF)/vascular permeability factor (VPF), interleukin-3 (IL-3), interleukin 7 (IL-7), interleukin-8 (IL-8), ephrins, matrix metalloproteinases (such as MMP2 and MMP9), or any other compound known in the art to promote survival, proliferation or differentiation of endothelial cells.

Further processing of the cells may also include: cell expansion (of one or more regenerative cell types) and cell maintenance (including cell sheet rinsing and media changing); sub-culturing; cell seeding; transient transfection (including seeding of transfected cells from bulk supply); harvesting (including enzymatic, non-enzymatic harvesting and harvesting by mechanical scraping); measuring cell viability; cell plating (e.g., on microtiter plates, including picking cells from individual wells for expansion, expansion of cells into fresh wells); high throughput screening; cell therapy applications; gene therapy applications; tissue engineering applications; therapeutic protein applications; viral vaccine applications; harvest of regenerative cells or supernatant for banking or screening, measurement of cell growth, lysis, inoculation, infection or induction; generation of cell lines (including hybridoma cells); culture of cells for permeability studies; cells for RNAi and viral resistance studies; cells for knock-out and transgenic animal studies; affinity purification studies; structural biology applications; assay development and protein engineering applications.

In general, a system useful for isolating a cell population comprising LECs and/or pre-LECs comprises a) a tissue collection container including i) a tissue collecting inlet port structured to receive adipose tissue removed from a subject, and ii) a filter disposed within the tissue collection container, which is configured to retain a cell population comprising LECs and/or pre-LECs from said subject and to pass adipocytes, blood, and saline; b) a mixing container or cell processing chamber coupled to the tissue collection container by a conduit such that a closed pathway is maintained, wherein said mixing container receives said cell population comprising LECs and/or pre-LECs and said mixing container comprises an additive port for introducing at least one additive to said cell population comprising LECs and/or pre-LECs; and an outlet port configured to allow removal of said cell population comprising LECs and/or pre-LECs from the mixing container or cell processing chamber for administration to a patient. In some embodiments, said mixing container or cell processing container further comprises a cell concentration device such as a spinning membrane filter and/or a centrifuge. Aspects of the invention also include a cell sorter, which is attached to said mixing chamber or cell processing chamber by a conduit and is configured to receive cells from said mixing chamber or cell processing chamber, while maintaining a closed pathway. Aspects of the embodiments above may also include a centrifuge attached to said mixing chamber or cell processing chamber by a conduit and configured to receive said cell population comprising LECs and/or pre-LECs, while maintaining a closed pathway, wherein said centrifuge comprises a gradient suitable for further separation and purification of said LECs and/or pre-LECs (e.g., ficoll-hypaque). Said centrifuge containing said gradient, which is configured to receive said cell population comprising LECs and/or pre-LECs may also be contained within said mixing container or cell processing chamber.

Exemplary cell processing systems or devices are described with reference to the figures. Referring now to the Figures, a system 10 of the present invention is generally comprised of one or more of a tissue collection chamber 20, a processing chamber 30, a waste chamber 40, an output chamber 50 and a sample chamber 60. The various chambers are coupled together via one or more conduits 12 such that fluids containing biological material may pass from one chamber to another while maintaining a closed, sterile fluid/tissue pathway. The conduits may comprise rigid or flexible bodies referred to interchangeably herein as lumens and tubing, respectively. In certain embodiments, the conduits are in the form of flexible tubing, such as polyethylene tubing conventionally used in clinical settings, silicone or any other material known in the art. The conduits 12 can vary in size depending on whether passage of fluid or tissue is desired. The conduits 12 may also vary in size depending on the amount of tissue or fluid that is cycled through the system. For example, for the passage of fluid, the conduits may have a diameter ranging from about 0.060 to about 0.750 inches and for the passage of tissue, the conduits may have a diameter ranging from 0.312 to 0.750 inches. Generally, the size of the conduits is selected to balance the volume the conduits can accommodate and the time required to transport the tissue or fluids through said conduits. In automated embodiments of the system, the foregoing parameters, i.e., volume and time for transport, must be identified such that the appropriate signals can be transmitted to the processing device of the system. This allows the device to move accurate volumes of liquid and tissue from one chamber to another. The flexible tubing used should be capable of withstanding negative pressure to reduce the likelihood of collapse. The flexible tubing used should also be capable of withstanding positive pressure which is generated by, for example, a positive displacement pump, which may be used in the system.

All the chambers of the system can include one or more ports, e.g., outlet 70 or inlet 21 ports, which accept standard IV, syringe and suction tubing connections. The ports can be a sealed port such as a rubber septum closed syringe needle access port 51. The inlet ports can be coupled to one or more cannulas (not shown) by way of conduits. For example, a tissue inlet port 21 can be coupled to an integrated single use liposuction cannula and the conduit can be a flexible tubing. The conduits are generally positioned to provide fluid passageways from one chamber of the system to another. Towards this end, the conduits and ports can be coupled to, for example, a suction device (not shown) which may be manually or automatically operated. The suction device can be, e.g., a syringe or an electric pump. Desirably, the suction device can be capable of providing sufficient negative pressure to aspirate tissue from a patient. Generally, any suitable suction device known to one of ordinary skill in the art, e.g., a surgeon, can be used in the embodiments described herein.

In some embodiments, the conduits 12 can further comprise one or more clamps (not shown) to control the flow of material among various components of the system. The clamps can be used to maintain the sterility of the system by effectively sealing different regions of the system. In other embodiments, the conduits 12 can comprise one or more valves 14 that control the flow of material through the system. The valves 14 are identified as open circles in the Figures. In some embodiments, the valves can be electro-mechanical pinch valves. In other embodiments, the valves can be pneumatic valves. In yet other embodiments, the valves can be hydraulic valves or mechanical valves, including cam valves. The valves are preferably activated by a control system which may be coupled to levers. The levers may be manually manipulated such that the levers are activated. In automated embodiments, the control system can be coupled to the levers as well as to a processing device which may activate the valves at pre-determined activation conditions. In embodiments wherein the system is fully or partially automated, activation of the valves can be partially automated and partially subject to the user's preference such that the process can be optimized. In yet other embodiments, certain valves can be activated manually and others automatically through the processing device. The valves 14 can also be used in conjunction with one or more pumps, e.g., peristaltic pumps 34 or positive displacement pumps (not shown). The conduits 12 and/or the valves 14 can comprise sensors 29, e.g., optical sensors, ultrasonic sensors, pressure sensors or other forms of monitors known in the art that are capable of distinguishing among the various fluid components and fluid levels that flow through the system. In a preferred embodiment, the sensors 29 may be optical sensors In some embodiments, the system can also include a plurality of filters 36. In certain embodiments, the filters can be within a chamber of the system 28. Different chambers within the system can be comprised of different filters. The filters can be configured to separate the regenerative cells, e.g., stem cells and/or progenitor cells, from undesirable cells and disaggregation agents that can be used in accordance with the system. In one embodiment, a filter assembly 36 includes a hollow fiber filtration device. In another embodiment, a filter assembly 36 can include a percolative filtration device, which can optionally be used with a sedimentation process. In a further embodiment, the filter assembly 36 can include a centrifugation device, which can optionally be used with an elutriation device and process. In yet another embodiment, the system can include a combination of these filtering devices. The filtration functions of the present invention can be two-fold, with some filters removing things from the tissue and/or cell suspension such as collagen, free lipid, free adipocytes and residual collagenase, and with other filters being used to concentrate the final product. The filters of the system can include a plurality of pores ranging in diameters and/or length from 20 to 800 µm. In a preferred embodiment, the collection chamber 20 has a prefixed filter 28 with a plurality of pores ranging from 80 to 400 µm. In another preferred embodiment, the collection chamber 20 can include a prefixed filter 28 with a plurality of 265 µm pores. In other embodiments, the filters can be detachable and/or disposable.

The system can also include one or more temperature control devices (not shown) that are configured to adjust the temperature of the material contained within one or more chambers of the system. The temperature control device can be a heater, a cooler or both, i.e., it can be configured to switch between a heater and a cooler. The temperature device can adjust the temperature of any of the material passing through the system, including tissue, disaggregation agents, resuspension agents, rinsing agents, washing agents or additives. For example, temperature control device heating of adipose tissue facilitates disaggregation whereas the cooling of the regenerative cell output is desirable to maintain viability. For example, the temperature control device can be used to store the cells at 4 degrees Celsius for future use. Also, if pre-warmed reagents are needed for optimal tissue processing, the temperature device can be used to maintain the pre-determined temperature rather than to increase or decrease the temperature.

Ports and valves can include closures that maintain the sealed configuration of the system. The closure can be a membrane that is impermeable to fluid, air and other contaminants or it can be any other suitable closure known in the art. Furthermore, all ports of the system can be configured to accommodate syringes, needles or other devices for delivering or withdrawing materials in the chambers without compromising the sterility of the system. In some embodiments, the collection chamber 20 can include one or more caps (not shown), such as a top cap and a bottom cap to further ensure that the system remains sterile while solutions and agents and other material is delivered into the collection chamber and/or waste is transported out. The ports 21 may be provided on the caps of the collection chamber or on a sidewall of the collection chamber.

Figure 5:
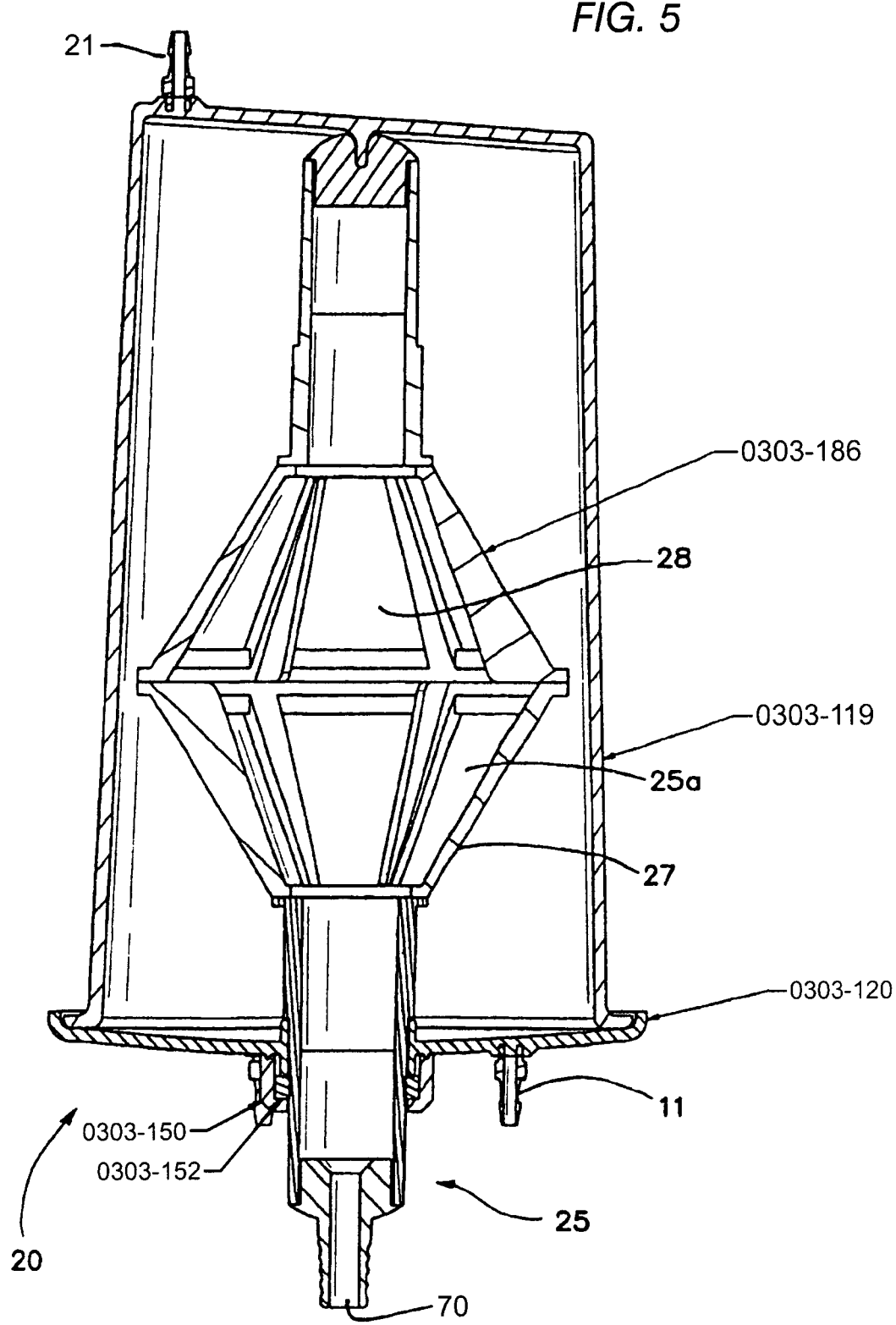
FIG. 5 is a sectional view of a collection chamber including a prefixed filter utilized in a system for separating and concentrating regenerative cells from tissue.

As set forth herein, tissue may be extracted from a patient via any art recognized method. In some embodiments, the tissue can be extracted from the subject prior to being placed in the system for processing. In some embodiments, tissue can be transferred to the collection chamber 20 through conduits 12 via a sealed entry port, such as a rubber septum closed syringe needle access port (not shown on collection chamber). In other embodiments, the system is configured to aseptically remove tissue from the subject, and transfer the removed tissue into the collection chamber 20 while maintaining a closed system. For example, as shown in FIG. 5, the collection chamber 20 can include of a vacuum line 12 to facilitate tissue removal using a standard cannula inserted into the patient, such that the entire system is attached to the patient. In some embodiments, the tissue can be introduced into the collection chamber 20 through an inlet port 21 via a conduit such as 12a which are part of a closed sterile pathway. The collection chamber 20 can include a plurality of flexible or rigid canisters or cylinders or combinations thereof. For example, in some embodiments, the collection chamber 20 can include one or more rigid canisters of varying sizes. The chamber can have size and shape specifications, e.g., height to width ratio, that provide the best result for the specific use at hand. For example, with respect to processing of adipose tissue, the chamber can be constructed to provide the best cell yield and viability while requiring a relatively short processing time. In one embodiment, particularly for agitation in an upright position, the chamber has a bottom surface that is angled, i.e., slanted, relative to the top surface. In some embodiments, the collection chamber 20 can include one or more flexible bags. In such systems, the system can include a support, such as in internal or external frame that helps reduce the likelihood that the flexible bag will collapse upon the application of suction to the bag. In some embodiments, the collection chamber 20 can be sized to hold the requisite amount of saline to wash and disaggregate the tissue prior to transfer to a processing chamber 30 or mixing chamber. By way of example, a tissue collection chamber can be configured to hold 800 ml of lipoaspirate and 1200 ml of saline. Accordingly, in one embodiment, the collection chamber 20 can be configured to accommodate at least 5 mL, 10 mL, 25 mLs 50 mL, 100 mL, 150 mL, 200 mL, 250 mL, 300 mL, 350 mL, 400 mL, 450 mL, 500 mL, 550 mL, 1 liter, 1.25 liters, 1.5 liters, 1.75 liters, 2 liters, 2.5 liters, 3 liters, or more, or any number in between, of material. For smaller tissue volumes, e.g., 5 mls to 100 mls, the tissue may be gathered in a syringe prior to transfer to the collection chamber 20. In some embodiments, the tissue collection chamber is configured such that the volume of tissue or fluid present in the collection chamber 20 is easily ascertainable to the naked eye.

The collection chamber 20 can be constructed out of any suitable biocompatible material that can be sterilized. In some embodiments, the collection chamber 20 can be made from disposable material that meets biocompatibility requirements for intravascular contact, for example, as described in the ISO 10993 standard. For example, in some embodiments, the collection chamber can be made from polycarbonate acrylic or ABS. The fluid path of the collection chamber 20 is preferably pyrogen free, i.e., suitable for blood use without danger of disease transmittal. In one embodiment, the collection chamber 20 is made from a material that allows the user to visually determine the approximate volume of tissue present in the chamber. In other embodiments, the volume of tissue and/or fluid in the collection chamber 20 is determined by automated sensors 29. For example, a load cell can be used to detect volume based on the weight of the tissue in the collection chamber 20. The collection chamber 20 can be configured such that in an automated embodiment, the system can determine the volume of tissue and/or fluid within the chamber with a reasonable degree of accuracy, for example with an accuracy of plus or minus 25%, 20%, 15% or less.

In some embodiments, the collection chamber 20 can be in the form of a rigid chamber, for example, a chamber constructed of a medical grade polycarbonate containing a roughly conical prefixed filter 28 of medical grade polyester with a mesh size of about 265 μm (See, e.g., FIG. 5). The rigid tissue collection container can be approximately eight inches high and approximately five inches in diameter; the wall thickness may be about 0.125 inches. The interior of the cylinder may be accessed through, for example, one or more ports for suction tubing, one or more ports with tubing for connection through sterile docking technology, and/or one or more ports for needle puncture access through a rubber septum. The prefixed filter 28 in the interior of the collection chamber 20 can be structured to retain tissue, such as adipose tissue and to pass non-adipose tissue as, for example, the tissues are removed from the patient. More specifically, the filter 28 can be configured to allow passage of free lipid, blood, and saline, while retaining fragments of adipose tissue during, or after, the initial harvesting of the adipose tissue. For example, in some embodiments, the filter 28 can include a plurality of pores of either the same or different sizes. In some embodiments, the filter can include a plurality of pores of either the same or different sizes ranging from about 20 μm to 5 mm. For example, in one embodiment, the filter 28 can include a plurality of 400 μm pores. In a preferred embodiment, the filter 28 is a medical grade polyester mesh of around 200 μm thickness with a pore size of around 265 μm and around 47% open area. This material can hold the tissue during rinsing while allowing cells to pass out through the mesh following tissue disaggregation. Thus, when the tissues are aspirated from the patient, non-adipose tissue such as saline, blood cells, mature adipocytes and the like may be separated from adipose tissue aggregates and fragments that include, for example, regenerative cells. In other embodiments, different materials, mesh size, filter positions and configurations, and the number and type of ports can be used to facilitate the separation of components as desired, e.g., blood, saline and mature adipocytes from adipose tissue aggregates and fragments. For example, mesh pore sizes smaller than 100 μm or as large as several thousand microns would achieve the same purpose of allowing passage of saline and blood cells while retaining adipose tissue aggregates and fragments. Similarly, the separation can be achieved by use of an alternative rigid plastic material, or by many other modifications that would be known to those skilled in the art.

In embodiments, the filter can comprise, e.g., a mesh oriented at any angle, including horizontally, at or close to the outlet port of the collection chamber 20. The mesh is positioned over the outlet port, such that fluid draining through the outlet port will necessarily pass through the mesh. Such a mesh can be positioned, e.g., in the bottom half or third of the chamber, depending on the size of the chamber and the volume of tissue to be processed. The mesh can also be positioned at an angle over an output port situated near the edge of the bottom collection chamber surface, or it can be a cylindrical filter, such as an inverted mesh cup, positioned directly over the outlet. In embodiments, the outlet port over which a filter is positioned can be used as an inlet port to receive, e.g., saline. In this embodiment, fluid added to the chamber serves to flush or clean the filter of potentially obstructing material such as cell or tissue debris. A filter can also be positioned in or near the inlet port for collection chamber 20, wherein said inlet port is used for adding tissue to the chamber.

In some embodiments providing an automated or partially automated cell processing device or system, the user may enter the estimated volume of tissue directed to the collection chamber 20. The tissue is introduced into the collection chamber 20 through an inlet port 21 which is part of a closed fluid pathway that allows the tissue, saline and other agents to be added to the tissue in an aseptic manner. In some embodiments, an optical sensor of the system, e.g., sensor 29, can detect when the user input volume of tissue is present in the collection chamber 20. In certain embodiments, if less tissue is present in the collection chamber than the user input, the user will have the option to begin processing the volume of tissue which is present in the collection chamber 20. In certain embodiments, a portion of the tissue removed from the patient may be directed to the sample chamber 60 through the use of a pump, e.g., a peristaltic pump, via a conduit, which may be activated via user input utilizing the user interface.

The system 10 can also include one or more solution sources 22. The solution source may comprise a washing solution source 23, and a tissue disaggregation agent source 24, such as collagenase. In some embodiments the collection chamber 20 includes fluid pathways that allows for the washing and disaggregating solutions or agents to be added to the tissue in an aseptic manner.

The containers for the washing solution 23 and the disaggregation agents 24 can be configured to hold their contents in a sterile manner. For example, the container 23 can be a collapsible bag, such as an IV bag used in clinical settings. The containers can have conduits 12, such as conduit 12*e*, coupled to the collection chamber 20 so that the washing solution and the disaggregation agent can be delivered to the interior of the collection chamber 20. The washing solution and the disaggregation agent can be delivered to the interior of the collection chamber 20 through any art-recognized manner, including, for example, simple gravity pressure applied to the outside of the containers or by placement of a positive displacement pump on the conduits. See, e.g., conduit 12*d* in FIG. 4.

In some embodiments, the system is configured such that solutions and materials such as saline, washing solutions, and the like can enter collection chamber 20.

The tissue collection chamber can be configured to mix the extracted tissue and any solutions, e.g., washing solutions, disaggregation agents and the like. In some embodiments, the tissue collection chamber 20 can be configured to agitate the tissue and any solutions or agents. (which maximizes cell viability and minimizes the amount of free lipid released). For example, the system can be configured to rotate the entire collection chamber 20 through an arc of varying degrees (e.g., through an arc of about 45 degrees to about 90 degrees) at varying speeds, e.g., about 30 revolutions per minute. In certain embodiments, the rotation arc and/or speed are kept constant. In other embodiments, the system can be configured to rotate the entire collection chamber 20, wherein the collection chamber 20 is comprised of one or more paddles or protrusions rigidly attached to an inside surface of the collection chamber, through an arc of varying degrees (e.g., through an arc of about 45 degrees to about 90 degrees) at varying speeds, e.g., about 30 revolutions per minute. In some embodiments, the system comprises a drive mechanism attached to or in operable communication with the collection chamber 20. In some embodiments, the drive mechanism can be a simple belt or gear or other drive mechanism known in the art.

In some embodiments, the system is configured to mix the contents of the tissue collection chamber or in the cell processing or mixing container (e.g., tissue, agents, solutions, and the like) through a rotatable shaft 25 inside the collection chamber 20. In some embodiments, the rotatable shaft can include one or more paddles 25*a* or protrusions rigidly attached to the rotatable shaft 25 which can pass through the mixture as the shaft is being rotated. In certain embodiments, the rotatable shaft 25 with rigidly attached 25a paddles can be rested on the bottom of the collection chamber 20. This can be accomplished, for example, by placing the paddle-like device into a spinning magnetic field (e.g., magnetic stirrer). Alternatively, agitating of the tissue in any of these chambers can be accomplished using a simple agitator known in the art, including but not limited to a device implementing shaking up and down without rotation. The skilled artisan will appreciate that any mechanism used to rock, stir or invert the contents of the chamber (e.g., tissue, solutions, agents, etc.) can be used in the systems described herein. In a specific embodiment, the contents of the processing chamber are agitated using a mechanism that rotates the processing chamber within the system. In embodiments, the collection chamber is horizontally positioned and rocked through an arc of about 30 to 90 degrees, with the center of the arc being, e.g., the horizontal position.

In some embodiments, the system is configured to deliver a tissue disaggregation agent to the collection chamber 20 or a mixing chamber to liberate the LECs and/or pre-LECs from the remaining adipose tissue components. In some embodiments, the system is configured for the delivery of more than one solution or agent to the cell collection chamber or mixing chamber. For example, in some embodiments, the system includes a saline source 23. The system can be configured, for example, to agitate washed adipose tissue and tissue disaggregation agent in manners similar to the agitation methods described above, until the washed adipose tissue is disaggregated. For example, the washed adipose tissue and a tissue disaggregation agent may be agitated by rotating the entire collection chamber through an arc of approximately 90 degrees, by having a shaft which contains one or more paddles which pass through the solution as the shaft is being rotated, and/or by rotating the entire collection chamber which contains paddles or protrusions on the inside surface of the collection chamber.

In some embodiments, the system is configured to produce a buoyant fraction and a non-buoyant fraction before treatment of the tissue with a disaggregation agent. The non-buoyant fraction can include blood, collagen, lipids and other components of the tissue, and the buoyant fraction can include cells such as LECs and/or pre-LECs. In some embodiments, the collection chamber 20 includes an outlet port 22 at the lowest point of the chamber such that blood and other non-buoyant components of the tissue may be drained to one or more waste containers 40 via one or more conduits 12.

In some embodiments, the collection chamber 20 can be in an upright position such that an outlet port 70 is located at the bottom of the collection chamber. The system can be configured to drain components into the waste container 40 either passively or actively. For example, in some embodiments, the system is configured such that blood, collagen, lipids, and used solutions or agents, can be drained using gravity. In some embodiments, the system is configured so as to apply positive or negative pressure, for example, by pumps 34 and/or by vents 32 to drain components into the waste container 40. In some embodiments, the system can be configured to retain components including non-buoyant components of disaggregated tissue, e.g., cell populations comprising LEC and/or pre-LECs.

In some embodiments, the system also includes a processing chamber 30. In some embodiments, the system is configured such that, after tissue disaggregation, material (e.g., the non-buoyant fraction comprising regenerative cells) can be transferred to the processing chamber 30. In some embodiments, the system comprises a conduit that allows for the transport of material from the tissue collection chamber to the cell processing chamber while maintaining a closed system. For example, in some embodiments, the processing chamber 30 of the invention can be positioned within the system such that the regenerative cell composition moves from the collection chamber 20 to the processing chamber 30 by way of tubing 12, valves 14 and pump 34 in a sterile manner.

In some embodiments, the processing chamber 30 is configured to further separate and/or concentrate cells or material of interest (e.g., cell populations comprising LEC and/or pre-LECs, etc.) from other cells and materials present in the components in the material transferred from the tissue collection chamber (e.g. collagen, residual collagenase, other connective tissue, etc.). In some embodiments, the processing chamber can be sized to accommodate tissue/fluid mixtures ranging from 10 mL to 2.0 L. In some embodiments, the processing chamber is configured to accommodate 800 mLs of material.

In some embodiments, the system is configured to receive the entire mixture from the collection chamber 20 or mixing container. In other embodiments, the system is configured such that a first portion of the mixture from collection chamber 20 or mixing container is directed to the processing chamber 30, and a second portion is directed to a different region of the system, e.g., the sample chamber 60, where the second portion can be recombined with cells processed in the processing chamber 30 at a later time.

The processing chamber 30 can be made from any suitable biocompatible material known to those skilled in the art that can be sterilized. In some embodiments, the processing chamber 30 can be made from disposable material that meets biocompatibility requirements for intravascular contact, for example, as described in the ISO 10993 standard. By way of example, in some embodiments, the processing chamber 30 can be made from polycarbonate, acrylic, ABS, ethylene vinyl acetate or styrene-butadiene copolymers (SBC). In some embodiments, the fluid path of the disposable processing chamber is pyrogen free. In some embodiments, the processing chamber can be in the form of a plastic bag, such as those conventionally used in processing blood in blood banks; or in other embodiments, it may be structurally rigid (See, e.g., FIG. 6). In one embodiment, the processing chamber 30 may be similar to the processing chamber disclosed in U.S. application Ser. No. 10/316,127, filed Dec. 7, 2001 and U.S. application Ser. No. 10/325,728, filed Dec. 20, 2002, the contents of which in their entirety are hereby incorporated by reference.

In embodiments wherein the processing chamber comprises one or more filters 36, the filter can be configured to allow the separation of one or more types of cells such as LEC and/or pre-LECs, from adipocytes, non-cellular components such as collagen, or contaminants any agent or solution such as collagenase. The skilled artisan will appreciate that variables such as, pore size of the filter media, geometry (shape) of the pore, surface area of the filter, flow direction of the solution being filtered, trans-membrane pressure, dilution of the particular cell population, particulate size and shape as well as cell size and cell viability of the components to be filtered can be configured to obtain optimal separation and concentration of the cells of interest from disaggregated tissue.

Figure 3:
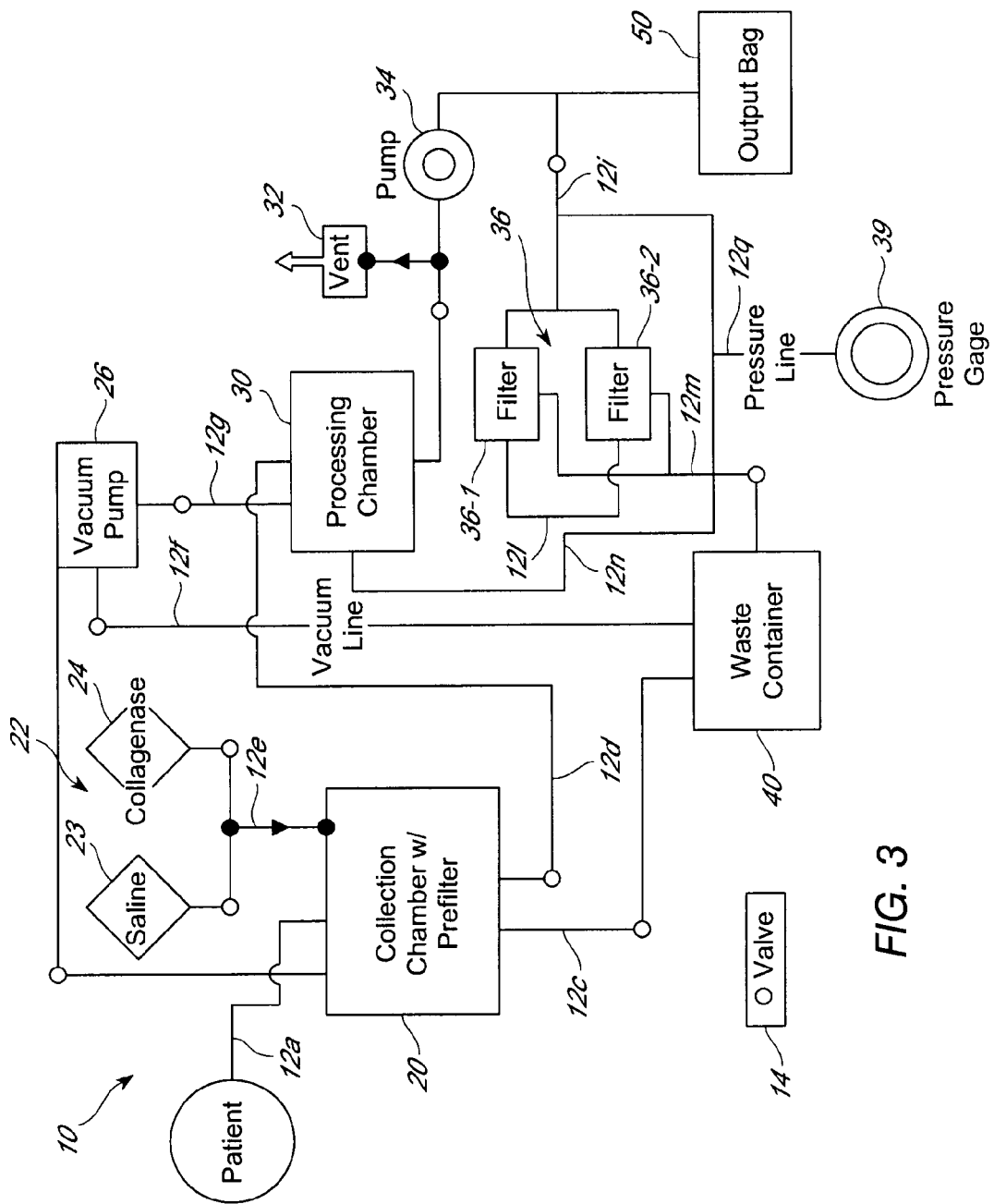
FIG. 3 is an illustration of a system similar to FIG. 1 having a plurality of filter assemblies in a parallel configuration.

In some embodiments, the system comprises a filter assembly 36. In certain embodiments, the filter assembly 36 comprises a plurality of filters which are structured to perform different functions and separate the cells of interest, e.g., a regenerative cell composition into distinct parts or components. For example, one of the filters can be configured to separate collagen from the cell population comprising LEC and/or pre-LECs, one of the filters can be configured to separate adipocytes and/or lipid components from the cell population comprising LEC and/or pre-LECs, and one of the filters can be configured to separate residual enzymes, such as the tissue disaggregation agent, from the cell population comprising LEC and/or pre-LECs. In certain embodiments, one of the filters can be configured to perform more than one function, such as separating collagen and the tissue disaggregation agent from the composition. The plurality of filters can be serially arranged. In some embodiments, at least a portion of the filters can be arranged in parallel. A serial arrangement of the filters of the filter assembly 36 is shown in FIG. 2. A parallel arrangement of the filters of the filter assembly 36 is shown in FIG. 3.

In one embodiment, the filter assembly 36 comprises a first filter, a second filter, and a third filter. The first filter can be configured to remove collagen particles present in the cell population comprising LEC and/or pre-LECs, for example. These collagen particles are typically approximately 0.1 microns in diameter and can be up to 20 microns long. The collagen particles may be of varying sizes depending on the digestion. They also may be fibrils, meaning they have twists and turns. Any of the filters described herein may be made 25 from polyethersulfone, polyester, PTFE, polypropylene, PVDF, or possibly cellulose. One method of filtering collagen can include removing the larger particles first, then letting the cells go through, which would require for example a filter in about the 10 micron range. In other embodiments, the system comprises a smaller size filter, such as 4.5 micron, with the intent that the collagen would be well digested, so as to trap the cells, and let the collagen pass through. In these embodiments, the system can also provide means to float the cells back 30 off the filter. In some embodiments, the system provides a filter which configured to attract and hold collagen fibers.

The second filter can be configured to remove, for example, free immature adipocytes which are not buoyant in the cell composition comprising LEC and/or pre-LECs. In one embodiment the second filter can be constructed of polyester and have a pore size between about 30 and about 50 microns, e.g., about a 40 micron pore size. Although referred to as a second filter, placement of such a device may be in a first, rather than second, position to facilitate an initial removal of larger cells and particles. The third filter can be configured to remove the contaminants such as unused or residual collagenase or other tissue disaggregation agent present in the composition. In some embodiments, the collagenase may degenerate over time. In one embodiment, the third filter comprises a plurality of pores having a diameter, or length less than about 1 μm. In some embodiments, the pores can have diameters ranging from about 10 kD and 5 microns. In some embodiments, the third filter can be configured to concentrate a cellular fraction, e.g., cell population comprising LEC and/or pre-LECs, into a small volume of saline or other washing solution. In some embodiments, the final filter in a series of filters can comprise a hollow fiber unit, configured to remove collagenase from the desired cellular component (e.g., the cell population comprising LEC and/or pre-LECs) while preserving the integrity of the desired cellular component. In some embodiments, other filters in the series of filters can also comprise a hollow fiber unit, whereas in other embodiments, the final filter is the only filter comprising a hollow fiber unit. In some embodiments, the filters within the filter assembly can be in separate housings. In other embodiments, some or all filters can be in the same housing.

The filters of the filter assembly 36 can be located in the processing chamber 30. In some embodiments, the system provides a filter assembly that is a separate component from the processing chamber 30. In some embodiments, filters of a filter assembly 36 can be provided in multiple processing chambers or in an inline fashion. In certain embodiments, the conduits or tubing can act as a processing chamber or chambers. The processing chamber can be reduced in size such that it becomes the inside volume of the conduits which connect the filters.

In some embodiments, processing chamber 30 can include multiple outlets. These outlets can serve to maintain the necessary pressure, as well as to provide connections via conduits to one or more other containers, such as the collection chamber 20, the output chamber 50, and the waste container 40.

Examples of filter media which can be used with the disclosed system 10 include polysulfone, polyethersulfone or a mixed ester material, and the like. These hollow fibers or hollow tubes of filter media may be contained in a cylindrical cartridge of the filter assembly 36. The individual tubes or fibers of filter media can have an inside diameter ranging from about 0.1 mm to about 1 mm. For example, in some embodiments, fibers of filter media can have a diameter of about 0.5 mm. The diameter and length of a suitable cylindrical cartridge will determine the number of individual tubes of filter media which can be placed inside the cartridge. A non-limiting example of a suitable hollow fiber filter cartridge is the FiberFlo® Tangential Flow Filter, catalog #M-C-050-K (Minntech, Minneapolis, Minn.). Pore sizes of the filter media can range between about 10 kDa and about 5 microns. In some embodiments, the pore size can be about 0.5 microns.

Figure 12A:
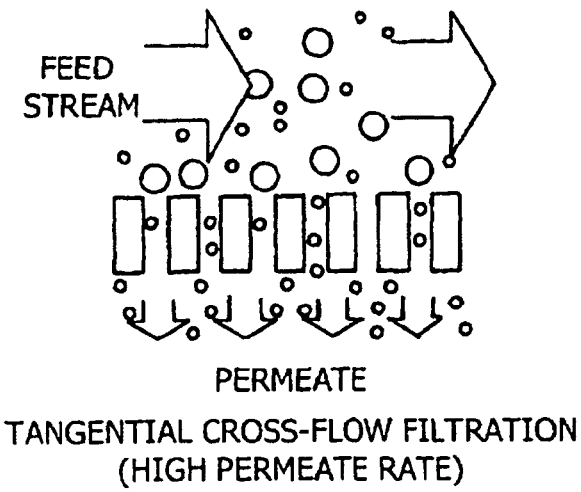
FIG. 12A illustrates a filtration process in which the feed stream of fluid flows tangentially to the pores of the filter.
Figure 12B:
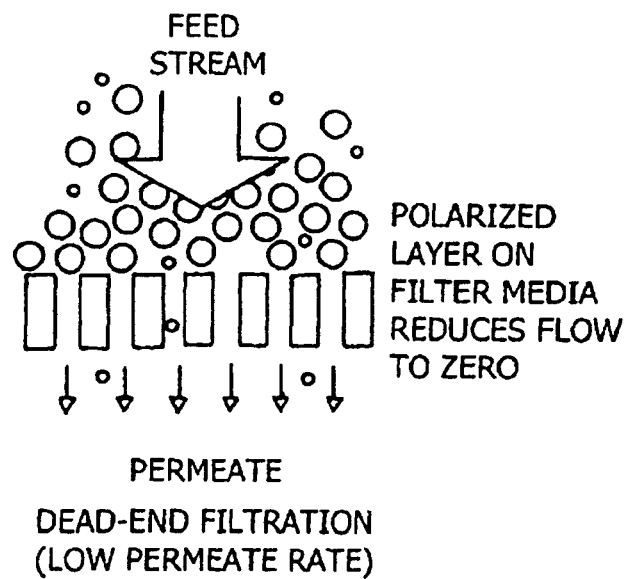
FIG. 12B illustrates a filtration process in which the feed stream of fluid flows perpendicular to the pores of the filter.

In the hollow-fiber filter, each hollow tube has a body with a first end, a second end, and a lumen located in the body and extending between the first end and second end. The body of each hollow tube includes a plurality of pores. The pores can be oriented in the body such that a cellular composition, e.g., a cell population comprising LEC and/or pre-LECs, can be filtered by flowing through the lumen of the body, and the products to be filtered tangentially pass through the pores, as shown in FIG. 12A. In other words, the smaller particles in the liquid pass tangentially through the pores relative the flow of fluid through the lumen of the body. The cell population comprising LEC and/or pre-LECs can pass through the lumen of each hollow tube when the composition is being filtered. Preferably, the flow of the composition is tangential to the pores of the body of each hollow tube. Tangential flow of fluid can increase the efficiency of the filtration relative to other filtration techniques, such as perpendicular flow, as shown in FIG. 12B.

In some of the embodiments disclosed herein, in the hollow fiber configuration of the present system 10, the fluid which is being filtered flows inside the lumen of the hollow tube. The portion of the fluid which has the ability to pass through the pores of the body of the filter does so with the aid of the positive pressure of the fluid on the inside of the body as well as a negative pressure which is applied on the outside of the body. In this embodiment, the cells typically are not subjected to the pressure of the fluid flow or the weight of other cells, and therefore, the shear forces on the stem cells can be reduced, thereby enhancing the efficiency and effectiveness of the filtration and reducing clogging rates cell lysis. The filters can be configured such that saline and unwanted protein molecules and other small components pass through the pores of the bodies of the hollow tubes to the outside of the hollow tubes and are directed to the waste container 40. In one embodiment, a vacuum can be located on the outside of the hollow tube filter media to enhance filtration. In some embodiments, the pore size of the filters is such that cells such as LEC and/or pre-LECs cannot pass through the pores of the filter body. The cells that cannot pass through the filter can remain on the inside of the hollow tube filter (e.g., in the lumens of the tubes) and can be directed back to the processing chamber 30 via a conduit between the filter and the processing chamber, or to the output chamber 50. In one embodiment, the hollow fiber filter can have about a 0.05 micron pore size, and contain approximately 550 $cm^2$ surface area of filter media. An individual media tube can have a diameter of about 0.5 mm.

In some embodiments, the system is configured to reduce the amount of collagenase in a composition (e.g., a cell population comprising LEC and/or pre-LECs) approximately by three logs. In some embodiments, the filter system provides for the reduction in collagenase levels. For example if the initial concentration of collagenase in the compositions, (e.g., a cell population comprising LEC and/or pre-LECs), which is transferred from the collection chamber to the processing chamber is 0.078 U/ml the collagenase concentration of the final regenerative cell composition would be 0.000078 U/ml. The collagenase can be removed from the compositions (e.g., a regenerative cell composition), in the hollow fiber filter, and the hollow fiber filter corresponds to the third filter discussed above.

FIGS. 1-3 depict exemplary processing chambers that include filtration means. With reference to FIGS. 1-3, some embodiments provide a pump 34 located between the processing chamber 30 and the filtering chamber of the filter assembly 36. In some embodiments, vent and pressure sensors, such as vent 32, and pressure sensor 39, can also be provided in line with the processing chamber 30 and the filter assembly 36. Some embodiments provide fittings for the output chamber 50. These components (e.g., the pump 34, the vent 32, the pressure sensor 39, and the fittings for the output chamber 50) can be positioned between the processing chamber 30 and the filter assembly 36 such that liquid contained in the processing chamber 30 can flow to one or more of these components before flowing through the filter assembly 36. For example, in some embodiments, liquid can flow through the pump 34 before it is passed to the filter assembly 36. In some embodiments, liquid may pass through the pressure sensor 39 before passing through the filter assembly to obtain a pre-filter liquid pressure in the system.

Figure 6:
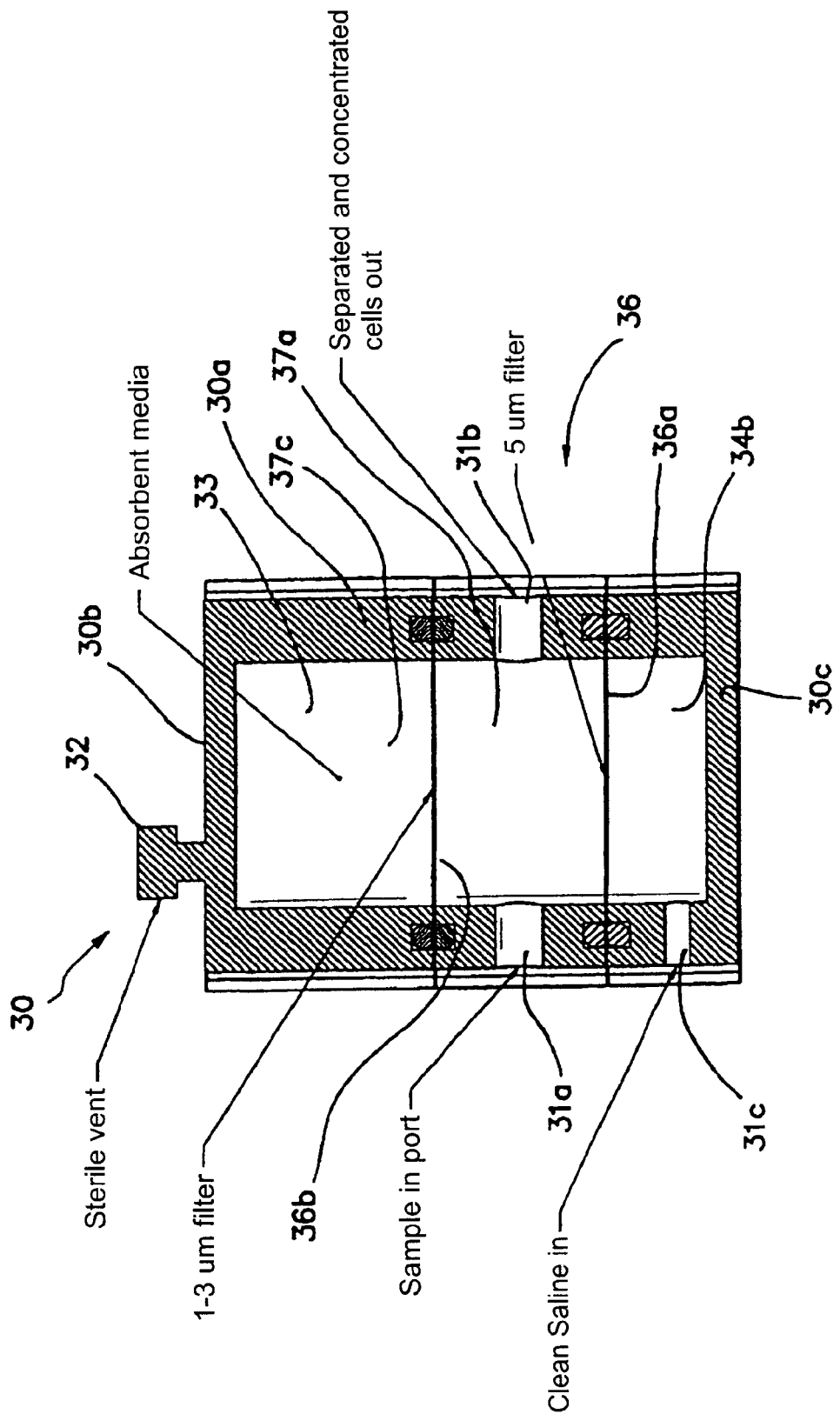
FIG. 6 is a sectional view of a processing chamber of a system for separating and concentrating regenerative cells from tissue utilizing a percolative filtration system.

In some embodiments, one or more of the components such as a pump 34, a vent 32, a pressure sensor 39, and fittings for the output chamber 50, can be provided as an element of the processing chamber 30, such as the vent 32 as illustrated in FIG. 6. In one embodiment, the pressure sensor 39 can be in line to determine the pressure of a compositions, e.g., a cell population comprising LEC and/or pre-LECs, which is generated by the pump 34 as it enters the filtering chamber of the filter assembly 36, to facilitate monitoring of the trans-membrane pressure across the filter membrane. In some embodiments, the system is configured to provide solutions and agents, such as saline or another buffer or washing solution to cell composition to assist in the removal of unwanted proteins as the composition is being filtered through the filter assembly 36. This repeated washing can be performed multiple times to enhance the purity of the cell population comprising LEC and/or LEC pre-LECs.

Figure 10:
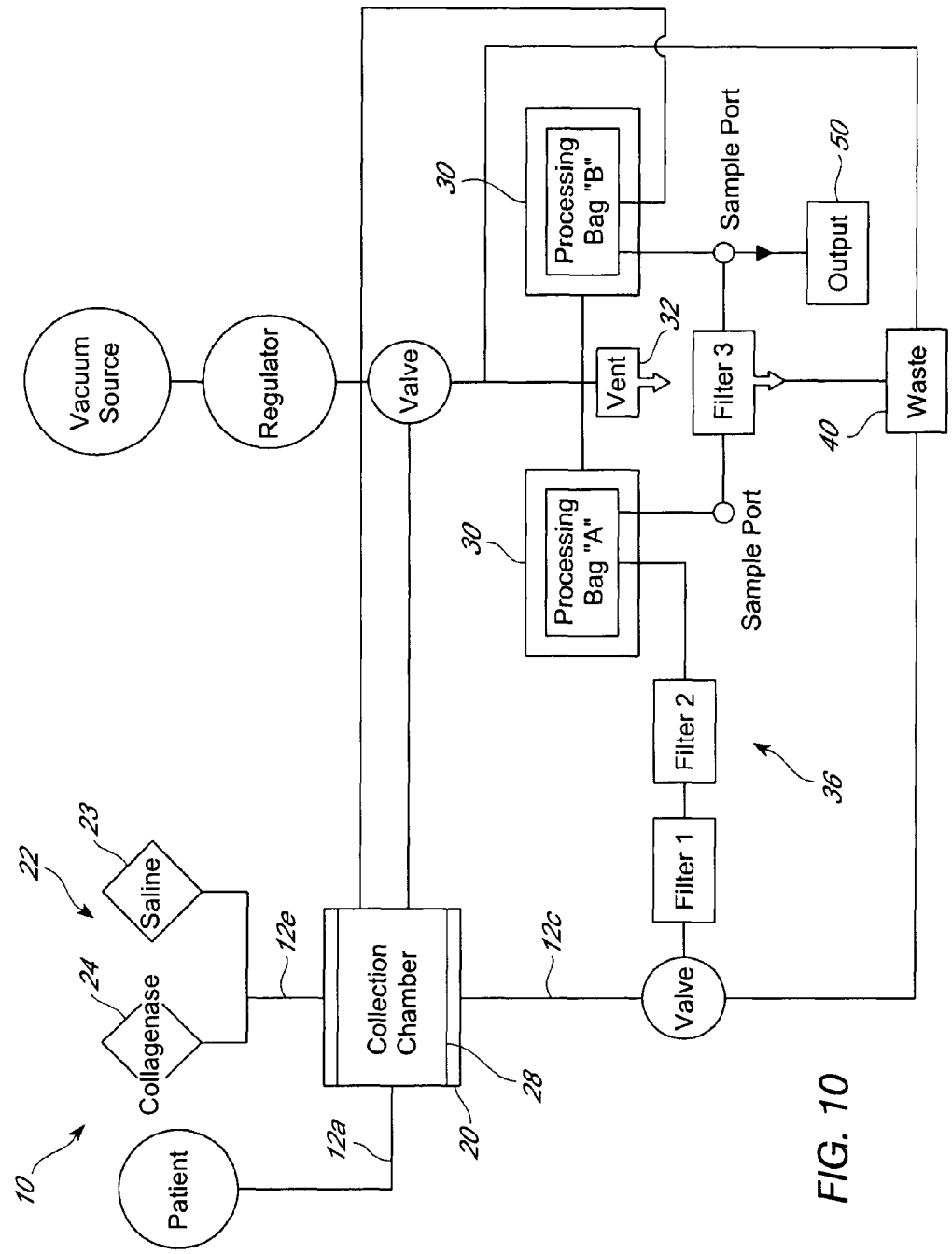
FIG. 10 is an illustration of a system for separating and concentrating regenerative cells from tissue utilizing vacuum pressure to move fluids through the system. A vacuum system can be constructed by applying a vacuum pump or vacuum source to the outlet of the system, controlled at a predetermined rate to pull tissue and fluid through, using a system of stopcocks, vents, and clamps to control the direction and timing of the flow.
Figure 11:
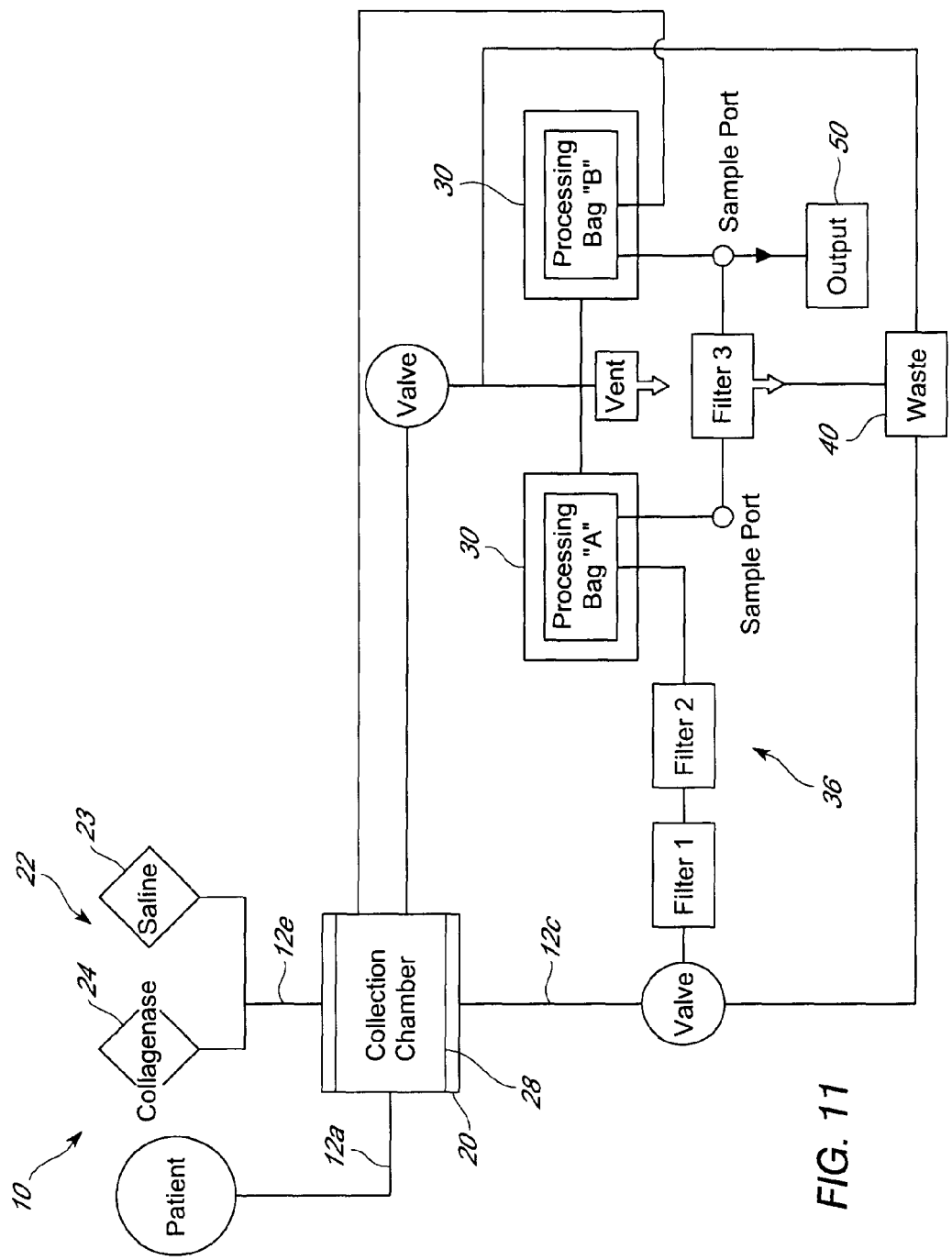
FIG. 11 is an illustration of a system for separating and concentrating regenerative cells from tissue utilizing positive pressure to move fluids through the system. A positive pressure system uses a mechanical means such as a peristaltic pump to push or propel the fluid and tissue through the system at a determined rate, using valves, stopcocks, vents, and clamps to control the direction and timing of the flow.

As shown in FIGS. 10 and 11, in some embodiments, the system is configured such that the composition, e.g. a cell population comprising LEC and/or pre-LECs, as well as collagen and connective tissue particles or fragments, adipocytes, and collagenase, can be cycled through a series of filters until a minimum volume is reached. The minimum volume is a function of the total hold up volume of the system and some predetermined constant. The hold up volume is the volume of liquid which is contained in the tubing and conduits if all of the processing chambers are empty. For example, in some embodiments, the system is configured such that the minimum volume is about 15 ml. When the minimum volume is reached, a predetermined volume of washing solution can be introduced into the system to be mixed with the composition, e.g., a cell population comprising LEC and/or pre-LECs. This mixture of washing solution and the composition, e.g., a cell population comprising LEC and/or pre-LECs can then be cycled through the filters until the minimum volume is reached again. This cycle can be repeated multiple times to enhance the purity of the LEC and/or pre-LECs, or in other words, to increase the ratio of cells e.g., LEC and/or pre-LECs, in the composition to the other materials in the composition. See FIGS. 10 and 11.

In some embodiments, the system can include an output chamber 50, such as an output bag. In some embodiments, the output chamber 50 can be connected to an outlet port of the processing chamber 30 and/or the filter assembly 36, depending on the specific embodiment. A vent, such as the vent 32, can provided such that when the vent is opened, output of the concentrated cell population is facilitated. With the vent 32 open, a pump, such as the pump 34, can function to transfer the concentrated cell population comprising LEC and/or pre-LECs into the output bag. In one embodiment, the output bag 50 can be similar to an empty blood bag which has a tube with a fitting on one end. In a sterile fashion, the fitting on the output bag can be attached to the outlet port, and the concentrated regenerative cells can be transferred to the output bag.

As illustrated in FIGS. 1-3, in some embodiments, the system includes a vacuum pump 26 for example to change the pressure in the system, among other things. For example, a vacuum pump 26 can be coupled to the collection chamber 20 via a conduit, such as conduit 12, to cause a decrease in pressure within the collection chamber 20. Vacuum pump 26 may also be coupled to a processing chamber 30 by way of a conduit, such as conduit 12g. Regarding the operation of vacuum pump 26 in connection with pump 34, two separate vacuum pumps or sources may be implemented, or a single one may be implemented by using valves which direct the vacuum pull to the different conduits that need it at specific points in the process. In addition, vacuum pump 26 may be coupled to the waste container 40 via a conduit, such as conduit 12f. The vacuum can be generated by a vacuum pump that is within the system or external, e.g., a house vacuum connected to chamber 20 by a vacuum line.

With reference to FIGS. 10 and 11, the pressure generated by the vacuum pump 26 can be used to direct the flow of fluids, including compositions such as a composition including a cell population comprising LEC and/or pre-LECs, through the conduits 12. This pressure can be supplied in multiple directions, for example, by automatically or manually controlling the position of one or more valves 14 in the system 10. The system 10 can be configured to use positive pressure or negative pressure, or combinations thereof. For instance, the cells including LEC and/or pre-LECs can be pulled through filters such as the first and second filters described above into a soft sided container which is connected to a third filter. The soft-sided container can be in line (serial) connected ahead of a third filter. The final output chamber may be a soft sided container which is on the other side (e.g., the downstream side) of the third filter. In this embodiment, pressure, e.g., from vacuum pump 26 can be used to move the cells, e.g., LEC and/or pre-LECs from one soft sided container to a second soft sided container through the filter.

In another embodiment the system can be configured to use both percolative filtration and sedimentation in order to separate and concentrate cells such LEC and/or pre-LECs. For example, such a system uses saline that is passed through a tissue cell composition (e.g., the composition containing the LEC and/or pre-LECs) and then through a filter. Some of the variables which are associated with percolative filtration of cells from a regenerative cell composition include, but are not limited to, pore size of the filter media, pore geometry or shape, surface area of the filter, flow direction of the regenerative cell composition being filtered, flow rate of the infused saline, trans-membrane pressure, dilution of the cell population, cell size and viability.

In one embodiment of the system 10, the processing chamber 30 uses a filter assembly 36 which implements percolative filtration and sedimentation to separate and concentrate the LEC and/or pre-LECs. By way of example, and not by way of limitation, the processing chamber 30 can be a generally cylindrical body having a sidewall 30*a*, a top surface 30*b*, and a bottom surface 30*c*, as shown in FIG. 6. A sterile vent 32 is provided in the top surface 30*b*.

In the embodiment of FIG. 6, the processing chamber 30 is illustrated as including a filter assembly 36, which includes two filters, such as large pore filter 36*a*, and small pore filter 36*b*. The pore sizes of the filters 36*a* and 36*b* can range from between about 0.05 microns and about 10 microns. A large pore filter 36*a* may comprise pores with a diameter of about 5 μm, and the small pore filter 36*b* may comprise pores with a diameter of about 1-3 μm. In one embodiment, the filters have a surface area of about 785 mm². In some embodiments, the system can be configured such that filters 36*a* and 36*b* can divide an interior of the processing chamber 30 to include a first chamber 37*a*, a second chamber 34*b*, and a third chamber 37*c*. As shown in FIG. 6, first chamber 37*a* can be located between second chamber 34*b* and third chamber 37*c*. In some embodiments, the first chamber 37*a* can have an inlet port 31*a* and an outlet port 31*b*. The processing chamber 30 can include a plurality of ports to provide communication paths from an exterior of the processing chamber 30 to the interior of the processing chamber 30, such as ports 31*a*, 31*b*, and 31*c*. The ports 31*a*, 31*b*, and 31*c* can be disposed in the sidewall 30*a* of a body of the processing chamber 30. In other embodiments, the ports 31*a*, 31*b*, and 31*c* can be positioned in other regions of the cell processing chamber or in other chambers, as well. In FIG. 6, port 31*a* can function as a sample inlet port, which can be coupled to a conduit so that a composition containing LEC and/or pre-LECs can be passed into the interior of the processing chamber 30. Port 31*b* can function as an outlet port constructed to be coupled to a conduit so that the separated and concentrated cells may be removed from the interior of the processing chamber 30. Port 31*c* can function as an inlet port constructed to be coupled to a conduit for delivery of a fresh washing solution, such as saline into the interior of the processing chamber 30.

As such, compositions, such as compositions that include the LEC and/or pre-LECs (e.g., the buoyant component of disaggregated tissue) can be introduced into the central chamber 37*a* via inlet port 31*a*. In some embodiments, the system can be configured such that saline or other buffer can be introduced into the bottom chamber 34*b* through inlet port 31*c*. In some embodiments, the system is configured so that solutions such as saline can be directed through the composition, (e.g., the cell population comprising LEC and/or pre-LECs), in chamber 37*a* particular rate, e.g., at a rate of about 10 ml/min. In some embodiments, the system is configured to allow for the adjustment of the flow rate of a solution such as saline is such that it counteracts the force of gravity. The flow of saline gives the cells in the chamber the ability to separate based on the density of the cells. For example, larger cells in the composition can settle to the bottom of the central chamber 37*a*, and smaller cells and proteins can be carried away through the second filter 36*b* into the top chamber 37*c*. This filtering can be accomplished by adjusting the flow rate of the saline such that the larger cells are rolled in place which allows the smaller particles to be liberated and carried off with the saline.

In some embodiments, a sterile vent 32 is included in the chamber 30 to ensure that the correct pressure gradient is maintained in the three chambers within the processing unit. The upper chamber 37*c* can comprise an absorbent media 33. Absorbent media can be used to trap the unwanted proteins in the solution to ensure that they do not cross the filter media back into the processing solution, if, for example, the saline flow rate decreases. An absorbent media can be a type of filter material that is absorbent, or attracts materials or components to be filtered out. In some embodiments, and outflow port be added above the top filter to help draw off the waste. Another embodiment of this may be to apply a gentle vacuum from the top to help pull off waste. Absorbent media can be implemented when, as in the illustrated embodiment, the flow rates are relatively small. Excess saline and proteins are then carried away to a waste container.

In some embodiments, the system can be configured to further concentrate cells (e.g., regenerative cells or the like) following removal from chamber 37*a* through outlet port 31*b*, or while it is in the chamber 37*a*. For example, in one embodiment, after the cells have been sufficiently separated, the filters, (e.g., filters 36*a* and 36*b*), can be moved towards each other. This movement has the effect of reducing the volume between the two filters (e.g., the volume of chamber 37*a*). In some embodiments, a vibrating member can be provided in connection with the processing chamber 30 to facilitate concentrating of the cells in the composition. In one embodiment, the vibrating member may be coupled to the filter 36*b* (e.g., the small pore filter). Vibrating can reduce an incidence of cells becoming trapped in the filters. The reduction in volume of the composition allows the excess saline to be removed as waste and the cells to be concentrated in a smaller volume. In other embodiments, the system can comprise another chamber to facilitate the further concentration of the composition (e.g., a cell population that comprises LEC and/or pre-LECs). For example, in some embodiments, the system includes a chamber that is configured to use gravity and/or sedimentation to filter out excess solutions such as excess saline. In some embodiments, the system is configured to carry out sedimentation and percolation at the same time. For example, in some embodiments, sedimentation can be accomplished by introducing the composition on top of a filter which has a pore size ranging from about 10 kD to about 2 microns. In one embodiment, a suitable filter has a pore size of about 1 micron. The force of gravity can allow saline and smaller particles to be passed through the filter while preventing the cells in the composition from flowing through the filter.

Figure 7:
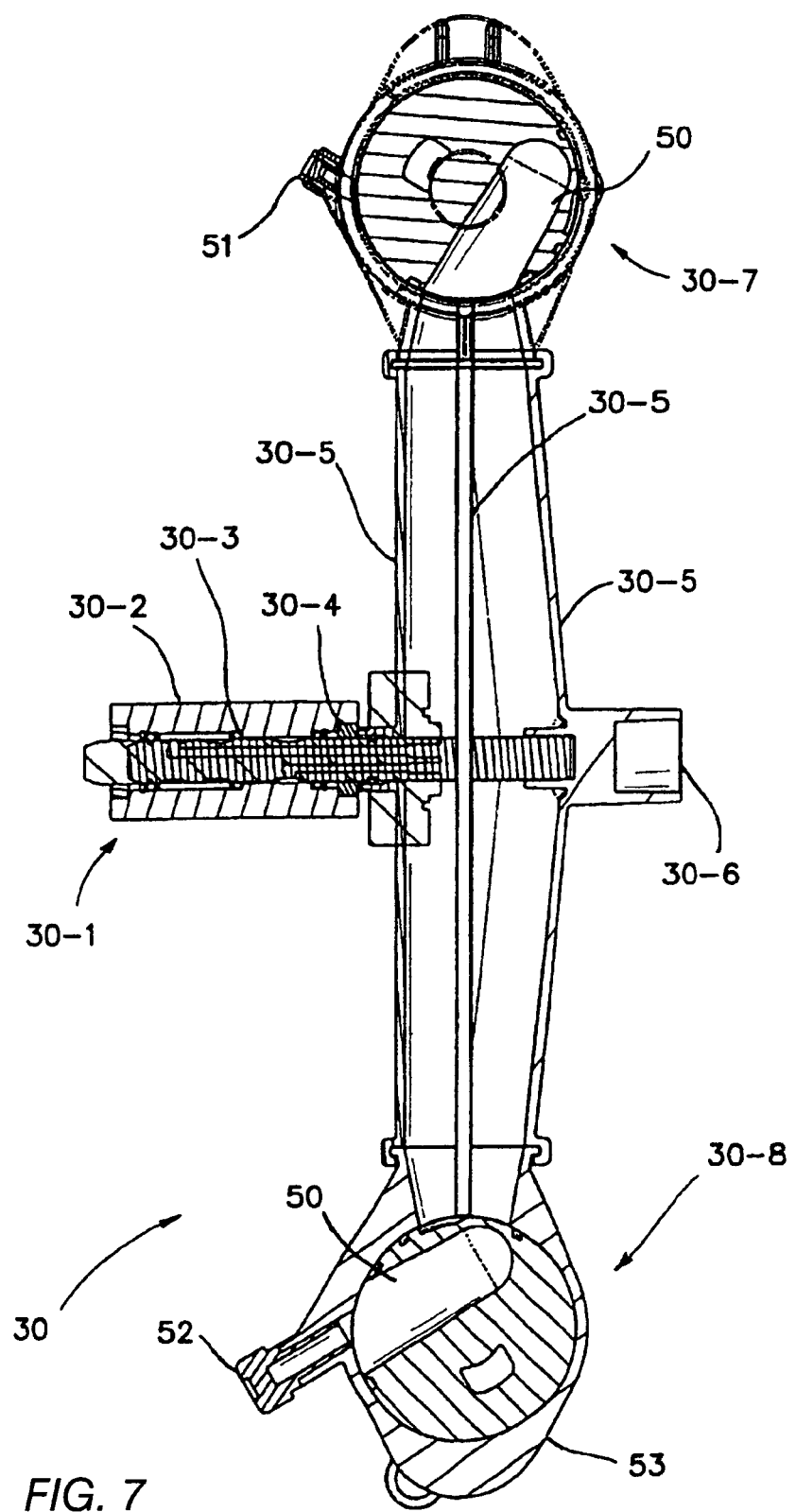
FIG. 7 is a sectional view of a processing chamber of a system for separating and concentrating regenerative cells utilizing a centrifuge device for concentrating the regenerative cells
Figure 8:
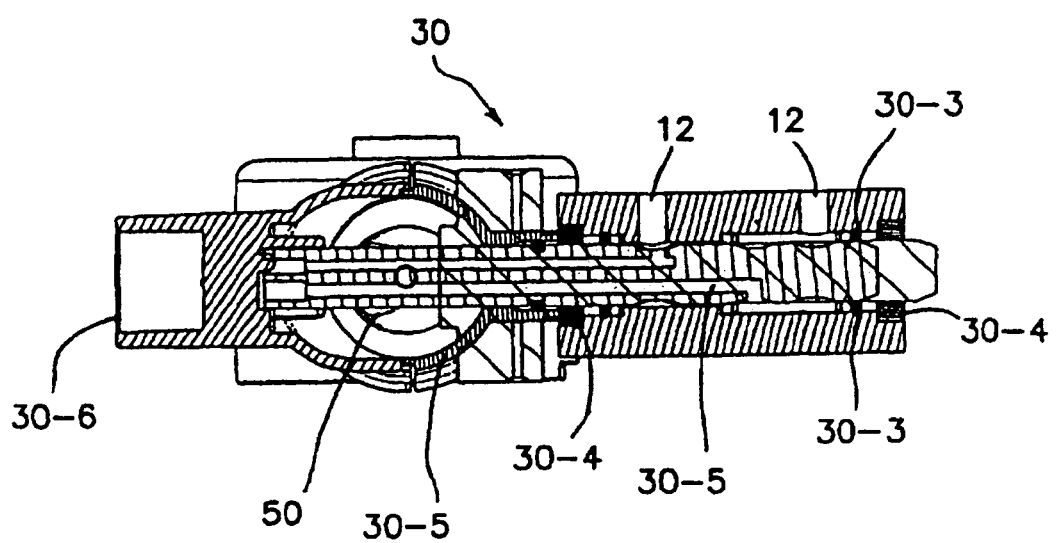
FIG. 8 is another sectional view of the processing chamber of FIG. 7.

In some embodiments, the cell processing chamber can include a centrifuge or centrifuge device to separate and concentrate the compositions (e.g a cell population comprising LEC and/or pre-LECs) from the tissue collection chamber. Standard, art-recognized centrifugation devices, components and parameters are useful in the embodiments described herein. An exemplary processing chamber for use as part of a centrifuge device is shown in FIGS. 7 and 8. The centrifuge device causes a centrifuge chamber (such as the one shown in FIG. 7) to spin around an axis thereby increasing the force on the cells in the solution to be greater than gravity. The denser or heavier materials in the solution typically settle to one end of the centrifuge chamber, i.e., an output chamber 50 of FIG. 7, to form a pellet (e.g., a pellet of cells comprising LEC and/or pre-LECs). The pellet may then be re-suspended to obtain a solution with a desired concentration of cells and/or a desired volume of cells and medium. In embodiments, additional cell composition is added to the processing chamber and further cycles of centrifugation are performed without resuspending the pellet after each cycle. The resulting pellet is resuspended only after the desired number of centrifugation cycles have been completed. The buffer or solution used for resuspension and/or washing can be selected as appropriate for each processing step, for example, if the cells are to be incubated with an enzyme, then a resuspension buffer in which that enzyme is active should be chosen. A solution designed to stop a reaction can be added directly to the incubation mix or can be used to resuspend the cells after pelleting. In some embodiments, the processing chamber can be constructed to separate and concentrate cells using both centrifugal and gravitational forces (See, e.g. FIG. 7). Specifically, during centrifugation, centrifugal force directs the denser components of the cell composition, e.g., the LEC and/or LEC pre-LECs, towards the outermost ends of the centrifuge chamber. By way of example, as the centrifuge chamber slows down and eventually stops, gravitational force can help the cells to remain in the outermost ends of the centrifuge chamber and form a cell pellet. Accordingly, the unwanted components of the composition such as waste, (e.g., collagenase, etc.), can be removed without disturbing the cell pellet.

Figure 4:
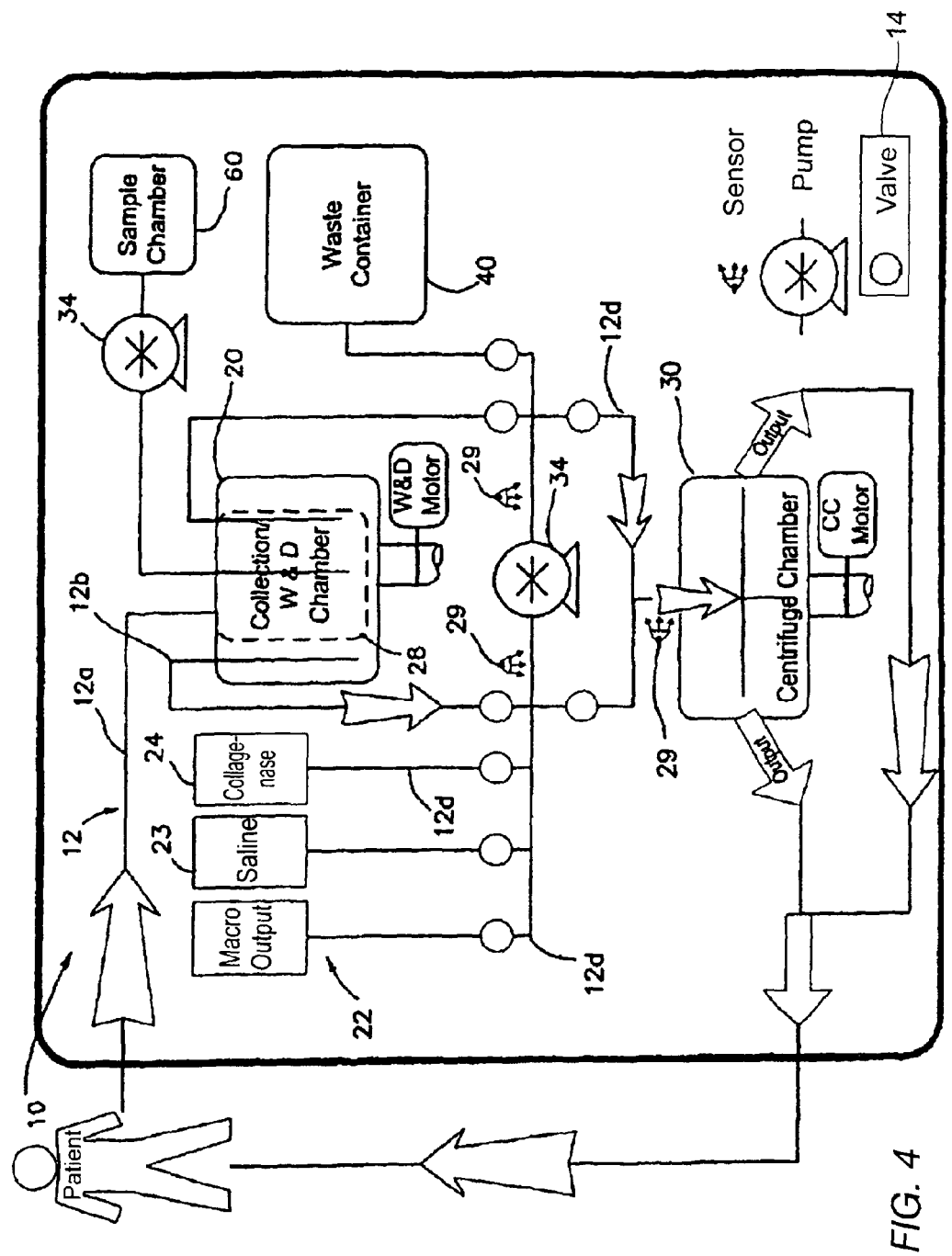
FIG. 4 is an illustration of a system for separating and concentrating regenerative cells from tissue which includes a centrifuge chamber.

The processing chamber 30 shown in FIG. 4 is in the form of a centrifuge chamber. A detailed illustration of the processing chamber of FIG. 4 is shown in FIGS. 7 and 8. Such a processing chamber 30 can include a rotating seal network 30.1 that can include an outer housing 30.2, one or more seals 30.3, one or more bearings 30.4 and an attachment point 30.6 for connecting the processing chamber to the centrifuge device; one or more fluid paths 30.5 in the form of conduits extending out from the rotating seal and ending in a centrifuge chamber on each end which is in the form of an output chamber 50 housed in a frame 53 wherein the frame is comprised of one or more ports 52 and one or more handles to manually re-position the output chamber 50.

In another embodiment, the cell processing chamber can include a cell concentrator in the form of a spinning membrane filter. In a further embodiment of the centrifugation process, centrifugal elutriation may also be applied. In this embodiment, the cells may be separated based on the individual cell sedimentation rate such that the directional (e.g., outward) force applied by centrifugation causes cells and solutes to sediment at different rates. In elutriation, the sedimentation rate of the target cell population is opposed by an opposite (e.g., inward) flow rate applied by pumping solution in the opposite direction to the centrifugal force. The counterflow can be adjusted so as to separate the cells and particles within the solution.

Figure 9A:
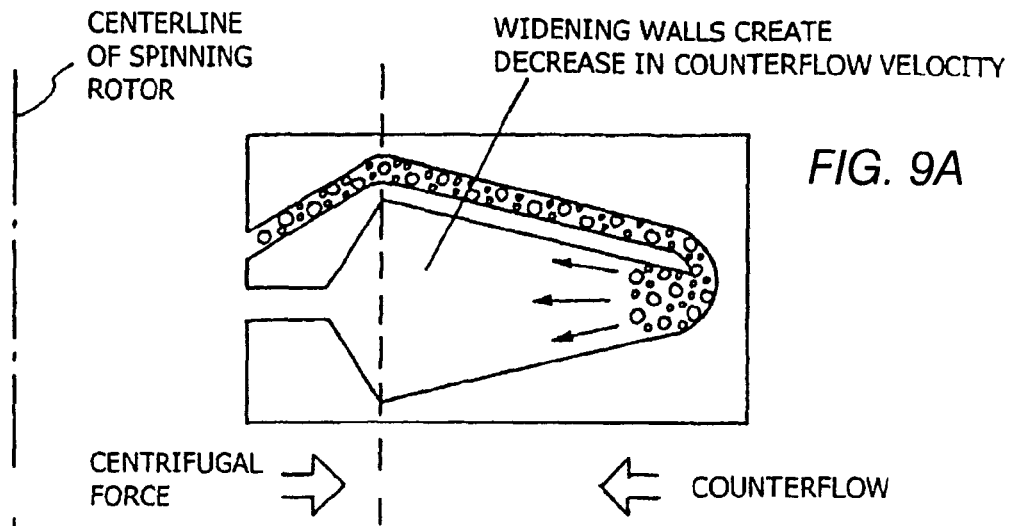
FIGS. 9A, 9B and 9C illustrate an elutriation component in use with the system of the invention.
Figure 9B:
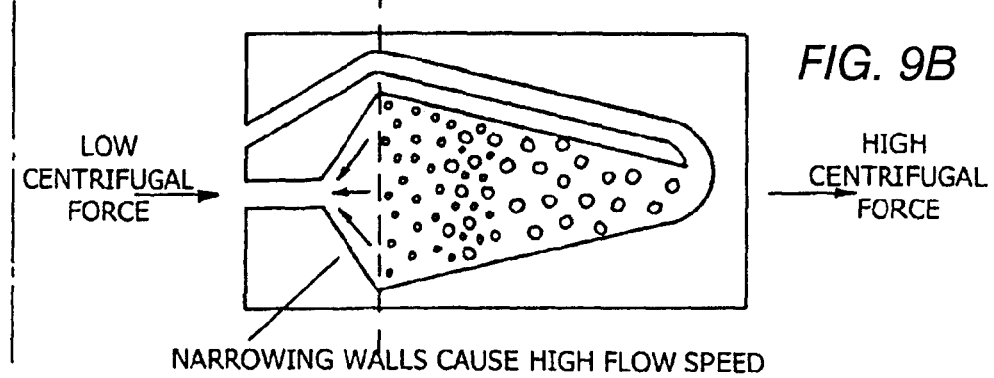
Figure 9C:
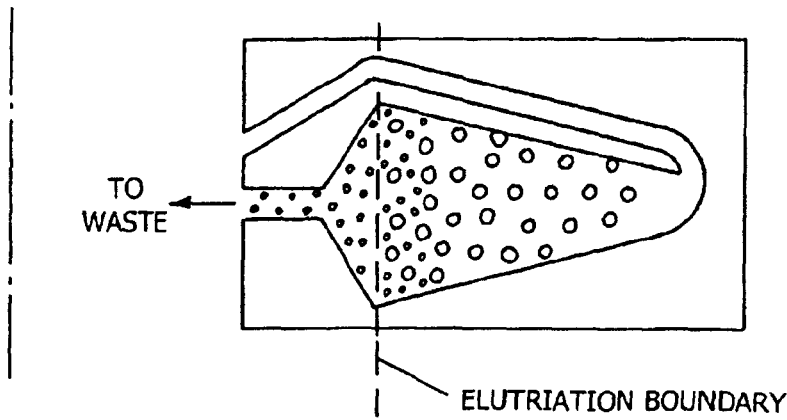

FIG. 9 illustrates how elutriation is useful in the embodiments described herein. Briefly, the system can include a spinning rotor to apply force to a composition (e.g., a composition comprising a cell population of LEC and/or pre-LECs). Some of the variables which are associated with the presently embodied elutriation separation include, but are not limited to, the size and shape of the spinning chamber, the diameter of the rotor, the speed of the rotor, the diameter of the counter flow tubing, the flow rate of the counter flow, as well as the size and density of the particles and cells which are to be removed from solution. As in centrifugation, cells such as LEC and/or pre-LECs can be separated based on individual cell densities.

In one embodiment compositions such as disaggregated tissue containing LEC and/or pre-LECs and, for example, residual collagenase, can be introduced into a chamber of a spinning rotor, as shown in FIG. 9.1. After the composition is added to the chamber additional saline can be added to the chamber at a predetermined flow rate. The flow rate of the saline can be predetermined as a function of the speed of the rotor, the cell diameter, and the chamber constant which has been established empirically. In some embodiments, the system includes a device similar to an IV pump, which can be used to control the flow rate of solutions such as saline and the like into the rotor chamber. A purpose of the additional saline is to provide a condition inside the rotor chamber where the larger particles will move to one side of the chamber and the smaller particles will move to the other, as illustrated in FIG. 9.2. The flow can be adjusted so that, the smaller particles will exit the chamber and move to a waste container, as shown in FIG. 9.3. After it has been determined that the cells have been separated from the rest of the items in the solution (with unwanted proteins and free lipids having been removed from the chamber), the counter flow can be stopped. The cells inside the chamber will then form a concentrated pellet on the outside wall of the chamber. The counter flow is reversed and the cell pellet is transferred to the output bag.

As previously set forth herein, the processing chamber 30 or the output chamber 50 may include one or more ports, e.g., ports 51 or 52. One or more of these ports may be designed to transport the cells, such as a cell population of LEC and/or pre-LECs obtained using any combination of methods described above, or a portion thereof, via conduits to other surgical devices, cell culturing devices, devices for pretreating the cells, e.g., with additives, gene therapy devices or purification devices, and combinations thereof. In some embodiments, these ports can also be designed to transport the regenerative cells via conduits to additional chambers or containers within the system or as part of another system for the same purposes described above. The ports and conduits can also be used to add one or more additives, e.g., growth factors, re-suspension fluids, cell culture reagents, cell expansion reagents, cell preservation reagents or cell modification reagents including agents that transfer genes to the cells. Cell treatment with additives can take place in chamber 20, chamber 30, or in another chamber connected to the system through the ports and/or conduits. The ports and conduits may also be used to transport the cells, such as regenerative cells to other targets such as implant materials (e.g., scaffolds or bone fragments) as well as other surgical implants and devices Potential additives include, but are not limited to, cell differentiation factors, cell de-differentiation factors, growth promoters, immunosuppressive agents, anti-apoptotic agents, anti-inflammatory agents, medical devices, nucleases, or any combinations thereof. For example, other cells, tissue, tissue fragments, growth factors such as VEGF and other known angiogenic or arteriogenic growth factors, biologically active or inert compounds, e.g., cardiogenol C or creatine, resorbable scaffolds, or other additives intended to enhance the delivery, efficacy, tolerability or function of the population of regenerative cells may be added. The nuclease human DNAse I (deoxyribonuclease I) can be added to the washed, disaggregated tissue in processing chamber 30 and digestion allowed to take place in saline, Lactated Ringer's solution or another effective solution at an appropriate temperature, e.g., at room temperature. Nuclease digestion can continue for a period of time, e.g., 10 minutes, 20 minutes, or until extracellular nucleic acid has been eliminated to a level of satisfaction, as determined by methods known in the art. Following digestion or treatment with an additive, any residual additive can be removed using a washing procedure known in the art, e.g. by centrifugation and subsequent resuspension of the cells in an appropriate solution one or more times.

In some embodiments, the system can be adapted by reconfiguring the interconnections of the disposable sets of the system, re-programming the processing device of the existing system, by providing different or additional containers and/or chambers for the existing system, by transporting the cells to a one or more additional systems or devices and/or any combinations thereof. For example, the system can be reconfigured by any of the means described above such that the cells (e.g., regenerative cells) obtained using the system may be subject to one or more of the following: cell expansion (of one or more regenerative cell types) and cell maintenance (including cell sheet rinsing and media changing); sub-culturing; cell seeding; transient transfection (including seeding of transfected cells from bulk supply); harvesting (including enzymatic, non-enzymatic harvesting and harvesting by mechanical scraping); measuring cell viability; cell plating (e.g., on microtiter plates, including picking cells from individual wells for expansion, expansion of cells into fresh wells); high throughput screening; cell therapy applications; gene therapy applications; tissue engineering applications; therapeutic protein applications; viral vaccine applications; harvest of regenerative cells or supernatant for banking or screening, measurement of cell growth, lysis, inoculation, infection or induction; generation of cells lines (including hybridoma cells); culture of cells for permeability studies; cells for RNAi and viral resistance studies; cells for knockout and transgenic animal studies; affinity purification studies; structural biology applications; assay development and protein engineering applications.

In some embodiments the cell pellet from the system (e.g., from the cell processing chamber), can be removed from an output chamber and placed into a second system providing a cell culture component. This could be in the form of a conventional laboratory tissue culture incubator or a Bioreactor-style device such as that described by Tsao et al., U.S. Pat. No. 6,001,642, or by Armstrong et al., U.S. Pat. No. 6,238,908. In an alternative embodiment, the cell expansion or cell culture component could be added to the existing system, e.g., into the output chamber, allowing for short-term adherence and/or cell culture of the adipose derived cell populations. This alternate embodiment would permit integration of the cell culture and/or cell expansion component to the system and remove the need for removing the cells from this system and placement within another.

As described above, in some embodiments, the system is configured such that one or more additives can be added to or provided with the various chambers or containers while maintaining a closed system. In some embodiments, a separate but associated system can be provided in the form of, for example, a new container or chamber comprising the additives connected to a port of the system in a sterile manner. In yet other embodiments, the additives are added or provided in a second system or device that is not connected to the system of the present invention.

In some embodiments, the system is configured to separate and concentrate cells using, for example cell-specific antibodies that recognize and bind antigens present on, for example, LEC and/or pre-LECs, such as the markers described herein. In some embodiments, for example, the system is configured to separate cells based on positive selection (selecting the target cells), negative selection (selective removal of unwanted cells), or combinations thereof. In some embodiments, the system is configured such that intracellular markers such as enzymes can be used in the selection and or separation of cells, e.g., molecules which fluoresce when acted upon by specific enzymes. In some embodiments, the system can include a solid phase material with adhesive properties selected to allow for differential adherence and/or elution of a particular population of cells, such as regenerative cells, within the final cell pellet could be inserted into the output chamber of the system. For example, in some embodiments, the system is configured such that antibodies are directly or indirectly attached to a solid phase support structure. In other embodiments, the system is configured such that cells such as LEC and/or pre-LECs can be separated from other cells using fluorescence activated cell sorting (FACS). Accordingly, in some embodiments, the system is configured such that a FACS apparatus is attached to an output chamber via a conduit to maintain a sterile, closed pathway.

In another embodiment the cell pellet could be re-suspended, layered over (or under) a fluid material formed into a continuous or discontinuous density gradient and placed in a centrifuge for separation of cell populations on the basis of cell density. In a similar embodiment continuous flow approaches such as apheresis (Smith, 1997), and elutriation (with or without counter-current) (Lasch et al., 2000) (Ito and Shinomiya, 2001) may also be employed.

In some embodiments, the system can include a cryopreservation unit. In some embodiments, the cryopresesrvation unit can be connected to the system 10 via a conduit, to provide for a closed system. For example, in some embodiments, a cryopreservation unit can be connected to the processing chamber, the output chamber, or any other container.

In some embodiments, the system can be configured for manually retrieval of the cells from the output chamber. For example, in some embodiments, the system is configured such that the cells can be loaded into a delivery device, such as a syringe, for placement into the recipient by either, subcutaneous, intramuscular, or other technique allowing delivery of the cells to the target site within the patient. In some embodiments, the system is configured to deliver the cell onto a scaffold, such as a preformed matrix as described herein. In some embodiments, the loading device is attached to the output chamber via a conduit, thereby providing a closed system. In some embodiments, the system is configured to deliver the cells into a container to store the cells for later use or for cryopreservation. Preferably, all retrieval methods can be performed in a sterile manner.

In some embodiments, (e.g., the embodiment shown in FIG. 4), the system can be automated. In another embodiment, the system has both automated and manual components. The system can include one or more disposable components connected to or mounted on a re-usable hardware component or module. The automated systems of the invention can provide screen displays (see FIG. 16) that prompt proper operation of the system. The automated systems can also provide a screen that provides status of the procedure and/or the step by step instructions as to the proper setup of the disposable components of the system. The screen can also be configured to indicate problems or failures in the system if they occur and provide "troubleshooting" guidance if appropriate. In one embodiment, the screen can be a user interface screen that allows the user to input parameters into the system through, e.g., a touch screen.

In some embodiments, the partial and fully automated systems can include a processing device (e.g., microprocessor or personal computer) and associated software programs that provide the control logic for the system to operate and to automate one or more steps of the process based on user input. In certain embodiments, one or more aspects of the system may be user-programmable via software residing in the processing device. The processing device may have one or more pre-programmed software programs in Read Only Memory (ROM). For example, in some embodiments, the processing device can have pre-programmed software tailored for processing blood, another program for processing adipose tissue to obtain small volumes of LEC and/or pre-LECs and another program for processing adipose tissue to obtain larger volumes of regenerative cells. In some embodiments, the processing device can also have pre-programmed software which provides the user with appropriate parameters to optimize the process based on the user's input of relevant information such as the amount of regenerative cells required, the type of tissue being processed, the type of post-processing manipulation required, the type of therapeutic application, etc.

In some embodiments, the system provides software that can allow for the automation of steps such as controlling the ingress and egress of fluids and tissues along particular tubing paths by controlling pumps and valves of the system; controlling the proper sequence and/or direction of activation; detecting blockages with pressure sensors; mixing mechanisms, measuring the amount of tissue and/or fluid to be moved along a particular pathway using volumetric mechanisms; maintaining temperatures of the various components using heat control devices; and integrating the separation and concentration process with timing and software mechanisms. For example, in some embodiments, the processing device of the system calculates various parameters, e.g., the volume of solutions such as saline and time or number of cycles required for washing as well as the concentration or amount of disaggregation agent and the time required for disaggregation based on information initially entered by the user (e.g., volume of tissue being processed). Alternatively, parameters such as amounts of agents, time and number of cycles etc. can be manually manipulated by the user. In some embodiments, the processing device can also control centrifuge speeds based on the tissue type being processed and/or the cell population or sub-population being harvested, and the types of procedures to be performed. For example, in some embodiments, the processing device can signal certain valves and/or pumps to drain, for example, the non-buoyant layer of disaggregated tissue from the collection chamber 20.

In some embodiments, the automated system can also include probes or sensors 29 which can detect when the interface between the buoyant and non-buoyant liquids has been reached. In some embodiments, the system can include a probe or sensor 29, e.g., an optical sensor, which may be capable of detecting a change in the light refraction of the effluent which is flowing in the conduit leading out of the collection chamber. The appropriate change in the light refraction may signal the presence of the buoyant layer in the outgoing conduits which indicates that the non-buoyant layer has been drained. The sensor 29 can then signal the processing device to proceed with the next step. In one embodiment, the system can be configured such that a determination of when a minimum concentration of desired cells has been reached is made empirically, for example, after experiments have been run and programmed into the electronic controls of the device. The determination can be an input into the process of what is desired to yield, i.e., how many LEC and/or pre-LECs are desired, or range of cell concentration. Based on scientific data, a predefined amount of adipose tissue needs to be obtained and placed into the system to achieve the desired output.

In some embodiments, the system can include one or several automated sampling probes or sensors placed in line with digested adipose tissue at various stages in the processing, including, but not limited to the final cell suspension, in order to sample the digested adipose tissue materials for potentially unsafe contaminants, or for the detection of cell markers such as FLT-4, CD45, CD31, CD34, podoplanin, LYVE-1 or Prox-1, or the like. Such a probe or sensor may be used to test the supernatant or cell suspension of the final cell preparation. Such a probe is designed to either dispense a cell suspension directly into a testing chamber or into a cell concentration device, such as a centrifuge or elutriator, in order to isolate the supernatant of the cell suspension, which is subsequently dispensed into a testing chamber.

In some embodiments, the sampling probe described above for sampling the final regenerative cell suspension may be used with a testing chamber for adipocytes. In some embodiments, the testing chamber comprises a FACS machine. In other embodiments, the testing chamber can include any one of the following components; (1) a stage for holding a microscope slide, and (2) an automated cover slipping unit. The sampling probe can be positioned in such as way as to obtain a sample of the final cell suspension from the main compartment and then to deliver the sample into a component of the testing chamber. The operation of such a testing chamber would proceed as follows: (1) the operator has pre-placed a microscope slide onto the stage, (2) a sample of the cell suspension is obtained by the sampling probe, (2) the probe then moves in an automated fashion above the microscope slide, (3) the stage is then automatically set to move slowly in a lateral plane while (4) the sampling probe dispenses a thin layer of the cell suspension across the microscope slide, and (5) the automated cover slipping unit places a cover slip atop of the slide after the sample has been dispensed onto the slide. The slide is then held in place until the operator removes it from the testing chamber, stains it with Oil Red O, and stains it for FLT-4, CD45, CD31, CD34, podoplanin, LYVE-1 or Prox-1, or some other adipocyte selective or LEC or pre-LEC antibody based or non-antibody based stain, and quantifies the cells microscopically.

In some embodiments, the sampling probe or sensor described above for sampling the final cell suspension may also be used with a testing chamber to test for free lipid in the cell suspension. This testing chamber may consist of the following components; (1) a conduit that is a port which connects the outside of the entire device with the testing chamber (2) a spectrophotometer or fluorimeter that houses a unit that holds tube(s) or well(s) for placement of the cell sample and a triglyceride reactive chromagen or fluorogen and that can be connected to a digital display on the outside of the entire device that converts the chromogenic or fluorometric signal into triglyceride content, a measure of free lipid. In some embodiments, the operation of such a testing chamber could proceed as follows: (1) the probe samples the cell suspension, and (2) dispenses it into the tube or well; (3) the operator injects an appropriate amount of the chromagen or fluorogen into the port, such that the solution is dispensed into tube(s) or well(s); (4) the tube or well and its contents incubate for an appropriate, designated period of time under controlled temperature; (5) the spectrophotometer or fluorimeter reads the contents of the tube or well, and; (6) the lipid content in the sample is displayed digitally on the outside of the device.

A sampling probe in line with the final cell suspension may also be used with a testing chamber to test for residual, soluble proteolytic activity in the supernatant of the cell suspension. Such a chamber would consist of the following major components; (1) a centrifuge that separates out the cell pellet from the supernatant, 2) a spectrophotometer or fluorimeter that houses a unit that holds tube(s) or well(s) for placement of the cell sample and a colorigenic or fluorigenic protease substrate, and is connected to a digital display on the outside of the entire device that converts the chromogenic or fluorometric signal into proteolytic activity, such as collagenase or thermolysin activity as measured by gelatin or casein digestion, respectively. The operation of such a testing chamber can proceed as follows: (1) The probe samples the final regenerative cell suspension and (2) dispenses it into a chamber within the centrifuge which then automatically begins revolving at a predefined g force and time to separate out the cell pellet and supernatant, (3) the sampling probe then obtains a sample of the supernatant from the final cell suspension (4) the operator injects an appropriate amount of the chromagenic or fluorogenic protease substrate into the port, such that the solution is dispensed into the spectrophotometer or fluorimeter tube(s) or well(s), (5) the tube(s) or well(s) and its contents incubate for an appropriate, designated period of time under controlled temperature, (6) the spectrophotometer or fluorimeter reads the contents of the tube(s) or well(s), and (7) the proteolytic activity in the sample can be displayed digitally of the device.

In some embodiments, a sampling probe in line with the final cell suspension can be used with a testing chamber to test for soluble factors from the supernatant of the final cell suspension, or cells from the final regenerative cell suspension, that can induce platelet aggregation. Such a chamber can include the following major components; (1) a centrifuge that separates out the cell pellet from the supernatant, (2) a temperature controlled aggregometer that contains a unit for holding tube(s) or well(s) and is connected to a digital display on the outside of the entire device that converts the amount of turbidity associated with platelet aggregation into a unit of platelet aggregation that is then displayed digitally on the outside of the entire device, and that has two separate ports; (a) one port that delivers the supernatant of the final cell preparation into the testing chamber and (b) one port that connects the outside of the entire device to the testing chamber. In some embodiments, the operation of such a testing chamber can proceed as follows: (1) The operator injects platelet rich plasma (PRP) into the port connected between the chamber and the outside of the device such that the PRP is dispensed into the tube(s) or well(s) within the aggregometer, (2) the sampling probe obtains a sample of the final cell suspension and performs the step "3" if measuring soluble agonists of platelet aggregation or performs step "4" if measuring cell agonists of platelet aggregation, (3) the sampling probe dispenses the sample into a chamber within the centrifuge which then automatically begins revolving at a predefined g force and time to separate out the cell pellet and supernatant, then the sampling probe obtains a sample of the supernatant and dispenses into the tube(s) or well(s) within the aggregometer (4) the sampling probe dispenses a sample of the final regenerative cell suspension directly into the tube(s) or well(s) within the aggregometer, (5) the tube(s) or well(s) and its contents incubate for an appropriate, designated period of time under controlled temperature, (6) the aggregometer reads the contents of the tube(s) or well(s), and (7) platelet aggregation activity of the sample is then displayed digitally on the outside of the device.

In some embodiments, the processing device can include standard parallel or serial ports or other means of communicating with other computers or networks. Accordingly, the processing device can be a stand alone unit or be associated one or more additional devices for the further processing methods described herein.

In some embodiments, the software can allow for automated collection of "run data" including, for example, the lot numbers of disposable components, temperature and volume measurements, tissue volume and cell number parameters, dose of enzyme applied, incubation time, operator identity, date and time, patient identity, etc. In some embodiments, the device or system can include a character recognition system, such as a bar code reading system would be integrated to permit data entry of these variables (for example disposable set lot number and expiration date, lot number and expiration date of the collagenase, patient/sample identifiers, etc.) into the processing device as part of documentation of processing. This could reduce the opportunity for data entry errors. Such a bar code reading system can be incorporated into the processing device using a USB or other interface port and system known to the art. In this way the device would provide integrated control of the data entry and documentation of the process. A print-out report of these parameters could then be part of the user-defined parameters of a programmed operation of the system. In some embodiments, the system is configured to integrate a printer component (hardware and driver) or printer driver in software plus an interface output connector for a printer (e.g., a USB port) in the hardware of the device.

In some embodiments, the system can be a fully automated system. For example, the user can initially select the amount of tissue to be processed, attach the system to the patient and the system may automatically aspirate the required tissue and separate and concentrate cells, e.g., LEC and/or pre-LECs in an uninterrupted sequence without further user input. The user may also input the amount of cells, e.g., LEC and/or pre-LECs required and allow the system to aspirate the requisite amount of tissue and process the tissue. In some embodiments, the fully automated system can also include a system which is capable of being reconfigured based on a number of (e.g., two or more) user input parameters, e.g., number of wash cycles, speed of centrifugation etc. In some embodiments, the system can be configured to run in semi-automatic mode during which the system goes through certain steps without user intervention but requires user intervention before certain processes can occur. In other embodiments, the system can be a single integrated system that displays instructions to guide the user to perform predetermined operations at predetermined times. For example, the processing device can be configured to prompt users through the steps necessary for proper insertion of tubing, chambers and other components of the system. Accordingly, the user can ensure that the proper sequence of operations is being performed. In some embodiments, the system is configured to require confirmation of each operational step by the user to prevent inadvertent activation or termination of steps in the process. In a further embodiment, the system may initiate automated testing to confirm correct insertion of tubing, chambers, absence of blockages etc. In yet another embodiment, the system of the present invention can be configured to be programmed to perform multiple separation and concentration processes through automated control of tissue flow through the system. This feature may be useful, for example, during surgery on a patient where tissue that would otherwise be lost is collected into the system, and LEC and/or pre-LECs from the tissue are separated and concentrated and returned to the patient.

Figure 13:
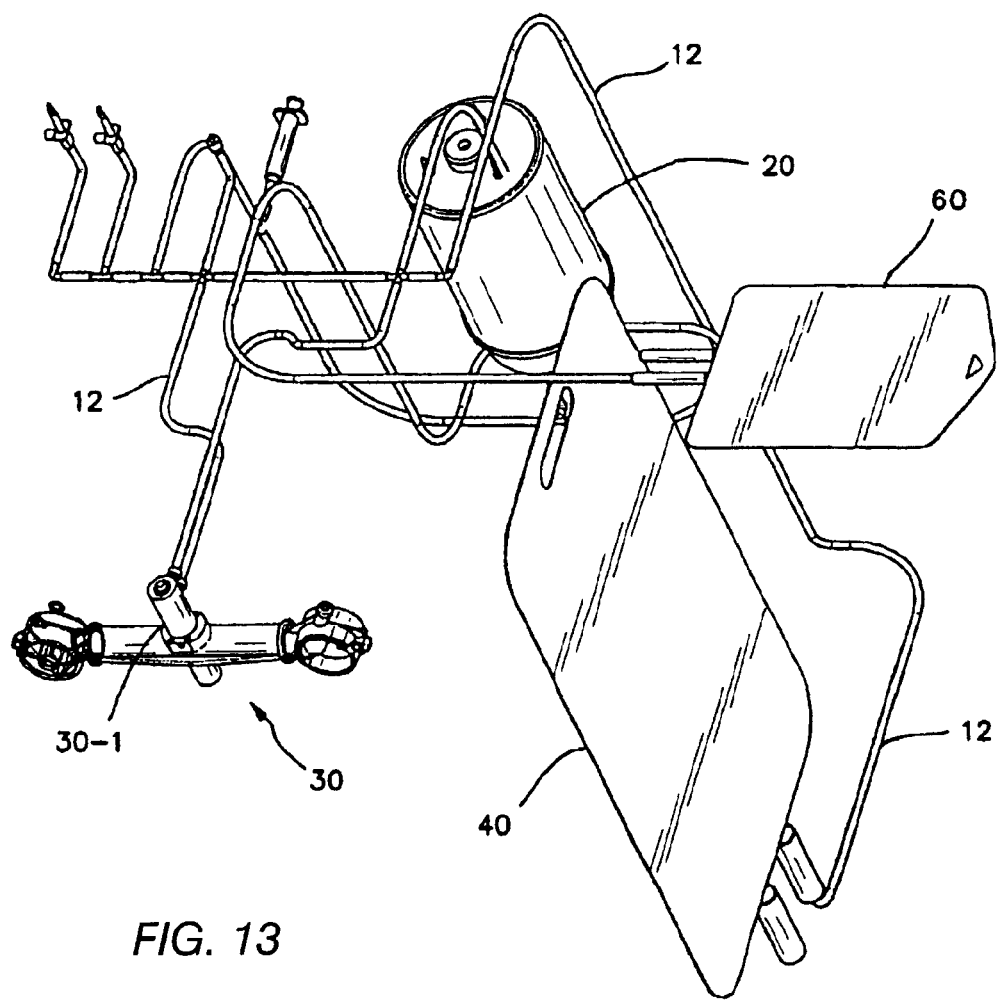
FIG. 13 is an illustration of an exemplary disposable set for a system of the invention.

As set forth above, in some embodiments, components of the system can be disposable (referred to herein as "disposable set(s)"), such that portions of the system can be disposed of after a single use. Systems with disposable components can be useful to ensure that any surface which comes in contact with the patient's tissue will be disposed of properly after being used. An exemplary disposable set is illustrated in FIG. 13. In a preferred embodiment, the disposable components of the system can pre-sterilized and packaged so as to be usable "off the shelf" that are easy to use and easy to load and that eliminate the need for many tubing connections and complex routing of tubing connections. Such disposable components are relatively inexpensive to manufacture, and therefore, do not create a substantial expense due to their disposal. In one embodiment, the disposable system (referred to interchangeably herein as "disposable set(s)") comprises, consists essentially of, or consists of, the collection chamber 20, the processing chamber 30, the waste chamber 40, the output chamber 50, the filter assemblies 36, the sample bag 60 and the associated conduits 12 or tubing. In preferred embodiments of the disposable sets of the system, the collection chamber 20 and the processing chamber 30 are connected by way of conduits 12 that are housed in a rigid frame. In some embodiments, the rotating seal network (shown in FIGS. 7 & 8) of a processing chamber 30 may also be housed in the same rigid frame. In another preferred embodiment, the various chambers and containers of the disposable set can include the necessary interfaces that are capable of communicating with the processing device of the system such that the pumps, valves, sensors and other devices that automate the system are appropriately activated or de-activated as needed without user intervention. The interfaces also reduce the time and expertise required to set up the system and also reduce errors by indicating how to properly set up the system and alerting the user in the event of an erroneous setup.

In some embodiments, the disposable sets may include one or more needles or syringes suitable for obtaining adipose or other tissue from the patient and returning LEC and/or pre-LECs to the patient. The type number and variety of the needles and syringes included will depend on the type and amount of tissue being processed. The disposable sets may further include one or more rigid or flexible containers to hold washing fluids and other processing reagents used in the system. For example, the disposable sets may comprise containers to hold saline, enzymes and any other treatment or replacement fluids required for the procedure. In addition, suitable washing solutions, re-suspension fluids, additives, agents or transplant materials can be provided with the disposable sets for use in conjunction with the systems disclosed herein.

In some embodiments, the system components, equipment or supplies described herein can be provided in the form of a kit. For example, in some embodiments, a kit can include, e.g., the optimal length and gage needle for the syringe based liposuction and sterile syringes which contain the preferred filter media which allows for the processing of small volumes of tissue. Other exemplary equipment and supplies which are useful in the system described herein and which can be included with the kits of the invention are listed in Tables 1 and 2 below.

Table 1 below identifies examples of supplies that can be used in to obtain adipose derived regenerative cell in accordance with the systems and methods of the present invention:

TABLE 1

| Description | Vendor | Quantity | Note |
|---|---|---|---|
| 10 mL syringe | Becton Dickinson | as req'd | Optional, used for liposuction |
| 14GA blunt tip needle | Becton Dickinson | as req'd | Optional, used for liposuction |
| Single blood pack (600 mL) | Baxter Fenwal | 1 | Main cell processing bag; bag has spike adaptor on line and two free spike ports |
| Transfer pack with coupler (150 mL) | Baxter Fenwal | 1 | Quad bag set |
| Transfer pack with coupler (1 L) | Baxter Fenwal | 1 | Waste bag |
| Sample Site Coupler | Baxter Fenwal | 2 | |
| 0.9% Saline (for injection) | Baxter Fenwal | 1 | |
| 14GA sharp needle | Monoject | as req'd | For adding liposuction tissue to bag |
| 20GA sharp needle | Monoject | 3 | For adding collagenase and removing cell compositions |
| 0.2 µm Sterflip filter | Millipore | 1 | For filtering collagenase |
| Teruflex Aluminum sealing clips | Terumo | 4 | ME*ACS121 for temporary tube sealing |

TABLE 1-continued

| Description | Vendor | Quantity | Note |
|---|---|---|---|
| Providone Iodnine prep pad | Triadine | as req'd | 10-2301 |
| Liberase H1 | Roche | | |
| Collagenase | Roche | | |
| TSCD wafers | Terumo | 2 | ISC*WO17 for use with TSCD Sterile Tubing Welder |

TABLE 2

| Description | Vendor | Quantity | Note |
|---|---|---|---|
| Sorvall Legend T Easy Set Centrifuge | Fischer Scientific | | 75-004-367 |
| Rotor | Kendro/Sorvall | | TTH-750 rotor |
| Rotor Buckets | Kendro/Sorvall | | 75006441 round buckets |
| Adaptor for 150 mL bags | Kendro/Sorvall | | 00511 |
| Plasma expressor | Baxter Fenwal | | 4R4414 |
| Tube sealer | Sebra | | Model 1060 |
| TSCD Sterile Tubing Welder | Terumo | | 3ME*SC201AD |
| LabLine Thermal Rocker | LabLine | | 4637 |
| Disposable plastic hemostat-style clamp | Davron | | |
| Balance bag sets | | | Water filled bags used to balance centrifuge |
| Biohazard sharps container | | | |
| Biohazard waste container | | | |

Figures 2, 14:
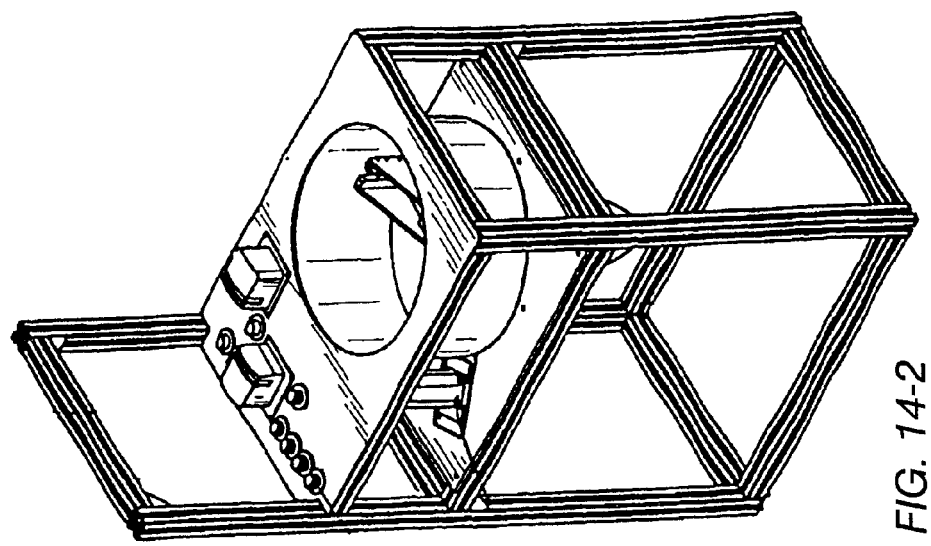
Figures 1, 14:
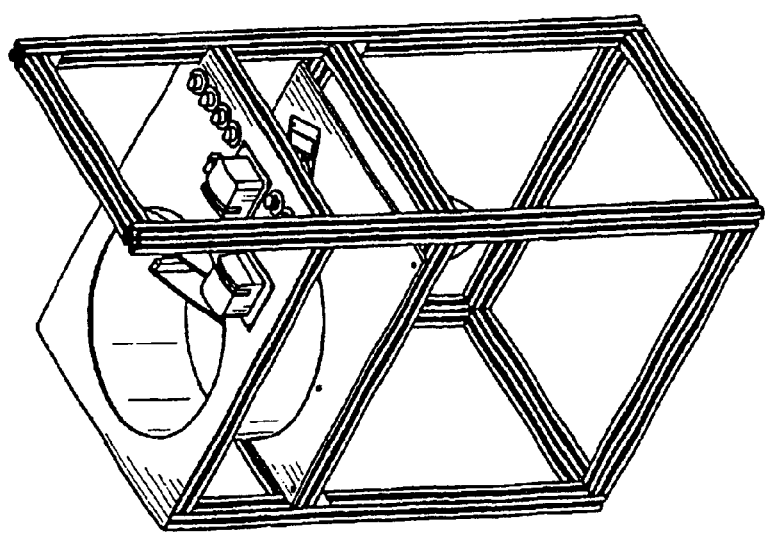
Figures 2, 15A:
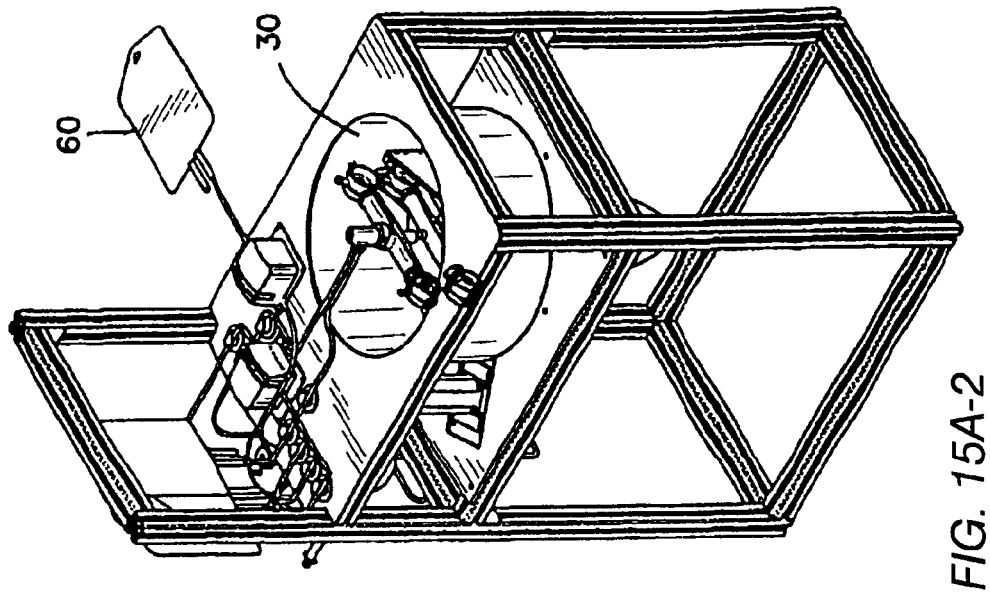
Figures 1, 15A:
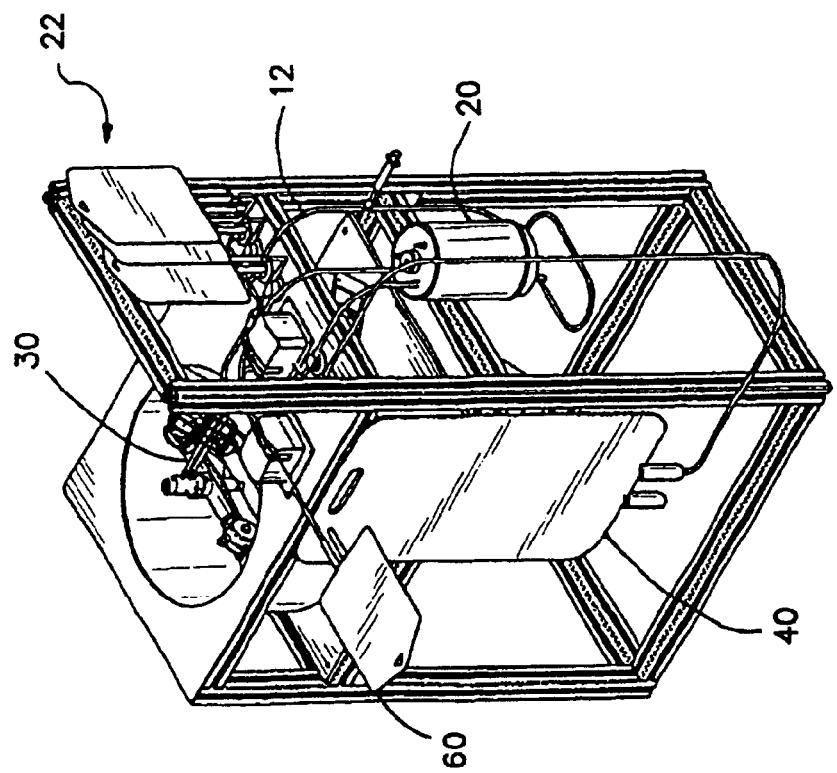

In some embodiments, the system includes a re-usable component. The re-usable component of the system can comprise, consist essentially of, or consist of an agitation mechanism for the collection chamber, a pump, and assorted sensors which activate valves and pump controls, a centrifuge motor, a rotating frame of the centrifuge motor, a user interface screen and USB ports, an interlocking or docking device or configuration to connect the disposable set such that the disposable set is securely attached to and interface with the re-usable hardware component and other associated devices. An exemplary re-usable component is illustrated in FIG. 14. In some embodiments, the re-usable component includes a means for separating and concentrating the cells, e.g., regenerative cells from a composition (e.g., a composition comprising a cell population of LEC and/or pre-LECs). For example, in some embodiments, the re-usable component includes a rotating centrifuge. In this embodiment, the re-usable component is designed connect to and interface with a portion of the processing chamber (comprising a centrifuge chamber) of the disposable set as shown in FIG. 15A. In some embodiments, the means for separating and concentrating cells (e.g., LEC and/or pre-LECs) in the re-usable component is not limited to a rotating centrifuge but may also include any other configuration described herein, including a spinning membrane filter. In some embodiments, the re-usable component can also house a processing device as described herein which contains pre-programmed software for carrying out several different tissue processing procedures and selectively activating the various pumps and valves of the system accordingly. The processor can also include data storage capability for storing donor/patient information, processing or collection information, and other data for later downloading or compilation. The re-usable component can be used with a variety of disposable sets. Disposable and re-usable components can be connected through, e.g., an interlocking device or configuration such that the disposable set is securely attached to and interfaces with the re-usable hardware component in a manner that the processing device present on the re-usable component can control, i.e., send and receive signals to and from the various components of the disposable set as well as various components of the re-usable component and other associated devices and systems.

In a specific embodiment, the disposable component of the system can include a collection chamber 20 which can accommodate about 800 mL of tissue; a processing chamber 30 configured to process the cell composition generated by about 800 mL of tissue washed and digested in the collection chamber 20; an output chamber 50 which can accommodate at least 0.5 mL of cells (e.g., regenerative cells); and a waste container 40 which can accommodate about 10 L of waste. In this embodiment, the hardware device is no larger than 24"L×18"W×36"H. The skilled artisan will readily appreciate, however, that the system can be configured with alternative dimensions of the various components of the disposable sets as well as the hardware device.

An illustration of an exemplary disposable set assembled together with a re-usable component is illustrated in FIG. 15A. In some embodiments, the system can be configured such that it can detect an improperly loaded disposable component. For example, in some embodiments, the components of each disposable set can have color-guided marks to properly align and insert the tubing, chambers etc. into appropriate places in the system. In additional embodiments, the system disclosed herein can be a portable unit. For example, the portable unit can be configured to be moved from one location where adipose tissue harvesting has occurred, to another location for adipose tissue processing. In certain other embodiments, the portable unit is suitable for harvesting and processing of adipose tissue by a patient's bedside. In some embodiments, the portable unit can be part of a system which can be moved from patient to patient.

Accordingly, the portable unit can be on wheels which lock in place and, thus, can be easily placed and used in a convenient location in a stable and secure position throughout the procedure. In other embodiments, the portable unit can be designed for set-up and operation on a flat surface such as a table top. The portable unit can also be enclosed in a housing unit. The portable unit can also include hangers, hooks, labels, scales and other devices to assist in the procedure. Each of the re-usable components of the system described herein such as the centrifuge, processing device, display screen can be mounted on the portable unit of the system.

Figure 15B:
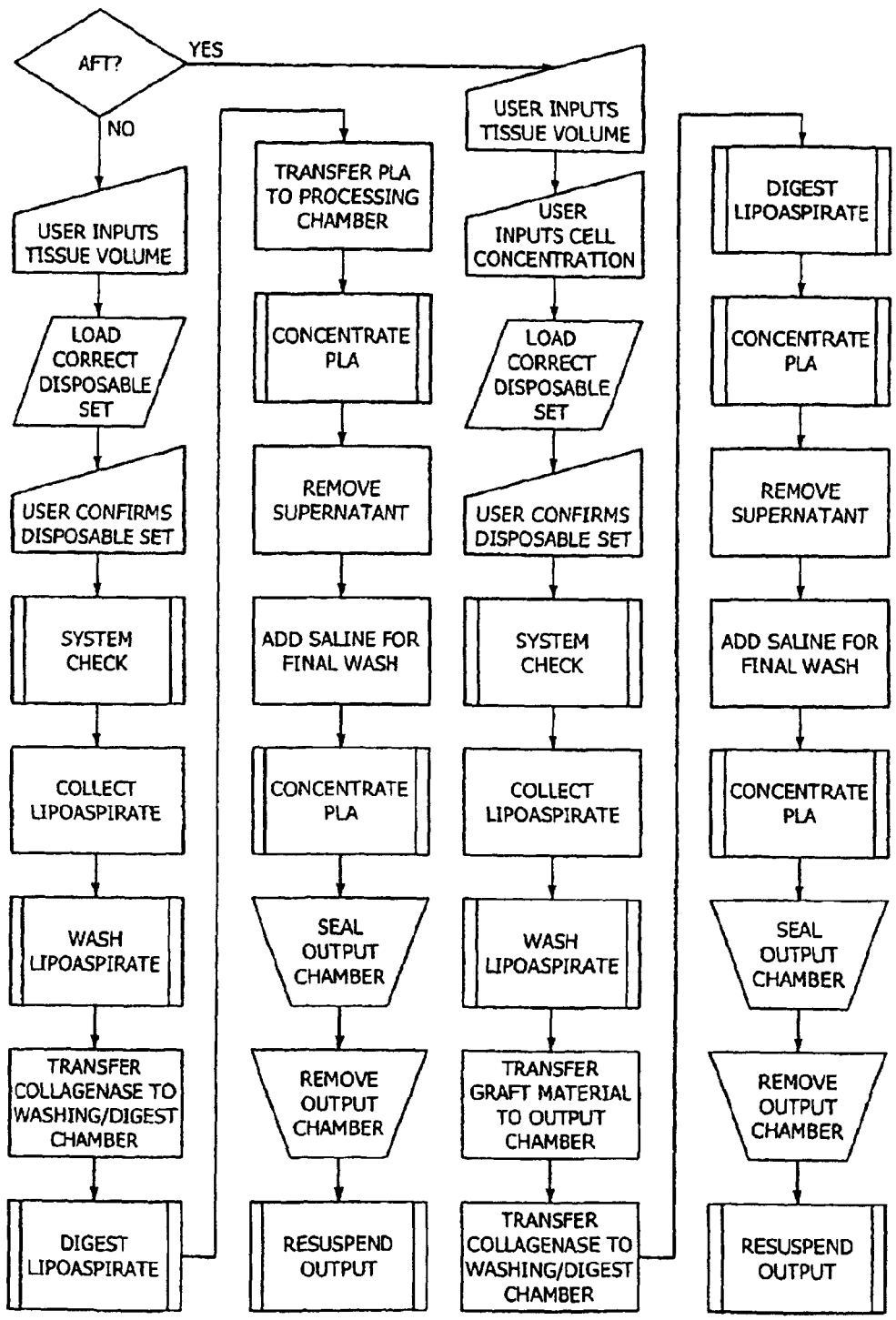
FIG. 15B is a flowchart depicting exemplary pre-programmed steps, implemented through a software program, that control automated embodiments of a system of the present invention. Two alternative processing parameters are shown indicating the versatility of the system.

In some embodiments, the system or cell processing device is configured such that the user can connect the disposable set to the re-usable component, input certain parameters using the user interface, e.g., the volume of tissue being collected, attach the system to the patient, and the system automatically performs all of the steps shown in FIG. 4 in an uninterrupted sequence using pre-programmed and/or user input parameters. One such sequence is illustrated in FIG. 15B. Alternatively, the tissue may be manually aspirated from the patient by the user and transported to system for processing, i.e., separation and concentration of regenerative cells.

A sensor 29 can signal the processing device present in the re-usable component to activate the steps needed to wash and disaggregate the tissue. For example, the processing device can introduce a pre-set volume of washing agent based on the volume of tissue collected using automated valves and pumps. This cycle can be repeated in the collection chamber until the optical sensor determines that the effluent liquid is sufficiently clear and devoid of unwanted material. For example, an optical sensor 29 along the conduit 12b/12d leading out of the collection chamber can be used to determine that the unwanted materials have been removed and can signal the processing device to close the required valves and initiate the next step.

In some embodiments, the processing device can introduce a pre-programmed amount of disaggregation agent based on the volume of tissue collected. The processing device may also activate agitation of the tissue in the collection chamber for a preset period of time based on the initial volume of tissue collected or based on user input. In the embodiment shown in FIG. 4, once the disaggregation agent, e.g., collagenase, is added to the collection chamber 20 through the collagenase source 24, the motor in the collection chamber 20 is activated via the processing device. The motor activates the rotatable shaft 25 which is comprised of a magnetic stirrer and a paddle-like device wherein one or more paddles 25a are rigidly attached to the filter cage 27 of a filter prefixed to the collection chamber 28. The paddles agitate the in the presence of the disaggregation agent such that the LEC and/or pre-LECs can be liberated from the tissue.

The solution in the collection chamber 20 is then allowed to settle for a preset period of time. The buoyant portion of the solution is allowed to rise to the top of the solution. Once the preset period of time elapses, the necessary valves and pumps are activated by the processing device to remove the non-buoyant portion to the processing chamber 30. The transfer into the processing chamber 30 continues until a sensor 29 along the conduit 12b/12d leading out of the collection chamber can detect that the buoyant fraction of the solution is about to be transferred to the processing chamber 30. For example, a sensor 29 along the conduit 12b/12d leading out of the collection chamber can be used to determine when to signal the processing device to close the required valves.

At this time the non-buoyant fraction of the solution, i.e., the cell composition comprising LEC and/or LEC regenerative cells, is moved to the processing chamber 30. This can be accomplished through the use of the necessary valves and peristaltic pumps. In certain embodiments, before transfer of the regenerative cell composition to the processing chamber 30, an additional volume of saline may be added to the buoyant fraction of solution remaining in the collection chamber 20, and another wash cycle may be performed. After this or sufficient additional wash cycles, the solution is allowed to settle and the non-buoyant fraction (which contains the cell population comprising LEC and/or pre-LECs) is transported to the processing chamber 30 and the buoyant fraction is drained to the waste chamber 40. An additional wash cycle can optimize transfer of all the separated cell population comprising LEC and/or pre-LECs to the processing chamber 30.

Once the cell composition comprising a population of cells that comprise LEC and/or pre-LECs is transported to the processing chamber 30 by way of conduits 12, the composition may be subjected to one or more additional washing steps prior to the start of the concentration phase. This ensures removal of waste and residual contaminants from the collection chamber 20. As described above, the composition can be subjected to treatment with one or more additives, e.g., with a nuclease such as DNAse I, in one or more steps, while in processing chamber 30 or any other chamber as appropriate. Following treatment, the additive can be removed by one or more washing steps, e.g., centrifugation and resuspension in a different solution. Subsequent to a concentration step, the cell composition comprising a cell population that comprises LEC and/or pre-LECs may be subjected to one or more additional washing steps to remove residual contaminants. The unwanted materials may be removed from the processing chamber 30 to the waste chamber 40 in the same manner, i.e., control of valves and pumps via signals from the processing device, as described above.

The various embodiments of the processing chamber 30 shown in FIG. 4 are described in detail below. The rotating seal network 30.1 is included to ensure that the fluid pathways of the processing chamber can be maintained in a sterile condition. In addition, the fluid pathways of the processing chamber can be accessed in a sterile manner (e.g., to add agents or washing solution) at any time, even while the centrifuge chamber of the processing chamber is spinning.

The rotating seal network 30.1 shown in FIGS. 7 and 8 includes a rotating shaft comprised of two or more bearings 30.4, three or more lip seals 30.3, and an outer housing 30.2. In this embodiment, the bearings 30.4 further comprise an outer and inner shaft (not shown) referred to herein as races. These races may be separated by precision ground spheres. The races and spheres comprising the bearings are preferably fabricated with material suitable for contact with bodily fluid, or are coated with material suitable for contact with bodily fluid. In a preferred embodiment, the races and spheres are fabricated using, for example, silicone nitride or zirconia. Furthermore, in this embodiment, the three lip seals can be in the form of a circular "U" shaped channel (not shown) as well as a circular spring (not shown). The circular "U" shaped channel can be fabricated using flexible material such that a leakage proof junction with the rotating shaft of the rotating seal network 30.1 is formed. In some embodiments, the lip seals can be oriented in a manner such that pressure from the cell composition comprising LEC and/or pre-LECs flowing through the processing chamber causes the seal assembly to tighten its junction with the rotating shaft by way of increased tension. In some embodiments, the seals can be secured in position by way of one or more circular clips (not shown) which are capable of expanding and/or collapsing as needed in order to engage a groove in the outer housing 30.2 of the rotating seal network 30.1. The heat generated by or near the rotating seal network 30.1 can be controlled to prevent lysis of the cells in the solution which is being moved through the passage. This may be accomplished by, for example, selecting a hard material for constructing the rotating shaft, polishing the area of the rotating shaft which comes in contact with the seals and minimizing contact between the rotating shaft and the seal.

In another embodiment the rotating seal network 30.1 can include a single rubber seal 30.3 and an air gasket (not shown). This seal and gasket provide a tortuous path for any biologic matter which could compromise the sterility of the system. In another embodiment the rotating seal network 30.1 is comprised of multiple spring loaded seals 30.3 which isolate the individual fluid paths. The seals 30.3 are fabricated of a material which can be sterilized as well as seal the rotating shaft without lubricant. In another embodiment the rotating seal network 30.1 can include of a pair of ceramic disks (not shown) which create the different fluid paths and can withstand the rotation of the system and not cause cell lysis. In another embodiment the fluid pathway is flexible and is allowed to wind and unwind with respect to the processing chamber. This is accomplished by having the flexible fluid pathway rotate one revolution for every two revolutions of the processing chamber 30. This eliminates the need for a rotating seal altogether.

The cell composition comprising a cell population comprising LEC and/or pre-LECs can be pumped from the collection chamber 20 along a fluid path through the axis of rotation of the rotating seal network 30.1 and then divided into a minimum of two fluid pathways 30.5 each of which radiate outward from the central axis of the processing chamber 30 and terminate near the outer ends of the processing chamber 30, i.e., within the centrifuge chambers which house the output chambers 50 (FIGS. 7 and 8).

Accordingly, in a preferred embodiment, the processing chamber 30 can include two or more output chambers 50 as shown in FIGS. 7 and 8. The output chambers 50 can be positioned such that they are in one orientation during processing 30.7 and another orientation for retrieval of concentrated cell populations comprising LEC and/or pre-LECs 30.8. For example, the output changes are tilted in one angle during processing and another angle for cell retrieval. The cell retrieval angle is more vertical than the processing angle. The two positions of the output chamber 50 can be manually manipulated through a frame 53 which protrudes out of the processing chamber 30. The concentrated cell population comprising LEC and/or pre-LECs can be manually retrieved from the output chambers 50 when they are in the retrieval orientation 30.8 using a syringe. In another embodiment, fluid path 30.5 is constructed such that it splits outside the processing chamber and then connects to the outer ends of the processing chamber 30, i.e., within the centrifuge chambers which house the output chambers 50 (not shown). In this embodiment, large volumes of cell composition comprising LEC and/or pre-LECs and/or additives, solutions etc. can be transported to the centrifuge chamber and/or the output chambers directly.

With reference to FIGS. 4 and 7-9, between the collection chamber 20 and the processing chamber 30, a pump 34 and one or more valves 14 can be provided. In a preferred embodiment, the valves 14 can be electromechanical valves. In addition, sensors, such as pressure sensor 29, may be provided in line with the processing chamber 30 and the collection chamber 20. The valves, pumps and sensors act in concert with the processing device present on the re-usable component (FIG. 14) to automate the concentration steps of the system.

In some embodiments, sensors detect the presence of the cell composition comprising LEC and/or pre-LECs in the centrifuge chambers and activate the centrifuge device through communication with the processing device of the system. The cell composition is then subjected to a pre-programmed load for a pre-programmed time based on the amount of tissue originally collected and/or user input. In certain embodiments, this step may be repeated either automatically or through user input. For example, the composition is subjected to a load of approximately 400 times the force of gravity for a period of approximately 5 minutes. The output chamber 50 is constructed such that the outer extremes of the chamber form a small reservoir for the dense particles and cells. The output chamber 50 retains the dense particles in what is termed a "cell pellet," while allowing the lighter supernatant to be removed through a fluid path, e.g., a fluid path which is along the axis of rotation of the rotating seal network 30.1 and travels from the low point in the center of the processing chamber 30 through the rotating seal network 30.1 to the waste container 40. The valves 14 and pumps 34 signal the processing device to activate steps to remove the supernatant to the waste container 40 without disturbing the cell pellet present in the output chamber 50.

In some embodiments, the cell processing device or system also includes a testing chamber. The testing chamber can be coupled to one or more of the chambers, e.g., a tissue collection chamber, a cell processing chamber, a cell collection chamber, an output bag, or the like. In preferred embodiments, the testing chamber is connected to the system via a conduit so as to maintain a sterile, closed pathway. In some embodiments, the testing chamber can include a buffer comprising a detectably labeled antibody to detect the presence or absence of markers that differentiate LEC and/or LEC precursor cells from other cell types, e.g., FLT-4, and/or CD45, and/or CD31, and/or CD34, and/or podoplanin, and/or LYVE-1, and/or Prox-1, etc. The testing chamber can be coupled to solution input chambers, and to waste containers via conduits that maintain a sterile, closed pathway.

The cell pellet that is obtained using the system shown in FIG. 4 comprises the concentrated cell population comprising LEC and/or pre-LECs. In some embodiments, after the supernatant is removed and directed to the waste chamber 40, a fluid path 30.5 may be used to resuspend the cell pellet that is formed after centrifugation with additional solutions and/or other additives. Re-suspension of the cell pellet in this manner allows for further washing of the cells to remove unwanted proteins and chemical compounds as well as increasing the flow of oxygen to the cells. The resulting suspension may be subjected to another load of approximately 400 times the force of gravity for another period of approximately 5 minutes. After a second cell pellet is formed, and the resulting supernatant is removed to the waste chamber 40, a final wash in the manner described above may be performed with saline or some other appropriate buffer solution. This repeated washing can be performed multiple times to enhance the purity of the cell solution. In certain embodiments, the saline can be added at any step as deemed necessary to enhance processing. The concentrations of LEC and/or pre-LECs obtained using the system shown in FIG. 4 may vary depending on amount of tissue collected, patient age, patient profile etc.

The final pellet present in the output chamber 50 may then be retrieved in an aseptic manner using an appropriate syringe after the output chamber 50 is positioned in the orientation appropriate for cell removal. In other embodiments, the final pellet may be automatically moved to a container in the in the output chamber 50 which may be removed and stored or used as needed. This container may be in any appropriate form or size. For example, the container may be a syringe. In further embodiments, the cell output can be moved to another container, e.g., collection chamber 20, and mixed therein with other materials. In embodiments the output is mixed with undigested or partially digested adipose tissue before being returned to the patient. In certain embodiments, the output container 50 itself may be heat sealed (either automatically or manually) and isolated from the other components of the processing chamber for subsequent retrieval and use of the regenerative cells in therapeutic applications as described herein including re-infusion into the patient. The cells may also be subject to further processing as described herein either prior to retrieval from the output chamber or after transfer to a second system or device. The re-usable component shown in FIG. 14 is constructed such that it can be connected to one or more additional systems or devices for further processing as needed.

To obtain certain compositions in which the composition primarily contains one type of cell (e.g., adipose tissue-derived LECs or adipose tissue-derived pre-LECs), any suitable method for further separating the different cell types may be employed, such as the use of cell-specific antibodies that recognize and bind antigens present on either cell type, gradient sedimentation through a selective media (e.g., ficoll-hypaque), cell sorting (e.g., FACS) or filtration. Similarly, LECs and pre-LECs may be isolated by use of negative selection approaches in which other cells are specifically removed. For example, LEC-specific markers such as podoplanin or FLT-4 or other markers may be used to immunoselect LECs and/or pre-LECs from the heterogeneous cell population as described by Kriehuber, et al. (Kriehuber, et al., 2001). In some embodiments, the obtained, refined, enriched, isolated, or purified adipose-derived cell population comprising LECs and/or pre-LECs has a cell population that is greater than or equal to 0.5%-1%, 1-2%, 2%-4%, 4%-6%, 6%-8%, 8%-10%, 10%-20%, 20%-30%, 30%-40%, 40%-50%, 50%-60%, 60%-70%, 70%-80%, 80%-90%, or 90%-100% LECs and/or pre-LECs, as compared to the total adipose-derived cell population. Many other positive and negative selection approaches can be utilized to isolate and purify LECs and pre-LECs, as described below. It is desired that after obtaining, enriching, concentrating, isolating, or purifying an adipose-derived cell population comprising LECs and/or pre-LECs, a measurement, analysis, or characterization of the cell population to determine the presence or absence of said LECs and/or pre-LECs is made. Several approaches to identify, measure, evaluate, or confirm the presence or absence of LECs and/or pre-LECs in an adipose-derived cell population are provided in the following section.

Measuring LECs and/or Pre-LECs in an Isolated Adipose-Derived Cell Population

A measurement, analysis, or characterization of said LECs and/or pre-LECs to determine the presence of these cells in an adipose-derived cell population can be undertaken within the closed system of a cell processing unit or outside of the closed system of a cell processing unit using any number of protein and/or RNA detection assays available in the art. Additionally, the measurement, analysis, or characterization of said LECs and/or pre-LECs can be part of or can accompany the isolation procedure (e.g., cell sorting using an antibody specific for LECs and/or pre-LECs or gradient separation using a media selective for LECs and/or pre-LECs).

In some embodiments the measurement or characterization of the isolated cell population is conducted by detecting the presence or absence of a protein marker that is unique to LECs and/or pre-LECs or is otherwise considered to confirm the presence of LECs and/or pre-LECs by those of skill in the art. In addition to conventional Western blots using antibody probes specific for said proteins or markers, immunoselection techniques that exploit on cell surface marker expression can be performed using a number of methods known in the art and described in the literature. Such approaches can be performed using an antibody that is linked directly or indirectly to a solid substrate (e.g., magnetic beads) in conjunction with a manual, automated, or semi-automated device as described by Watts, et al., for separation of CD34-positive cells (Watts, et al., 2002, Variable product purity and functional capacity after CD34 selection: a direct comparison of the CliniMACS (v2.1) and Isolex 300i (v2.5) clinical scale devices," Br J. Haematol. 2002 July; 118(1):117-23), by panning, use of a Fluorescence Activated Cell Sorter (FACS), or other means.

Pre-LECs can be measured, characterized and quantified, e.g., by detection of cells that express FLT-4 but express markers characteristic of terminally differentiated LECs, such as CD31, at low levels or not at all. Thus, one phenotype that could include pre-LECs is the phenotype $FLT-4^+/CD31^-$. Pre-LECs can also be measured, characterized and quantified by expression of FLT-4 and the presence of markers of immature cells such as CD133 (Salven, et al., 2003). (check the previous three sentences with respect to our current knowledge) It is recognized in the art that these phenotypes might not identify all pre-LECs and that some cells with the above phenotypes might not be LEC progenitors; rather, these phenotypes are used by way of example and can be used as surrogate measures of actual pre-LEC frequency similar to the same way that expression of the CD34 molecule on hematopoietic cells is frequently used as a surrogate measure of hematopoietic stem cells (Bender, et al. 1991).

Separation, measurement, and characterization can also be achieved by positive selection using antibodies that recognize cell surface markers or marker combinations that are expressed by LECs and pre-LECs, but not by one or more of the other cell sub-populations present within the cell population. Separation, measurement, and characterization can also be achieved by negative selection, in which non-LECs and/or non-pre-LECs are removed from the isolated cell population using antibodies or antibody combinations that do not exhibit appreciable binding to LECs and pre-LECs. Markers that are specifically expressed by LECs and putative pre-LECs have been described (for example by Kriehuber, et al., 2001), and include, e.g., CD45, CD133, FLT-4, D2-40, podoplanin, LYVE-1, and Prox-1. See, e.g., Breiteneder-Geleff, February 1999, "Angiosarcomas Express Mixed Endothelial Phenotypes of Blood and Lymphatic Capillaries," Am. J. Path. 154(2): 385-394; U.S. Pub. No. 2005/0271636; Wilting, et al., August 2002, "The transcription factor Prox1 is a marker for lymphatic endothelial cells in normal and diseased human tissues," The FASEB J. 16:1271-1273; Podgrabinska, et al., Dec. 10, 2002, "Molecular characterization of lymphatic endothelial cells," PNAS 99(25):16069-16074; Chen, et al., December 2005, "Novel Expression and Characterization of Lymphatic Vessel Endothelial Hyaluronate Receptor 1 (LYVE-1) by Conjunctival Cells," Invest. Ophthalmol. Vis. Sci. 46(12):4536-4540; Banerji, et al., (Feb. 22, 1999). "LYVE-1, a New Homologue of the CD44 Glycoprotein, Is a Lymph-specific Receptor for Hyaluronan." J. Cell. Bio. 144(4): 789-801, and; Garrafa et al., 2006, all incorporated herein by reference. Examples of antibodies that could be used in negative selection include, but are not limited to, markers expressed by red blood cells (glycophorin A) or endothelial cells (CD31 and VE cadherin). There are many other antibodies well known in the art that could be applied to negative selection. The relative specificity of FLT-4 for LECs and pre-LECs can also be exploited in a purification and/or characterization or measurement strategy. For example, a fluorescently-labeled FLT-4 ligand can be used in FACS-based sorting of cells, or an FLT-4 ligand conjugated directly or indirectly to a solid substrate can be used to separate in a manner analogous to the immunoselection approaches described above.

Measurement and characterization of the adipose-derived cell population to determine the presence or absence of LECs and/or pre-LECs can also involve analysis of one or more RNAs that encode a protein that is unique to or otherwise considered by those of skill in the art to be a marker that indicates the presence or absence of an LEC and/or pre-LEC. In some embodiments, for example, the isolated cell population or a portion thereof is analyzed for the presence or absence of an RNA that encodes one or more of, e.g., FLT-4, and/or CD45, and/or CD31, and/or CD34, and/or podoplanin, and/or LYVE-1, and/or Prox-1. The detection of said RNAs can be accomplished by any techniques available to one of skill in the art, including but not limited to, Northern hybridization, PCR-based methodologies, transcription run-off assays, gene arrays, and gene chips.

The measurement and characterization of an adipose-derived cell population that comprises LECs and/or pre-LECs can also include an analysis of the cell population's ability to form lymphatic structures, e.g., lymphatic cords or lymphatic vessels in vitro or in vivo. For example, the presence or absence of LECs and/or pre-LECs can be measured or evaluated in a cord formation assay using the protocol set forth in Garrafa, et al., 2006, hereby expressly incorporated by reference in its entirety. Briefly, an adipose-derived cell population isolated in accordance with a method described herein can be placed in 200 µl of Cultrex BME (10 mg/ml) (Biodesign International, Saco, Mass.) at 4° C. in pre-chilled 24-well culture plates using sterile tips that are cooled to −20° C. before use. After gentle agitation to insure coating, the plates are incubated for 1 hour at 37° C. to allow the Cultrex BME to solidify. The isolated adipose-derived cell population is then seeded at a concentration of $6 \times 10^4$/well in EGM containing VEGF-C. The presence or absence of LECs and/or pre-LECs in an isolated adipose-derived cell population prepared as described herein can be measured, characterized, or otherwise confirmed by the appearance of cord or cord-like structures, which will form after 24 hours of incubation.

By introducing said adipose-derived cell population that comprises LECs and/or pre-LECs into an experimental animal and determining the presence or absence of expansion of LECS and/or pre-LECs, formation of lymphatic vessels, or formation of lymphatic tissue, one can also measure, characterize, and determine the presence or absence of LECs and/or Pre-LECs. Whereas the measurement and analysis of expansion of an adipose-derived cell population that comprises LECs and/or pre-LECs and formation of lymphatic vessels and lymphatic tissues in rodents is contemplated, other animals are also suitable. For example, in some embodiments, an approach used by Daniels, et al., (published online Jan. 2, 2003), "Regenerating lizard tails: A New Model for Investigating Lymphangiogenesis," FASEB Journal express article 10.1096/fj.02-0579fje, hereby expressly incorporated by reference in its entirety, is used to evaluate the presence or absence of an adipose-derived cell population that comprises LECs and/or pre-LECs. By one approach, for example, a regenerating lizard tail is used to evaluate, characterize, and measure lymphangiogenesis in the presence and absence of an adipose-derived cell population that comprises LECs and/or pre-LECs. Histological analysis (staining and video camera imaging) can be used visualize and count lymphatic and blood vessel formation in the presence and absence of an adipose-derived cell population that comprises LECs and/or pre-LECs.

The teachings of U.S. Pat. No. 6,689,352, hereby expressly incorporated herein by reference in its entirety, can also be used to measure, characterize, or evaluate the presence or absence of LECs and/or pre-LECs in an adipose-derived cell population. By one approach, for example, a measurement of the increase in lymph vessel endothelial cell formation based on the presence, quantity or distribution of VEGF receptor-3 in the presence and absence of an adipose-derived cell population comprising LECS and/or pre-LECs is conducted. In the presence of LECs and/or pre-LECs, a greater presence, quantity, and distribution of the VEGF receptor-3 will be seen. A variety of methods known in the art for evaluating parameters indicative of lymphatic function are also described, e.g., in U.S. Pat. App. Pub. No. 2006/0025338, hereby expressly incorporated by reference in its entirety.

There are also a large number of methods, which can be used to compare lymphatic vessel growth and architecture in experimental animals in the presence and absence of an adipose-derived cell population that comprises LECs and/or pre-LECs. For example, lymphatic vessels can be studied with the aid of lymphography. In lymphography, X-ray contrast medium is injected directly into a lymphatic vessel. The contrast medium is distributed along the efferent drainage vessels of the lymphatic system and is collected in the lymph nodes. The contrast medium can stay for up to half a year in the lymph nodes, during which time X-ray analyses allow the follow-up of lymph node size and architecture. This diagnostic has been used in cancer patients with metastases in the lymph nodes and in lymphatic malignancies, such as lymphoma. The use of radioactive tracers, e.g., in lymphoscintigraphy, can also be used. Preferably, a plurality of the aforementioned measurements are conducted to determine the presence or absence of LECs and/or pre-LECs in an isolated cell population.

Compositions Comprising Adipose-Derived LECs and/or Pre-LECs

In accordance with the aforementioned approaches, raw adipose tissue is processed to substantially remove mature adipocytes and connective tissue thereby obtaining a heterogeneous plurality of adipose tissue-derived cells comprising LECs and/or pre-LECs suitable for placement within the body of a subject. The extracted LECs and/or pre-LECs and/or LEC progenitors may be provided in a neat composition comprising these cells substantially free from mature adipocytes and connective tissue or in combination with an inactive ingredient (e.g., a carrier) or a second active ingredient (e.g., adipose-derived stem cell and/or adipose-derived endothelial cell). The cells may be placed into the recipient alone or in combination (e.g., in a single composition or co-administered) with biological materials, such as cells, tissue, tissue fragments, or stimulators of cell growth and/or differentiation, supports, prosthetics, or medical devices. The composition may include additional components, such as cell differentiation factors, growth promoters (including FLT-4 ligands, e.g., as disclosed by Alitalo, et al., in U.S. Pat. No. 6,730,658), immunosuppressive agents, or medical devices, as discussed herein, for example. In some embodiments, the cells, with any of the above mentioned additives, are placed into the person from whom they were obtained (e.g., autologous transfer) in the context of a single operative procedure with the intention of providing a therapeutic benefit to the recipient.

Accordingly, aspects of the invention include compositions that comprise, consist, or consist essentially of a refined, enriched, concentrated, isolated, or purified adipose-derived cell population comprising LECs and/or pre-LECs and mixtures of these cells with a biological material, additive, support, prosthetic, or medical device, including but not limited to, unprocessed adipose tissue, collagen matrix or support, cell differentiation factors, growth promoters, immunosuppressive agents, processed adipose tissue containing adipose-derived stem cells and/or progenitor cells, and cell populations already containing an enriched amount of LECs and/or pre-LECs. In some embodiments, the aforementioned compositions comprise an amount or concentration of refined, isolated, or purified adipose-derived LECs and/or pre-LECs that is greater than or equal to 0.5%-1%, 1-2%, 2%-4%, 4%-6%, 6%-8%, 8%-10%, 10%-20%, 20%-30%, 30%-40%, 40%-50%, 50%-60%, 60%-70%, 70%-80%, 80%-90%, or 90%-100% LECs and/or pre-LECs, as compared to the total adipose-derived cell population. In some embodiments, the adipose-derived LEC and/or pre-LEC cells express an amount of, e.g., FLT-4, and/or CD45, and/or CD31, and/or CD34, and/or podoplanin, and/or LYVE-1, and/or Prox-1.

In some embodiments, the adipose-derived cell population that comprises LECs and/or pre-LECs described herein is formulated in compositions that include at least one pharmaceutically acceptable diluent, adjuvant, or carrier substance, using any available pharmaceutical chemistry techniques. Generally, this entails preparing compositions that are essentially free of impurities that could be harmful to humans or animals.

Appropriate salts and buffers can be employed to stabilize and to facilitate uptake of the adipose-derived cell population that comprises LECs and/or pre-LECs. Compositions contemplated herein can comprise an effective amount of the LECs or pre-LECs in a pharmaceutically acceptable carrier or aqueous medium.

Administration of the compositions described herein can be via any common route so long as the target tissue is available via that route. Compositions administered according to the methods described herein may be introduced into the subject by, e.g., by intravenous, intradermal, intramuscular, intramammary, intraperitoneal, intrathecal, retrobulbar, intrapulmonary (e.g., term release); by oral, sublingual, nasal, anal, vaginal, or transdermal delivery, or by surgical implantation at a particular site. The introduction may consist of a single dose or a plurality of doses over a period of time. Vehicles for cell therapy agents are known in the art and have been described in the literature. See, for example Remington's Pharmaceutical Sciences, 18th Ed. (1990, Mack Publ. Co, Easton Pa. 18042) pp 1435-1712, incorporated herein by reference. Sterile solutions are prepared by incorporating the adipose-derived cell population that comprises LECs and/or pre-LECs in the required amount in the appropriate buffer with or without various of the other components described herein.

Combination therapy with any two or more agents described herein also is contemplated as an aspect of the invention. Similarly, every combination of agents described herein, packaged together as a new kit, or formulated together as a single composition, is considered an aspect of the invention. Compositions for use according to aspects of the invention preferably include the adipose-derived cell population that comprises LECs and/or pre-LECs formulated with a pharmaceutically acceptable carrier. The cells can also be applied with additives to enhance, control, or otherwise direct the intended therapeutic effect. For example, in some embodiments, the adipose-derived cell population that comprises LECs and/or pre-LECs can be further purified by use of antibody-mediated positive and/or negative cell selection to enrich the cell population to increase efficacy, reduce morbidity, or to facilitate ease of the procedure. Similarly, cells can be applied with a biocompatible matrix, which facilitates in vivo tissue engineering by supporting and/or directing the fate of the implanted cells. In the same way, cells can be administered following genetic manipulation such that they express gene products that are believed to or are intended to promote the therapeutic response provided by the cells. Examples of manipulations include manipulations to control (increase or decrease) expression of factors promoting lymphangiogenesis (for example VEGF-C) or expression of developmental genes promoting differentiation (for example Prox-1).

The adipose-derived cell population that comprises LECs and/or pre-LECs can be applied alone or in combination with other cells, tissue, tissue fragments, growth factors such as VEGF-C and other known lymphangiogenic growth factors, biologically active or inert compounds, resorbable plastic scaffolds, or other additive intended to enhance the delivery, efficacy, tolerability, or function of the population. The adipose-derived cell population that comprises LECs and/or pre-LECs can also be modified by insertion of DNA or by placement in cell culture in such a way as to change, enhance, or supplement the function of the cells for derivation of a structural or therapeutic purpose.

A number of molecules have been reported to be involved in LEC differentiation, including, but not limited to, VEGF-C, VEGF-D, VEGFR-3, Prox-1, Syk/SLP76, podoplanin, Ang-2, Nrp2, FOXC2, etc. In addition, the importance of extracellular matrix (ECM) molecules in lymphangiogenesis, and molecules including hyaluronan, integrins, reelin, IL-7, and matrix metalloproteinases in LEC growth, migration, tube formation and survival, have been reported. (See, e.g., Ji, R. C., 2006, "Lymphatic Endothelial Cells, Lymphangiogenesis, and Extracellular Matrix," Lymphat. Res. Biol. 4(2):83-100.) In some embodiments, one or more of these molecules is used to enhance or modify the activity of the cells, e.g., by use in culture of the cells or by co-administration.

In more embodiments, the adipose-derived cell population that comprises LECs and/or pre-LECs are combined with a gene encoding a pro-drug converting enzyme which allows cells to activate pro-drugs within the site of engraftment, that is, within a tumor. Addition of the gene (or combination of genes) can be by any technology known in the art including but not limited to adenoviral transduction, "gene guns," liposome-mediated transduction, and retrovirus or lentivirus-mediated transduction, plasmid, or adeno-associated virus. Cells can be implanted along with a carrier material bearing gene delivery vehicle capable of releasing and/or presenting genes to the cells over time such that transduction can continue or be initiated in situ. Particularly when the cells and/or tissue containing the cells are administered to a patient other than the patient from whom the cells and/or tissue were obtained, one or more immunosuppressive agents can be administered to the patient receiving the cells and/or tissue to reduce, and preferably prevent, rejection of the transplant.

Still more embodiments concern the ex vivo transfection of an adipose-derived cell population that comprises LECs and/or pre-LECs and subsequent transfer of these transfected cells to subjects. It is contemplated that such embodiments can be an effective approach to upregulate in vivo levels of the transferred gene and for providing relief from a disease or disorder resulting from under-expression of the gene(s) or otherwise responsive to upregulation of the gene (see e.g., Gelse, et al., 2003, "Articular cartilage repair by gene therapy using growth factor-producing mesenchymal cells," Arthritis Rheum. 48:430-41; Huard, et al, 2002, "Muscle-derived cell-mediated ex vivo gene therapy for urological dysfunction," Gene Ther. 9:1617-26; Kim, et al., 2002, "Ex vivo gene delivery of IL-1Ra and soluble TNF receptor confers a distal synergistic therapeutic effect in antigen-induced arthritis," Mol. Ther. 6:591-600, all incorporated herein by reference). Delivery of an adipose-derived cell population that comprises LECs and/or pre-LECs to appropriate cells is effected ex vivo, in situ, or in vivo by use of vectors, and more particularly viral vectors (e.g., adenovirus, adeno-associated virus, or a retrovirus), or ex vivo by use of physical DNA transfer methods (e.g., liposomes or chemical treatments). See, for example, Anderson, 1998, "Human Gene Therapy," Nature Suppl. to vol. 392 (6679): 25-20, incorporated by reference herein. Gene therapy technologies are also reviewed by Friedmann, 1989, "Progress toward human gene therapy," Science 244(4910):1275-1281, Verma (1990), "Gene therapy." Scientific American 263(5): 68-84, and Miller (1992), "Human gene therapy comes of age," Nature, 357:455-460, all incorporated by reference herein. An adipose-derived cell population that comprises LECs and/or pre-LECs can be cultured ex vivo in the presence of an additive (e.g., a compound that induces differentiation or lymphatic vessel formation) in order to proliferate or to produce a desired effect on or activity in such cells. Treated cells can then be introduced to a subject.

In some embodiments, the ex vivo gene therapy is conducted locally, e.g., to the site of edema. For example, by using catheter-mediated transfer an adipose-derived cell population that comprises LECs and/or pre-LECs can be transferred into a lymphatic vessel of the mammalian subject. Materials and methods for local delivery are reviewed, e.g., in Lincoff, et al. (1994), "Local drug delivery for the prevention of restenosis. Fact, fancy, and future," Circulation, 90: 2070-2084, hereby expressly incorporated by reference. For example, adipose-derived cell population that comprises LECs and/or pre-LECs can be provided to a subject by an infusion-perfusion balloon catheter (preferably a microporous balloon catheter), such as those that have been described in the literature for intracoronary drug infusions. See, e.g., U.S. Pat. No. 5,713,860 (Intravascular Catheter with Infusion Array); U.S. Pat. No. 5,087,244; U.S. Pat. No. 5,653,689; Wolinsky, et al. (1990) (Wolinsky Infusion Catheter), "Use of a perforated balloon catheter to deliver concentrated heparin into the wall of the normal canine artery," J. Am. Coll. Cardiol. 15: 475-481; and Lambert et al., 1993, "Local drug delivery catheters: functional comparison of porous and microporous designs," Coron. Artery Dis. 4: 469-475; all of which are incorporated herein by reference in their entirety. Use of such catheters for site-directed somatic cell gene therapy is described, e.g., in Mazur, et al., 1994, "Coronary restenosis and gene therapy," Texas Heart Institute Journal 21: 104-111, hereby expressly incorporated by reference.

Aspects of the invention also concern the ex vivo transfection of LECs or pre-LECs with a gene encoding a therapeutic polypeptide, and administration of the transfected cells to the mammalian subject. Procedures for seeding a vascular graft with genetically modified endothelial cells are described in, e.g., U.S. Pat. No. 5,785,965, "VEGF gene transfer into endothelial cells for vascular prosthesis," hereby expressly incorporated by reference in its entirety.

U.S. Pat. App. Pub. No. 2006/0088532, titled "Lymphatic and blood endothelial cell genes," provides methods for transforming cells with genes for use in treating impaired lymphatic function, and lists, inter alia, selected classes of genes differentially expressed in BECs and LECs, and a list of LEC-specific genes (Tables 1 and 2, respectively). For example, hereditary lymphedema with distichiasis has been attributed to mutations in the FOXC2 gene, and a predictive mutational model reported by Berry, et al., 2005, "The Establishment of a Predictive Mutational Model of the Forkhead Domain through the Analyses of FOXC2 Missense Mutations Identified in Patients with Hereditary Lymphedema with Distichiasis," Human Molecular Genetics 14(18):2619-2627. Screening and therapy for hereditary lymphatic disorders is also described in, e.g., U.S. Pat. App. Pub. No. 2003/026759, "Screening and Therapy for Lymphatic Disorders Involving the FLT-4 Receptor Tyrosine Kinase (VEGF-R3)," hereby expressly incorporated by reference. It is contemplated that any one or more of the aforementioned genes can be expressed in an adipose-derived cell population that comprises LECs and/or pre-LECs.

In some embodiments, the administering step comprises implanting a prosthetic or medical device (e.g., intravascular stent) in the mammalian subject, where the stent is coated or impregnated with an adipose-derived cell population that comprises LECs and/or pre-LECs. Exemplary materials for constructing valves, stents or grafts coated or seeded with transfected endothelial cells are described in Pavcnik, et al., 2004, "Second-generation percutaneous bioprosthetic valve: a short-term study in sheep," Eur. J. Endovasc. Surg. 40:1223-1227, and Arts, et al., 2002, "Contaminants from the Transplant Contribute to Intimal Hyperplasia Associated with Microvascular Endothelial Cell Seeding," Eur. J. Endovasc. Surg. 23:29-38, incorporated herein by reference. See also U.S. patent application Ser. No. 11/317,422, entitled CELL-LOADED PROSTHESIS FOR REGENERATIVE INTRALUMINAL APPLICATIONS, filed Dec. 22, 2005, incorporated herein by reference. For example, in one variation, a synthetic valve that comprises an adipose-derived cell population that comprises LECs and/or pre-LECs is sutured to a square stainless steel stent. The square stent has a short barb at each end to provide anchors for the valve during placement, and the submucosa membrane is slit at the diagonal axis of the stent to create the valve opening.

Surfaces of the synthetic valve can be coated with a transfected or non-transfected adipose-derived cell population that comprises LECs and/or pre-LECs, e.g., by placing the synthetic valve in an appropriate cell culture medium for 1-3 days prior to implantation to allow for complete coverage of valve surface with the cells.

In another embodiment, the administering step comprises implanting an intravascular stent in the mammalian subject, where the stent is coated or impregnated, as described in literature cited above and reviewed in Lincoff, et al., 1994. A metal or polymeric wire for forming a stent is coated with a composition such as a porous biocompatible polymer or gel that is impregnated with (or can be dipped in or otherwise easily coated immediately prior to use with) a transfected or non-transfected adipose-derived cell population that comprises LECs and/or pre-LECs. The wire is coiled, woven, or otherwise formed into a stent suitable for implantation into the lumen of a vessel using conventional materials and techniques, such as intravascular angioplasty catheterization. Exemplary stents that may be improved in this manner are described and depicted in U.S. Pat. Nos. 5,800,507 and 5,697,967 (Medtronic, Inc., describing an intraluminal stent comprising fibrin and an elutable drug capable of providing a treatment of restenosis); U.S. Pat. No. 5,776,184 (Medtronic, Inc., describing a stent with a porous coating comprising a polymer and a therapeutic substance in a solid or solid/solution with the polymer); U.S. Pat. No. 5,799,384 (Medtronic, Inc., describing a flexible, cylindrical, metal stent having a biocompatible polymeric surface to contact a body lumen); and U.S. Pat. Nos. 5,824,048, 5,679,400 and 5,779,729; all of which are hereby expressly incorporated herein by reference in their entirety.

As disclosed herein, the adipose-derived cell population that comprises LECs and/or pre-LECs may be provided to the subject, or applied directly to the damaged tissue, or in proximity to the damaged tissue, without further processing or following additional procedures to further purify, modify, stimulate, or otherwise change the cells. For example, the cells obtained from a patient may be provided back to said patient without culturing the cells before administration. In several embodiments, the collection and processing of adipose tissue, as well as, administration of the adipose-derived cell population that comprises LECs and/or pre-LECs is performed at a patient's bedside. In a preferred embodiment the cells are extracted from the adipose tissue of the person into whom they are to be implanted, thereby reducing potential complications associated with antigenic and/or immunogenic responses to the transplant. However, the use of cells extracted from another individual is also contemplated.

In accordance with the invention herein disclosed, the adipose tissue-derived cells can be delivered to the patient soon after harvesting the adipose tissue from the patient. For example, the cells may be administered immediately after the processing of the adipose tissue to obtain a composition of adipose tissue-derived stem cells. In one embodiment, the preferred timing of delivery should take place on the order of hours to days after diagnosis of edema or of a procedure likely to place the patient at risk for developing edema. In another embodiment, the harvest and, in certain cases the treatment, can take place in advance of a procedure likely to induce a lymphatic disorder or edema. Ultimately, the timing of delivery will depend upon patient availability and the time required to process the adipose tissue. In another embodiment, the timing for delivery may be relatively longer if the cells to be delivered to the patient are subject to additional modification, purification, stimulation, or other manipulation, as discussed herein. Furthermore, the adipose-derived cell population that comprises LECs and/or pre-LECs may be administered multiple times. For example, the cells may be administered continuously over an extended period of time (e.g., hours), or may be administered in multiple injections extended over a period of time. In certain embodiments, an initial administration of the adipose-derived cell population that comprises LECs and/or pre-LECs will be administered within about 12 hours after diagnosis of lymphatic disease or disorder or performance of a procedure likely to induce development of lymphatic insufficiency, such as at 6 hours, and one or more doses of cells will be administered at 12 hour intervals.

The number of the adipose-derived cell population that comprises LECs and/or pre-LECs administered to a patient may be related to the cell yield after adipose tissue processing. In addition, the dose delivered will depend on the route of delivery of the cells to the patient. Fewer cells may be needed when intra-lymphatic delivery systems are employed, as these systems and methods can provide the most direct pathway for treating lymphatic conditions. The cell dose administered to the patient will also be dependent on the amount of adipose tissue harvested and the body mass index of the donor (as a measure of the amount of available adipose tissue). The amount of tissue harvested will also be determined by the extent of the injury or insufficiency. Multiple treatments using multiple tissue harvests or using a single harvest with appropriate storage of cells between applications are within the scope of this invention.

A portion of the total number of cells may be retained for later use or cryopreserved. Portions of the processed adipose tissue may be stored before being administered to a patient. For short term storage (e.g., less than 6 hours) cells may be stored at or below room temperature in a sealed container with or without supplementation with a nutrient solution. Medium term storage (e.g., less than 48 hours) is preferably performed at 2-8° C. in an isosmotic, buffered solution (for example Plasmalyte®) in a container composed of or coated with a material that prevents cell adhesion. Longer term storage is preferably performed by appropriate cryopreservation and storage of cells under conditions that promote retention of cellular function, such as disclosed in PCT App. No. PCT/US02/29207, filed Sep. 13, 2002 and U.S. Pat. App. Ser. No. 60/322,070, filed Sep. 14, 2001, the contents of both of which are hereby expressly incorporated by reference.

In some embodiments, the amount of adipose derived cells (e.g., an enriched, concentrated, isolated, or purified population of the adipose-derived cells comprising LECs and/or pre-LECs), which is provided to a subject in need thereof is greater than or equal to about 10,000, 20,000, 30,000, 40,000, 50,000, 60,000, 70,000, 80,000, 90,000, 100,000, 110,000, 120,000, 130,000, 140,000, 150,000, 160,000, 170,000, 180,000, 190,000, or 200,000 cells and the amount of LECs and/or pre-LECs in said population of adipose derived cells can be greater than or equal to 0.5%-1%, 1%-2%, 2%-4%, 4%-6%, 6%-8%, 8%-10%, 10%-20%, 20%-30%, 30%-40%, 40%-50%, 50%-60%, 60%-70%, 70%-80%, 80%-90%, or 90%-100% of the total population of adipose derived cells. The dose can be divided into several smaller doses, e.g., for administering over a period of time or for injection into different parts of the affected tissue, e.g., by local injection. However, this dosage can be adjusted by orders of magnitude to achieve the desired therapeutic effect.

The cells can also be subjected to cell culture on a scaffold material prior to being implanted. Thus, tissue engineered valves, lymph vessels, and other structures such as lymph nodes could be synthesized on natural or synthetic matrices or scaffolds using ADC prior to insertion or implantation into the recipient.

Many routes of administration can be suitable for the therapeutics described herein. In some variations, oral, intravenous, intraarterial, and other systemic administrations are used. In some variations, local delivery to an edematous limb or other portion of the body, such as administered subcutaneously at a site of edema, is contemplated.

In some embodiments, direct administration of cells to the site of intended benefit is preferred. This can be achieved by local injection into the tissue, direct injection into a lymph node or lymph vessel, the spleen, through insertion of a suitable cannula, by arterial or venous infusion (including retrograde flow mechanisms) or by other means disclosed herein or known in the art.

The adipose-derived cell population that comprises LECs and/or pre-LECs can be applied by several routes including systemic administration by venous or arterial infusion (including retrograde flow infusion) or by direct injection into the lymphatic system. Systemic administration, particularly by peripheral venous access, has the advantage of being minimally invasive relying on the natural transport of cells from the blood to the lymph. The adipose-derived cell population that comprises LECs and/or pre-LECs can be injected in a single bolus, through a slow infusion, or through a staggered series of applications separated by several hours or, provided cells are appropriately stored, several days or weeks. The adipose-derived cell population that comprises LECs and/or pre-LECs can also be applied by use of catheterization such that the first pass of cells through the area of interest is enhanced by using balloons to manage lymph flow. As with peripheral venous access, the adipose-derived cell population that comprises LECs and/or pre-LECs may be injected through the catheters in a single bolus or in multiple smaller aliquots. Cells can also be injected into interstitial space.

As previously set forth above, in a preferred embodiment, the adipose-derived cell population that comprises LECs and/or pre-LECs is administered directly into the patient. In other words, the active cell population (e.g., the LECs, LEC progenitors, stem cells and/or combinations thereof) are administered to the patient without being removed from the system or exposed to the external environment of the system before being administered to the patient. Providing a closed system reduces the possibility of contamination of the material being administered to the patient. Thus, processing the adipose tissue in a closed system provides advantages over existing methods because the active cell population is more likely to be sterile. In some embodiments, the only time the adipose-derived cell population that comprises LECs and/or pre-LECs are exposed to the external environment, or removed from the system, is when the cells are being withdrawn into an application device and administered to the patient. In other embodiments, the application device can also be part of the closed system. Accordingly, a complete closed system is maintained from removal of the adipose tissue from the subject (e.g., cannula) to introduction to the subject (e.g., application device). Thus, the cells used in these embodiments are may be processed for culturing or cryopreservation and may be administered to a patient without further processing, or may be administered to a patient after being mixed with other tissues, cells, or additives.

In other embodiments, at least a portion of the adipose-derived cell population that comprises LECs and/or pre-LECs can be stored for later implantation/infusion. The population may be divided into more than one aliquot or unit such that part of the population of cells is retained for later application while part is applied immediately to the patient. Moderate to long-term storage of all or part of the cells in a cell bank is also within the scope of this invention, as disclosed in U.S. patent application Ser. No. 10/242,094, entitled PRESERVATION OF NON EMBRYONIC CELLS FROM NON HEMATOPOIETIC TISSUES, filed Sep. 12, 2002, which claims the benefit of U.S. App. Ser. No. 60/322,070, filed Sep. 14, 2001, the contents of both expressly incorporated herein by reference. At the end of processing, the concentrated cells may be loaded into a delivery device, such as a syringe, for placement into the recipient by any means known to one of ordinary skill in the art. The adipose-derived cell population that comprises LECs and/or pre-LECs with or without an additive can be used in several therapeutic methods as described in the following section.

Therapeutic Methods

Aspects of the invention concern methods of tissue transplantation, methods of inducing expansion of lymphatic vessels, and methods of treatment of various lymphatic diseases, which entail providing an adipose-derived cell population that comprises LECs and/or pre-LECs to a subject that has been identified as one in need of tissue transplantation, an induction of lymphatic vessels, and/or a subject suffering from a lymphatic disease. The identification of a subject in need of a tissue transplantation, an induction of expansion of lymphatic vessels, or treatment of a lymphatic disease (e.g., a patient suffering from a disease of the lymphatic system) can be accomplished by a clinician or physician using evaluation techniques known in the field of medicine (e.g., biopsy, clinical evaluation, and diagnostic procedures). Evaluation methods are described in, e.g., U.S. Pat. App. Pub. 2006/0025338, including: examination of tissue biopsies, e.g., for the presence of tortured lymphatic vessels and/or the presence of SMCs/PCs through appropriate microscopy techniques; identification of markers for lymphatic endothelia, SMCs/PCs, and other cell types; immunohistochemistry and fluorescence microlymphangiography to assay for arterial endothelial cell markers including ephrinB2, notch1-notch4, jagged1, Dll1, Dll4, transcription factors Hey1 and Hey2, hyaluronan receptor CD44, and neuropilin-1, venous endothelial cell markers including EphB4 and neuropilin-2, lymphatic endothelial markers including VEGFR-3 and LYVE-1, podoplanin and PROX1; computed tomography (CT) to show the presence of edema; X-ray lymphography involving the injection of a substance into the lymphatic vessels and viewing by X-ray; assessing capillary density using simultaneous dual-site fluorescence angiography (fluorescence microlymphography FML); measuring the diameter of lymphatic vessels using FML; computer analysis of images generated by FML; isotope lymphography (lymphoscintigraphy or lymphangioscintigraphy), to provide images of lymphatics and lymph nodes as well as quantitative data on tracer (lymph) transport; direct oil contrast lymphography; non-invasive duplex-Doppler studies; phlebography to examine the deep venous system; magnetic resonance imaging; ultrasonography, indirect (water soluble) lymphography; lymph node biopsy; CVI diagnosis based on physical examination; and Doppler bidirectional flow studies and Doppler color-flow studies.

Other methods to identify a subject in accordance with the methods provided herein include the teachings of U.S. Pat. App. Pub. No. 2004/0127790, titled "Measurement of Capillary Related Interstitial Fluid Using Ultrasound Methods and Devices," herein expressly incorporated by reference, which describes the use of ultrasound to measure capillary related interstitial fluid. Accordingly, the methods as described can be used for continuous or intermittent monitoring, and applied to assessment of cardiac, renal, capillary and hepatic function. U.S. Pat. No. 5,957,861, "Impedance Monitor For Discerning Edema Through Evaluation Of Respiratory Rate," incorporated herein by reference, describes an implantable device that measures electrical impedence in tissue to evaluate edema. Methods for screening patients for genetic mutations associated with or responsible for lymphatic dysfunction, whether or not the patients are symptomatic, are described in, e.g., U.S. Pat. App. Pub. No. 2006/0088532, "Lymphatic and Blood Endothelial Cell Genes," incorporated herein by reference. U.S. Pat. No. 5,114,703, incorporated herein by reference in its entirety, describes the use of contrast agents of a smaller size that are suitable for use in imaging, which agents are in particulate form and are adapted to be preferentially taken up by the lymphatic system upon percutaneous administration. This patent discloses as contrast agents, e.g. radiopaque materials, MRI imaging agents, and ultrasound imaging agents. Any one or a combination of the aforementioned approaches can be used to identify a subject in need of tissue transplantation, an induction of lymphatic vessels, and/or a subject suffering from a lymphatic disease. Methods of screening for an endothelial cell disorder in a mammalian subject are also known. Evaluation can be performed by measuring the growth rate of the cells and correlating the growth rate with a disorder. The growth rate determined in the method is the rate of cell division per unit time, determined by any one of a number of techniques known in the art. The correlation of the growth rate with a disorder can involve a positive or negative correlation.

Once a subject in need is identified, the identified subject is provided a therapeutically effective amount of an adipose-derived cell population that comprises LECs and/or pre-LECs. In some embodiments, a method of treating a patient includes steps of: a) providing a tissue removal system; b) removing adipose tissue from a patient using the tissue removal system, the adipose tissue having a concentration of therapeutic cells; c) processing at least a part of the adipose tissue to obtain a concentration of therapeutic cells other than the concentration of therapeutic cells of the adipose tissue before processing; and d) administering the therapeutic cells to a patient without removing the therapeutic cells from the tissue removal system before they are ready to be administered to the patient using several methods known to one of ordinary skill in the art, including but not limited to, injection into lymph nodes, into the lymphatic vessels, into the blood system, and into tissues and tissue space.

In some embodiments, an adipose-derived cell population that comprises LECs and/or pre-LECs used to treat conditions, diseases, and disorders of the lymphatic system. Adipose tissue-derived cells of the invention have properties that can contribute to modulating expansion, repair, or regeneration of lymph vessels. These properties include, among other things, the ability to synthesize and secrete growth factors that modulate LEC expansion, as well as the ability to proliferate and differentiate into cells directly participating in lymphangiogenesis. The methods and compositions described herein can also be used to modulate re-growth or permeability of lymphatic vessels in, for example, organ or tissue transplant patients. LECs, LEC progenitors and/or pre-LECs can be used to mitigate the loss of axillary lymphatic vessels following surgery in cancer patients, e.g., breast cancer patients. Changes in lymph flow caused by radiation therapy can also be treated using the methods of the invention. The methods and compositions described herein can be useful in treating or preventing inflammation, edema, or aplasia of the lymphatic vessels, lymphatic obstruction, elephantiasis, and Milroy's disease. LECs, LEC progenitors and/or pre-LECs can further be used to stimulate lymphocyte production and maturation, and to promote or inhibit trafficking of leukocytes between tissues and lymphatic vessels or to affect migration in and out of the thymus.

Conditions specifically contemplated for treating using the methods described herein include, but are not limited to: obesity; lymphatic vessel aplasia; edema; lymphatic vessel loss or damage due to surgical intervention; lymphatic vessel loss, damage or deficiency due to organ or tissue transplant; reduced lymphatic vessel function due to lymphatic vessel blockage; lymphatic vessel occlusion; elephantiasis; cardiovascular disease; heart disease; chronic granulomatous disease (CGD); lymphatic malignancies, including Hodgkin's Disease, non-Hodgkin's lymphoma, and Castleman Disease; non-lymphatic malignancies, including breast cancer, ovarian cancer, colorectal cancer, lung cancer, liver cancer, stomach cancers, pancreatic cancer, and CNS cancer.

Myocardial edema can result in compromised cardiac function (see, e.g., Mehlhorn, et al., 2001, "Myocardial Fluid Balance," Eur. J. Cardio-thoracic Surg. 20:1220-1230). Causes of myocardial edema include cardiac surgery, e.g., cardiopulmonary bypass and cardioplegia, as well as myocardial ischemia, arterial hypertension, pulmonary hypertension, and cardiac transplantation. Some of the methods described herein can be used to increase lymphatic function either directly, e.g., through cell engraftment, or indirectly, e.g., by secreting factors that stimulate growth or activity of the existing lymphatic system. Secreted factors can act on host cells and/or cells administered according to the methods of the invention. Regenerative cells can be administered by methods described in the art and herein, e.g., by intracoronary or intramyocardial injection. In disorders where damage to the blood vessel endothelial cells results in increased vessel permeability, the cells of the invention can penetrate the blood vessel walls to enter the surrounding tissue.

Some of the methods described herein can be used in conjunction with tissue or cell transplantation (e.g., pancreatic islet transplantation) to expedite the formation of lymphatics in and around the transplant. Depending on the type of tissue or cells to be transplanted, lymphatic regenerative cells can be provided with the transplant material as a mixture or they can be administered separately by other methods described herein and in the literature, e.g., intravenously, subcutaneously, intraarterially, etc. Additives, e.g., growth factors and immunosuppressive agents, can be co-administered as desired. Administration of the additives as well as the adipose-derived cell population that comprises LECs and/or pre-LECs can take place before, during or after the tissue transplantation procedure. The adipose-derived cell population that comprises LECs and/or pre-LECs can also be administered via a scaffold, e.g., a resorbable scaffold known in the art.

The methods described herein are contemplated for use in treating obesity related to lymphatic defects. Obesity has also been related to defective lymphatic system function. For example, mice having a defect in Prox1, a gene needed for lymphatic vascular development, were reported to develop adult-onset obesity (Harvey, et al., 2005, "Lymphatic Vascular Defects Promoted by Prox1 Haploinsufficiency Cause Adult-Onset Obesity," Nature Genetics 37[10]:1072-1081). According to the report, defects in the lymphatic vasculature of the mice were the cause of the obesity phenotype. For lymphatic system disorders resulting from genetic defects, treatment using non-autologous lymphatic regenerative cells might prove beneficial. Administration of non-autologous cells using the methods of the invention can be accomplished using methods known in the art and described herein and in the literature.

Wound-healing is also dependent on lymphatic function. For example, impaired wound healing is a common complication of diabetes. Maruyama, et al., in "Decreased Macrophage Number and Activation Lead to Reduced Lymphatic Vessel Formation and Contribute to Impaired Diabetic Wound Healing" (Am J. Pathol. 170(4):1178-91, April 2007), reported that both the presence of activated macrophages and the formation of lymphatic vessels are rate-limiting to the healing of diabetic wounds. They further reported that cells that co-stain for the macrophage marker F4/80 and the lymphatic markers LYVE-1 and podoplanin contribute to lymphatic vessels in full-thickness wounds, and that LYVE-1-positive lymphatic vessels and CD31-positive blood vessels were significantly reduced in corneal wound healing in diabetic mice compared with control mice.

Aspects of the present invention are also useful for treating patients with wounds including incisional ulcerous or other cutaneous or internal wounds, wounds of diabetic patients, radiation necrosis, skin wounds following surgery, skin abrasions caused my mechanical trauma, caustic agents or burns, cornea following cataract surgery or corneal transplants, mucosal epithelium wounds following infection or drug therapy (e.g., respiratory, gastrointestinal, genitourinary, mammary, oral cavity, ocular tissue, liver and kidney), skin wounds following grafting, and regrowth of blood vessels following angioplasty.

Cells may be administered to a patient in any setting in which lymphatic function is insufficient or abnormal. Examples of such settings include, but are not limited to, primary and secondary edema, and risk of developing edema, among other things. Endothelial cell disorders contemplated by the invention include, but are not limited to, physical loss of lymphatic vessels (e.g., surgical removal of axillary lymph tissue), lymphatic vessel occlusion (e.g., elephantiasis), and lymphangiomas. In a preferred embodiment, the subject, and the adipose-derived cell population that comprises LECs and/or pre-LECs are human. The adipose-derived cell population that comprises LECs and/or pre-LECs may be provided in vitro, or in vivo. The cells may be extracted in advance and stored in a cryopreserved fashion or they may be extracted at or around the time of defined need.

Methods of Screening Compounds

It is contemplated that screening techniques using an adipose-derived cell population that comprises LECs and/or pre-LECs will be useful for the identification of compounds that will augment, stimulate or otherwise increase the effects of the LECs and pre-LECs of the present invention on the lymphatic system and be useful in the treatment of lymphatic disorders in general. It is similarly contemplated that such screening techniques will prove useful in the identification of compounds that will inhibit the ability of LECs and pre-LECs to modulate expansion of the lymphatic system within a developing tumor and thereby reduce the likelihood of metastasis of the tumor via the lymphatic system. In these embodiments, the present invention is directed to a method for determining the ability of a candidate substance to modulate the growth or activity of the lymphatic system.

Another aspect of the invention concerns methods of identifying compounds that modulate expansion of lymphatic cells, the formation of lymphatic vessels or the formation of lymphatic tissue. By some approaches, a test compound is contacted with a composition comprising an adipose-derived cell population that comprises LECs and/or pre-LECs (preferably, a population having FLT-4$^+$ cells). Next, the ability of said test compound to modulate expansion of lymphatic cells, the formation of lymphatic vessels or the formation of lymphatic tissue is determined or measured. A candidate compound that increases or decreases the ability of said adipose-derived cell population that comprises LECs and/or pre-LECs cells to modulate expansion of lymphatic cells, the formation of lymphatic vessels or the formation of lymphatic tissue in comparison to control cells not exposed to the candidate compound is then identified. In some embodiments the adipose-derived cell population that comprises LECs and/or pre-LECs (for example, a population having FLT-4$^+$ cells) is identified as a source of LECs and/or pre-LECs.

In other embodiments, a method of screening for an agent that inhibits lymphatic growth within a tumor is provided. Accordingly, a test compound is contacted with an adipose-derived cell population that comprises LECs and/or pre-LECs (preferably, a population having FLT-4$^+$ cells) and the ability of said compound to modulate expansion of lymphatic cells, the formation of lymphatic vessels or the formation of lymphatic tissue is measured. A candidate compound that inhibits the ability of said cells to modulate expansion of the lymphatic system in comparison to control cells not exposed to the candidate drug is then identified.

To identify a candidate substance as being capable of promoting or inhibiting the growth of a lymphatic endothelial cell network, one could, e.g., measure or determine the presence of growth of LECs, LEC progenitors and pre-LECs of the present invention in the absence of the added candidate substance. One could then add the candidate substance to the co-cultured cells and determine the response of the co-culture in the presence of the candidate substance. A candidate substance that modulates the expansion of lymphatic vessels in the co-culture is indicative of a candidate substance having the desired activity. In in vivo screening assays, the compound can be administered to a model animal, over a period of time and in various dosages, and an alleviation of the symptoms associated with edema or tumor progression or tumor metastasis monitored. Any improvement in one or more of these symptoms can be indicative of the candidate substance being a useful agent.

As used herein the term "candidate substance" refers to any molecule that may potentially act as a modulator of lymphatic vessel expansion. Such an agent may be a protein or fragment thereof, a small molecule inhibitor, or even a nucleic acid molecule.

Additionally, one can acquire from commercial sources small molecule libraries that are believed to meet the basic criteria for useful drugs in an effort to identify useful compounds. Screening of such libraries, including combinatorially generated libraries (e.g., peptide libraries), is a rapid and efficient way to screen large number of related (and unrelated) compounds for activity. Combinatorial approaches also lend themselves to rapid evolution of potential drugs by the creation of second, third and fourth generation compounds derived from active, but otherwise undesirable compounds. The application of such libraries to the adipose-derived cell population that comprises LECs and/or pre-LECs prepared as described herein is also contemplated.

Candidate compounds may include fragments or parts of naturally-occurring compounds or may be found as active combinations of known compounds which are otherwise inactive. It is proposed that compounds isolated from natural sources, such as animals, bacteria, fungi, plant sources, including leaves and bark, and marine samples may be assayed as candidates for the presence of potentially useful pharmaceutical agents. It will be understood that the pharmaceutical agents to be screened could also be derived or synthesized from chemical compositions or manmade compounds.

As described, the LECs, pre-LECs, and LEC progenitors of the present invention can be cultured according to methods known in the art, and the cultured cells used in drug screening assays. "Effective amounts" of the candidate agent in certain circumstances are those amounts effective to reproducibly produce an alteration in the modulation of expansion of lymphatic vessels. Significant changes in activity and/or expression will be those that are represented by alterations in activity of, e.g., 30%-40%, and preferably, by changes of at least about 50%, with higher values of course being possible.

The following examples are provided to demonstrate particular situations and settings in which this technology may be applied and are not intended to restrict the scope of the invention and the claims included in this disclosure.

EXAMPLES

Example I

Isolation of an Adipose-Derived Cell Population that Comprises LECs and/or Pre-LECs Cell processing procedures that employed either a cell processing unit as described herein, or a manual method, were used to successfully isolate an adipose-derived cell population comprising LECs and/or pre-LECs. In manual processing, lipoaspirate removed from the patient was warmed in a sterile container in a 37° C. water bath. At this point, if bloody, the lower portion (blood-saline mixture) was removed aseptically using vacuum suction and discarded. The remaining material was then placed in a sterile separatory funnel with an equal volume of pre-warmed sterile saline, shaken gently, and the phases allowed to separate. Upon completion of separation, multiple layers were observed, with the adipose tissue floating on top and the blood-saline mixture below the adipose tissue layer. The stopcock was then opened to allow removal of the blood-saline mixture into a waste container. The washes were repeated until most of the red blood cells have been removed from the lipoaspirate.

The lipoaspirate was then removed to a sterile bottle and digested with collagenase and thermolysin. A volume of pre-warmed sterile buffered saline, equal to the volume of lipoaspirate was added. Enzyme was then combined with the washed lipoaspirate/saline solution. The enzyme was added through a sterile 0.2 μm syringe filter. Digestion was allowed to take place with gentle shaking, e.g., on a thermal shaker, pre-warmed to 35-38° C., for 20±5 minutes. When digestion was complete (e.g., after approximately 5% of the initial amount of adipose tissue remained), the solution was poured into a fresh sterile glass separatory funnel and incubated for 5-10 minutes for phase separation to occur. The undigested adipose tissue and free lipid floated.

The non-buoyant solution was then removed, without the buoyant later, through a sterile 265 μm filter and rinsed with buffered-saline. The mixture was shaken gently and allowed 5-10 minutes for phase separation again. Undigested adipose tissue and free lipid floated. The non-buoyant solution was removed through a new, sterile 265 μm filter and placed into centrifuge tubes. The tubes were centrifuged at 400×g for 5 minutes at room temperature with a low-medium brake speed. The supernatant was removed without disturbing the pellet, and the cells were resuspended in the remaining supernatant or a desired amount of buffered saline. The tubes were centrifuged a second time at 400×g for 5 minutes at room temperature with a low-medium brake speed. The supernatant was removed and the cells resuspended as necessary for further processing. Care was taken throughout the process to ensure that sterility was maintained.

The example below provides an approach to further isolate and purify an adipose-derived cell population that comprises LECs and/or pre-LECs.

Example II

Purification of a Cell Population that Comprises LECs and/or Pre-LECs by Density Gradient This example describes one approach to purify LECs and/or pre-LECs from an adipose-derived cell population that comprises LECs and/or pre-LECs. An adipose-derived cell population that comprises LECs and/or pre-LECs can be obtained as described in Example I. A cell population was further purified by density gradient centrifugation using ficoll-hypaque as follows. The adipose-derived cell population that comprises LECs and/or pre-LECs obtained in Example I was layered onto "Lymphocyte Separatium Medium" (LSM—Mediatech, Inc) and subjected to density gradient centrifugation. The cell suspension was diluted to $10^7$ cells/mL into DPBS ($Ca^{++}$ and $Mg^{++}$ free) and carefully overlayed on top of the LSM to create a sharp cell suspension/LSM interface in 50 mL conical tubes. The tubes were then centrifuged at 400 g with the brake off. For each volume of LSM, 2-3 volumes of cell suspension were used. Centrifugation sediments most of the red blood cells and polymorphonuclear cells, and the mononuclear fraction forms a distinct layer between the PBS and the LSM. After aspiration of the top layer (DPBS), the mononuclear fraction was collected in a new flask and washed using DPBS. Cells were resuspended at $10^7$ cells/mL in Dulbecco's phosphate buffered saline (DPBS). The data provided by the experiments done using these cells confirmed that an adipose-derived cell population comprising LECs and/or pre-LECs is present in adipose tissue. The results also confirmed that an adipose-derived cell population that comprises LECs and/or pre-LECs can be effectively isolated from adipose tissue using a cell processing unit and/or density gradient centrifugation. The example below provides another approach that can be used to isolate or purify LECs and/or pre-LECs from an adipose-derived cell population.

Example III

Purification of a Cell Population that Comprises LECs and/or Pre-LECs by Cell Sorting This example describes a cell sorting approach that was used to further purify the LECs and/or pre-LECs from an adipose-derived cell population that comprises LECs and/or pre-LECs. It should be noted that this approach can be performed in lieu of the density gradient sedimentation procedure provided in Example II or, as presented in this example, in addition to the procedure provided in Example II. An adipose-derived cell population comprising LECs and/or pre-LECs obtained in accordance with the procedure provided in either Example II was strained using a 100 μm cell strainer and resuspended in sorting buffer, which contained D-PBS solution (Ca/Mg++ free) supplemented with 1 mM EDTA, 25 mM HEPES, 1% BSA (or 1% fetal bovine serum) and 10 U/ml DNAse I. FLT-4+ and FLT-4− cells were sorted using the FACSAria according to the manufacturer's instructions.

Example IV

Measurement of FLT-4+ Cells in ADC Preparation

The mononuclear cells were then stained for cytofluorometric assays. The Fc receptors on the adipose-derived cell population were blocked using normal mouse immunoglobulin. Aliquots of 100 µl of the cell suspension were transferred into 12×75 mm centrifuge tubes containing the sorting buffer (D-PBS solution (Ca/Mg++ free) supplemented with 1 mM EDTA, 25 mM HEPES, 1% BSA (or 1% fetal bovine serum) and 10 U/ml bovine DNAse I) described in Example III above, and incubated in the presence of the target-conjugated antibodies for 30 minutes at 4° C. protected from the light. Following this incubation, the unbound antibody was removed by washing the cells twice in 500 µl of DPBS. The cells were then fixed using FACS Lysis buffer (Becton Dickinson) and the data was acquired in the FACSAria cytometer no more than 24 hours after fixation.

Flow cytometry data were evaluated using FACSDiva software. From a plot of FSC-A vs SSC-A, a gate (P1) was drawn to include the nucleated cells. Cells inside this gate were then displayed in a SSC-H vs SSC-W plot and a second gate around low SSC-W cells was drawn (P2). Cells inside P2 were then displayed in a FSC-H vs FSC-W plot and a gate (P3) was drawn around low FSC-W. This strategy was used to eliminate double events from being analyzed as single events. Only cells that fell in P3 were evaluated relative to their reactivity with the target antibodies. Fluorescence minus one (FMO) or isotype controls were used to set up the gates to evaluate positive events. Negative controls were used for all markers. The negative gates were set up to include at least 99.5% of the cells in the control tubes.

Low density cells were evaluated as described above. Between 11.9% and 39.8% of cells in the fraction analyzed were found to express FLT-4 (Table 3).

TABLE 3

| Sample ID | Cells Expressing FLT-4 (%) |
|---|---|
| 471 | 22.9 |
| 468 | 23.2 |
| 469 | 39.8 |
| 473 | 18.5 |
| 512 | 22.6 |
| 529 | 11.9 |

Thus, in this sample population, between 11.9% and 39.8% of the adipose-derived cell population expressed FLT-4, a marker of adult lymphatic endothelial lineage cells. Accordingly, the data provided in this example demonstrate that adipose tissue is a rich source of LECs and/or pre-LECs, which can be isolated using a cell processing unit and further purified using gradient sedimentation and/or cell sorting technology. Further, the data in this example confirms that either the procedures employed in Example II (selective media gradient centrifugation) or this example (cell sorting) can be used to measure the presence or absence of LECs and/or pre-LECs in an adipose-derived cell population.

More approaches to measure and characterize the presence of LECs and/or pre-LECs in an adipose-derived cell population are provided below.

Example V

Characterization of LECs and Pre-LECs Using Flow Cytometry

LEC and pre-LECs were further defined and quantified by multicolor flow cytometry as described in this example. An adipose-derived cell population was obtained and processed using the methods provided in Examples I and II, using antibodies specific for a plurality of markers that are characteristic of LECs and pre-LECs.

As described above, the tissue was collected through vacuum liposuction and rinsed with saline to remove excess blood. An adipose-derived cell population comprising LECs and/or pre-LECs was obtained by enzymatic digestion and centrifugation, and the pelleted nucleated fraction was isolated, washed and stained for cytofluorometric assays. Cells were resuspended at $10^7$ cells/mL in Dulbecco's phosphate buffered saline (DPBS) and the Fc receptors on the cells were blocked using normal mouse immunoglobulin. Aliquots of 100 µl of the cell suspension were then transferred to 12×75 mm centrifuge tubes containing sorting buffer and were incubated in the presence of one of the following antibodies: antibody to CD34 (a marker of mature and immature endothelial cells) conjugated to APC-A; antibody to CD45 (a marker of hematopoietic cells that has been suggested to be associated with circulating LEC progenitor cells (Kerjaschki, et al., 2006)) conjugated to APC-Cy7-A; antibody to CD31 (a marker of mature endothelial cells) conjugated to FITC; and the conjugated FLT-4 antibody used in Example III.

Following the incubation, the unbound antibody was removed by washing the cells twice in 500 µl of DPBS. The cells were then fixed using FACS Lysis buffer (Becton Dickinson) and the data was acquired in the FACSAria cytometer no more than 24 hours after fixation.

Flow cytometry data were evaluated for each tube using FACSDiva software. As described above, from a plot of FSC-A vs SSC-A, a gate (P1) was drawn to include the nucleated cells. Cells inside this gate were then displayed in a SSC-H vs SSC-W plot and a second gate around low SSC-W cells was drawn (P2). Cells inside P2 were then displayed in a FSC-H vs FSC-W plot and a gate (P3) was drawn around low FSC-W. This strategy was used to eliminate double events from being analyzed as single events. Only cells that fell in P3 were evaluated relative their reactivity with the target antibodies. Fluorescence minus one (FMO) or isotype controls were used to set up the gates to evaluate positive events. Negative controls were used for all markers. The negative gates were set up to include at least 99.5% of the cells in the control tubes.

In the three samples, 36.9%, 21.5%, and 5.1% of cells exhibited FLT-4 expression, indicating that the adipose-derived cell population was rich in lymphatic endothelial cells. The percentages of cells found to express certain combinations of the markers tested, as calculated using the FACSDiva software, are shown in Table 4.

TABLE 4

| Markers Expressed | Patient Sample #503 | Patient Sample #523 | Patient Sample #529 |
|---|---|---|---|
| FLT4 | 36.9 | 21.5 | 5.1 |
| FLT4+/CD45+ | 18.6 | 13.8 | 3.8 |
| FLT4+/CD45− | 18.3 | 7.7 | 1.4 |
| FLT4+/CD45+/CD34+ | 2.9 | 1.9 | 1.5 |
| FLT4+/CD45+/CD34− | 15.8 | 11.9 | 2.2 |
| FLT4+/CD45−/CD34+ | 14 | 5.3 | 1.2 |
| FLT4+/CD45−/CD34− | 4.2 | 2.3 | 0.2 |
| FLT4+/CD31bright | 4.5 | 3.5 | 1.5 |
| FLT4+/CD31dim | 22.7 | 14.6 | 2.6 |
| FLT4+/CD31neg | 9.7 | 3.6 | 1.2 |
| FLT4+/CD34+ | 16.9 | 7.3 | 2.7 |
| FLT4+/CD34− | 20 | 14.2 | 2.4 |
| FLT4+/CD34+/CD31bright | 4.4 | 3 | 1.1 |
| FLT4+/CD34+/CD31dim | 5.5 | 2.5 | 0.6 |
| FLT4+/CD34+/CD31neg | 7.1 | 1.8 | 1.1 |
| FLT4+/CD34+/CD31$^{bright}$/CD45+ | 0.7 | 0.7 | 0.8 |
| FLT4+/CD34+/CD31$^{bright}$/CD45− | 3.6 | 2.3 | 0.3 |
| FLT4+/CD34+/CD31$^{dim}$/CD45+ | 1.6 | 0.8 | 0.5 |
| FLT4+/CD34+/CD31$^{dim}$/CD45− | 3.9 | 1.7 | 0.1 |
| FLT4+/CD34+/CD31$^{neg}$/CD45+ | 0.5 | 0.4 | 0.3 |
| FLT4+/CD34+/CD31$^{neg}$/CD45− | 6.6 | 1.4 | 0.8 |
| FLT4+/CD34−/CD31$^{bright}$/CD45+ | 0 | 0.4 | 0.4 |
| FLT4+/CD34−/CD31$^{bright}$/CD45− | 0.1 | 0 | 0 |
| FLT4+/CD34−/CD31$^{dim}$/CD45+ | 14.7 | 11 | 1.9 |
| FLT4+/CD34−/CD31$^{dim}$/CD45− | 2.5 | 1.1 | 0.1 |
| FLT4+/CD34−/CD31$^{neg}$/CD45+ | 1 | 0.6 | 0 |
| FLT4+/CD34−/CD31$^{neg}$/CD45− | 1.6 | 1.2 | 0 |

FIG. 1 shows an analysis of marker expression observed in Sample 503. In general, the population of FLT-4+ cells could be split into three populations based on CD34, CD31, and CD45 expression. One population exhibited high expression of CD31 and CD34 and low to absent expression of CD45 (Gate Q1, FIGS. 16A, 16B). This phenotype is consistent with mature LECs. A second population exhibited expression of CD34 and low to absent expression of both CD45 and CD31, a phenotype that is consistent with one class of pre-LECs (Gate Q2, FIGS. 16A, 16C). The remaining cells exhibited intermediate to absent expression of CD34, intermediate CD31 expression, and were largely positive for CD45 expression (Gate Q1, FIGS. 16A, 16D). This phenotype is consistent with a second class of pre-LECs (Kerjaschki, et al. 2006). Accordingly the adipose-derived cell population obtained using the cell processing unit as described herein yielded appreciable quantities of LECs and pre-LECs.

The percentages of cells observed in the three general populations described are shown in Table 5.

TABLE 5

| Sample ID | FLT-4+ CD31+ CD34+ LECs | FLT-4+ CD31− pre-LECs | FLT-4+ CD45+ pre-LECs |
|---|---|---|---|
| 503 | 4.4 | 7.1 | 20.0 |
| 523 | 3.0 | 1.8 | 14.2 |
| 529 | 1.1 | 1.1 | 2.4 |

In one sample, dual staining with antibodies to FLT-4 and CD14 showed that approximately 56% of FLT-4+ ADC co-expressed CD14. In this analysis, approximately 51% of all ADC expressed FLT-4. Accordingly, the results provided in this example provide more support for the conclusion that an adipose-derived cell population containing LECs and/or pre-LECs can be efficiently isolated from adipose tissue using a cell processing unit as described herein and further isolation and purification can be obtained by isolated and various techniques in cell sorting. The example below provides more evidence of the presence of LECs and/or pre-LECs in an adipose-derived cell population isolated as described herein.

Example VI

Measurement of the Presence or Absence of Markers for LECs and Pre-LECs in an Adipose-Derived Cell Population Using Immunohistochemistry This example provides an immunohistochemistry approach that was used to measure the presence or absence of LEC and/or pre-LEC specific markers on an adipose-derived cell population prepared as described herein. An adipose-derived cell population that comprises LECs and/or pre-LECs was prepared as described in Example II. A cell suspension having approximately a concentration of $10^7$ cells/ml was then prepared from the adipose-derived cell population that comprises LECs and/or pre-LECs. The adipose-derived cell population comprising LECs and/or pre-LECs was subsequently stained for the lymphatic endothelial cell-specific antigens Prox-1 and Lyve-1 as follows. Cytospins were prepared from 100 μl of this suspension, and immunohistochemistry was performed using the Vectastain® Universal Elite ABC Kit (Vector Labs). Conjugated antibodies specific for Prox-1 and Lyve-1 were employed and the cells were costained with hematoxylin.

FIG. 17 shows staining of nucleated cells with Lyve-1 and Prox-1 at 100× magnification, indicating the presence of the lymphatic endothelial cell-specific antigens Prox-1 and Lyve-1 on the isolated adipose derived cell population. The data provided in this example further demonstrates that the adipose-derived cell population prepared as described in Example II contains LECs and/or pre-LECs. This example also provides another approach by which one of skill in the art can measure the presence or absence of LECs and/or pre-LECs in an adipose-derived cell population. The next example teaches yet another approach by which to measure the presence or absence of LECs and/or pre-LECs in an adipose-derived cell population.

Example VII

Further Characterization and Measurement of the Presence or Absence of LECs and Pre-LECs in an Adipose-Derived Cell Population Using a CFU-F Assay As described in this example, an adipose-derived cell population containing LECs and/or pre-LECs was isolated (Example I) and further purified using density gradient centrifugation (Example II) and cell sorting (Example III). Once the cells were sorted into FLT4+ and FLT4− populations, the purified cells were then measured for development of CFU-F.

More specifically, the source of the adipose-derived cell population was 400 ml liposuction fat removed from the hips, thighs and abdomen of a 20-year-old woman. Tissue processing, performed as described in Example I, yielded $6.175×10^6$ cells/ml, or $0.42×10^6$ cells/ml of fat tissue, in Lactated Ringer's Solution. Density gradient centrifugation was conducted as described in Example II and the viability of the cells was determined to be 84.6% (pre-ficoll), and 80.2% (post-ficoll). The LEC and/or pre-LEC population removed from the gradient was then sorted in accordance with Example III and the FLT4+ and FLT4− sorted populations were determined by flow cytometry analysis to be 94.5% pure and 99.7% pure, respectively.

Aliquots of 1000 cells (each in 5 ml) of the sorted populations were then plated in uncoated six-well plates. Samples were plated in each of three different media: DMEM F12 (Cellgro), Media 231 (Smooth muscle media, Cascade Biologics), and EGM-2 MV (Cambrex). A CFU-F was defined as a colony of fifty or more fibroblastic-like cells. The observed CFU-F frequencies are shown in Table 6.

TABLE 6

| Population | Medium | Well 1 | Well 2 | Well 3 | Well 4 | Well 5 | Well 6 | Ave CFU-F Freq |
|---|---|---|---|---|---|---|---|---|
| FLT4+ | DMEM-F12 | 0 | 0 | 0 | 0 | 0 | 0 | 0 |
| FLT4+ | EGM-2 MV | 0 | 0 | 0 | 0 | 0 | 0 | 0 |
| FLT4+ | Media 231 | 0 | 0 | 0 | 1 | 0 | 0 | 0 |
| FLT4− | DMEM-F12 | 0 | 0 | 1 | 0 | 0 | 0 | 0.01 |
| FLT4− | EGM-2 MV | 0 | 4 | 5 | 1 | 3 | 1 | 0.23 |
| FLT4− | Media 231 | 0 | 1 | 0 | 1 | 0 | 1 | 0.05 |

The data in this example demonstrate that fibroblastic-like cells are, in general, absent from the purified adipose-derived cell population comprising LECs and/or pre-LECs. This example also provides an approach by which to measure the presence and absence of LECs and/or pre-LECs in an adipose-derived cell population. The next example provides even more evidence of the presence of LECs and/or pre-LECs in an adipose-derived cell population prepared, as described herein, and teaches yet another approach by which to measure the presence or absence of LECs and/or pre-LECs in an adipose-derived cell population.

Example VIII

Further Characterization and Measurement of the Presence or Absence of LECs and Pre-LECs in an Adipose-Derived Cell Population Using a CFU-Endo Assay As described in this example, an adipose-derived cell population containing LECs and/or pre-LECs was isolated (Example I) and further purified using density gradient centrifugation (Example II) and cell sorting (Example III). Once the cells were sorted into FLT4+ and FLT4− populations, the purified cells were then measured for development of CFU-Endo.

As in the CFU-F assays above, once the cells were isolated (Example I) and purified (Examples II and III), the FLT4+ and FLT4− populations were plated in each of the three different media, DMEM-F12, EGF-2 and Media 231. Additionally, three different substrates (gelatin, fibronectin, and laminin) were used with each medium. CFU-F was also assayed on the same substrates for comparison.

The results showed that the DMEM-F12 cultures and the 231 cultures produced very few or no colonies. Although the frequency of colonies detected was highest when the cells were cultured on gelatin-coated plates in EGM2-MV medium, it was only possible to expand colonies sufficiently for use in morphology assays or cytofluorometric analysis in Media 231 on fibronectin or laminin.

CFU-Endo was defined as a colony of ten or more cells having a rounded, cobblestone formation. Table 7 shows the CFU frequencies at 28 days of culture in EGM2-MV media.

TABLE 7

| CFU | Gelatin | Fibronectin | Laminin |
|---|---|---|---|
| Endothelial (CFU-Endo) | 0.08% (10 of 12 wells) | 0.025% (3 of 12 wells) | 0.06% (7 of 12 wells) |
| Fibroblastic (CFU-F) | 0.008% (1 of 12 wells) | None (0 of 12 wells) | 0.017% (2 of 12 wells) |

Most FLT-4+ CFU-Endo colonies were found to present a cobblestone formation, consistent with an endothelial cell phenotype. (See FIG. 18.) Accordingly, the data provided in this example provide even more evidence that the procedures described herein can effectively isolate LECs and/or pre-LECs from an adipose-derived cell population. This example also provides another approach that can be used to identify, measure, or characterize the presence or absence of LECs and/or pre-LECs in an adipose-derived cell population. The following example describes experiments that were performed to further characterize cell obtained from the CFU-Endo colonies prepared in this example.

Example IX

Cytofluorometric Analysis of Cells Derived from CFU-Endo Colonies

This example describes experiments that were performed to further characterize the cells obtained from the CFU-Endo colonies prepared in Example VIII. Two CFU-Endo colonies observed in the CFU-Endo assay described above were further expanded and evaluated by flow cytometry for expression of surface markers typically expressed by endothelial cells. One of these two colonies was first detected at 7 days of culture (on a laminin-coated plate) and the other at 28 days of culture (on a fibronectin-coated plate).

Several lymphatic endothelial cell-specific markers have been described in the literature. Anti-podoplanin antibodies have been described, e.g., by Breiteneder-Geleff, et al. 1999. Anti-Prox1 antibodies have been described, e.g., in U.S. Pub. No. 2005/0271636. Anti-LYVE-1 antibodies have been described, e.g., by Banerji, et al., 1999, "LYVE-1, a New Homologue of the CD44 Glycoprotein, Is a Lymph-specific Receptor for Hyaluronan," J. Cell Biology 144(4):789-801.

FACS analysis was performed using methods similar to those described in the above examples.

Following expansion for cytofluorometric analysis, the FLT-4 antigen was no longer detectable in either cultured population. Interestingly, there were more CD31⁻ cells identified in the colony that arose at day 28. As shown in Table 8, 25.7% of the cells from the Day 28 colony were CD31⁻, whereas 10.1% of those from the Day 7 colony were CD31⁻. The two populations expressed CD105 and CD146 at about the same level, and both failed to express detectable levels of CD144, CD11b, CD133, and podoplanin. The cytofluorometric analysis data are shown in FIG. 19. The example below provides more evidence of the presence of LECs and/or pre-LECs in the adipose-derived cell populations prepared as described herein and provides yet another approach to measure and/or characterize the adipose-derived cell population.

TABLE 8

| Colony | CD31⁻ | CD105⁺ | CD146⁺ |
|---|---|---|---|
| Day 7 | 10.1% | 93.5% | 86.7 |
| Day 28 | 25.7% | 79.6% | 82.2 |

Example X

In Vitro Analysis of Adipose-Derived LECs and/or Pre-LECs

This example describes experiments that were conducted to analyze and measure the ability of the expanded cells obtained from the two populations described in Example IX for their ability to proliferate, migrate, and form capillary-like structures (tubes).

Cells obtained from the Day 7 and Day 28 colony (Example IX) were analyzed for the ability to form tubes on Matrigel, previously described by, e.g., Pounce ML, 2001, "In vitro Matrigel Angiogenesis Assays." In: Methods in Molecular Medicine," Vol 46: Angiogenesis Protocols, Edited by J C Murray, Humana Press, Totowa, N.J. Matrigel is composed of basement membrane components, and is an extract of the Engelbreth-Holm-Swarm tumor. When plated in Matrigel, cells derived from both the colonies (detected in days 7 and 28) formed tube-like structures, as shown in FIG. 20. This result provides further evidence that cells derived from the FLT-4⁺ population of the adipose-derived cell population isolated in accordance with the methods described herein are functional endothelial cells. This example offers yet another method by which the presence or absence of LECs and/or pre-LECs can be evaluated in an adipose-derived cell population.

Example XI

RNA Analysis of Adipose-Derived LECs and/or Pre-LECs

This example describes several approaches that can be used to measure the presence or absence of LEC and/or pre-LEC-specific RNAs in an adipose derived cell population so as to confirm the presence of these cells in an adipose-derived cell population and differentiate said cells from LECs and/or pre-LECs present in dermis and tonsil tissue. Lymphatic endothelial cells and their precursors that are derived from adipose tissue are phenotypically distinct from those derived from other tissues, for example, the dermis or tonsil. One approach by which this is demonstrated is to isolate FLT4-positive cells from adipose tissue, dermis, and tonsils (e.g., using the procedures described in Examples I, II, or III), extract RNA from the cells, and perform a differential expression analysis, for example, a microarray. For each analysis RNA is extracted using TRIzol® (Invitrogen) followed by clean-up using the RNEasy Mini kit (Qiagen). cDNA is generated, pooled, labeled, and hybridized onto the Affymetrix GeneChip Human Genome U133A 2.0 Array or the Affymetrix Gene Chip rat Expression Set 230 according to the manufacturer's recommendations (GeneChip Expression Analysis: Technical Manual, Affymetrix). Normalization and analysis is performed using GeneSight software package from BioDiscovery. Heat mapping is performed with HEATMAP BUILDER (Stanford University, Palo Alto, Calif.).

Differences detected using this approach are validated using alternate strategies such as polymerase chain reaction (PCR) and, preferably, by immunoassay for expressed protein. For example, differences in the level of expression of a particular cell surface marker are demonstrated by flow cytometry demonstrating that certain markers are reproducibly expressed in adipose LECs or their progenitors but are not expressed in dermal LECs (or vice versa). Relative differences, for example, markers that are expressed at higher levels in one population or the other can also be determined by this approach. It is expected that the data produced from these experiments will show that LECs and/or pre-LECs isolated from adipose tissue are functionally different than LECs and/or pre-LECs isolated from, e.g., dermis or tonsil. The following example describes more approaches that can be used to measure and characterize the presence or absence of LECs and/or pre-LECs in an adipose-derived cell population and differentiate these cells from LECs and/or pre-LECs isolated from dermis and/or tonsil tissue.

Example XII

Immunophenotyping Adipose-Derived LECs and/or Pre-LECs

This example describes more approaches that can be used to measure the presence or absence of LEC and/or pre-LEC-specific RNAs in an adipose derived cell population so as to confirm the presence of these cells in an adipose-derived cell population and differentiate said cells from LECs and/or pre-LECs present in other tissues, e.g., dermis and tonsil. By employing techniques in immunophenotyping, the expression of lineage specific proteins that are characteristic of lymphatic endothelial cells can be exploited to distinguish LECs and/or pre-LECs isolated from adipose tissue from LECs and/or pre-LECs from other tissues. For example, pure populations of LECs and/or pre-LECs are isolated from dermis, tonsils, and adipose tissue using the techniques described in Examples I, II, or III. The FLT-4+ cells are then cultured using a specific endothelial cell growth medium. For the immunophenotyping, the cultured cells are then harvested from the culture vessels using a detachment enzyme, such as trypsin or similar, and incubated with antibodies recognizing different proteins. Differences in the level of expression of, e.g., CD34, CD31, vWF, KDR, VE-cadherin, CD54, CD58, FLT1, CD133, endoglin, macrophage mannose receptor, desmoplakin, podoplanin, prolyl-hydroxilase, CD36, Prox-1, LYVE-1, CD40, CD80, MHC class I and II molecules, ICAM-1, P-selectin, E-selectin, CD146, thrombomodulin, Tie-2 are then evaluated by flow cytometry. It is expected that the data produced from these experiments will show that LEC and pre-LEC cells isolated from adipose tissue are functionally different than LEC and/or pre-LEC cells isolated from dermis or tonsil. The following example describes more approaches that can be used to measure and characterize the presence or absence of LECs and/or pre-LECs in an adipose-derived cell population.

Example XIII

Transplantation of Adipose-Derived LECs and/or Pre-LECs into lacZ Animals

This example describes an approach that can be used to measure the ability of an adipose derived cell population comprising LECs and/or pre-LECs to expand lymphatic cells and induce formation of lymphatic vessels and lymphatic tissue. It is contemplated that an adipose-derived cell population comprising LECs and/or pre-LECs, prepared as described herein, can induce the repair and/or expansion of lymphatic cells, lymph vessels, and lymphatic tissue in a subject (e.g., a mammal such as a human). Preferably, the adipose-derived cell population comprising LECs and/or pre-LECs, prepared as described herein, are introduced into such existing lymphatic vessels in said subject. This can be in the context of repair of an existing vessel in a setting where a lymph vessel has become fully or partially denuded of lymphatic endothelial cells and it can be in a setting where lymph vessels are being replaced or generated de novo.

By one approach, de novo generation of lymph vessels is performed in a tissue transplant in which anastomosis of blood and lymphatic vessels is not performed surgically. In this context, vessels within the tissue either connect with adjacent, active vessels by biologic processes or they atrophy and are replaced by new vessels. In the related case where a tissue-engineered construct lacking lymphatic vessels is implanted into a subject the implanted tissue will become colonized by newly formed lymph vessels.

For example, free adipose tissue grafts (that is, portions or fragments of adipose tissue that are implanted without the surgical generation of connections with host lymph vessels) are implanted into syngeneic mice. One group of animals receives free adipose tissue grafts alone, the second receives similar grafts that are supplemented with an adipose-derived cell population comprising LECs and/or pre-LECs, prepared as described herein. In order to allow definitive determination of supplemental cell fate the supplemental cells are obtained from donor mice that carry the lacZ transgene in all cells. The product of this transgene, Betagalactosidase, is not expressed in non-transgenic mice, and can be detected by histologic staining with colorigenic substrates such as X-gal.

Several weeks after implantation the free adipose grafts are harvested and prepared for histologic evaluation of donor cell fate. Co-staining with X-gal and markers specific for lymphatic cells (for example, Prox-1, Lyve-1, Podoplanin, and FLT-4) is performed. Detection of cells that exhibit co-staining for these markers is evidence that supplemental cells have developed a lymph vessel-associated cell fate. It is expected that the data produced from these experiments will show that the adipose-derived cell population comprising LECs and/or pre-LECs are capable of inducing the expansion and proliferation of lymphatic cells in vivo, and said cells will induce the formation of lymphatic vessels and lymphatic tissue in transplanted mammals more effectively than the unprocessed adipose tissue. The following example describes another approach that can be used to measure and characterize the presence or absence of LECs and/or pre-LECs in an adipose-derived cell population.

Example XIV

Transplantation of Adipose-Derived LECs and/or Pre-LECs and Detection of Lymphatic Tissue Formation by Histology This example describes another approach that can be used to measure the ability of an adipose derived cell population comprising LECs and/or pre-LECs to expand lymphatic cells and induce formation of lymphatic vessels and lymphatic tissue. By this approach, the ability of an adipose derived cell population comprising LECs and/or pre-LECs to expand lymphatic cells and induce formation of lymphatic vessels and lymphatic tissue is determined by measuring the frequency or density of such vessels in the mammal in the presence and absence of the inventive cell population.

In these studies a wound is formed in recipient mammals. The wound is a cutaneous, full thickness skin wound, a myocardial wound formed by occlusion of the coronary artery for approximately 45 minutes followed by release of the occlusion and reperfusion of the ischemic capillary bed, or an ischemic limb injury model. In this latter injury model, sections of the femoral artery serving one hind limb are resected and/or ligated. Over approximately two weeks perfusion is at least partially restored by development of new blood and lymph vessels.

Within 48 hours of the creation of each injury type, the animals are divided into two groups, a control group (that receives saline vehicle only) and a cell-treatment group (to which an adipose derived cell population comprising LECs and/or pre-LECs are administered). For the cutaneous wound, the adipose derived cell population comprising LECs and/or pre-LECs are administered by direct application to the wound bed and intra- and sub-cutaneous injection into the surrounding area. For myocardial injury, the adipose derived cell population comprising LECs and/or pre-LECs are delivered into the vascular system. For the hind limb wound, the adipose derived cell population comprising LECs and/or pre-LECs are delivered either by direct injection into the muscles of the affected hind limb or into the vasculature.

One to three weeks following cell delivery, the recipient animal is euthanized and injured tissues are excised and prepared for histology. The frequency and density of lymph vessels is determined by immunostaining sections with lymphatic-specific antibodies. Computer-aided analysis is performed to determine the number of positive staining structures present within a defined surface area. Detection of a statistically significant difference in lymph vessel density between the cell-treated and control group for any wound type is expected and such evidence will indicate that the adipose derived cell population comprising LECs and/or pre-LECs, prepared as described herein, can expand lymphatic cells and induce formation of lymphatic vessels and lymphatic tissue in vivo. The following example describes approaches that can be used to treat patients having post-surgery lymphedema.

Example XV

Use of an Adipose-Derived Cell Population Comprising LSCs and/or Pre-LECs for the Treatment of Post-Surgery Lymphedema This example provides methods of treating patients having post-surgery lymphedema by providing patients identified as having post-surgery lymphedema with an adipose derived cell population comprising LECs and/or pre-LECs. In some embodiments, patients having post-surgery lymphedema are identified as individuals in need of an adipose derived cell population comprising LECs and/or pre-LECs prior to administration of said cells. Identification of patients in need of an adipose derived cell population comprising LECs and/or pre-LECs and/or patients having post-surgery lymphedema can be accomplished using clinical evaluation. For example, following partial mastectomy for breast carcinoma, patients suffer from lymphedema due to axillary lymph node removal and these patients can be identified as patients in need of an adipose derived cell population comprising LECs and/or pre-LECs through routine clinical evaluation by the surgeon or physician.

Identified patients, as described above, are then injected with cells in the affected area in one or more injections.

Lymph circulation in the breast is then measured by $^{99m}$Tc-nanocolloid clearance and skin circulation by Laser Doppler Fluxmetry (LDF), as described, e.g., by Perbeck, et al., in "Lymph Circulation in the Breast after Radiotherapy and Breast Conservation," Lymphology. 2006 March; 39(1):33-40. Measurements are made prior to cell injections and at other times as desired. The lymph circulation is measured 2 cm above and medial or lateral to the areolar border in the quadrant not operated on for carcinoma. Skin circulation is measured at corresponding sites. The lymph circulation is expressed as the ratio of $^{99m}$Tc-nanocolloid clearance and compared with that in patients who did not receive cell injections. These experiments can show that transplantation of an adipose-derived cell population comprising LECs and/or pre-LECs will expand lymphatic cells and induce formation of lymphatic vessels and lymphatic tissue in the patient and thereby treat post-surgery lymphedema. The following example provides an approach to use adipose-derived cell population comprising LECs and/or pre-LECs in breast augmentation procedures.

Example XVI

Use of an Adipose-Derived Cell Population Comprising LECs and/or Pre-LECs in Breast Augmentation This example describes the use of an adipose-derived cell population comprising LECs and/or pre-LECs in breast augmentation procedures. Accordingly, a patient in need of breast augmentation is identified as one in need of an adipose-derived cell population comprising LECs and/or pre-LECs. The identification of a patient that desires breast augmentation as one in need of an adipose-derived cell population comprising LECs and/or pre-LECs can be accomplished using clinical analysis by a physician or surgeon. U.S. Pat. App. Pub. No. 20050025755, entitled "Methods of Using Adipose Tissue-Derived Cells in Augmenting Autologous Fat Transfer," hereby expressly incorporated by reference, details a breast augmentation approach that may be applicable in some embodiments. Accordingly, a patient is identified as one in need of an adipose-derived cell population comprising LECs and/or pre-LECs and adipose tissue is collected from said identified patient. Adipose tissue is selected to be harvested from the lateral and medial thigh regions of the patient. The area to be harvested is injected subcutaneously with a standard tumescent fluid solution, which may or may not contain a combination of lidocaine, saline, and/or epinephrine in different standardized dosing regimens.

Using an 11-blade scalpel (or other standard blade), a small puncture wound is made in order to transverse the dermis. The blade is turned 360 degrees to complete the wound. A blunt tip 14-gauge (or appropriately sized) cannula is then inserted into the subcutaneous adipose tissue plane. The cannula may be connected to a power assisted suction device or to a syringe for manual aspiration. The cannula is then moved throughout the plane to disrupt the connective tissue architecture. The volume of aspirate obtained is between 700 cc and 1000 cc. A fraction of the adipose tissue collected in this manner is provided to an adipose cell processing unit for isolation and concentration of an adipose-derived cell population comprising LECs and/or pre-LECs. The remainder of the adipose tissue is processed for re-implantation into the breast. Alternatively, the patient may have adipose tissue removed through a lipectomy procedure.

After removal of adipose tissue, hemostasis of the patient is achieved with standard surgical techniques and the wound closed primarily. The collection of adipose tissue occurs about 1-2 hours prior to augmentation mammoplasty in a clinical office. However, the timing of collection is expected to vary and will depend on quality of care standards. Ultimately, the practitioner responsible for administering care to the patient will determine the timing of collection.

A portion of the adipose tissue is used to prepare an enriched or concentrated population of adipose-derived cells comprising LECs and/or pre-LECs (e.g., by using the procedure in Example I). While the adipose-derived cell population comprising LECs and/or pre-LECs prepared in accordance with, e.g., Example I, can be provided to the patients identified above with adipose tissue, collagen matrix or another material suitable for breast augmentation without further processing, it is oftentimes more desirable to further purify the adipose-derived cell population comprising LECs and/or pre-LECs by using the procedures detailed in Example II and/or III. That is, in some embodiments, the isolated adipose-derived cell population comprising LECs and/or pre-LECs obtained from the cell processing unit (e.g., Example I) are provided with adipose tissue, collagen matrix, or another material suitable for breast augmentation to said identified patient without further purification and in some embodiments, the purified adipose-derived cell population comprising LECs and/or pre-LECs obtained after density gradient centrifugation (e.g., Example II) or cell sorting (e.g., Example III) or a combination of density gradient centrifugation and cell sorting (e.g., Example III) are provided with adipose tissue, collagen matrix, or another material suitable for breast augmentation to said identified patient. Preferably, cell suspensions are mixed with a unit of adipose tissue (approximately 100-300 cc) to be transplanted. After tissue processing is complete, the patient is prepared to undergo augmentation mammoplasty. The cell dose delivered to the patient is determined from the cell yield after adipose tissue processing. For example, approximately $5.5 \times 10^5$ cells per 50 cc of autologous fat is transplanted into the breast. The composition is delivered through a standard 14-gauge blunt tip cannula inserted into the breast tissue through a periareolar incision. The regenerative-cell-enhanced adipose tissue is administered in a tear-like fashion to increase the surface area to volume ratio. The results in these studies can show that the use of an adipose-derived cell population comprising LECs and/or pre-LECs will improve breast augmentation procedures (e.g., by inducing the expansion of lymphatic cells, formation of lymphatic vessels, or the formation of lymphatic tissue). The following example describes approaches that can be used to treat diabetic ulcers.

Example XVII

Use of an Adipose-Derived Cell Population Comprising LSCs and/or Pre-LECs to Treat Patients Having Diabetic Ulcers This example provides an approach by which an adipose-derived cell population comprising LECs and/or pre-LECs is used to treat diabetic ulcers. As above, an adipose-derived cell population comprising LECs and/or pre-LECs is provided by using a cell processing unit (e.g., Example I), density gradient sedimentation (e.g., Example II), cell sorting (e.g., Example III) or a combination of any of these approaches. Once the adipose-derived cell population comprising LECs and/or pre-LECs is obtained it can be combined with any number of growth factors or additives as known in the art, preferably additives described in WO 2006/014157, entitled "Methods of Using Regenerative Cells to Promote Wound Healing," by Vojtassak, et al., 2006; "Autologous Biograft and Mesenchymal Stem Cells in Treatment of the Diabetic Foot," Neuro Endocrinol Lett. 27 Suppl 2:134-7 (reporting use of a method for treatment of chronic non-healing wound (diabetic ulcer) using an autologous biograft composed of autologous skin fibroblasts on biodegradable collagen membrane (Coladerm) in combination with autologous mesenchymal stem cells (MSC) derived from the patient's bone marrow); and by Cavallini, M., 2007, "Autologous Fibroblasts to Treat Deep and Complicated Leg Ulcers in Diabetic Patients," Wound Repair Regen. 15(1):35-8, incorporated herein by reference.

Patients suffering from a diabetic ulcer are identified as ones in need of an adipose-derived cell population comprising LECs and/or pre-LECs using techniques available in routine clinical evaluation and said identified patients are provided an effective amount of an adipose-derived cell population comprising LECs and/or pre-LECs. The adipose-derived cell population comprising LECs and/or pre-LECs can be prepared using a cell processing unit (e.g., Example I), density gradient sedimentation (e.g., Example II), cell sorting (e.g., Example III) or a combination of any of these approaches and the cells can include an additive as described herein. In patients that receive said adipose-derived cell population comprising LECs and/or pre-LECs with or without an additive, an improvement in the ability to heal the diabetic ulcer will be seen.

It is to be understood that this invention is not limited to particular formulations or process parameters, as these may, of course, vary. It is also to be understood that the terminology used herein is for the purpose of describing particular embodiments of the invention only, and is not intended to be limiting. Further, it is understood that a number of methods and materials similar or equivalent to those described herein can be used. Any feature or combination of features described herein are included within the scope of the present invention provided that the features included in any such combination are not mutually inconsistent as will be apparent from the context, this specification, and the knowledge of one of ordinary skill in the art. The above-described embodiments have been provided by way of example, and the present invention is not limited to these examples. Multiple variations and modification to the disclosed embodiments will occur, to the extent not mutually exclusive, to those skilled in the art upon consideration of the foregoing description. Additionally, other combinations, omissions, substitutions and modifications will be apparent to the skilled artisan in view of the disclosure herein. Accordingly, the present invention is not intended to be limited by the disclosed embodiments, but is to be defined by reference to the appended claims.

The contents of all cited references, including literature references, issued patents, published patent applications, and co-pending patent applications, cited throughout this application are hereby expressly incorporated by reference in their entirety. Those skilled in the art will recognize, or be able to ascertain using no more than routine experimentation, many equivalents to the specific embodiments of the invention described herein. Such equivalents are intended to be encompassed by the appended claims.

What is claimed is:

1. A method of treating edema in a subject in need thereof, comprising:
identifying a subject having edema; and
administering to said subject an isolated population of adipose-derived cells comprising lymphatic endothelial cells (LECs) and pre-LECs, wherein greater than 5% of said population of adipose-derived cells express FLT-4.

2. The method of claim 1, wherein the edema is lymphedema.

3. The method of claim 1, wherein said subject has a wound.

4. The method of claim 3, wherein said wound is a burn.

5. The method of claim 3, wherein said wound is a skin wound following grafting.

6. The method of claim 3, wherein said wound is a radiation wound.

7. The method of claim 1, wherein said isolated population of adipose-derived cells comprising lymphatic endothelial cells (LECs) and pre-LECs is administered by injection into a lymph node.

8. The method of claim 1, wherein said isolated population of adipose-derived cells comprising lymphatic endothelial cells (LECs) and pre-LECs is administered by injection into lymphatic vessels.

9. The method of claim 1, wherein said isolated population of adipose-derived cells comprising lymphatic endothelial cells (LECs) and pre-LECs is administered by injection into tissue space.

10. The method of claim 1, wherein greater than 5% of said population of adipose-derived cells also express CD45.

11. The method of claim 1, wherein greater than 5% of said population of adipose-derived cells also express CD34.

12. The method of claim 1, wherein greater than 5% of said population of adipose-derived cells also express CD14.

13. The method of claim 1, wherein said isolated population of adipose-derived cells is mixed with an additive prior to administering the adipose-derived cells to the subject.

14. The method of claim 13, wherein said additive is selected from the group consisting of an anti-apoptosis agent, a growth factor, a tissue graft, a portion of unprocessed adipose tissue, a population of adipose-derived stem cells, a population of adipose-derived endothelial cells, population of adipose-derived progenitor cells, a cell differentiation factor.

15. The method of claim 1, wherein said identification comprises examination of a tissue biopsy, fluorescence micorlymphangiography, computed tomography, X-ray lymphography, dual0site fluorescence angiography, isotope lymphography, laser-Doppler analysis, magnetic resonance imaging, ultrasonography, or any combination thereof.

16. The method of claim 1, wherein said isolated population of adipose-derived cells is not cultured prior to providing the isolated population of adipose-derived cells to the subject.

17. The method of claim 1, wherein said isolated population of adipose-derived cells is cultured in vitro prior to providing the isolated population of adipose-derived cells to the subject.

18. The method of claim 1, wherein said isolated population of adipose-derived cells is obtained by processing adipose tissue in a cell processing device configured to maintain a closed pathway.

19. The method of claim 1, further comprising analyzing said edema following the administration of said isolated population of adipose-derived cells.

20. The method of claim 1, wherein the isolated population of adipose-derived cells comprising LECs and pre-LECs is cryopreserved.

* * * * *

UNITED STATES PATENT AND TRADEMARK OFFICE
CERTIFICATE OF CORRECTION

PATENT NO. : 9,486,484 B2
APPLICATION NO. : 14/336755
DATED : November 8, 2016
INVENTOR(S) : Alfonso et al.

Page 1 of 1

It is certified that error appears in the above-identified patent and that said Letters Patent is hereby corrected as shown below:

In the Claims

In Column 88, Line 64, In Claim 15, change "micorlymphangiography," to --microlymphangiography,--.

In Column 88, Line 65, In Claim 15, change "dual0site" to --dual-site--.

Signed and Sealed this
Tenth Day of April, 2018

Andrei Iancu
*Director of the United States Patent and Trademark Office*